US012195738B2

(12) United States Patent
Ben Khaled et al.

(10) Patent No.: US 12,195,738 B2
(45) Date of Patent: Jan. 14, 2025

(54) METHOD FOR MODIFYING ALKALOID CONTENT IN PLANTS

(71) Applicant: BRITISH AMERICAN TOBACCO (INVESTMENTS) LIMITED, London (GB)

(72) Inventors: Sara Ben Khaled, London (GB); Francisco Anastacio De Abreu E Lima, London (GB)

(73) Assignee: BRITISH AMERICAN TOBACCO (INVESTMENTS) LIMITED, London (GB)

( * ) Notice: Subject to any disclaimer, the term of this patent is extended or adjusted under 35 U.S.C. 154(b) by 175 days.

(21) Appl. No.: 17/597,249

(22) PCT Filed: Jul. 3, 2020

(86) PCT No.: PCT/GB2020/051603
§ 371 (c)(1),
(2) Date: Dec. 30, 2021

(87) PCT Pub. No.: WO2021/001659
PCT Pub. Date: Jan. 7, 2021

(65) Prior Publication Data
US 2022/0340921 A1    Oct. 27, 2022

(30) Foreign Application Priority Data

Jul. 3, 2019 (GB) .................................. 1909563

(51) Int. Cl.
*C12N 15/82* (2006.01)
*C07K 14/415* (2006.01)

(52) U.S. Cl.
CPC ........ *C12N 15/8243* (2013.01); *C07K 14/415* (2013.01); *C12N 15/8218* (2013.01)

(58) Field of Classification Search
None
See application file for complete search history.

(56) References Cited

U.S. PATENT DOCUMENTS

| | | | |
|---|---|---|---|
| 6,376,750 | B1 | 4/2002 | Yu et al. |
| 7,798,153 | B2 * | 9/2010 | Lawrence, Jr. ........ A24B 15/10 131/352 |
| 8,455,719 | B2 | 6/2013 | Frankard et al. |
| 9,290,773 | B2 | 3/2016 | Edgerton |
| 9,878,004 | B2 | 1/2018 | Williams et al. |
| 9,879,275 | B2 * | 1/2018 | Nadzan .............. C12N 15/8261 |
| 10,138,492 | B2 | 11/2018 | Nadzan et al. |
| 10,167,482 | B2 | 1/2019 | Coffin |
| 2006/0195934 | A1 | 8/2006 | Apuya et al. |
| 2009/0222957 | A1 | 9/2009 | Apuya et al. |
| 2012/0090052 | A1 | 4/2012 | Sanz Molinero et al. |
| 2014/0325710 | A1 | 10/2014 | Abad et al. |
| 2015/0259699 | A1 | 9/2015 | Nadzan et al. |
| 2016/0032299 | A1 | 2/2016 | Hashimoto et al. |
| 2017/0137835 | A1 | 5/2017 | Qu et al. |
| 2018/0037902 | A1 | 2/2018 | Le et al. |

FOREIGN PATENT DOCUMENTS

| | | | |
|---|---|---|---|
| CN | 101824429 A | 9/2010 | |
| KR | 101460741 B1 | 11/2014 | |
| WO | 2003020936 A1 | 3/2003 | |
| WO | 2004013295 A2 | 2/2004 | |
| WO | 2006109197 A2 | 10/2006 | |
| WO | WO-2010125036 A2 * | 11/2010 | ........... C07K 14/415 |
| WO | 2015085299 A1 | 6/2015 | |
| WO | 2015131053 A1 | 9/2015 | |
| WO | 2018237107 A1 | 12/2018 | |
| WO | WO-2019046756 A1 * | 3/2019 | ............... A01H 5/10 |

OTHER PUBLICATIONS

Moldoveanu, Serban C., Wayne A. Scott, and Darlene M. Lawson. "Nicotine analysis in several non-tobacco plant materials." Contributions to Tobacco & Nicotine Research 27.2 (2016): 54-59. (Year: 2016).*
Keskin, Ozlem, et al. "A new, structurally nonredundant, diverse data set of protein-protein interfaces and its implications." Protein Science 13.4 (2004): 1043-1055. (Year: 2004).*
Guo, Haiwei H., Juno Choe, and Lawrence A. Loeb. "Protein tolerance to random amino acid change." Proceedings of the National Academy of Sciences 101.25 (2004): 9205-9210. (Year: 2004).*
Thornton, Janet M., et al. "From structure to function: approaches and limitations." nature structural biology 7.11 (2000): 991-994. (Year: 2000).*
Köster et al., "RNA-Binding Proteins Revisited—The Emerging *Arabidopsis* mRNA Interactome", Trends Plant Sci., vol. 22, No. 6, pp. 512-526, 2017.
Marondedze et al., "The RNA-binding protein repertoire of *Arabidopsis thaliana*", Scientific Reports, vol. 6, 29766, pp. 1-13, 2016.
International Searching Authority in connection with PCT/GB2020/051603 filed Jul. 3, 2020, "The International Search Report and the Written Opinion of the International Searching Authority, or the Declaration", 19 pages, mailed Nov. 5, 2020.
Ben Saad et al., "AlSRG1, a novel gene encoding an RRM-type RNA-binding protein (RBP) from Aeluropus littoralis, confers salt and drought tolerance in transgenic tobacco," Environmental and Experimental Botany, Mar. 2018, vol. 150, pp. 25-36.

(Continued)

*Primary Examiner* — Amjad Abraham
*Assistant Examiner* — Kelsey L McWilliams
(74) *Attorney, Agent, or Firm* — McKee, Voorhees & Sease, PLC

(57) ABSTRACT

The present invention relates to a method of modulating the alkaloid content of a plant or a part thereof, the method comprising modifying the plant by modulating the activity or expression of at least one gene encoding an RNA binding protein. The present invention also relates to a method of reducing the content of at least one tobacco specific nitrosamine (TSNA) precursor in tobacco, the method comprising modulating the activity or expression of at least one gene encoding an RNA binding protein.

18 Claims, 36 Drawing Sheets

Specification includes a Sequence Listing.

(56) References Cited

OTHER PUBLICATIONS

Bollenbach et al., "CSP41a, a multifunctional RNA-binding protein, initiates mRNA turnover in tobacco chloroplasts," The Plant Journal, Nov. 2003, vol. 36, No. 6, pp. 842-852.
Hakkinen et al., "Functional characterisation of genes involved in pyridine alkaloid biosynthesis in tobacco," Phytochemistry, Nov.-Dec. 2007, vol. 68, Issues 22-24, pp. 2773-2785.
Rushton et al., "Tobacco Transcription Factors: Novel Insights into Transcriptional Regulation in the Solanaceae," Plant Physiology, May 2008, vol. 147, Issue 1, pp. 280-295.
Voelckel et al., "Herbivore-induced ethylene burst reduces fitness cost of jasmonate- and oral secretion-induced defenses in Nicotiana attenuata," Oecologia, Jan. 2001, vol. 127, No. 2, pp. 274-280.
Edwards et al., "A reference genome for Nicotiana tabacum enables map-based cloning of homeologous loci implicated in nitrogen utilization efficiency," BMC Genomics, Jun. 19, 2017, vol. 18, No. 448, 14 pages.
Feng et al., "Research Progress on Nitrate Accumulation and Regulation During Tobacco Plant Development," Chinese Journal of Tobacco, Apr. 13, 2019, vol. 25, No. 2, pp. 109-120.
Hirose et al., "Nicotiana sylvestris mRNA for RNA-binding glycine-rich protein-1a, complete cds," Genbank, Jan. 23, 2008, 2 pages.
Hirose et al., "RNA-binding glycine-rich protein-1a [Nicotiana sylvestris]," Genbank, Jan. 23, 2008, 1 page.
Saurabh et al., "RNA interference: concept to reality in crop improvement," Planta, Jan. 9, 2014, vol. 239, No. 3, pp. 543-564.
Zhao et al., "Progress in the Application of Proteomics Techniques in Tobacco Research," Chinese Journal of Tobacco, Feb. 28, 2014, vol. 20, No. 1, pp. 103-110.

\* cited by examiner

Figure 3

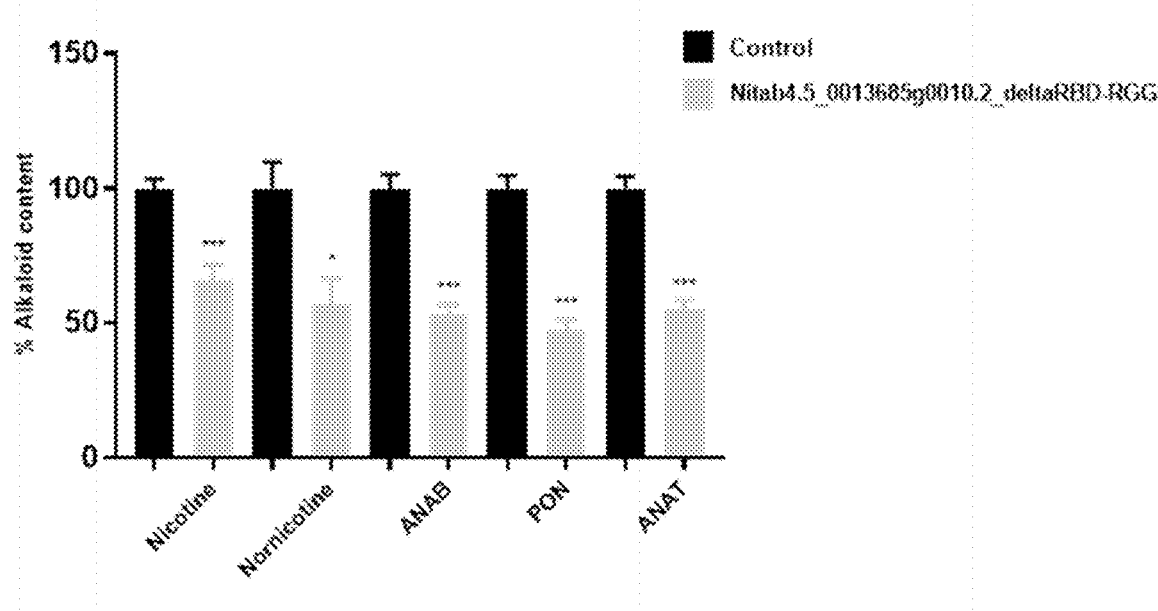

Figure 4

Nitab4.5_0013685g0010.2 amino acid sequence (SEQ ID NO. 1):

MAEVEYRCFVGGLAWATTDQTLGEAFSQFGEILDSKIINDRETGRSRGFGFVTFKDEKAMRDAIEGMNGQDL
DGRNITVNEAQSRGSGGGGGGGGGYRGGSGGGYGGGGRREGGYGGGGGYGGGRREGGYGGGGGGGYGGGRREG
GYGGGSEGNWRS

Figure 5

Nitab4.5_0013685g0010.2 coding sequence (SEQ ID NO. 2):

ATGGCAGAAGTTGAATACAGGTGCTTCGTCGGTGGGCTAGCATGGGCTACCACGACCAAACACTTGGGGAG
GCTTTTTCTCAGTTCGGCGAAATTCTCGACTCGAAGATTATCAATGACAGAGAAACTGGTAGATCTAGAGGA
TTTGGATTTGTTACCTTCAAGGATGAGAAAGCCATGAGGGACGCTATTGAAGGGATGAACGGCCAGGACCTT
GACGGTCGTAACATCACCGTCAACGAAGCTCAGTCTCGCGGAAGCGGCGGAGGTGGAGGCGGTGGCGGTTAC
CGTGGTGGTAGCGGTGGAGGCTACGGAGGTGGTGGCCGTCGTGAAGGTGGATACGGTGGTGGCGGCGGTTAC
GGAGGTGGCCGCCGTGAAGGTGGTTATGGTGGTGGTGGCGGCGGCGGTTATGGAGGTGGCCGTCGTGAAGGT
GGTTACGGTGGTGGCTCTGAAGGAAACTGGAGGAGTTAG

Figure 6
Nitab4.5_0013685g0010.2 genomic sequence (SEQ ID NO. 3):

ACAGCTCTCTCTCTTTACTTCATTTTTAGGGTTTCTTCTTATTAATCAGAAAAAAAAATGGCAGAAGTTGAA
TACAGGTGCTTCGTCGGTGGGCTAGCATGGGCTACCACCGACCAAACACTTGGGGAGGCTTTTTCTCAGTTC
GGCGAAATTCTCGACTCGAAGGTCTGTTGCAAAACAGAGCAGAGATCGGATTCGAGCCGATTTGAATCGGCT
TCGTTGACCCTCTGTTACTGGAAAAATTGATCTGTTACTACTCTCTCTGTTACTGTTACTGTTACTACTCTC
TGGTTTATCTGTTACTGTTACTGTTTGTTACTATTATTCCACTTTCCCCGAAACGGTACGTTCCGTCTTCCT
CTGTTTATACAAGAGATGAAGATAGATCGATTTTAATGTTTCTCCCTATTTTTTTATTTTATATTTTATG
GATTTACCTATTTTTGGATGTTATGTTGTAGATCTGGTTAGATCTGATGTGTTTTTTTAATGATATTTGAAT
TTTTCAGATTATCAATGACAGAGAAACTGGTAGATCTAGAGGATTTGGATTTGTTACCTTCAAGGATGAGAA
AGCCATGAGGGACGCTATTGAAGGGATGAACGGCCAGGACCTTGACGGTCGTAACATCACCGTCAACGAAGC
TCAGTCTCGCGGAAGCGGCGGAGGTGGAGGCGGTGGCGGTTACCGTGGTGGTAGCGGTGGAGGCTACGGAGG
TGGTGGCCGTCGTGAAGGTGGATACGGTGGTGGCGGCGGTTACGGAGGTGGCCGCCGTGAAGGTGGTTATGG
TGGTGGTGGCGGCGGCGGTTATGGAGGTGGCCGTCGTGAAGGTGGTTACGGTGGTGGCTCTGAAGGAAACTG
GAGGAGTTAGATTTTCCGTTGCCTTTAGATTTATTTTTTGGTTTGAAATTTATGGTTCTAAGTTTGGTTGA
AGTTCCGTTATGGTTTACTGTGGTTCCTGCTACTGTCCTCGTTTTTGACCGTGAGATTGTTACCGTGATGTT
ACGTTGTGGATCTGTATTTACAAAGTTCTCTGGAATGAAGTGAATGAAGATTTACCGTTTACAATTAACAAT
TCATGTGTGTGTTATTATTTAGTTTAGTAAATGGAGATATATCCCTTTATGT

Figure 7
Nitab4.5_0000308g0150.2 amino acid sequence (SEQ ID NO. 4):

MADAEYRCFVGGLAWATTDQTLGDAFSQYGEIVDSKIINDRETGRSRGFGFVTFKDEQAMRDAIEGMNGQDL
DGRNITVNEAQSRGSGGGGGRGGGGGGYGGGGGYGGGGRREGGYGGGGGGYGGGRRDGGYGGGGGYGGGRRE
GGYGGGSEGSWRS

Figure 8
Nitab4.5_0000308g0150.2 coding sequence (SEQ ID NO. 5):

ATGGCAGATGCTGAATACAGGTGCTTCGTCGGTGGGCTAGCATGGGCTACCACCGACCAAACACTTGGGGAT
GCTTTTTCTCAGTACGGTGAAATTGTCGACTCGAAGATTATCAATGACAGAGAAACTGGTAGATCTAGAGGA
TTTGGATTTGTTACCTTCAAGGATGAGCAAGCTATGAGGGACGCTATTGAAGGGATGAACGGTCAGGACCTT
GACGGTCGTAACATCACCGTCAACGAAGCCCAGTCTCGCGGAAGCGGCGGAGGCGGCGGTCGCGGTGGTGGC
GGTGGAGGCTACGGAGGTGGTGGAGGCTACGGAGGTGGTGGCCGCCGTGAAGGTGGATACGGTGGCGGCGGT
GGCGGTTACGGAGGTGGCCGCCGTGATGGTGGTTACGGTGGTGGTGGAGGTTATGGAGGTGGCCGTCGTGAA
GGTGGTTACGGTGGTGGCTCTGAAGGAAGCTGGAGGAGTTAA

Figure 9

Nitab4.5_0000308g0150.2 genomic sequence (SEQ ID NO. 6):

CGGAGTTTTCTCAGTAACCAAACGGACAATTTTTTTAACCAGACCCCTAAACCCGAGTTGCATTGAAGTTAG
GAAAAGAACCGCCGTGCACGATTAACTTAACCAGCCCTAGACTCAACCCTAGGCTCCTCAACCAGCCTATAA
AAACCGGCGTTTTCTACTCTCGTATCCACAGCTCTCTCTTCACTTTGTTTTTAGGTATTCTTCTTATTATTA
ATCGGGAAATAATGGCAGATGCTGAATACAGGTGCTTCGTCGGTGGGCTAGCATGGGCTACCACCGACCAAA
CACTTGGGGATGCTTTTCTCAGTACGGTGAAATTGTCGACTCGAAGGTCTGTTGGAAAACAGAGCAGAGAT
CGGATTCGAGCCGATTTGAATCGGCTTCGTTGACCCTCTGTTACTGGAAAAATTGATCTGTTACTACTCTCT
CTGTTACTGTTACTGTTACTGTTACTACTCTCTGGTTTATCTGTTACTGTTACTATTGTTACTGTTATTCC
ACTTTCCCCGAAACGGTACGTTCCGTCTTCCTCTGTTTATACAAGAGATGAAGATAGATCGCTTTTAATGTT
TCTCCCCTATTTTTTTGATTTTTGATTTTATGGTTTTACCTTTTTTGGATTTTATGTTGTAGATCTGGTTA
GATCTGATGTTTTTTTTTTTTTATGATTTGGACTTTTTCAGATTATCAATGACAGAGAAACTGGTAGATCT
AGAGGATTTGGATTTGTTACCTTCAAGGATGAGCAAGCTATGAGGGACGCTATTGAAGGGATGAACGGTCAG
GACCTTGACGGTCGTAACATCACCGTCAACGAAGCCCAGTCTCGCGGAAGCGGCGGAGGCGGCGGTCGCGGT
GGTGGCGGTGGAGGCTACGGAGGTGGTGGAGGCTACGGAGGTGGTGGCCGCCGTGAAGGTGGATACGGTGGC
GGCGGTGGCGGTTACGGAGGTGGCCGCCGTGATGGTGGTTACGGTGGTGGTGGAGGTTATGGAGGTGGCCGT
CGTGAAGGTGGTTACGGTGGTGGCTCTGAAGGAAGCTGGAGGAGTTAAATTTTCCGTTGCCTTCAGATCTTT
TGTTTGAAATTTATGGTTCTAAGTTTTGTTGAAGTTCCGTTATGGTTTACTGTTGTTCCTGTTACTGTCCTC
GTTTTTGACCGCGAGATTGTTACCGTGATGTTACCTTTGTGGATCTGTATTTACGAAGTTATCTGGAATTAA
GTGAATTTAGATTTACAGTCTACAATTGCATACCTGTTAACTCTTGCGC

Figure 10

Nitab4.5_0003919g0010.2 amino acid sequence (SEQ ID NO. 7):

MAEVEYRCFVGGLAWATTDRTLGEAFSQYGEVLESKIINDRETGRSRGFGFVTFGDEKSMRDAIEGMNGQDL
DGRNITVNEAQSRGSGGGGGGGGGFRGGRREGGGGYGGGGYGGGRREGGGGGYGGGGYGGGRDRGYGGGDRGY
GGDGGSRYSRGGGDSDGNWRN

Figure 11

Nitab4.5_0003919g0010.2 coding sequence (SEQ ID NO. 8):

ATGGCTGAAGTTGAATACCGGTGCTTCGTCGGTGGGCTCGCATGGGCTACCACTGATCGAACCCTAGGTGAA
GCTTTCTCTCAGTACGGCGAGGTTCTTGAATCGAAGATAATCAATGACCGTGAAACCGGTAGATCTAGAGGA
TTTGGCTTTGTTACCTTCGGTGATGAGAAATCCATGAGGGACGCTATCGAAGGGATGAACGGCCAAGACCTT
GACGGTCGTAACATCACCGTTAACGAAGCTCAATCACGCGGAAGCGGCGGCGGCGGCGGCGGTGGTTTC
CGCGGTGGACGTCGTGAAGGAGGCGGCGGATACGGAGGTGGAGGATATGGAGGTGGAAGACGCGAGGGCGGC
GGTGGTGGTTACGGCGGCGGCGGTTATGGTGGTGGCCGTGACCGTGGATATGGCGGTGGTGACCGTGGATAC
GGTGGTGATGGCGGATCACGCTACTCAAGGGGTGGTGGTGACTCTGATGGAAACTGGAGGAATTAG

Figure 12

Nitab4.5_0003919g0010.2 genomic sequence (SEQ ID NO. 9):

AAAAATTTTCCCAACGCGTGAAAAAGAGTTTCTCAAGTCTCAACGCGTCTTCAACGACGGCAAAGAAAAAG
AAATCGCGTTGAATAACTTTTACTTTTGCAAGAAATTCGGAAAAAACAAGAGCCGAAACCAGACCTCTAACC
CAAGTTGAATAGAGTGCTAAATTAACTCAACCGCCCTGCTTAACCCTAGCATCCTCCTCCTCCCTATAAATA
TATAGCCTTTCCTCATATTTTTCCTCATCCCTTTCTCCTCCGTTGTCATCTCTCTCTATAATTTAAAAAAAA
ATCAATGGCTGAAGTTGAATACCGGTGCTTCGTCGGTGGGCTCGCATGGGCTACCACTGATCGAACCCTAGG
TGAAGCTTTCTCTCAGTACGGCGAGGTTCTTGAATCGAAGGTCCGTTTGTCGGTCGCAGAGCAGAGATCGGA
ATCCGAGCCGTGATTTGGCTTCGTTTACCCCTCTGTTACTGTTGATTCATCTGTTACTGTTACTATGTCTCT
CTCTGTTACTGTTGCTTCATCTGTTACTGTTACTATTTGATACTATTATTCGTTCTCTTAACGGTACGTT
CCGTCTTACTTCTCTTCTTAAAAAAGAGATGAAGATAGATCGGTTATTTCTATTTTTGGTCCAGTTTGATT
GGAATGAATGTTAGTTTCCGAGCAAGCTCGGACATAGTCCTTTTGCTTTGTTTTTCCTGTGACAAGTGTGG
ATCTGGCAGATCTGATGTTTTTGTTGTGGATTTTGATTTTACAGATAATCAATGACCGTGAAACCGGTAGAT
CTAGAGGATTTGGCTTTGTTACCTTCGGTGATGAGAAATCCATGAGGGACGCTATCGAAGGGATGAACGGCC
AAGACCTTGACGGTCGTAACATCACCGTTAACGAAGCTCAATCACGCGGAAGCGGCGGCGGCGGCGGCGGCG
GTGGTTTCCGCGGTGGACGTCGTGAAGGAGGCGGCGGATACGGAGGTGGAGGATATGGAGGTGGAAGACGCG
AGGGCGGCGGTGGTGGTTACGGCGGCGGCGGTTATGGTGGTGGCCGTGACCGTGGATATGGCGGTGGTGACC
GTGGATACGGTGGTGATGCGGATCACGCTACTCAAGGGGTGGTGGTGACTCTGATGGAAACTGGAGGAATT
AGATAATTGAGAAGATGTGGATTTTAGTTATTTTGATCGCATTTTAAGTTGGGTATATCTTAATGTTAAGTG
TGACTGTCTTTTTTGACCGTTATTGGCTCGTTACTTTACTGTGTTTTTCTGTTTACAGAGTTCTTATGGAAT
GAATTAAATGAAGTCTACAAATTAAATCTTTCTTTTG

Figure 13

Nitab4.5_0002978g0020.2 amino acid sequence (SEQ ID NO. 10):

MAEVEYSCFVGGLAWATTDRTLADAFGTYGEVLDSKIINDRETGRSRGFGFVTFKDEKCMRDAIEGMNGQEL
DGRSITVNEAQARGSGGGGGYGGGRREGGGGYGGGGGYGGGRREGGGGYGGGRREGGGGYGGGYGG
GGRY

Figure 14

Nitab4.5_0002978g0020.2 coding sequence (SEQ ID NO. 11):

ATGGCTGAAGTAGAATACAGTTGCTTCGTCGGTGGGCTCGCATGGGCTACCACCGATAGAACCTTAGCTGAT
GCTTTCGGTACATACGGCGAAGTTCTCGACTCGAAGATCATTAACGACAGAGAAACTGGCAGATCTAGAGGA
TTTGGCTTTGTTACCTTTAAGGATGAGAAATGCATGAGGGATGCAATCGAAGGGATGAACGGTCAGGAACTT
GACGGCCGTAGCATTACCGTTAACGAAGCTCAGGCTCGTGGAAGTGGAGGCGGCGGCGGTGGTTACGGAGGT
GGCCGACGTGAAGGAGGAGGCGGTGGTTACGGAGGTGGTGGTGGTGGCTACGGAGGTGGCCGACGTGAGGGA
GGAGGCGGTGGCTACGGAGGTGGCCGACGTGAAGGAGGAGGCGGTGGTTACGGAGGTGGCGGTTATGGCGGT
GGTGGTCGTTATTAG

Figure 15

Nitab4.5_0002978g0020.2 genomic sequence (SEQ ID NO. 12):

ACCCCATCTCTTCTTTCTGATATTTTCCTTTAGGGTTTATCCTCTTCTCTCTTTTCTCAGTGTAGTAAAATG
GCTGAAGTAGAATACAGTTGCTTCGTCGGTGGGCTCGCATGGGCTACCACCGATAGAACCTTAGCTGATGCT
TTCGGTACATACGGCGAAGTTCTCGACTCGAAGGTCCGTTTGTTGCGCAGAGCAGAAATCGAATCCGGGCCC
ATTTTTTGGCTTTGTTGATGACCTTCTGTTACTGATTACTGTTTATTAATCTCTGGTTTACTTGATTCATCT
GTTACTGTTACTGTTACTGTTATTACTGTTATACCCTTGAAACGGTACGTTCCGTCTTTTTCTCTTTTTGT
CAAGAGATGAAGATAGATCGGTTAATTATTTTGCGTGTAAACGTTGTAGATCTGTTAGATCTGAGCTTAGTT
TTGTTTTACTTTTATTTTTCAGATCATTAACGACAGAGAAACTGGCAGATCTAGAGGATTTGGCTTTGTTAC
CTTTAAGGATGAGAAATGCATGAGGGATGCAATCGAAGGGATGAACGGTCAGGAACTTGACGGCCGTAGCAT
TACCGTTAACGAAGCTCAGGCTCGTGGAAGTGGAGGCGGCGGCGGTGGTTACGGAGGTGGCCGACGTGAAGG
AGGAGGCGGTGGTTACGGAGGTGGTGGTGGTGGCTACGGAGGTGGCCGACGTGAGGGAGGAGGCGGTGGCTA
CGGAGGTGGCCGACGTGAAGGAGGAGGCGGTGGTTACGGAGGTGGCGGTTATGGCGGTGGTGGTCGTTATTA
GATTAAATTTACTTAATTTTGGCCTATTGTTAAATTGGCCTTTAGATTAGTATCCATTACTGTTTTAGTGTG
GTTGGTGTTATTGTCCTTTATATTTGGTTAAGATACTGTGAATCTGTATTTTACAAAGTTCCATGGAATCAA
GTAAATGATGGTTTACGAAATAACTGTGTCGGCTTCTTAGTTCATTACTAGTTGAGGAACTCTCTTATATTC
ATTACTTTTTAAATGAAGTTTAAAGGATTAAATTAATTGAGTTATTAAAGAGTGAGTACTTG

Figure 16

Nitab4.5_0001361g0220.2 amino acid sequence (SEQ ID NO. 13):

MAAEVEYSCFVGGLAWATTDRTLADAFGTYGEVLDSKIINDRETGRSRGFGFVTFKDEKCMRDAIEGMNGQE
LDGRNITVNEAQARGSGGGGGGGYGGGRREGGGGGYGGGGYGGGRREGGGGGYGGGRREGGGGGYGGGGYGGG
GRY

Figure 17

Nitab4.5_0001361g0220.2 coding sequence (SEQ ID NO. 14):

ATGGCTGCTGAAGTAGAATACAGTTGCTTCGTCGGTGGGCTCGCATGGGCTACCACCGATAGAACCTTAGCT
GACGCTTTTGGTACATACGGCGAAGTTCTCGACTCGAAGATCATTAACGACAGAGAAACTGGCAGATCTAGA
GGATTTGGCTTTGTTACCTTTAAGGATGAGAAATGCATGAGGGATGCAATCGAAGGGATGAACGGTCAGGAA
CTTGACGGCCGTAACATTACTGTTAACGAAGCTCAGGCTCGTGGAAGTGGAGGCGGCGGCGGTGGTTACGGA
GGTGGCCGTCGTGAAGGGGAGGCGGTGGTTACGGTGGTGGTGGATACGGAGGTGGCCGACGTGAGGGAGGC
GGCGGCGGTTACGGAGGTGGTCGACGTGAAGGAGGAGGCGGTGGTTACGGAGGTGGTGGTTATGGCGGTGGT
GGGCGTTATTAG

Figure 18

Nitab4.5_0001361g0220.2 genomic sequence (SEQ ID NO. 15):

ACCCCATCTCTTCTTTCTGATATATTTTTCATTTAGGGTTTATCTTAGTCTCTCGTTTCACAGTATAGTAAA
TGGCTGCTGAAGTAGAATACAGTTGCTTCGTCGGTGGGCTCGCATGGGCTACCACCGATAGAACCTTAGCTG
ACGCTTTTGGTACATACGGCGAAGTTCTCGACTCGAAGGTCCGTTTGTTGCGCAGAGCAGAAATCGAATCCG
AGCCCATTTTTTGGCTTCGTTGATGACCTTCTGTTACTGATTACTGTTATTACTCTCTGGTTTACTTGATTC
ATCTGTTACTGTTACTGTTATTACTATTATACCCTTGAAACGGTACGTTCCATCTTTTCTCTTTTTGTCAAG
AGATGAAGATAGATCGGTTAATTATTTAGCTTGTAAACGTTGGAGATCTGTTAGATCTGAGCATAGTTTGT
TTTGTTTTATTTTTCAGATCATTAACGACAGAGAAACTGGCAGATCTAGAGGATTTGGCTTTGTTACCTT
TAAGGATGAGAAATGCATGAGGGATGCAATCGAAGGGATGAACGGTCAGGAACTTGACGGCCGTAACATTAC
TGTTAACGAAGCTCAGGCTCGTGGAAGTGGAGGCGGCGGCGGTGGTTACGGAGGTGGCCGTCGTGAAGGGG
AGGCGGTGGTTACGGTGGTGGTGGATACGGAGGTGGCCGACGTGAGGGAGGCGGCGGCGGTTACGGAGGTGG
TCGACGTGAAGGAGGAGGCGGTGGTTACGGAGGTGGTGGTTATGGCGGTGGTGGGCGTTATTAGATTTAATG
TACTTAATTTTGGCCTAATGTTTAATTGGCCTTTAGATTAGTATTCATTACTGTTTTAGTGTGGTTGGTGT
GATTGTCCTTTATAATTTGGTTGTTAAAGTTACTGTGAATCTGTATTTTACAAAGTTCCGTGGAATCAAGTA
AATGATGGTTTACGAAATAACTGTGTCGACTTCCTTTTGTATCCCAGTTATTTAGCCTCCAAGGTAGTTTAG
GAATCTCTTAGGGTTCGTTTTGGCACGAGGATAATTTAGTTCGCATATCAAATGTTTCCTTAGCTTATTAGT
TTTTAAATGAAGTTTCAACAATTAAATTAATTGTATTATTAAAGAGTGAGTACATGATACTATGATAGTATT
AGTAGATGATAATTTATTGGGTTTTTATTAAAATAT

Figure 19

Nitab4.5_0002978g0030.2 amino acid sequence (SEQ ID NO. 16):

MAAEVEYRCFVGGLAWATTDRTLGDAFAHYGEVVDSKIINDRETGRSRGFGFVTFNDEKAMRDAIEGMNGQN
LDGRNITVNEAQSRGSGGGGGGFGGGRREGGYSGGGGYGGGGGYGGGRREGGYSGGGYGGSYGGGRDRGYG
GGYGGGDGGSRYSRGGGASEGSWRN

Figure 20

Nitab4.5_0002978g0030.2 coding sequence (SEQ ID NO. 17):

ATGGCAGCTGAGGTTGAGTACAGGTGCTTTGTAGGTGGGCTGGCATGGGCTACCACCGATAGAACTTTAGGA
GATGCTTTTGCTCACTACGGCGAAGTTGTCGACTCGAAGATCATTAACGATCGTGAAACTGGAAGATCAAGG
GGATTTGGCTTTGTTACCTTCAATGATGAGAAAGCTATGAGGGACGCAATTGAAGGAATGAACGGCCAGAAC
CTTGACGGTCGTAACATCACCGTTAATGAAGCTCAATCACGCGGAAGCGGCGGCGGTGGCGGTGGTTTTGGA
GGTGGCAGACGCCGTGAGGGTGGATACAGTGGTGGTGGCGGATACGGTGGCGGCGGCGGCTATGGAGGTGGC
AGACGTGAGGGTGGCTACAGCGGTGGTGGCTACGGTGGTAGTTATGGAGGTGGCCGTGACCGTGGATATGGT
GGAGGTTATGGCGGTGGTGATGGTGGGTCCCGCTACTCAAGAGGTGGTGGTGCGTCCGAGGGAAGCTGGAGG
AATTAA

Figure 21

Nitab4.5_0002978g0030.2 genomic sequence (SEQ ID NO. 18):

CCACATCGTAACCATTGTTAGCTACCGCCTACCAGTGGTTATCCATTACCGTCGCAATCGGTAACGACCCCC
TTCCCGGTTAAAATTAACCGCCATAGCATAAACTTTCGCCTATAAAAGCCAGCATTTGCTACCCATAAAATT
CACATCAGCTCTTCTCTTCTATTAATTGTTTACATTCATATTCTCTCTTAAGAAAACAATGGCAGCTGAGG
TTGAGTACAGGTGCTTTGTAGGTGGGCTGGCATGGGCTACCACCGATAGAACTTTAGGAGATGCTTTTGCTC
ACTACGGCGAAGTTGTCGACTCGAAGGTCCGTTTGTTGCACTGCAGAGCTGAGATCGGATCCGAGCCGATCT
GATCATTGATCTCTCTGTTACTGTTACTGTTACTTTCACTCTCTGGTTTACTTGATTCACTCTGTTACTATG
TTACTATTTGTTACTGTTACGTTATTCCGTTCCCTTATACGGTACGTTCCGATCTTCCATAGATTTGAACAT
TGATCGCTTTTATATATATATGGAAAATTCGTATTTTAATTCACGAAAATTAGATGAATTGTTCACTTGTTT
CCTATTTTCAGTGACATAATTTATTCTTGTAACGGATGGAGTATTATTTCTATATACCATGCATGTTTAAAT
CTGTTTGTTTTTTTGTTGTAATTCATGTAGATCTGTTTAGATCTGATCTTTTACGGATTTTGATTTCAGATC
ATTAACGATCGTGAAACTGGAAGATCAAGGGGATTTGGCTTTGTTACCTTCAATGATGAGAAAGCTATGAGG
GACGCAATTGAAGGAATGAACGGCCAGAACCTTGACGGTCGTAACATCACCGTTAATGAAGCTCAATCACGC
GGAAGCGGCGGCGGTGGCGGTGGTTTTGGAGGTGGCAGACGCCGTGAGGGTGGATACAGTGGTGGTGGCGGA
TACGGTGGCGGCGGCGGCTATGGAGGTGGCAGACGTGAGGGTGGCTACAGCGGTGGTGGCTACGGTGGTAGT
TATGGAGGTGGCCGTGACCGTGGATATGGTGGAGGTTATGGCGGTGGTGATGGTGGGTCCCGCTACTCAAGA
GGTGGTGGTGCGTCCGAGGGAAGCTGGAGGAATTAATAAGATTCTGAAACTGGGTTTGATTGTGTCAAATAT
ATGTCCTCCTTTAGATAGTTTTTTTTTAAAAAATAAAAATAAAAATTTGGTGATTATGTTTCTGGGTTGGG
TAAGAGTCTATTTTTGATACTGTATTTCGTGTTACTGTTCTGGTTTCTCGCTATCGGTTCTCGTTATGTTAC
TGTGTGGATCTGTACTTACAAGGTTAAATGAAAGTTACCAATGATCACTCATTTGTAAGTGCCTAAGTATTT
AAATGCTTTTTTAATTACTCGATGATTTTTATGTAATTCCTTCAACCGAAGAGTTTTATGTACTTCCTACT
TGAATCAAAGACTAGTCACTCGGTTGTTATTAGCTTATAATGATCATTTCCACCTCCAGGAGGGATTTGGAC
AATGTTGGAAGAACAATTGAAATTTTATTATAAATAGACTTTTATTTAAAGTTTTTTTTATAAATAAA

Figure 22

Nitab4.5_0001361g0225.2 amino acid sequence (SEQ ID NO. 19):

MAAEVEYRCFVGGLAWATTDRTLGDAFAHYGEVVDSKIINDRETGRSRGFGFVTFSDEKAMRDAIEGMNGQN
LDGRNITVNEAQSRGSGGGGGGFGGGRREGGYSGGGGYGGGGSYGGGRREGGYSGGGGYGGGYGGGRDRG
YGGGYGGGDGGSRYSRGGGASEGSWRN

Figure 23

Nitab4.5_0001361g0225.2 coding sequence (SEQ ID NO. 20):

ATGGCAGCTGAGGTTGAGTACAGGTGCTTCGTCGGTGGGCTGGCATGGGCTACCACCGATAGAACGTTAGGA
GATGCTTTTGCTCACTACGGCGAAGTGGTCGACTCGAAGATCATCAACGATCGTGAAACTGGTAGATCAAGG
GGATTTGGCTTTGTTACCTTCAGTGATGAGAAAGCAATGAGGGATGCGATTGAAGGAATGAACGGCCAGAAC
CTTGACGGCCGTAACATCACCGTTAATGAAGCTCAATCACGCGGCAGCGGTGGTGGTGGCGGTGGTTTCGGA
GGTGGCAGACGCCGTGAGGGTGGATACAGTGGAGGTGGCGGATACGGTGGTGGTGGTAGTTACGGAGGTGGC
AGACGCGAGGGTGGCTACAGTGGCGGCGGTGGTGGCTATGGTGGTGGTTACGGAGGTGGCCGTGACCGTGGA
TATGGTGGCGGTTATGGTGGTGGTGATGGTGGGTCCCGCTACTCAAGAGGTGGAGGTGCATCCGAGGGAAGC
TGGAGGAATTAG

Figure 24

Nitab4.5_0001361g0225.2 genomic sequence (SEQ ID NO. 21):

GCATTAATCACCACATTTTAACCATAGTTAGCTACCGCCTACCAGTGGTTATCCATTACCGTCGCAATCGGT
AACCACCCCTTCCGGTTAAAATTAACCGCAATAGCAAAATTTAGTCCCCTCACGCCTATAAAGCCAGCGT
TTGCTACCCACAAAATTCACATCAGCTCTTCTCTTCTATTATATTAATTCTCTCTTGTATGTTTACATTCAT
ATTCTCTTCAAAAAAGAAAAACAATGGCAGCTGAGGTTGAGTACAGGTGCTTCGTCGGTGGGCTGGCATGG
GCTACCACCGATAGAACGTTAGGAGATGCTTTTGCTCACTACGGCGAAGTGGTCGACTCGAAGGTCCGTTTG
TTGCACTGCAGAGCAGAGATCGGATCCGAGCCGATCTGATCATTGATCTCTCTGTTACTGTTACTGTTACTG
TTACTGTTACTTCACTCTGGTTTACTTGATTCACTCTGTTACTATGTTACTATTTGTTACTGTTACGTTATT
CCATTCCCTTATACGGTACGTTCCGATCTTCCATAGATTTGAACAATTGATGGCTTTTATGATTCTCTTCCT
TTTTTTTACTTTCACTGTTTTAATTTATGGAGGAATTTTGATTGCTGTTGTATTACGATTTTCAAAATTGT
TGTTATTACTAGTTTTTAACGGATGGACTGTTATTTTTAGCATGCATGTGCAAAATCTGTTTGTTTTTAGCT
TATAATTCATGTAGATCTGTTTAGATCTAAATTTTTTTTATGGATTTTGATTTCAGATCATCAACGATCGT
GAAACTGGTAGATCAAGGGGATTTGGCTTTGTTACCTTCAGTGATGAGAAAGCAATGAGGGATGCGATTGAA
GGAATGAACGGCCAGAACCTTGACGGCCGTAACATCACCGTTAATGAAGCTCAATCACGCGGCAGCGGTGGT
GGTGGCGGTGGTTTCGGAGGTGGCAGACGCCGTGAGGGTGGATACAGTGGAGGTGGCGGATACGGTGGTGGT
GGTAGTTACGGAGGTGGCAGACGCGAGGGTGGCTACAGTGGCGGCGGTGGTGGCTATGGTGGTGGTTACGGA
GGTGGCCGTGACCGTGGATATGGTGGCGGTTATGGTGGTGGTGATGGTGGGTCCCGCTACTCAAGAGGTGGA
GGTGCATCCGAGGGAAGCTGGAGGAATTAGATTTAAGATTCTGAAACTGGGTTTAATTAATTGTGTCTAATA
TATGTCCTCCTTTAGATAGTTTTTAAATTTGGTGACTATATTTCTGGGTTGGGTAAAAGTCTATTTTTGTTA
TAGTTTTTAAATTTGGTGACTATATTTCTGTGTTGGGTAAAAGTCTATTTTTGTTACTGTGGCTCGTGTTAC
TGTTCTGGTTTCTCGTTATTGGTTCTCGTTATGTTACTGTGTGGATCTGTACTTACAAGTTTAAACGAAGGT
TACCAATGATCACTCATTTTTAAGTGCCTATATATTGGATGGAATTTGATGTAATTGCTTCACTGAAGAGTT
TTATGTATTTTCTACTTGAATCAAGACTAGTAATCAATTGTTATTAGCTTATAGGGATAATTTCCACCTCCA
AAAGGAATTTGGAAAACTGGAAGAACAAATTGAAATTTCTATATATTTTAAATCATTTTTGGCAAAACATTA
CTGGAAAAGGTAGTACTTCTCTTTTTGTATTCATACGCGTTCATTCAACAAATTTACTAAAACTTACTCGTG
TATAGTGGATATGGATATAAATCGACAGATTTTTATATAAATTTATAACCGTATCGAT

Figure 25

Nitab4.5_0003978g0020.2 amino acid sequence (SEQ ID NO. 22):

MAAEVEYSCFVGGLAWATTDRTLADAFGTYGKVLDSKIINDRETGRSRGFGFVTFKDEKCMRDAIVRMNGQE
LDDRNITVNEAQARGSGGSGGGYGGGRREGGGCCKF

Figure 26

Nitab4.5_0003978g0020.2 coding sequence (SEQ ID NO. 23):

ATGGCTGCAGAAGTAGAATACAGTTGCTTCGTCGGTGGGCTCGCATGGGCTACCACCGATAGAACCTTAGCC
GATGCTTTCGGTACATACGGCAAAGTTCTCGACTCGAAGATCATTAACGATAGAGAAACTGGCAGATCTAGA
GGATTTGGCTTTGTTACCTTTAAGGATGAGAAATGCATGAGGGATGCAATCGTAAGGATGAACGGTCAGGAA
CTTGACGACCGTAACATTACCGTTAACGAAGCTCAGGCTCGTGGAAGTGGAGGCAGCGGTGGTGGTTACGGA
GGTGGCCGACGTGAAGGAGGAGGATGCTGCAAGTTCTGA

Figure 27

Nitab4.5_0003978g0020.2 genomic sequence (SEQ ID NO. 24):

AAATGGCTGCAGAAGTAGAATACAGTTGCTTCGTCGGTGGGCTCGCATGGGCTACCACCGATAGAACCTTAG
CCGATGCTTTCGGTACATACGGCAAAGTTCTCGACTCGAAGATCATTAACGATAGAGAAACTGGCAGATCTA
GAGGATTTGGCTTTGTTACCTTTAAGGATGAGAAATGCATGAGGGATGCAATCGTAAGGATGAACGGTCAGG
AACTTGACGACCGTAACATTACCGTTAACGAAGCTCAGGCTCGTGGAAGTGGAGGCAGCGGTGGTGGTTACG
GAGGTGGCCGACGTGAAGGAGGAGGATGCTGCAAGTTCTGAAGCAATT

Figure 28

Nitab4.5_0000078g0240.2 amino acid sequence (SEQ ID NO. 25):

MGEDAEYRCFIGNLSWSTSDRGLKDAFRKFGNLLDAKIVVDKFSGRSKGFGFVTFDEKKAMEEAIEEMNGMD
LDGRAITVDKAQPQQGSGREYDSDRPRDRDRGRDHGRSNREYGGGRGSGGGECFKCGKPGHFARECPSEGGR
GGRYGGRDDRYGGGGGGGRSSGHYGPDRNGDRFGSRSSRDGGGHGGERYNRDSGPYDRR

Figure 29

Nitab4.5_0000078g0240.2 coding sequence (SEQ ID NO. 26):

ATGGGGGAGGATGCTGAGTACCGCTGTTTCATTGGAAACTTATCATGGTCAACATCTGATCGAGGACTAAAA
GACGCATTTAGGAAGTTTGGAAATCTTCTTGATGCAAAGATTGTAGTTGACAAGTTCTCAGGCCGATCTAAA
GGATTTGGTTTTGTTACATTTGATGAAAAGAAAGCAATGGAAGAAGCCATTGAAGAAATGAATGGGATGGAT
TTGGATGGCCGTGCTATTACTGTGGACAAAGCCCAGCCCCAACAAGGTTCAGGTAGAGAATATGATAGTGAT
CGGCCCCGTGACCGAGATCGAGGTCGTGATCACGGTCGCAGTAATCGTGAATATGGAGGTGGACGTGGATCT
GGTGGTGGAGAGTGCTTTAAGTGTGGCAAGCCAGGACACTTTGCCAGAGAATGCCCAAGTGAAGGAGGTCGA
GGTGGTCGGTATGGCGGCAGAGATGATAGGTATGGCGGCGGAGGTGGTGGTGGTAGATCAAGTGGCCATTAT
GGACCTGATAGAAATGGAGATCGTTTTGGAAGCCGCAGCAGCAGGGATGGTGGTGGACATGGGGGAGAACGA
TATAACCGTGATCGTTCTGGTCCATACGATCGTCGTTAA

Figure 30A

Nitab4.5_0000078g0240.2 genomic sequence (SEQ ID NO. 27):

```
GGTCAAGAAGGATGACTGCATCAAGTCATCAACTATAGTGCAGGACACCCGCCAAGAAAATATATCTTCTTC
TATAATACCCTAATATTCCCATTCAGATTTCAGACTCTACAAAAACGCTACCTTAAGCTTCTCTCTCTCTCT
TTTGCGGCTCTTCACTCTTGAAGGTATCGATCAATTGCTAAATCTTTAATTTTCAGCAACAGTTGTATCTTA
ATTCTTGTTTTGCCGGCACTTTTCTACGGATCTACTTTGGTTTTTGTCGCTAATTAGGGCAATTCACGATTT
TCGTATTAGGAAAGTGTAGAATTGATGTACGACGTTTGATTCTTTAATTTCAGAACGTTTTGTTTTTTTGTG
AAAAATGTTTTGGCATGTGTTGTCTGTTAAATTTGTGGGACTAAAAGATAGATGCATTTTTGTTAATTACT
AATAAATGTGACAAAGTGAAAAAAAAGGCATCCATATTCCGCAGTTCCATATCGATTGTTGGTGTCAATTTT
GACCCATTAATGTGTAAAGCTGTCCCAATCTTGGATAGTTTGGGTGCGTGGTGTTAATTAGAAGACTAATGT
TGGTTTCACCCAGATTCAATCCACCCAAAAGATTGGTTTCAACTCAGGCTACATTACTTGCATTTTCTTTGT
TAATTATGGTGGTATCCGGGCAAAGTTTGTGCACCTCAACTACTCCACCGGGACCCTGCTATCTTCCATCAG
CACAAGTACTCTAGTACTTAGGCAGATGAGAAGAAATCACATAGTAGTATTTTCTTGCCTCTGCTGGGATTT
GAATCTTAGACTTTTTCCTCACCCCAAAAAGAAGAAGAAGCAAATGGATAAGTATTTTGGGCTGGCCAG
TCCTCAACCCTTTTAACCATTTCATTGAAGAAACAAGCATTTCTCTCCTCTCATTCTGATTTTGAATAATTT
ACGTTAATATTGATAATTTATTGTGGTGATAGTTAGGTGCAGGCATTACTGGGTCAACCCTTTTTTATGTT
AAAAGAATAATGCAAATCTCTTGTTCTCCTAGATGCTTAAATTTGTAGCAGGTTCTGCGGCAGGATACTATT
TTATTTGATGAACTATATGTCAAGAATTTCAAGGGGAAATATCTTAACATGCTAGGCTGGTGTTTTATGATT
CTTCTCTTTAGGGAGATTAGGGCCGACATGTCGGCTGTCTGCATGCTTTTGAGTTCATTTTATGTCAGAATA
TGGTTATTTTGAACTTAATGTACCATTCTATAAAGAAAGTTATTTTGAACTTTCTATTTGGGACATTTGCCC
ATGTTTGGGCTTGGCACCTACTTTCATCCCTTTTTTTATTTGCTCATGGTAATTTTCAACTCTCAAGCATAT
CATTCTGAACTCAATTGCTCAAATTTAGATTTCTAGAAGCTACTTTGTGCAAAACTCAGAACTTCTTAACGA
AACCATTGACGAGCTACTTAAAGGAATACAATAACATGATATCTATGTCCAGGCACACATATATTTGATAAG
CGGAGACATGATATTCTTTTTAGGGATATTTACACAATTAGCCGGCCAAATTCACTGGTTGCTTTTTTTTTT
CTCTAGCTGATATATATAGATTATTCACTGATTATATATGGTTATACACATATCATACATGGATTATACATA
TATTATACATAAGCGGTTGGGTGGGCGGCTATTTAGGTTAATTCTTCTTCTTTTAACTAGACCAAAGCATA
AGAATGTCTTTTGTCTCTACATTTTCAAAATTTGTCCAATAGATCAATAATTAGGAAACCATACCGCTGAT
GATATTGAGAGCACTTTTTGATTGGTCCGTTTAAGCTTAAATGTCATACTATGAGACAATGGGTCTCATAGT
AAAACTCATATAAACAAGACCTGCTGTAACAACATTTTGAAATTTTGTTTTGCTGTGTTCCACCTCTGGATC
ATTCTTGAATTTTCTCACCCCCTTCCCTGTCCACCTCTCTCTCTTTGTCTTTCCTTTTCAGTTGCAAAAGT
TGTGTGATAAATGGGGGAGGATGCTGAGTACCGCTGTTTCATTGGAAACTTATCATGGTCAACATCTGATCG
AGGACTAAAAGACGCATTTAGGAAGTTTGGAAATCTTCTTGATGCAAAGGTAAGGATGAGTCATTCTTTAAA
ATACTGTCTTACTATTCTTCTATTTGTTTGGCTTCTTTCACCCTCCCCCACCTCCTATGCATACCCAACTTG
TACTTTTGAGGTGCAAATTATATCTTTTACAGAGCTTATCTCAGTGTAGTGCTGTACTCCCTTCTCATGCTT
AAGGGAAAATCAAAGAAAATGTGTTTTCTCCTGTGGAGTAGCAGAAGATTTTTAAGATCACTAAGAGGCAAT
TGAGCAGGAAAATAAATGTTCAACTGCAAAAATAAATGTAACTACTTATCTCAACAGAAAAAGGGGTAAATG
TGAGCAGCTACAAGAGCTTGATAGTCTATTGGTACGTGAGTACCTGTATTCTTTGTGATAAAACCTGTGTAT
CCCGCATACAGTCTGGGGGTTCAGGAAAAGCATCAGTTTCCTTTGTAGACTAATAATGGACCAAAATATTAC
AAACCTGTAGGATCAGTCATCTTAGCCAGAACCAAAACTCCAATGCCTGTAGGATTTATTCATCATAGCCAT
AACCAAAACTCCAGAGCCTTTTCAGTGAAGAAATTATTCAATTTATTTTGGATTATGCAATTTCAGCCAATG
CATGAAACCTCCACCGCCACAAACATCCATCAGTGCGAGAATAAACAGCAATGTGATACAGTCATGTTGTGA
GCACTTTACTTACCAATGTTGCAGAATACATTTTGGCTTCTTTGTATCATTAAGTCTGTGGCAACACTTGCG
TGACTACTTCTCTGTCTCTTTCCTTTTTCCTTATTTTGTTTCCTTCTTTCTCATACTTTATCTGGATATAGA
TTTTAAACATGTCTACGCCTCTATCATTTAAACTCTTTCCGTTTGGTTTAGATTGTAGTTGACAAGTTCTCA
GGCCGATCTAAAGGATTTGGTTTTGTTACATTTGATGAAAAGAAAGCAATGGAAGAAGCCATTGAAGAAATG
AATGGGATGGATTTGGATGGCCGTGCTATTACTGTGGACAAAGCCCAGCCCCAACAAGGTTCAGGTAGAGAA
TATGATAGTGATCGGCCCCGTGACCGAGATCGAGGTCGTGATCACGGTCGCAGTAATCGTGAATATGGAGGT
GGACGTGGATCTGGTGGTGGAGAGTGCTTTAAGTGTGGCAAGCCAGGACACTTTGCCAGAGAATGCCCAAGT
GAAGGAGGTCGAGGTGGTCGGTATGGCGGCAGAGATGATAGGTATGGCGGCGGAGGTGGTGGTGGTAGATCA
AGTGGCCATTATGGACCTGATAGAAATGGAGATCGTTTTGGAAGCCGCAGCAGCAGGGATGGTGGTGGACAT
GGGGGAGAACGATATAACCGTGATCGTTCTGGTCCATACGATCGTCGTTAATGCTTTAAGGTGCAATAGTTA
TTTTGGACTTCTAATTTTTGCTGTCTGATATTTGTGAATCATTTCATTGTAGTAACTGAAATTTTAACCTG
TCTGTTGCAGCTAAAGAGTTAGGCGCCAACCAAGCTGGATACTAAGGGTTTGAACTTTGAAGTATGTCCGAT
GGCATCTTGTTTCCTTGGCCTGTTAGCAGAAGTGGATCAATCTTTTGAACTCATGAAACATGGCACTTTAAT
CTACTGTTCTATGTCCGTAAAATGCTCAATAGTGTGGTTTGATTGGGATCTTATGCGTGCTTAATTTACGAA
TTTGAATATGGTCTCACACTTTTGAATGCTACTATGGCTGCTGGTTATTTGCTTTGTTCGCTTGGAAAGTAG
AATACTGATGTTTGCTGCTGGAATCAATGGTTTCTTGTGTTCACAATTGCACCTCTAATTGTGGTGATATAG
ATGGGTCTGATGAATTGCCAGAATTTTGTACTGGTGATAAAATTCTGAGGCTCACCAGCTTGTTTATGTCAA
```

Figure 30B

```
ATTGGGAAGCGAGGGTGAATTAGCAGTGGTTTTCCTGTTCTGTTCTCTTAGAATCTCTTAACAGTTAATTGG
AGTTAAAACGGGTAATCTATTGCATTATTCCTCCATTTAGTCAGTTCCTACTTTGCAGCTTTACAGTATTAA
TGATGTTAACCTTTTGACAGGCTGCCTGTGTTCAAATGACCTTTTTGGGTACATGATTGGGTCTCTTTGCT
AGTTGGTCCAGTTAAACATAATTAATTTGAGAAAGCATTTTGGACAGCGACAATCCTTCTGCCAGTAATTAC
ACCACTAATTGCTCTTATGTTCTGCAAGGATTTCCTGAGGACGAGTTAGTTTCCTCTTAGATGACAAGTTAT
TAGTTACTCTTGAGTTCAGCAACTGAGGTCCATTTATTTTGTTCTGATTTGATGTTCCTCCTCCATGGAGA
AGGATCTTGTTCGTCGTCGTGGTTTCCACATTTGAGACCAAGACGATTGTCGCTTTGCTTCAAAGTCGGGCT
TCATTTCCATGTCAGCTTGTGATTCTTGGTATCTCTCCGGTAATGGTTCTGCTTTTTAATTTCGGCTGGAGA
GCATGGCCTATTTGTTACACAAGGGTTCTGAAGGGGGATGTGGTTATCTGGATATTCAGTACTTCATCTGTG
TTTTTCTCATCTTGGGCCGGGGGGGGGGGGGGGGGTTGCATATTCGTGCATTTACTCCTCTTCTTAGAAACA
TCACAGAATTCTATTTCTTGTTTCGCTTTATTACTGGTAACCCGTCATCCGCAGGCAGATCAAAGATAGGTG
CAACCTTTAAGGTTCTTAATGTGGAGCATATTGTTTTTCCCAAAATTATGGGTTCAAAACTTAATTTTTTTT
GAAATTGTAGTAGTCTTTC
```

Figure 31

Nitab4.5_0005079g0050.2 amino acid sequence (SEQ ID NO. 28):

```
MGDDAEYRCFIGNLSWSTSDRGLKDAFRKFGNLLDAKIVVDKFSGRSKGFGFVTFDEKKAMEEAIEEMNGMD
LDGRAITVDKAQPQQGSGREFDSDRPRDRDRGRDHGRDNREYGGGRGSGGGECFKCGKPGHFARECPSEGGR
GGRYGGRDDRYGGGGGGGRSSGHYGPDRNGDRFGSRSSRDGGGHGGERYNRDRSGPYDRH
```

Figure 32

Nitab4.5_0005079g0050.2 coding sequence (SEQ ID NO. 29):

```
ATGGGCGACGATGCTGAGTACCGCTGTTTCATTGGAAACTTATCATGGTCAACATCTGATCGAGGACTAAAA
GATGCATTTAGGAAGTTTGGCAATCTTCTTGATGCAAAGATTGTAGTTGACAAGTTCTCTGGCCGATCTAAA
GGATTTGGTTTTGTTACATTTGATGAAAAGAAAGCAATGGAAGAAGCCATTGAAGAAATGAATGGGATGGAT
TTGGATGGCCGCGCTATTACTGTGGACAAAGCCCAGCCCCAACAAGGTTCAGGTAGAGAATTTGATAGTGAT
CGGCCCCGTGACCGAGATCGAGGTCGTGATCACGGTCGTGATAATCGTGAATATGGAGGTGGGCGTGGATCT
GGTGGTGGAGAGTGCTTTAAGTGTGGCAAGCCAGGACACTTTGCCAGAGAATGCCCAAGTGAAGGAGGTCGT
GGTGGTCGGTATGGCGGCAGAGATGATAGGTATGGCGGCGGCGGAGGTGGTGGTGGTAGATCAAGTGGCCAT
TATGGACCTGATAGAAATGGAGATCGTTTTGGAAGCCGCAGCAGCAGGGATGGTGGTGGACATGGGGGAGAA
CGATATAATCGTGATCGTTCTGGTCCGTACGATCGTCATTAA
```

Figure 33A

Nitab4.5_0005079g0050.2 genomic sequence (SEQ ID NO. 30):

```
CTGAGCCCTTAAATCTTCACGACTTCACCGCTTGGAACCGGTCATTACGGGTCAAGTAGGATGATTGCATCA
AGTCATCAACTATAGTGCAGAATATATGCTCTTCTATAATAATACCCTAATATTCCCCATTCAGGCTCCACA
AAAACGCTACCTAAAGCTTTCGGCTCTTCACTCTTGAAGGTATCAATCAATCTCTAATTCTTTAATTTTCAG
CAACAGTTGTATCTTAATTCTTGTTTTGCCGGTACTTTTCTACCGATCTACTTAGGTTTTTGTCGCTAATTA
GGGCATTTCACGATTTTCGTATTAGGAAAGTGTAAAATTGATGTACGACGTTTGATTCTTTAATTTCAGAAC
GTTTTGTTTTTTTTGTTAAAAATGTTTTGGCATGTGTTGTCTGTTAAATTTGTGGGACTAAAAGATAAATG
CATTTTTTGTTAATTGCTAAATATCATGTGACAAAGTGAAAGAAAGGCATCCATATTCCACATTTCCATATC
GATTGTTGGTGTCAGTTTTGACCCATTAATGTGTAAAGCTGTCCCAATCTTGGATGGTTTGGGTGCATGATG
TTAATTAGAAGACTAATGTTGGTTTCACCCAGATTCAACCCACCCGAAAGATTGGTTTCAACGCAGGCTACA
TTACTTGCATTTTCTTTTGTTAATGATGGTGGTGTCCGGGCAAAGCTTGTGCACCTCAACTATTCCATCGGG
AGCCTGCTATCTTCCATTCTGCTATCGAGTACTTAGGCAGATGAGAAGAAATCACATAGTAGTATTTTCTTG
CCTCTGTTGGGATTTGAATCTTAGACTTTTTCCTCACACCCTTGGCTACATGCTACATTAATTGCCTTACC
CATCCCATAAGGGAGTTTTTTACCAATATGGAAAAGCAGTAAGACAAAAAGATGATTTTGAACTTGGGGATA
TAATTTTACTTTCTTGTTGGTAACTCACCTTTTTTGCAACTCAATTATCTAGTTAAGTTAACCCCCCCCCAC
CCCCATCGCAAAAAAATAAAAGGAAAAAAAAAGAACGNNNNNNNNNNNNNNNNNNNNNNNNNNNAGAAGCAAAG
GGATAAGTATTTTTGGGCTGGACGGTCTTCAACCCTCTTAACCATTTCATTGAAGAAACAAGCATTTCTCTC
CTCTCATTCTGATTTTGAATAATTTACGTTAATATTGATAATTTGTTGTGGTGATAGCTGGGTGAAGGCATT
ACTGGGTCAACCCTTTTTTTATGTTAAAAGAATAATGCAAATCTCTTGTTCTCCTAGATGCTTAAATTTGT
AGCAGGTTCAGTGGCAGGATACTATTTTATTTGATGAACTATATGTCAAGGGGAAATATCTTAACATGCTAG
GCTGGTGTTTATGATTCTTTTCTTTAGGGAGATTAGGACCGACATGTCGGCTGTCTGCAGGCTTTTGAGTT
CTTTTTATGTCAGAATATGGTTATTTTGAACTTAATGTACCATTCTATAAAGAAAGTGATTTTGAATTTTCT
ATTTGGGACCAGTGTTTTAAAAGGCGTGGGCGTAAAGCTAGGCGTTTTACATATGCCTCAGCGAGACGTAAG
CCCTTAGGCACGAGGCATATGGGTATTTAATTTTAATGTTTTATAAAATAATATAATTACAGTAAATATTTA
TAAATAAGTAAAATTACATAAAAATTGAAAAAAATTATAAATATGTGAAATATATATATATATAGATGTGCT
CCATCCCCATAAAAAACTAGTCGAAACAATCTATTATACGCTACTTACAAGTAACTTGAGTCGAAAAGAATA
AAGTTTCTACATGAAGGAACAAAAAGAATGACAAATATAACATGAATTGCTGCGCGTACGCCTCTTGAGATT
TTCGCCCGACGCCATCGTATCGGGGCATTTTTGGTAGGCCTCGCCCCAGGGCTTGCCCCGAAAACGCCTTTT
AAAATTAGACAAGATAAAGAATTGGGAAAGACTATAAATTAGAGCTTCAATCAATAAAAAGGTCTTTGACT
TTTAAATTTAATACATTTCAGTTCCTTTTTTAAATTTTTGAGTAATTACAAGCTGACTTTTGAGAATTTGGG
TATTATGTGAAGGACTTATTCAACAAATTTTGTTTTAATTTGAAAAAAGTCTCTGGGGCTTACGTCTCACTA
CAAAAATGCGCCCCAAACGCCCGACGTACGCCCCGAACACTTGGGCGTACGCCCCAAATTGCAGGGCGTACG
CCTCTTGAGACTTTCGCCCCACACCGCCTCGGGCATTTTTGGTGCGCCTCGCGCCTTGAAAATGCTTTTTAA
AACACTGTTTGGGACAATTGTCCATGTTTGGGCTTGGCACCAGCCCTTTTTCTGTTTGCTCATGGTAATTTT
CAACTTTCAAGCATATCATTCTGAACTCAATTACTCAAATTTAGATTTCTAGAAGCTACTTTGTGCAAAACT
CAGATCGTTTTAACGAAACCAAGTACCGTAGCATTGACGAGCTACTTAAAGGAATACGATAACATGATATTG
ATATCTATGCTCACGCACACATATATTTGATAAGCGGAGACATGATATTCTTTTTAGAGATATTTACACAAT
TAGCCGGCCAAATTCACTGTTTGCTTTTTTTTTCTTCTAGCTGATATATATATAGATTATTCACCGATTA
TACATGGTTATACACATATTATCCATGGATTATACATATATTATACATAAGCGGTTGGATGGGCGACTATTT
AGGTTAATTCTTCTTCTTTTTAACTAGGCCAAAGCATAAGAATGTCTTTTAGTCTCTACATTTTCAAAATTT
GTCCAACAGATGAATAGTTAGGAAACCATACTGCTGATGATACTGAGAGCACTTTTTGATTTGTCTGTTTAA
GCTTAAATGTCATACTATGAGACAACGGGTCTCATAGTAAAACTCACATAAACAGGACCTGCTGAAACAACA
TTTTGAAATTTTGTTTTGCTGTGTTCCACCTCTACCTCTGGATCATTCTTGAATTTTCTCACTCCCCTCCC
CCTCCACCCCTCTCTGTCTTTCCTTTTCAGTTGCAAAAAGCTGTTTGATAAATGGGCGACGATGCTGAGTAC
CGCTGTTTCATTGGAAACTTATCATGGTCAACATCTGATCGAGGACTAAAAGATGCATTTAGGAAGTTTGGC
AATCTTCTTGATGCAAAGGTAAGGATGAGTCATTCTTTAAAATACTGTCTTACTATTCTTCTATTTGTTTGG
CTTCTTTCACCCACCCCCACCTCCTATGCATACCCAACTTGTACTCCTGAGGTGCAAATTATATTTTTCACA
GAGCTTTTCTCAGTGTAGTGCTGTACTCCCTTCTCATGCTTAAGGGAAAATCAAAGAAATGTGTTTTCTCC
TGTGGAGTAGCAGAATTTTTTAAGAGCACTAAGAGGCAACTGAGCAGGAAATAAATGTTCAACTGCATAAA
TAAATGTAACTACTTATCTCAACAGAAAAGGGGTAAATGTGAGCAGCTACAAGTCATGTTGTGAGCACTTT
ACTTACCAGTGTTGCAGAATACATTTTGGTTTCTTTGTATCATTAAGTCTGTGGCAACACTTAAGTGACGAC
CTTTTTGTCTCTTTCCTTTTTTCCTTATTTTGTTTCCTTCTTTCTCATACTTTACCTGGATATAGAGTTTACA
CATGTCTACGCCACTATCATTTGAACTGTTTTTCCCTTTGGTTCAGATTGTAGTTGACAAGTTCTCTGGCCG
ATCTAAAGGATTTGGTTTTGTTACATTTGATGAAAGAAAGCAATGGAAGAAGCCATTGAAGAAATGAATGG
GATGGATTTGGATGGCCGCGCTATTACTGTGGACAAAGCCCAGCCCCAACAAGGTTCAGGTAGAGAATTTGA
TAGTGATCGGCCCCGTGACCGAGATCGAGGTCGTGATCACGGTCGTGATAATCGTGAATATGGAGGTGGGCG
TGGATCTGGTGGTGGAGAGTGCTTTAAGTGTGGCAAGCCAGGACACTTTGCCAGAGAATGCCCAAGTGAAGG
```

Figure 33B

```
AGGTCGTGGTGGTCGGTATGGCGGCAGAGATGATAGGTATGGCGGCGGCGGAGGTGGTGGTGGTAGATCAAG
TGGCCATTATGGACCTGATAGAAATGGAGATCGTTTTGGAAGCCGCAGCAGCAGGGATGGTGGTGGACATGG
GGGAGAACGATATAATCGTGATCGTTCTGGTCCGTACGATCGTCATTAATGCTTTAAGGTGCAATATTTATT
TTGGACTTTTAATGCTGTCTGATATTCGTGGAATCATTTCATTGTAGTAACTGAAATTTTAACCTGTCTGTT
GCAGCTAAAGAGTTAGGCGCCAACCAAGCTGGATACTAAGGGTTTGAAGTATGTCCGATGGCATCTTGTTTC
CTTGGCCTGTTAGCAGAAGTGGATCAATCTTTTGAACTCATGAAACATGGCACTTTAATCTACTGTTCTATG
TCCGTAAAATGTTCAATAGTGTGGTTTGATTGGGATCTTATGCGTGCTTAATTTATGAATTTGAATATGGTC
TCACACTTTTGAATGCTACTATGGCTGCTGGTTATTTGCTTTGTTCGCTTGGAAAGTAGAATACTGATGTTT
GCTGCTGGAATCAATGGTTTCTTGTGTTCACAATTGCACCTCTAATTGTGTGGTGATATAGATGGGTCTGAT
GAATTGCCAGGATTTTGTACTGATGATAAAATTCTGAGGTTCACCAGCGTGTTTATGTCAAATTGGGAAGCG
AGGGTGAATTAGCAGTGGTTTTCCTGTTCTGTTCTCTTAGAATCTCTTAACAGTTAATGGGAGTTAAAACGG
GTAATCTATTGCATTATTCCTCCATTTAGTCAGTTTTTACTTTGCAGCTTTACAGTATTAATGATGTTAACC
TTTTGACAGGCTGCCTGTGTTCAAATGACCTTTTTTGGGTACATGATTGGGTCTCTTTGCTAGTTGGTCCAG
TTAAACATAATTAATTTGAGAAAGCATTTTGGACAGCGACAATCCTTCTACAAGTAATTAGACCACTAATTG
CTCTTATGTTCTCTAAGGATTACCGGAGGACGAGTTAGTTTCCTCTTAGATGGCAAGTTATTAGTTACTCTT
GAGTTCAGCAACTGAGGTCCATTTATTTTGTTCTGGTTTTGATGTTCCTCCTCCATGGAGAAGGTTCTTGTT
CGTCGTCGTGGTTTCCACATTTGAGACCCAGACGATTGTCGCTTTGCTTCAAAGTCGGGCTTCATTGCCATC
TCAGCTTGTGATTCTTGGTATCTCTCCGGTAATGGTTCTGCTTTCTAATTCGGCTGGAGGAGCATGGCCTAT
TTGTTACACAAGGGTTCTGAAGGGGATGTGGTTATCTGGATATTCA
```

Figure 34

Amino acid sequence Nitab4.5_0008185g0030.2 (SEQ ID NO. 31)

```
MADDEYRCFIGNLSWSTSDRGLKDAFEKFGNLVDAKVVLDKFSGRSRGFGFVTFDEKRAMEDAIEAMNGVDL
DGRDITVDKAQPDKGSGRDFDSDRPRDRERDRDRGRDRDRGSRDYGGGRGSGGGGDCFNCGKPGHFARECPS
EGGRGGRYGGGGGGSRSSGYGPDRNGDRYGSRSGRDGGGRGGGERFSRDRSGPYERRSSGGSRAG
```

Figure 35

Coding sequence Nitab4.5_0008185g0030.2 (SEQ ID NO. 32)

```
ATGGCAGATGATGAATATCGCTGTTTTATTGGTAACTTGTCATGGTCAACTTCTGATCGAGGATTAAAAGAT
GCATTTGAGAAGTTTGGAAATCTTGTTGATGCAAAGGTTGTACTTGACAAGTTCTCTGGCCGATCTCGTGGA
TTTGGTTTTCTTACATTTGATGAAAGAGAGCAATGGAAGATGCCATTGAAGCAATGAATGGAGTGGACTTA
GATGGTCGTGATATTACTGTAGACAAAGCCCAGCCTGACAAAGGTTCAGGTAGAGATTTTGATAGTGATCGA
CCTCGTGACCGTGAACGTGACCGAGATCGGGGTCGCGATCGCGATCGTGGTAGCCGTGATTATGGAGGTGGA
CGGGGATCTGGTGGTGGTGGAGACTGCTTTAACTGTGGTAAGCCAGGACACTTTGCCAGAGAATGCCCTAGT
GAAGGGGGTAGAGGTGGTCGGTATGGTGGCGGTGGCGGAGGTAGTAGAAGCAGTGGCTATGGACCCGATAGG
AACGGAGATCGATATGGAAGCCGCAGCGGCAGAGATGGTGGTGGTCGTGGAGGAGGTGAACGGTTTAGCCGT
GATCGTTCCGGACCATACGAACGTCGCAGTTCTGGAGGCTCTCGAGCTGGCTGA
```

Figure 36

Nitab4.5_0008185g0030.2 genomic sequence (SEQ ID NO. 33)

```
GATTGGCATTTCTTCTTTGGAGTAAACGCTACTAAACTTTTCTGCATCTCTTCGTATCGCCGCCGCCCTCTC
ATCTCCGAATCTTCATTATTTTCAAAGGTAACATTTATTTCTAGTATCTACAACTTTTGTTTCTTGCTATCT
ACTTTTTGCATAGATTGTCTCGAAGATCTAATTCGTTTGCGAATTCTGAAGCTTTGATGGCTTATTTGGGGC
AATTGATGATTTGGGTTTTCATGAAAATGTTAAATTGACAGACCCATGTTCCTTTATATATATATATATCTT
GAAGCAATTTTCTGTACTGTTATGTTTCAGTTTGTACTTTATGAGTTGATAAAAGATAATGAATTTCTCTTA
TTAATCATTGAATAAAGTATCCAACTCATGCTTAATGTTGAAGAATGTCTCAAATAAATTTGTTCTTTTAAT
GTTATATGTTTTTGGCTATTTTTGTGCTGTGCATAATTTAATTTGGTGAAAGTATACTAAACAGTTAAAATA
GTTAAATGGGGATGGGGTATTTTTAACTGAATTGGGGTGATTGATTGGTTGGGCTTCTGGATTCTTTTCATG
TTTGCATATGATTATTCTGTACATATTTAGAAAAATTCATTCATGTTTCATGCTTAGGAAGGGGTCAATTTG
TTTCTTGGTGTCTGACAAAAGTAGGTTTTACAGTATGATTTTGTTGGTTGATGAGCTTTCTGCTTAGATTG
TTGAATTATATTGTTGAATTCACAATTAGAACACATAAGCTAATTGACTGCATAGAGGAGTATGGTGAAGTG
ATATTCCTTTTTGATAAAACCTAAAATAGTAGTAAAAATAGTGTGATTTTGTATTTGTTAAGTGGAACTGTA
TTTTGAATCATATATGGTTGATGATTATTTTGAGTGCTTGGCTTGTTTGTCTAATGCTATTGTTGTCTGGGG
GCAGAGAAAATGGATCTAATAGTATAATCCACATAAGCAGGCCCTATTATCATAACTGAATTAATCTTTTGG
TGCACTTTTTGACTCTTGGCTTGATTTTGCACCCCCCCCCCTCCCAAATCTATCTCGTTCTGTCTTCTTTTT
CAGTAGCAGCAGTCTGTTTCAGAAATGGCAGATGATGAATATCGCTGTTTTATTGGTAACTTGTCATGGTCA
ACTTCTGATCGAGGATTAAAAGATGCATTTGAGAAGTTTGGAAATCTTGTTGATGCAAAGGTAAGGATGGTT
TATTTTTTAGGTTTTCGAATTGGTTAATTTGTCAATGATCTCTTTTTTTTTTTGCTTCTCTTTTTTTTCTTC
TTTATTGTTTTTCGAGTATTGTTGCTGGGTGGATTATTTATGCGAAGGAGTTTGCCTCATCCTTTAGACTAG
GATTAGACCATTCATACCTGCAAACCTCCTTCCCTTTCAAGTGACGGTCAGGGTTTTGACCACTTTAGTGCA
ATCTCCCTTCTACTTATCTCTCAATGCACCTATTTTTAACCTCTTTACGTGAACAATTCAAATCTTTTGAGT
AATTTTCTTATTCTTGCTCTTTGAATGCTACAACATCTGCACTTTCATTGATATCATTTTAATCCTCAGTCC
TGACCTCACTCCCAACTTCTAATGAGGAATATGAAGGTAAATCAGTATCTTTTTCCCCTGGATGCGCACATA
CATCATCAGGGGATTCTGAAAATTCATGAAAATGTAGCTTAAGGTACTACATCAAACAAGTATTACCACCAA
ACTTTATCAAGGTGCATGCGAGATTAGACAAAATTGTGAATTCTTCCTGTCAAACTTCACCACAGAACCTCA
TTAGAAGGTTTCTTTGTGTTGTGAAGTCTATGACAAGAGTTAGAATTGCAACTGTCTACCTCCGTTTCCTCT
CTTTTTCTTATGTCATTCCCACTCTATTTTTTCTTTTTGTGGATGTTAAATTTCAATATTTCAATGCCTCT
ATCCTTTTTGGCTTAGGTTGTACTTGACAAGTTCTCTGGCCGATCTCGTGGATTTGGTTTTGTTACATTTGA
TGAAAAGAGAGCAATGGAAGATGCCATTGAAGCAATGAATGGAGTGGACTTAGATGGTCGTGATATTACTGT
AGACAAAGCCCAGCCTGACAAAGGTTCAGGTAGAGATTTTGATAGTGATCGACCTCGTGACCGTGAACGTGA
CCGAGATCGGGGTCGCGATCGCGATCGTGGTAGCCGTGATTATGGAGGTGGACGGGGATCTGGTGGTGGTGG
AGACTGCTTTAACTGTGGTAAGCCAGGACACTTTGCCAGAGAATGCCCTAGTGAAGGGGTAGAGGTGGTCG
GTATGGTGGCGGTGGCGGAGGTAGTAGAAGCAGTGGCTATGGACCCGATAGGAACGGAGATCGATATGGAAG
CCGCAGCGGCAGAGATGGTGGTGGTCGTGGAGGAGGTGAACGGTTTAGCCGTGATCGTTCCGGACCATACGA
ACGTCGCAGTTCTGGAGGCTCTCGAGCTGGCTGATGCTTTAAGTTGTGGTAAGTTTTAGGCTATTTGATTTT
CAATTATCCAATATTCAGGGTATTATTTACTTTTGAGCTGATTAAATTTTGATTCTTTCTGATGCAGCTGAA
GAGTTAGAAGTCCTACAAGCTGGATGCAAGTGATTTGATGTATGTCTACTTGGTGCTGTTTCCCTGGCCTGA
GCCAACAAAATGGATGAATCGTTTGAGCTCATGAAACCTGGCTCTTATAAACTACTGTTCTATGTCCGTAAA
TGTTCGATAATACAGTTTGATTGGGATTTTATGCTTGCTTAATTTGCAAATTTGAATATGGCCTTACACTTT
GAATGCCACTATGGTTGCTGGTTATTTGCTTACTTGGTTTGGAAATTTGGAAACCATTGTGTGGTGCTGGAT
TTATAATGCTTTCTTGCATGGCAATCGCACCTCTGAAACTTTGCCTTGTGATTGATGGGTCTGATGAATTGC
CTGAATTTAGTACTGGTGATAAAAATCTGGGCCAGCAGGTGTTCATGTCTAATTGGATTGTAGAACTGGAT
TAGGAGTGGCCTTTGTTGTGTTCTTGTAAAATCTCTTTAACAGTTAATGGGAGTGAACCGGGTAATTTATTC
CGTTTTACCCTCTATTGGTCCATTCTAAGTTCTCAACTGTTATGATATTAATGTTGTTAACCTTTTGGCAGG
CTATTTTGTTCCTTTGTCCTTTTCTGGGTACATGATTGGCTCTCTTGCTAGTTTTGGTGCGCATTTAAATTT
ATAGAGCGAGAATGCTTCTGCATGAAAGATCGTTGGTGGAAGAGTTAGTTTTCCTGTTAGATGGTGACATG
TTTAGATACTCTTGGAGGGTTCAGCAATATGGCTCCACTAATTTGTTCTGCTTTGTGTTTCTATTTCGCGG
GGACGGTTCTTGTTCTTTTCTTGTAGTCCTGGTGTCTGTTTTCAAGATCCAAATGAGTGCAAAACCAATACA
GCAAGACTTCATTTGCCAATGAGCTCCTGGTCCTAGGTATCTATTCTTTCTACTTGGCAGATCTGCTTTTGA
ACTCCAGTTGGAGACTTCGGCCTATTTTGAGTCACTAGTGCATTGAAGA
```

Figure 37
Nucleotide sequence of Nitab4.5_0013685g0010.2_deltaRBD-RGG (SEQ ID NO. 34)

ATGAGCGGTGGAGGCTACGGAGGTGGTGGCCGTCGTGAAGGTGGATACGGTGGTGGCGGCGGTTACGGAGGT
GGCCGCCGTGAAGGTGGTTATGGTGGTGGTGGCGGCGGCGGTTATGGAGGTGGCCGTCGTGAAGGTGGTTAC
GGTGGTGGCTCTGAAGGAAACTGGAGGAGTTAG

Figure 38

Amino acid sequence of Nitab4.5_0013685g0010.2_deltaRBD-RGG (SEQ ID NO. 35)

MSGGGYGGGGRREGGYGGGGGYGGGRREGGYGGGGGGGYGGGRREGGYGGGSEGNWRS

Figure 39
Amino acid sequence of an RNA-binding domain (RBD) (SEQ ID NO. 36)

YRCFVGGLAWATTDQTLGEAFSQFGEILDSKIINDRETGRSRGFGFVTFKDEKAMRDAIEGMNGQDLDGRNI
TVNEAQS

Figure 40
Amino acid RGG motif (SEQ ID NO. 37)

RGG

Figure 41
Nitab4.5_0005487g0030.2 amino acid sequence (SEQ ID NO. 38)

MNTQPNNLYDTASQPDTGNDAYTFLEFNTQGEEFDYPEFQELSQPIRSSAWPTPSDSLVSEAPDRPPSSDAS
PSKKTRGGSGGNVSGGGGNGNVIGSSSNNQAASVVVDALAAGMSGLNFEETVDDEGFEYGKGDFGVEHACKY
CGVTNPACVVRCNVPSCRKWFCNSRGNTSGSHIVNHLVRAKHKEVCLHKDSPLGETILECYNCGCRNVFLLG
FISAKAESVVVLLCREPCLSVNALKDMNWDLSQWCPLIDDRCFLQWLVKVPSEQEQLRARQISAQQINKVEE
LWKTNPDATLEDLEKPGVDDEPQPVALKYEDAYQYQNIFAPLIKLEADYDKMMKESQSKDNLTIRWDIGLNK
KRVAYFVFPKEDNELRLVPGDELRLRYSGDAVHPAWQSVGHVVKLTAQEEVALELRVSQGVPVDVTHGLSVD
FVWKSTSFDRMQSAMKTFAVDETSVSGYIYHHLLGHEVEMQMVRNALPRRFGAPGLPELNASQVFAVKSVLQ
KPISLIQGPPGTGKTVTSAAIVYHMAKQGQGQVLVCAPSNVAVDQLAEKISATGLKVVRLCAKSREAVSSPV
EHLTLHYQVRHLDTSEKSELHKLQQLKDEQGELSSSDEKKYKALKRATEREIAQSADVICCTCVGAGDPRLA
NFRFRQVLIDESTQATEPECLIPLVLGAKQAVLGDHCQLGPVIMCKKAARAGLAQSLFERLVFLGVKPIRL
QVQYRMHPALSEFPSNSFYEGTLQNGVTINERQSTGIDFPWPVPNRPMFFYVQMGQEEISASGTSYLNRTEA
ANVEKIVTTFLKGGVVPSQIGVITPYEGQRAYIVNYMARNGSLRQQLYKEIEVASVDSFQGREKDYIILSCV
RSNEHQGIGFLNDPRRLNVALTRARYGIVILGNPKVLSKQPLWNGLLTHYKEHECLVEGPLNNLKQSMVQFQ
KPKKIYNERRLFFGGGPGIPGDSFGSASGPNADRRNSRSRGSYMAPGVPNGTQKPGLHPAGYPMPRVAFPPY
HGGPPQPYAIPTRGAVHGPVGAVPHVQPGSRGFGAGRGNANAPIGSHLPHHQGAQQQAGSLGSFNFPALE
NPNSQPSVGGPLSQPGYASNIGIQGPGQTFRDGYSLGSMSQDFVGDDFKSQGSHVPYNVADFSTQASQSGYA
VDYVTQGAQAGFPGNFLNQNSQSGYSRFGSGNEFMSQDYMAHGSQGLFTQAGYNNPSQDDGSQNHFGMSNAS
LQSQSSLNPLYSQPFAHYNTQPFNMQSQPQQQQAPQGQGFQNQKLHYNS

Figure 42
Nitab4.5_0005487g0030.2 coding sequence (SEQ ID NO. 39)

```
ATGAATACTCAGCCGAACAATCTCTACGATACGGCGTCGCAGCCGGACACCGGGAACGATGCATACACATTC
CTCGAATTCAACACGCAAGGCGAAGAGTTCGATTATCCTGAATTTCAAGAGCTTTCACAGCCAATTCGATCG
TCAGCGTGGCCTACGCCGTCGGATTCTCTGGTTTCCGAAGCACCCGATCGGCCTCCGTCTTCTGACGCCTCT
CCGTCCAAAAAAACCCGCGGTGGAAGCGGCGGAAATGTCTCTGGTGGAGGCGGGAACGGAAATGTTATTGGT
AGTAGTAGTAATAATCAGGCGGCATCGGTGGTGGTGGATGCATTGGCGGCGGGGATGAGCGGGTTGAATTTT
GAGGAGACGGTGGATGATGAGGGTTTTGAGTATGGAAAGGGGGATTTTGGTGTTGAGCATGCTTGTAAGTAC
TGTGGAGTGACGAATCCTGCTTGTGTAGTTAGGTGCAATGTGCCGTCTTGCCGTAAGTGGTTTTGTAATTCA
AGGGGGAATACTTCGGGCTCACATATTGTTAATCACCTGGTGCGAGCAAAACACAAGGAGGTGTGCCTTCAT
AAAGATAGTCCACTTGGAGAAACGATTCTAGAGTGCTATAATTGTGGATGCCGAAATGTCTTTCTTCTTGGT
TTCATTTCTGCTAAGGCAGAGAGTGTCGTTGTTCTCCTCTGTAGGGAACCTTGTCTTAGTGTTAATGCATTG
AAGGATATGAACTGGGACCTAAGCCAGTGGTGCCCGCTCATTGATGACAGGTGCTTTTTGCAGTGGCTTGTT
AAGGTCCCCTCTGAGCAAGAACAGTTGAGGGCGCGCCAGATCAGTGCTCAACAAATCAACAAAGTAGAAGAA
TTGTGGAAGACAAATCCAGATGCTACCCTGGAAGATCTTGAGAAGCCTGGTGTAGATGATGAGCCTCAGCCC
GTTGCCTTGAAGTATGAAGATGCCTATCAGTATCAAAACATATTTGCACCATTGATCAAGCTCGAAGCTGAC
TACGACAAGATGATGAAAGAGTCTCAGAGTAAAGACAATCTTACTATTCGATGGGATATTGGTCTCAACAAG
AAGCGCGTTGCGTACTTTGTCTTCCCTAAGGAAGATAATGAGTTGCGTCTTGTACCTGGTGATGAGCTAAGG
CTGCGATATTCAGGGGATGCAGTACATCCAGCTTGGCAATCCGTGGGGCACGTGGTAAAATTAACTGCTCAA
GAGGAGGTTGCGCTTGAACTTCGTGTCAGCCAGGGGGTTCCTGTCGATGTGACCCATGGGCTTAGTGTTGAC
TTTGTTTGGAAAAGCACGAGCTTTGATCGGATGCAGAGTGCGATGAAAACCTTTGCAGTGGATGAGACTAGT
GTCAGTGGGTATATTTACCATCACCTGCTAGGTCATGAAGTTGAGATGCAGATGGTCCGCAATGCACTTCCT
CGTCGTTTTGGTGCCCCTGGTCTTCCAGAGCTTAATGCATCTCAGGTTTTTGCTGTAAAAAGTGTTCTTCAA
AAGCCCATCAGTTTAATTCAAGGTCCACCTGGAACGGGAAAAACTGTCACCTCTGCCGCCATTGTGTATCAT
ATGGCCAAACAAGGCCAAGGACAGGTTTTGGTTTGTGCCCCCAGTAATGTTGCTGTGGACCAATTAGCAGAG
AAGATAAGTGCTACTGGTCTGAAGGTGGTCAGGCTCTGTGCCAAGTCAAGGGAAGCTGTCAGTTCTCCTGTC
GAGCATTTAACCCTTCACTATCAGGTTCGCCATCTTGACACATCTGAGAAGAGTGAACTGCACAAGTTACAG
CAACTGAAGGATGAACAAGGAGAGCTCTCCAGCAGCGATGAGAAGAAATATAAAGCTTTGAAGCGGGCAACA
GAGAGGGAAATAGCTCAGAGTGCTGATGTAATTTGTTGCACATGCGTTGGTGCTGGAGACCCTAGATTGGCT
AACTTCAGATTCCGCCAGGTGCTTATTGATGAATCCACTCAGGCTACTGAGCCTGAATGTCTTATTCCTTTG
GTTCTTGGCGCAAAGCAGGCTGTTCTTGTCGGTGATCACTGCCAGCTTGGACCAGTCATTATGTGCAAGAAA
GCAGCCCGTGCTGGACTTGCTCAATCTCTATTTGAGCGCCTTGTGTTTCTAGGAGTGAAGCCAATTAGGTTA
CAGGTACAATACCGTATGCATCCTGCATTATCTGAGTTTCCATCAAATAGCTTTTATGAAGGTACACTCCAA
AATGGTGTAACCATCAATGAAAGGCAATCAACAGGCATTGATTTCCCTTGGCCTGTGCCCAACCGTCCCATG
TTCTTTTATGTTCAGATGGGACAAGAGGAGATCAGTGCTAGTGGAACTTCCTATCTGAATAGAACTGAAGCT
GCAAATGTGGAGAAGATTGTGACTACATTTCTTAAGGGTGGAGTAGTCCCTAGTCAGATTGGGGTCATAACA
CCATATGAGGGTCAACGAGCATACATTGTAAATTACATGGCAAGAAATGGTTCCTTGAGGCAACAACTTTAC
AAGGAAATTGAGGTTGCAAGTGTTGATTCATTTCAAGGGAGGGAAAAGGATTATATTATTTTGTCATGTGTC
AGGAGTAATGAACATCAGGGCATTGGATTCCTTAATGATCACGGAGGCTTAATGTTGCCCTTACACGTGCT
CGTTATGGTATTGTTATCCTTGGAAATCCTAAAGTTCTTAGCAAACAGCCTCTGTGGAATGGCTTGCTGACA
CACTACAAGGAGCATGAGTGCTTGGTAGAAGGTCCTCTGAATAACTTAAAGCAGAGCATGGTTCAATTTCAG
AAGCCCAAAAAGATCTACAATGAGCGCAGACTTTTCTTTGGTGGTGGACCTGGAATTCCAGGTGACAGTTTT
GGATCTGCTTCAGGCCCCAACGCTGACAGGAGAAATAGTCGTTCTAGGGGTTCTTATATGGCACCTGGTGTA
CCCAACGGTACTCAGAAACCTGGTCTTCATCCTGCTGGTTATCCAATGCCTCGGGTTGCCTTTCCACCTTAC
CATGGAGGCCCTCCACAACCGTATGCAATTCCTACTCGTGGTGCTGTCCATGGCCCTGTTGGAGCTGTTCCT
CATGTTCCACAGCCAGGTAGCCGGGGTTTTGGGGCTGGACGTGGCAATGCCAATGCCCCAATTGGTAGTCAT
CTCCCTCACCATCAAGGCGCCCAGCAACAGGCCGGAAGTCTTGGATCTAACTTCAACTTTCCTGCATTGGAG
AATCCAAACAGCCAGCCTTCTGTTGGAGGACCTTTATCTCAGCCTGGATATGCTTCTAATATTGGTATCCAG
GGGCCAGGCCAGACATTTCGGGATGGATATTCTTTGGGTAGCATGTCACAGGATTTCGTGGGAGATGATTTC
AAGAGCCAGGGGTCTCATGTTCCATATAACGTTGCTGACTTCTCTACACAGGCTTCTCAAAGTGGATATGCT
GTTGATTATGTAACTCAAGGAGCACAGGCTGGTTTTCCAGGGAACTTCTTAAACCAGAATTCGCAATCTGGA
TACTCCCGTTTTGGTTCAGGAAATGAATTCATGTCACAGGACTACATGGCTCATGGATCCCAAGGTCTCTTT
ACTCAAGCTGGATACAATAACCCGTCGCAAGATGATGGTTCACAGAATCATTTTGGCATGTCCAATGCATCT
CTTCAGTCTCAGAGTTCGCTTAATCCACTTTACTCCCAACCATTTGCTCACTACAACACGCAACCATTTAAC
ATGCAAAGCCAACCTCAACAGCAGCAAGCCCCACAAGGCCAGGGCTTCCAAAATCAGAAACTTCACTACAAT
AGTTGA
```

Figure 43A
Nitab4.5_0005487g0030.2 genomic sequence (SEQ ID NO. 40)

```
ATCATATCTTTCTCTCCCCCTCTCTCTCTTCTTCGCCCTTTTCACCGAACCCTAACTTTCCCCTTTCCAAA
CCCTAATTCTGAACACACTAAAAATCTCACTTCGAAATCGAAAACTTCAGCCTACATTAAATTCATATCATC
GATTTTTTGATTATACGATGAATACTCAGCCGAACAATCTCTACGATACGGCGTCGCAGCCGGACACCGGGA
ACGATGCATACACATTCCTCGAATTCAACACGCAAGGCGAAGAGTTCGATTATCCTGAATTTCAAGAGCTTT
CACAGCCAATTCGATCGTCAGCGTGGCCTACGCCGTCGGATTCTCTGGTTTCCGAAGCACCCGATCGGCCTC
CGTCTTCTGACGCCTCTCCGTCCAAAAAAACCCGCGGTGGAAGCGGCGGAAATGTCTCTGGTGGAGGCGGGA
ACGGAAATGTTATTGGTAGTAGTAGTAATAATCAGGCGGCATCGGTGGTGGTGGATGCATTGGCGGCGGGGA
TGAGCGGGTTGAATTTTGAGGAGACGGTGGATGATGAGGGTTTTGAGTATGGAAAGGGGGATTTTGGTGTTG
AGCATGCTTGTAAGTACTGTGGAGTGACGAATCCTGCTTGTGTAGTTAGGTGCAATGTGCCGTCTTGCCGTA
AGTGGTTTTGTAATTCAAGGGGGAATACTTCGGGCTCACATATTGTTAATCACCTGGTATGTAAGAGAGATG
CATTTTTTTCTCTCGCATATTTGATTCTTGTTGTGAATGCCTGTTTTTTGTGGTCTATAGAAATGTGCAGAA
TAGATGTTATCATACTACAACAACAATAACTATGCCAGTCCCAAACAAGTTGGGGTTGGTTCTATGAATCCT
TACAGAATATGTTACTCATATAAACTCATTGCCAATATCGTACAAAATAAAAATAAAAGGTACAAGAAGTTT
ATATTGCCTATTGACGTATAAGTATCTGCAAATAAATTTATCGTGCAACAATTATGCCTCAATCTCATACAA
GTTGGGGTTTGTTATGTGAATCCTTATTCACCATGTCACTCCATATAAACTCATATCAGCCCATTATTATAC
AAAATAAATATAAAAAGTACTACTAGAAGTTCGTTATCTTGTTGACATATAAATCTCTACAAAATAGGTTTT
ACCATAAAACAACTATGCCTCAATATCAAACAAGTTGGGGCCAATTCTCGCTGATCATGTTACTTCATATCA
ACTTATCTCAGGCCAATATTATACAAAATAATTTCACTCAGCCCCTAGTAGTTTTTTATATTTAAAGGAAAG
GTTGTGCCACCAACAACCTTTAGGTGTTTTGCGTGACAAGAATGTGCCACCAAAACTTAAAGGTAAGTTCTA
TAGAGCGGTTGTCAGACCGACTATGTTGTATGGGGTTGAGTGTTGGCCGATCAAGAACTCACATGTCCAGAA
GGTGAAGGTAGAAGAAATGAGGATGTTGAGATGAATATACAAGATAGATAAAATTAAGAATGAAGATATTCA
GGAAAAGGTGGGTGTGGCCCATGTGGAGGACAAGATGAGAGACGCGAGACTTACATGATTCAAGCATGTGAA
GATGAGAGGCACCGATGCCCCAGTGAGGAGGTGTGAGAGGTTGGCCTTGTAGAGCCTAAGAAGAGGTAGAGG
TAAGCCGGAGAAGTACTGGGGAGAGGTGATTAAGCATGACATGGCGATGCTCCAGCTTACCGAGGACATGAC
CTTTGATTGGAAGGTATGGAGGTCGAGAATTAGGGCAGAAGGTTCGGTAGCATTGCATTTTCCTTGTTCATA
CCAGAAGTATTAGTTTACTACTTAGTGTTAGTCTAGTATTTTTTGTTCTTAGATTTCTATTATTATTTGAA
GGGAGCCTTGGCGCAACTGGTGAAGTTGCTGCCATGTGACCAGGAGGTCACGGGTTCAAGCTGTGGAAACAA
CCTCTTGCAGAAATGCAGGGTAAGGTTGCGTACGAGAGACCCTTGTGGTCCGGCCCTTCCCCGGACCCCGCG
CATAGCGGGAGCTTAGTGCACCGGGTTGCGCTTTAGATTTCTATTATTACTTGTTGTCTCTTTCGCTTCGGT
TTTCTTATTGGTTGTTGGTGTCATTACTTGTTGTTACTCCTTTTATTTTATCTTTCTTGAGCCGAGGGTCTA
CCGCAAAAAGCCTCTCTACCTTCTCAAGGTAGGGGTAAGGTCTGCTTATACACTACCCTCCCTAGACCCCAC
TTGTGGGATTATACTGGGTTTTTTGTTGTTGTACGGGTTTTTTATATTTCCTATTAATGTGTAAATGTCTGC
AGAATAGGTTTTGTCATAACTACATTATTTTTTGACAAGTAGCTTACTAGCTTTATCATAATGAAATAGAAA
AAACTTGTATAGTAGCTTTATGGTATTTTCTTTTGTAGTTTATTTGGATGACTTGAAGTTGATTTACCAGTT
ATAATTGGGATGAAAAATAATTTTTCTGTCCTCATTTTGCTAAAGGAAGCAGGGTTTTAAGTGGAATACCTT
ATACCTCACACCCATTACTCCCCTGAGCTTAATATAGGTATATATATTTCAAGCTAAAGGCAGTAGTGTGCA
GCACTAGCTGCAGATAGGGTCTTGGGGCAGGGGCATGTTTATCATAATGTATGTAGTCTCCTTCCTCCTGTC
CTCCCTTTCTCTCTGGTACTTGTTTAGGAAAGGGAATAACATGGTTAAAAAGAAGTATGGAACCAGAAAT
ACTAGTATCGGATAGCACCAGAAAAGTGAACTAGTGAAGTAGATGAGGCTTATGCATTTGTCTTTGACCTAG
CGATTATTAATCGACTAACCAATTAGTCTTTATTCCGTTTCTTTATTCCTTTTAAATTCTTTAAATCAAGCA
GTTATTGGTAACTGCTGAGAAAATCTCCTTCCTTTTTTCTTGTTTGTGTGTTACCAATAAGGTTTTTAGCCG
AGTATAGTTCTTTTGTTTCATCTGGTGATTGATGGTCAATGCTGTGGATGTCGTTGGTTTTGAGCTCTCTT
TTATTTGCTTTTCTCCATATTTGGGATGCTATTGCCCCAGGGCTTCACTTTAACATAAAATGCAACATGT
GATGCGTGGGTTAGGCACTTCATGGGTTCGAGACCTGCCGCAGCCAAAAGCGCGAGTTTAAGTGGAGGAGTA
TAGAGGGACGGGCCCATTATCCACCGTTTTTGAACCATGCGCTACTGACCCTCGAGTGTTTCTTGGTCATTA
GAAAAAATCGGGATGCTATTACTCATGCAGCTTCTAGCTGTTATGCCATGGGATATAGATTTGCTGTTATAC
CATGGGATAGATTTGCTGCGTCCGTTATTCTTTGGGAAAGCATATTTTGAAGCAACAATGGAAAATTTAT
TTGATACAAATGTATAGTTTTGTCAGCCTTTTTCTGTAGTATGGTGAATGTACATTTACTAGGTATAATGCT
AGATTTCCACATGTCCTTATAAGTTAGTAAAGCAACAAGTTCTTTTCTCCTTTTGTAATGTATATTTCTAGC
ACCCTTTAGTGCTGGGATCTCTTCAATAAAAGATCTTTTATCCCAATAAAATATACATTTTTGTCAGATTC
ATGCAACTTCACCTCCACAAAATTCTTAATTTATGCATGTGGGATAAGTTAAAAGGGAAATTCTCTATATGT
TTTTCGAGGAGAAAAGCCAAAGCGCCACCTTTTCTTAGTTACTAAGGGAGTAGATTATCTCTAGTTGATACT
GCATTTTGGAATGTCAGTTGTCCAAACTGTAGAAATTAAATAAGGAATCTTAAATGCATATTATAATTTGAT
TGTTTCACCAGTGTATGCAGTGGGATCAGCTACTTGCATTTAATGGACTTACGTTGGGGTGTTATATTCATC
TTGCCTTTTCCTACAACTAACATGTCTATTATATTCTCCGGAAACAAGGCATTTATTGAGTATAATTTTT
GTATTGTTGGCATTTATTGAATATTCTCAATTTTTTCTAATAGGTGCGAGCAAAACACAAGGAGGTGTGCCT
```

Figure 43B

```
TCATAAAGATAGTCCACTTGGAGAAACGATTCTAGAGTGCTATAATTGTGGATGCCGAAATGTCTTTCTTCT
TGGTTTCATTTCTGCTAAGGCAGAGAGTGTCGTTGTTCTCCTCTGTAGGGAACCTTGTCTTAGTGTTAATGC
ATTGAAGGATATGAACTGGGACCTAAGCCAGTGGTGCCCGCTCATTGATGACAGGTGCTTTTTGCAGTGGCT
TGTTAAGGTCTGGATTCTCTTTCTTGTTCTCTCTTTTTGATCCTTTTGGTTTTTGTTTTCTGTCCTGTATTT
GTGACGTGTGGAGTGCTGCAGGTCCCTCTGAGCAAGAACAGTTGAGGGCGCGCCAGATCAGTGCTCAACAA
ATCAACAAAGTAGAAGAATTGTGGAAGACAAATCCAGATGCTACCCTGGAAGATCTTGAGAAGCCTGGTGTA
GATGATGAGCCTCAGCCCGTTGCCTTGAAGTATGAAGATGCCTATCAGGTTCTCACTGGATGATACTATTGT
ATTATCTCCTCTACCTTTTATGTGTAATAAATGCTGTGCAGGAATTGCTTTACTATGTATTTGTGAGTTGCC
TTCGTATTGACATTTTAACTAAGTTTGCCTTCACCCTTCTAATGTAGTATCAAAACATATTTGCACCATTGA
TCAAGCTCGAAGCTGACTACGACAAGGTATGTCAGGTTTTGAAGATGATTTTACATGCTGAAGCGTGAGTGC
GTCAATGAATACTGAATTTTGTCTATACAAATGTTGATTTATGAGGACAATTGTATTTATGCTTGCTTATC
TTTTTCTTCTTGATTCTTAACGTCCGTGACAATTGAGTTAAGGCATTCAAAGTTACTTCTCTCTATTGTCAC
TCTTGAGTAAAGATGTGAGCGTACTACTGTCACGACCCAAAATCTAACCATGGTCGTGATGGCGCTTATCGT
GTTACAAGGCAAGCCTACTTTTCAAAATATTACTACTAAACCGATTATAAGAATTTAATAAAACATTTCAAC
ATTTAAATTTTTCATAAACTAAATCAACTCTAAATATAATATAGAAAAATACGGNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNGATCTCTAACATGAAGGCAGACAAGTTCAA
CAACAAGTAACTATGTAAACACAGATGATGGCCATGAGGCCTCACGGGACGGACCAAGTCTCGATCCCTCGA
GGTATACACCCACACGCCCATCACCTAGCGTGGGTATCATCTCCAAACAGTCACACGATATCAAATTCTCCA
GGTTTATACCCTCAAAGCCAGAGTTAAAACTGTTACTTAACTTAACAACGTAAAATCCTACTCCGGGATGCC
CTCGTCTCTGGACTCGGTCTCCAAAAGCTCCAAATCTAACCATAATCTGATTAATACCATTCCACAATAAAA
ACTACAAAATATGCCAAAAATTCGAAACCGGCCAAAACCCGCCCCGGGCCCACGTCTCGAAATCAGTCAAA
AATGGCAGAATAATAAACCTCGTCCTCTCCCGAGTCTAACCATATAAAATTCATCAAAATCGGACTCCGTTT
GGTCCCTCAAATCCTCACTTAAACTCTCCAAAACTCAAACCCTAACTCCCTCAATTTCACTTTGAAATCATC
AATTAAATCCCAAAAACGAAGATGGATTCATGAAATATAACCAAAACTGAGTAGAGAACACTTACCCCAATC
CTTATGGTGAAAATCGCCCCCAAAATCGCCCAAATCCGAGCTCCCCAACTCAAAATATGACCGAATGAACAA
ACCCTCGTTTTATATATTTTTCTGCCAGCTATTCTGCCTCGTTTCTCGTGCCAAACGATCCCGAAACTCGTT
TTTTATGCCTCTAATGGATTCGTTGTGAAATTTTAGTCAAGTTAGGCTTTTGAATCACTCAATTTGACCTTA
TAATGAAGTAGATATGTAGGTTTTAATATTTGCAAATCGTGCAGATTTTTAAATACACCGTCAGAGGCAATT
TCGTAATTAATCTGAAAAATCTGGCAACCTAATTCTTAGTGAAATGACCATAAAATCCTCATACGATGTCCA
AATTCAACGATTCTTTTTGCTACGGGTCCGTAATTACAATTTACAATACGGATCTAATGCTTCAATCAAAAA
AGAAATCGGAGCTCATTTGTTCAATATGATATCATTTATGCTTGAAGAAACGACGTCGAAACATAAGAAAAA
CGAGCGTAACACAACCCAAACCTATCCGAAACTCTCCCGAGGCCCTCGGGACCTCAACCAATAATTCCAACA
AGTCATATATCACTACCCGAACTTAGTTGAACCTTCGGAACACCCAAAACAACACCAAAACACCAAATCAAC
CTCGGATTCAAGCCTAAGAACTTCTAAACTTCCAACTTTCGCCAATTCAAGCCTAATTCTACCACGGACTTC
CAAATTACATTCCGGACACACTTCTAAGTCTAAAATCACCCAACGAAGCTAATCGAATCATAAAAATTCACA
TCCGAATTCGTTTACTCATAAGTCAACTTCCGGTTGACTTTTCTAACTTAACTTTTTAACTAAGAGACTAAG
TGTTCATTTCACTCCAAAACTACTCCGGACCCAAACCTACCAACTCGATACAACTCAACACCGCTGAACAAC
```

Figure 43C

```
ACATAAAGAAGCAGGAATGGGGAAACATGGCTTTAACTCTCAGAACGACTGGCCGGTTCGTTACAACTACTT
ACCTAAGTTTACTTGATAGTGAGTTTTGTCCATACAAATGTTGATTTTATGCTGAATATCGTATTTAAGATT
GCTTTTCTTTTTCTTCTTGAATCTTAACCTCTGTGACAATTGAGCTAAGACGTGTGAAGTTACTTCTCTCTG
TTGTCATTCTTTTTGAGAATGTGATGTTTTCCCTTGTCAATTAATCTGCCCATCGTGTCTTCTTCGTCTCCA
AGTAGAGTTTATACTTGTGTTGAGATACTGCTTACAAGTTTTTGAGTTCTTTTTTCTGTTTGGTAGATGATG
AAAGAGTCTCAGAGTAAAGACAATCTTACTATTCGATGGGATATTGGTCTCAACAAGAAGCGCGTTGCGTAC
TTTGTCTTCCCTAAGGTATTTTCTTGTTATTTTTTCTGCTATGATTCTTCTAGATTCTTGGACTGTTATAGA
GCTTATTGCTGTCATTTACTATTAAATCTTGATATGGGAAATCTCTTGTGTCTTTCCCTATCTGAATTGAAG
ATGGTCTGCTGTTTTTAGGAAGATAATGAGTTGCGTCTTGTACCTGGTGATGAGCTAAGGCTGCGATATTC
AGGGGATGCAGTACATCCAGCTTGGCAATCCGTGGGGCACGTGGTATGGACATTTTGCTTGATCTCCAACTC
TTTTCGAGAGGGAAAATAATTTATGGAGTATAGCTAGCCATAAACCCTCTTAACAAGTAAATTGGTTGGAAT
GAAAAAGGCTCCCAGCATCATGGAAAATTTTCTTAAACGAGCTTCTCGGAAAGCTCCCTGCTTTTTGTTTTC
TTGGGTTGTTAAAGGCTTCTTTTGCGATTTCTAGCCTGAGATATTGATTGACTATTCAATTTTCAGGTAAAA
TTAACTGCTCAAGAGGAGGTTGCGCTTGAACTTCGTGTCAGCCAGGTACCTTAGTTTTTAGATTGCTAGTCT
CTTCGCGATTTTCTGTTTTCTTCTTTCACCATGTTTTGGCTTGTACTTTGGGCCTTTTCTAAACTAGTCCTG
TCTTATCAGGGGGTTCCTGTCGATGTGACCCATGGGCTTAGTGTTGACTTTGTTTGGAAAAGCACGAGCTTT
GATCGGATGCAGAGTGCGATGAAAACCTTTGCAGTGGATGAGACTAGTGTCAGTGGGTGAGTGAGAATGTCT
GGTTTCTGTGTAGAAAGATAAAAAACAATTGTGAAGATTTCATGTACTTTTAATTAATTATCTTACTTGCCT
AAGGTTTATTATTCCATCTAAACCTTTTCAAAAAGGTGTTCATCGAATTGGTTTGTCCCTTTTTATTTGTT
TATTGTAGGTATCTTGTAATGCTTATGATGATTATACATTTAGAGAAATGACTGCTCTTTCTTTAACTTTGC
CTCGTTGAATGTTTAAGATATACTACATCCTTTTTTTGGATGAAGCAATAAGGGATACTGCATCTTTTCTTT
TGTTGCCTAGTCATTGTATCCTGAATGAAACTTTGAATTCATCTATGTAGTACAAAGGAATGTCATATTCAT
GGATGTAACAACTTACTTTATTTGGGTCAACCAGTTGTAACTTTTATCGATGGAGCATTTAGTTTTGCGTTC
TCTTTACTTCTTGTGCAGGTATATTTACCATCACCTGCTAGGTCATGAAGTTGAGATGCAGATGGTCCGCAA
TGCACTTCCTCGTCGTTTTGGTGCCCCTGGTCTTCCAGAGCTTAATGCATCTCAGGTTGAGGGCGCTGTCTG
TTTGCTTGAACCTGTTACCTCTTTTCCCTCATTTCTGAAAAAGCATATTTCCTTTAGCTTCAATATTGATCA
CGCTTCCAAACCTTTTTCAGGGACACCTTATTGAACGGGATTTTTTGACAATGAAAATTCTTAGTAGTTCTC
TAAGTATACACATGTATCAAACATGTTATGATGGCATGTTTGCTTACAGTTGAGAATTATAGTGAATAGTCA
ACCCTGATTGCTGTGTTGGTTCATGTTACATTGTGAAACCCATTAACAAGCACATGCAATCCAAATTTTAGT
TGCTGTTTTGTTCTCTCTTTTCATAAAATTGCCCCCTCAATTTCGGCAGCTTACTCAATTAAGCTTAATGCA
GAAGTGGTGCCCCATTGTCAGTTGCTTCCCCTCACCCCCTTAACCAAAAAAATACCCCTTCACCACCAACAG
TGGAAAGAGGTTCTCAAAAGGAGTTCTTGATTCTGGTTGTCTTATTGATCCATGTTTGCATCCTTAGGTTTT
TGCTGTAAAAGTGTTCTTCAAAAGCCCATCAGTTTAATTCAAGGTCCACCTGGAACGGGAAAAACTGTCAC
CTCTGCCGCCATTGTGTATCATATGGCCAAACAAGGCCAAGGACAGGTAACTTTAAGTCATTTTTACTTATA
TTTGCTCTAGGTATTAGTCGCTTGATATAATGGCTCTTTACAATCATTTGCGGACTATTATTTCATCAGGTT
TTGGTTTGTGCCCCAGTAATGTTGCTGTGGACCAATTAGCAGAGAAGATAAGTGCTACTGGTCTGAAGGTG
AGGCACCAGCTATTTCTGTATCTCCTTCCCACCCTCCAACCCAAGAAAAATAAAGTGACGAAGATTGAAGAC
ATTTTGAACTGACTGGGAAATAACTATTTTGGTGTTTAATGCATATTTATGCAGCACGTGTTTCTAGTGGAA
GCATCTTGCAGAATGTTGGACTGTTGTCCACCTTTGACATAGTATATATATATATCTCCATCCCCTATCAGC
TCCTTTTATGGTATTGATTTAAAGAAAGAGTTCTATTTATATCCTCAGATGGATCGAGTATGGTTAACTGAA
GGATAAAAATGAATCTCCTATATCCATCCCAATCGGCCCTGTCCCACCAGTGGTAGATGTAACCTCGATATT
ACTAGGTTCAACCGAACCTACTATTTTGACAGGAGCATAAATATCTATATGTAAAAATCACTAAAATTTACT
TCTTAACCCATAATTTGAAATGTGCAATGTGTTCAGTGCCAAAAACCTTATAGGTTGAACCCATTGAGTTTT
AATTCTGGATCCGCCTCTGTCAGTCCAACCCATGAATACAAACTGAAGGCGAACGAAGGAAATTGGAGTCTA
AAAGTACTGGAAATATAATAAGAAATGTAATAAAAATGATCAGAAACTTCCAAATAACTCTTTTTTTTTTAA
TTTTTATTTGTGAGAATATTAGGTCCTTTCTCATATAATTTCTTTCTTCCAGGTGGTCAGGCTCTGTGCCA
AGTCAAGGGAAGCTGTCAGTTCTCCTGTCGAGCATTTAACCCTTCACTATCAGGTTAGTTTTTTAATTTGTT
ATCCTCAAATATTTTTTATATATCGTTCTATTTTAATGATATGTTGTAAACTTTTGTTTATACAGGTTCGC
CATCTTGACACATCTGAGAAGAGTGAACTGCACAAGTTACAGCAACTGAAGGATGAACAAGGTTTGTGTTGC
TTTCCTGGATTTTCTTTGGCCTCATATGTATTGGGGGGATTTAGCATTTACATGGTGATACTTTTAGCATAG
TGCTCGGTTTTTTTTTCTCTTTCTCATTATATATCCTTTATTAGAGCATTCTAAATATGTGATCATGATTCA
GAGTCATTTGGTTAATGAACTTTCAGGAGAGCTCTCCAGCAGCGATGAGAAGAAATATAAAGCTTTGAAGCG
GGCAACAGAGAGGGAAATAGCTCAGAGTGCTGATGTAATTTGTTGCACATGCGTTGGTGCTGGAGACCCTAG
ATTGGCTAACTTCAGATTCCGCCAGGTTGGTTTACCTTATTACTGAAGATTTGAGGATTTCCTAACTATTTT
AGATTTTCAGTTTCTTATTTTTGTTCTTATGTACTCATTCTGGATTCTTGCTGATTTTAACATTTCTGTTGT
GTTAAACCTCTTGGTAGGTGCTTATTGATGAATCCACTCAGGCTACTGAGCCTGAATGTCTTATTCCTTTGG
TTCTTGGCGCAAAGCAGGTCACTATTGCAATTAATGTCATGTTGAAATTCATTTATGAAAAATTTCATACT
```

Figure 43D

```
GAAATATAGTTCGATGTTGGGTCTTACTGTGAGTTTTGTGCTAGGCTGTTCTTGTCGGTGATCACTGCCAGC
TTGGACCAGTCATTATGTGCAAGAAAGCAGCCCGTGCTGGACTTGCTCAATCTCTATTTGAGCGCCTTGTGT
TTCTAGGAGTGAAGCCAATTAGGTTACAGGTGATTGCCTGTCTGTTGATGTGTTAACATGTCTATCAGGGTT
GGTAGTGGCTGAAGTTAAATTTAAGATTCTCTTTTTCCAGTTATTCTCTTGTTTCTCATATAGTTGGCATAG
TGATTGGAAGTGCTCTTCAGTCATCTATGAAGACTTGAGGAGTCTGCTTTGCATTTTCTTTTTTTGGGGGG
GTGGGGGGGTGTGTGGAGTAAGATGTTCCTGGTATTTTAACTCTTCTTCACTAATCTGCCACTTCCCATTTT
TTTTTTGGGCGGAGCTGCAACAAATCATGCTAATTTAAGGTTTTCTGATTTTTCTATGCTTCATGTAGCATT
ATGTTATTCGGTTTATGTCATTATCTAGTGTAGCTTGTGTATCTGAGCTGTTTTGAGTTTCTAAGCTTCTCA
TTCTAGCTGCTTTTATTTGCTTGCCAAGTAGTAATTGTTAATCCCCTCTTGCTTTTTTTTTTTTTTTAC
ATTTTGTTTCCTTGGACGTAGAGTTGCCTGGTCACTTCTTCTTTCAGAGTACTGTTTATCTTTATTTAGCTA
TTTTTTAAATCTGTAAAGCATCAGAATTCTTTTATTCCATTACTAATGTTGATTATGCTGTCTATTTGTTTG
CAATTCCAGGTACAATACCGTATGCATCCTGCATTATCTGAGTTTCCATCAAATAGCTTTTATGAAGGTACA
CTCCAAAATGGTGTAACCATCAATGAAAGGCAATCAACAGGCATTGATTTCCCTTGGCCTGTGCCCAACCGT
CCCATGTTCTTTTATGTTCAGGTATTATCAGATTATTTTAGCTGATTCTTCTTTGTTTTTCGTTTTTTGAGT
TGTGGAAAAACCTGTCATTTTTGTTTTGGGATGTTATTGTGATGGTTATGGTTACACTAAAGATTGTTTCTC
CTATATAGTTTATAGGAACTTTTTCCTGGTTTACTGATATATTCAAATTTGAATACTTGATTTGAATACTTG
GTAATTCATCTATAGATGGGACAAGAGGAGATCAGTGCTAGTGGAACTTCCTATCTGAATAGAACTGAAGCT
GCAAATGTGGAGAAGATTGTGACTACATTCTTAAGGGTGGAGTAGTCCCTAGTCAGGTAAATTCTTATATG
CATCTTTAAGGTTGAACACCTTCTTTTTGTGGCGAGGATGTAATTATTTTAAATTCACAGATTGGGTCATA
ACACCATATGAGGGTCAACGAGCATACATTGTAAATTACATGGCAAGAAATGGTTCCTTGAGGCAACAACTT
TACAAGGAAATTGAGGCAAGCATTAAATAGATGAGCTTTATGGTAGTCTTGGATTCTTAATACTTACTGTGA
GTATTTGCTATGTTCAGGTTGCAAGTGTTGATTCATTTCAAGGGAGGGAAAAGGATTATATTATTTTGTCAT
GTGTCAGGAGTAATGAACATCAGGTTGGTTTGCATATCCATTAATTCTCTCTTTTTGATGCTTCATGTTTTA
ACATATTCTGATTTGATTCGATCTGTTGAAGATTTATGCATCCTCCTGTGAACCATACCTCTGTTCTTTTTT
TCTCTCTAACCTCCCCCCCCTCTTCTGGTCCTTTTTGGAGTTTGTTTAACTTCATTTGCAAAAAGTTTCAG
TTCTTTTTTATTTCGGGGTGCAGGAGGTCGGGTGGAATTTTTGTTAGGCGTTAAGATATGTTTTTGCAATAA
CTTGCATGCTTAATATATAGTCAGTGTGGATCTCTGACTCTCTTGTGCTTAAGCTTTAATCTATTCCACCAG
TTCCCATATTTCACTGTTAAACTTTAAGTATTGAGAACATCTTTTACTTCTCTTTTTAGGGCATTGGATTCC
TTAATGATCCACGGAGGCTTAATGTTGCCCTTACACGTGCTCGTTATGGTATTGTTATCCTTGGAAATCCTA
AAGTTCTTAGCAAACAGCCTCTGTGGAATGGCTTGCTGACACACTACAAGGTAATTTCTTCAAAATGTTCTC
TTGTAATGCTTGTTAGGCATTTTTTCACTATTTCTCTACACTTCGGAGAAGTTATGAACCGGCAAAGTTGGC
ATAATATCAGGTGGTTAATTTTTTGGGATAATATATCATGTTGAATTGTTAGGCAATATTGTTACTGTCTG
TAGGCTTGGGGACGTATAAAGTAACGTCTCAGTAGGTTTTTCATGCTTTGAGATGCTCACACTTTAATGAAT
TTGTTTCTCAGGAGCATGAGTGCTTGGTAGAAGGTCCTCTGAATAACTTAAAGCAGAGCATGGTTCAATTTC
AGAAGCCCAAAAAGGTACTTATTGTGGTCAAATACTCTTCCAAAGTTATATGTTTGTGCTTGATTATGCATC
AGTACTCAGATTTCTTGTAACGTCGTTTGCAGATCTACAATGAGCGCAGACTTTCTTTGGTGGTGGACCTG
GAATTCCAGGTGACAGTTTTGGATCTGCTTCAGGCCCCAACGCTGACAGGAGAAATAGTCGTTCTAGGGTA
TGGTGGATCTGAACTTTCCCCCACTGACTGTTAGTTACTTGCTGAGATGTTGTATGATTGGAGCGTGTGTCT
CTTTCATCTGATAATGTGTCAGAGACCTGCTTTTGCTTTCTTATTGTACAGTTTTTCTCAAAGAAACTTTGG
AGTAACTAGAAAATTTTCATTATTATTATAATCTCATGGAATTTATATATGTATTTGTTTGTTTTGCTGAG
GATATGATTTTATGTGTAGGTTCTTATATGGCACCTGGTGTACCCAACGGTACTCAGAAACCTGGTCTTCAT
CCTGCTGGTTATCCAATGCCTCGGGTTGCCTTTCCACCTTACCATGGAGGCCCTCCACAACCGTATGCAATT
CCTACTCGTGGTGCTGTCCATGGCCCTGTTGGAGCTGTTCCTCATGTTCCACAGCCAGGTAGCCGGGGTTTT
GGGGCTGGACGTGGCAATGCCAATGCCCCAATTGGTAGTCATCTCCCTCACCATCAAGGCGCCCAGCAACAG
GCCGGAAGTCTTGGATCTAACTTCAACTTTCCTGCATTGGAGAATCCAAACAGCCAGCCTTCTGTTGGAGGA
CCTTTATCTCAGCCTGGATATGCTTCTAATGTTAGTAAATTTCAGTTTGATTTTTCGATCAATAGTAGATG
ATTTGCTGTAAGTATTTTCTCTCTTTTGAATTATAGATTGGTATCCAGGGGCCAGGCCAGACATTTCGGGAT
GGATATTCTTTGGGTAGCATGTCACAGGTGATTGATTCTGAACATTAAAATTGTTATTTTGATTTAATTTTT
CTATCATATTTACCTTAGATTTGTTCATCAGGATTTCGTGGGAGATGATTTCAAGAGCCAGGGGTCTCATGT
TCCATATAACGTTGCTGACTTCTCTACACAGGTTCTTGTCCTGCACATTTTCTAGTAATTGTATATTGGGCC
TGCACATCACTGCCCTTTTTATGCATAATTATTTGATTTTCTTGCTCCAATTAGTTTGCATAGGCATAGCAA
TATTAACTGGCCTTTTTTGTTGGTATTTAGGCTTCTCAAAGTGGATATGCTGTTGATTATGTAACTCAAGG
AGCACAGGCTGGTTTTCCAGGGAACTTCTTAAACCAGAATTCGCAATCTGGATACTCCGTTTTGGTTCAGG
AAATGAATTCATGTCACAGGTTAATTTTAATTGTTCACTCCTTTGCCCCTTAATGTCTCAAACTTTAAGGCC
TGGAAAACATGTATTTAAATATGTGAGTCTGGAATGTATTTAAATATGAGAGTCTGGAAGTTTTCACAAGTT
CATCGTACATGATGGGCTGATCTGTTAGCTCTTCTGACTGGGCGGCTTTGGTAGACAAGTTAATTGAAGTGG
TCTCTTATGATTTCTTTTCTCTTGATCTTCGGGTTGAACTTTTGCTTATCGGACTTTTTATTTTTGGTGCAG
```

Figure 43E

```
GACTACATGGCTCATGGATCCCAAGGTCTCTTTACTCAAGCTGGATACAATAACCCGTCGCAAGATGATGGT
TCACAGAATCATTTTGGCATGTCCAATGCATCTCTTCAGTCTCAGGTTAGTTTATTAAATAATTCTGCTTGA
GAGTTGGCTAAATTACTGAACACGCACAAAATAGGAAGTATGGATTAGGCGAAGTCCACTAGATTGCACAAA
TGATTCTTCACGGGAATATAATCAGGGGACTTCGCTTGTTAAAAATATTTTCTTCTTGCTATTAGTTTATT
TCAACTAGTCTAATGTGACTTGGATGATTGAGGTTTTCCTTGGAATAGCACTTGAATTTGATTCCACTTTTT
CCAGAGTTCGCTTAATCCACTTTACTCCCAACCATTTGCTCACTACAACACGCAACCATTTAACATGCAAAG
CCAACCTCAACAGCAGCAAGCCCCACAAGGCCAGGGCTTCCAAAATCAGAAACTTCACTACAATAGTTGAAG
ATCGCAGGCTTGTTTATGTGATGGGTTATAGTTTGCTTCCAGCAGTTTGGTTTATGTGTCAACGCGTGGACC
ATATTATCTGACCTAAGATGAGATTAAGAGTTTGCTAATAATTCAGGTCAAATGGTGACATATCCCTTGCCA
GTGATTCTGAATGTTGAGTCAGAGGGCTGGAGTGGTGGAAGGCTCTCTGCTCAAGTAAACCATGCACAGCAC
AACTGGTGCTGAGAAAGGAAAAATAACCCATGTTATCTTCGTGAAGTTTTACGTATTGTTTGAAGAGAGTAA
TACTATTTCTCCGGGAGAGTAAGGTTACATGGCATGGTATTGGCCGGAAGGGTGGGTTATTCAGGACACGGA
GCTTGCTACTTGCGCGTTGGAAGGAGTACAACATTGTTTGAAGCTGCGACCATATCTTTTGTACAGTGTCCA
GGCGAAAGTCAGCTAACCCTTTCAGCTCTTCCTGACATGTAGTTAAACTCTTTAGTATTTGTATTACGTGGA
TAATGACGATAATTATAGATGTGTTTATGTTTCAGCACTTGAGGTATTGGGTATATAAGCAGTTATTAGTCA
TTTGATTAAACTGGATTGCTTGTAATCCAGTATCATTTTTTGTGGATTTCTTTTAGCGTTTTGCTTGGAG
TAGTCGGTGAGAAAA
```

Figure 44
Nitab4.5_0007831g0020.2 amino acid sequence (SEQ ID NO. 41 )

```
MIPNGVEDEEKFLAAGIAGLQQNAFYMHRALDSNNLKDALKYSAQMLSELRTSRLSPHKYYELYMRAFDELR
KLEIFFKEETKRGCSIVELYELVQHAGNILPRLYLLCTVGSVYIKSKEAPARDILKDLVEMCRGIQHPLRGL
FLRSYLSQVSKDKLPDIGSEYEGDAETVVDAVEFVLQNFTEMNKLWVRMQHQGPAREKEKREKERSELRDLV
GKNLHVLSQIEGIDLEMYKETVLPRILEQVVNCKDEIAQGYLMDCIIQVFPDEYHLQTLETLLGACPQLQPS
VDIKMVLARLMERLSNYAALSTDVLPEFFQVEAFAKLNNAIGKVIEAQEDMPIAGVVTLYSSLLTFTLHVHP
DRLDYVDQILGACVKKLSGKGKLKDSKATKQIVALLSAPLEKYKDIDTALKLSNYPHVMEHLDDATSKEMAN
VLVQTILKSKTCISTAEKVEALFELMKGLIRDLDENLHDELDEEDFKEEQNSVARLIQMLHNDDPEEMLKII
STVKKHILTGGPKRLPFTVPPLIFNSLKLVRRLQNQDENAPEEEASAMPKKIFQILNLIIEALSSVPVPELS
LRLYLECAEAANDADLEPVAYEFFTQAYILYEEEISDSKAQVTAIHLIIGTLQRMHVFGVENRDTLTHKATG
YSAKLLKKPDQCKAVYSCSHLFWVDDQDNIKDGERVLLCLKRALRIANAAQQMSNATRGSSGSVLLFIEILN
KYLYFFEKGVTQITVASIQSLIELITTEMQSENTTSDPAADAFLASTLRYIQFQKDKGGAVGEKYESIKS
```

Figure 45
Nitab4.5_0007831g0020.2 coding sequence (SEQ ID NO. 42)

ATGATCCCTAACGGAGTTGAAGATGAAGAGAAATTTCTAGCAGCTGGAATCGCCGGCCTTCAACAGAACGCT
TTCTACATGCATCGCGCTCTTGATTCGAATAATCTGAAAGATGCACTCAAATACTCAGCTCAGATGCTATCG
GAGCTCCGAACTTCAAGGCTTTCCCCTCACAAATACTACGAGCTATATATGCGGGCATTTGATGAATTGAGA
AAGCTAGAAATTTTCTTTAAGGAGGAGACGAAGCGGGGTTGCTCGATTGTTGAGTTGTATGAACTCGTGCAG
CATGCTGGCAATATTTTGCCTAGACTGTATCTACTATGCACAGTGGGGTCTGTGTACATCAAATCCAAGGAG
GCGCCTGCCAGGGATATTCTTAAAGATCTGGTTGAAATGTGCCGTGGTATACAACATCCTTTGCGCGGACTC
TTCCTGAGGAGTTATCTTTCTCAAGTCAGCAAGGATAAATTACCTGATATAGGTTCTGAGTATGAAGGGGAT
GCTGAAACTGTTGTGGATGCTGTAGAGTTTGTTCTCCAAAATTTCACGGAAATGAACAAACTCTGGGTTAGA
ATGCAACATCAGGGACCTGCTCGCGAAAAGGAGAAACGAGAAAAGAAAGGAGCGAGCTTCGTGATCTCGTT
GGGAAGAACCTGCATGTTCTCAGTCAAATAGAAGGAATCGACCTGGAGATGTACAAAGAGACTGTGCTTCCA
AGAATTTTAGAGCAGGTTGTCAACTGTAAAGATGAGATTGCACAGGGCTATTTGATGGATTGCATAATTCAA
GTCTTCCCTGATAATATCACTTACAAACTCTTGAAACATTATTGGGTGCTTGTCCCCAGCTTCAGCCATCT
GTTGATATCAAGATGGTGCTTGCTCGGCTGATGGAAAGGCTCTCAAACTATGCTGCTTTAAGTACAGATGTT
TTACCAGAGTTTTTCCAAGTGGAAGCTTTTGCAAAACTAAATAATGCCATAGGGAAGGTGATAGAAGCACAA
GAAGACATGCCTATTGCTGGAGTTGTGACTTTATATTCATCTCTTCTAACTTTTACTCTTCATGTACACCCT
GATCGTCTTGATTATGTGGATCAGATCTTGGGTGCATGTGTTAAGAAACTTTCTGGTAAAGGAAAGCTCAAA
GACAGTAAAGCAACAAAACAGATTGTGGCTCTTTTAAGTGCTCCCCTGGAGAAGTATAAGGATATTGATACT
GCATTAAAGCTGTCAAATTATCCTCATGTTATGGAGCACCTTGATGATGCAACTAGTAAAGAGATGGCTAAT
GTTTTAGTTCAAACTATTTTAAAAAGTAAGACTTGCATTTCGACAGCTGAAAAGGTAGAGGCACTTTTTGAA
TTAATGAAAGGACTTATCAGGGATTTGGATGAGAATCTTCATGATGAGCTTGACGAAGAAGATTTCAAGGAA
GAGCAGAACTCTGTTGCACGGCTTATTCAAATGCTTCACAATGACGACCCTGAAGAGATGCTGAAGATAATT
TCTACTGTGAAGAAGCATATTCTGACAGGAGGACCGAAGAGGCTTCCCTTTACTGTCCCTCCCCTTATTTTC
AATTCTCTTAAGTTGGTTAGGCGACTGCAGAACCAAGATGAAAATGCTCCAGAGGAAGAGGCATCTGCTATG
CCTAAGAAAATTTTTCAGATTTTAAATCTGATAATTGAGGCTCTCTCAAGTGTTCCAGTACCTGAACTATCA
TTGAGGTTGTACTTGGAGTGTGCTGAGGCTGCCAATGACGCTGACCTAGAGCCTGTTGCCTACGAATTTTC
ACCCAAGCTTATATACTATACGAAGAAGAAATTTCGGACTCCAAAGCTCAGGTGACTGCAATACACTTAATT
ATAGGAACTCTTCAGAGAATGCACGTCTTTGGTGTTGAGAACAGGGACACATTAACACACAAGGCCACGGGG
TACTCGGCAAAACTCCTGAAGAAGCCTGATCAGTGCAAGGCTGTCTACTCCTGTTCGCATCTTTTCTGGGTT
GATGATCAGGACAACATCAAGGATGGAGAGAGGGTTTTGCTTTGCTTAAAACGGGCTTTAAGAATTGCGAAT
GCCGCTCAACAAATGTCCAATGCAACCCGAGGCAGCAGTGGATCGGTCTTGCTCTTTATAGAAATTCTAAAC
AAGTATTTATATTTCTTTGAAGGGGGTGACACAGATCACTGTTGCATCCATCCAAAGCCTAATTGAGCTA
ATAACAACTGAAATGCAAAGTGAAAATACAACTTCGGATCCTGCTGCAGATGCTTTCCTTGCAAGCACATTA
CGATATATCCAGTTCCAGAAGGATAAAGGTGGAGCAGTTGGTGAGAAATATGAATCCATCAAGTCTTAG

Figure 46A
Nitab4.5_0007831g0020.2 genomic sequence (SEQ ID NO. 43)

ATACGTAAAAGAACCCGATGCCCGCCCCGCCCCGACCCGCTCCCGTACTATGTCTGGCAGTTGGAACAAAGT
AATGGCAACCAAAACTGAAGTCAATACCAAGAACATAAAATCCCACAAAAAACTCGTCGATCGCGAATTTCC
CCCCTCGAAATCGATAAAAAACGCTATGATCCCTAACGGAGTTGAAGATGAAGAGAAATTTCTAGCAGCTG
GAATCGCCGGCCTTCAACAGAACGCTTTCTACATGCATCGCGCTCTTGTAATTTTCACAAAACTCCCCCAAA
TTTCTTTATATCTTTATGTACAATGAAATTACAGTTTTATTTGGTTTACATAAACCCTAATTTTGATTTTTC
TTTTTATGGTTATTGAATTGTAGGATTCGAATAATCTGAAAGATGCACTCAAATACTCAGCTCAGATGCTAT
CGGAGCTCCGAACTTCAAGGCTTTCCCCTCACAAATACTACGAGCTATGTGTGTACTTTTCACTGATCAGAT
CTTAATTATTGATTAATTAATAAATTGAAACTTAATTTCAAAATTTGATTTGTTGCTCTTTAACCTCAGTAT
TAAAACTGTATCGCTGTTGTTTGTTTGTTTGTTTTTATTTTGTTTTTCAATAACTTCAAATGCAC
ATTGCTGTTATGCTGAAAATTTTATATTCCAGCATTTGATTAGAAGCTCCTTAACCTCGGTGTTAGAACATT
GTTGTGTCTTTTCTTTTCCTTTTTTTTTTTAAATTTTAATTCTTTTAAAATTTTAAATGCGCATTGCTTTG
TTAGATATGCGGGCATTTGATGAATTGAGAAAGCTAGAAATTTTCTTTAAGGAGGAGACGAAGCGGGGTTGC
TCGATTGTTGAGTTGTATGAACTCGTGCAGCATGCTGGCAATATTTTGCCTAGACTGTAAGTTGTAGTGATG
ATCCAACTGTATTTTCCGCTTTAGCTCGATTTTTTAAAGCTTTATCTTGTAGTTCTTCAGCAACTGATCTT
ATGTTTGTGAATTGGCTTAAAGCTTGTACTGCTTAACTATATTATATGTCTCCAAAGAGAGGTACTTTTCGC
TTAGGTTGTCAGGAATAATGTTTCGTAGGAAAATCATGTGATTAAAGACTCAAATGAATCATATAGAAACA
CTATCAATGATGGCCGAACAGTCAGGAGGAGAATACTATACTCCATGGGTTATAACATTAGGAACCTACACC
CAAAAAAGCATTGCCAAAACAGTAGAGAAAATCAGAAACGGGTTCAGCGAGTAAGTTTTAACTTACATCTA
ACTTTGATGAAAGCAGTTACAAGTTTAGGTAGAAAGAGCAGCTAGTGTCAGAGAGACACATGAAGCGAAGTA

Figure 46B

```
TTTGAGTATCGTTCTGTTTGGCCTTTGCTGTGTTTCTTTTAAGTTCTTTTGCCATGCTAATCTTACTGTTGT
CCTGCGCTCAACTGCTTACAGACATCTCCTCTCTACCTTTGTTTAGCATAGGTTGGATGTGCCTTTACAACT
CACATGGACACAAGTGTTGCTGCTTTAACAGTTTGGTTACTGGGAATCAAGCTAGAGCTTGCATACATTTTA
TTAAAACTGGAAAAATTTCCAATAAGTTATTTGAATTTTTTGGGAGAGGACTGCCGTTTGGGGTAGTTAACA
GCAGCCTTTCAGATAATCAATAAATTTTTGGACTGGTTTTTGCTGAAGCAAACTGTAAGAGTAAATGTTTTT
TTTTTCCTTTTTTTCTTTCTTTATGGTAAATGGAAATTATGCTCCTTTTTCATTTGTTTAGATTGGGTTGGT
GGGAGAGGAGTTCAAGTAGTTAGAAGGATAGTTGAACTGAATCAGACGCAACTTCTTATGGGAAGGAACTAG
GAAGCTAAAAAGTTGCATTTGATAAAGTAGGATAAAGTCATGTTATGTAAGGAAAGGGGAAGTTTAGGTGTC
AGGGATCTTGGGCTCCACAATAAAAGCTTGCTCTCTGTGAAGATGGACTGATACCGGGAAGGAACAATGTAA
AGATTTAAAGGTTAAATACGGACTACAGAAGTATGGAGATACAACTGATATTACATCTCCCCATGGTATTGC
ATTCGAAGCATATTGCTCCCTTCTTTGCCAATTTATGTGACGCTCTTTCCTTTTAGTCAGTCCCAAAAAGA
ATGACACATTTCTTTATTTAGTAACAACTTAACTCTAAACTCCCCATTTTACCCTTATGAGATGATTTATAG
CCACAATTGTTTTTGGCTTATTTTGAACCATAAGTTTTAAAAGTCATTCTTTCCATCTTTGTTAAACTCTGT
GCCAAGTCAAACGCCATCACATAAATTGGAATGGAGGGAAGTAATAGTTTGTGGGATGAGTTCCAAGAGTAT
ACCAGACTAAAAATTGGAGATGGAGGAAGAATTAATTTCTGGCAAGAGAAATGGTTTAGAGAGGATATTTCA
GCTGCCTTAGTCTCGGAGCTGTATAGTATGGTGCTGAACGGAAACTGTGTCATTGCTGATTGTTGGGATGGG
ATTGCTTGGTCTTCTCAGGATTTAGTTGGAGAGTTTCAACAAGCTACTGGAAATTACTGAGAGCATATTACC
GATAAGCTCCCAGAATGATTCCTTCTGTGTGGATGGGCAAGAGTGTATGGTATTTTCAGTAAAGTCGAGCTA
TCAGTTAATGGTTAAGAACATGGCTGCAAACAGTGCAGATTGGTCATGGAAAATGCTGTGGAAAACTAAAGC
CCCAACTGAAGTTGCTTTTTCGGTTGGGTAGCAGCACCTGAGGCTTTCTTAAAACAGGAAGAGTTACAGAAA
ATAAGCTTTAATCTATTTTGGTGCTATTTATGCAGAGGATGGTGAATCGGTGAATCACTTACTGCTGAGCAA
ATATGTATGGTGCAACAACAACAACCCAGTATATTCCCACAAGTAGGGTCTTGGGAGGGTAGTGTGTACGCA
GACCTTACCCCTACCCTGGGGTAGAGAGGCTGTTTCCGATAGACCCTCGACACAAGAAGATGAAATGCGACA
ATATAATAATAACAACAACATAACCAGAAAGATAGTACCAACGAGCTAAGAACCAGAAAATATACCTGGAAA
ACAATATTAATAAAAAGTGCAGTGACAAGGTCCTAGAAAATAGTACGAGCACCACATGTACCACTAGCATAC
TAAAACACGACACAGGCCGACTAGACTTACACACAGAACGGAGTAGAAAAACGCTCAATTACCTGCTAACCT
TCAACCCTAATGCACCCCCTCCATACCTTCCTATTAAGGGCTATGTCGTCGGTGAGCTGGAGTCGCGCCATG
TCCTGTCTGATCACCTCTCCCCAATACTTCTTAGGTCGCCCTCTACCTCTTCTCATACCCGTCAGAGCCAAC
TGCTCGCACCTCGTAACCGGAGCATCTAGGTTTCTCCTCTGCACGTGCTCGAACGATCTAAGCCTTACTTCC
TGCATTTTGTCTTCCATGGGAGCCACGCCCACTCTTGCCCAAATATCTTCATTCTTAATCTTATCCAACCTC
GTGTGCCCGCACATCCATCTCAACGTCCTAATTTCTGCTACGTTCATCTTCTGGATATGGGCAATCTTGACT
GGCCAACATTCTGCCCCATACAACATGGCCGGTCTAACCACCGCTTTGTAGAGCCTGCCTTTAAGTTCCGAG
GTACCTTCTTGTCACATAAAACGCCAGATGCTAACCTCCGTTTCATCCAATCTGGTGCGTGACATCCTCGTT
GATCTCCTCGTTTCCCTGGATAATCGACCCAAGATACTTAAAACTTCCTTTTTTGTGGTCATGTTCCTCAAT
TTTTATGGGGTTCAATGGGTCATGCAAGCAAATGTAAGACTGATTCTGCATAGTTGGTAGAGTCAAAAAGTG
GGAAAGGAGATAAAAGGGAAGACCTGGAAGACCACTCATTTATGCATAATGTGGAATATTTGGCTTGAGAGA
AACAGAAGATGCTTCGAGGGGAAGGAAGAGAACATCCCGCTTTTGAAAAATAGATGTATACAATGTCTAAGA
TGCAATGCTGATTTTGCTATTAATATTGATGCAATGCTGGAGTCTTGGAATTCTTACAGCTTCAGAGGATCC
TTTTCCAGAAATTTTTTGTACATTATTCTTTAATAAAATTTTACCTTTATTGATCAAAAGAAGATTTTACT
CGGACTAATTTTGTTCAAGATCATGATTAAAGGTGGAATGGTTATAATCCTGCTTAGCTGCATTGTTTCCTT
TCTTCTTTAGTTGTTAACCTATGTCAAAGAGGATGTGTTCATTTTATCATCTGGTTGCTTTTAAGCCAGTCT
TAAATCTTGTTTTCTATTATTTGCTCATCAGGATTTCTACAGTTCATATGTTGCCTTTTTGTTTCTCAGGTA
TCTACTATGCACAGTGGGGTCTGTGTACATCAAATCCAAGGAGGCGCCTGCCAGGGATATTCTTAAAGATCT
GGTTGAAATGTGCCGTGGTATACAACATCCTTTGCGCGGACTCTTCCTGAGGAGTTATCTTTCTCAAGTCAG
CAAGGATAAATTACCTGATATAGGTTCTGAGTATGAAGGGTAAGGGTGTTACTCAGCTCCACAGTGGTTTAC
CATCAATTTAGTTACAAGAATCATGTGTCAATGTCCAGTTTTATGGGTTTCGTTTACAATGTTCTAGCTGAG
AGGTATAAGTGCTTGAGAGAGAAAATACTATGCTGAAGTGTCAACCTGAAGACATAAACACTGACATGACT
AAGCTAATTGGCAGTGCCTGCAGTGTAACCGTGTGTTAAGTTGAATTTATTTAAATAAAGATGCTAGTAGAT
TATGTTGTTCATGGTAACCGGTTGTTGTTGTTTTCTTACTGCCATAATGATTAATTGAGGATTTCCTCAACT
ATGTCAACATAGTATGATCTTAACTCAGAAGAAAGAAAATGAAAAGATAATAAACTATCTTACCTTCATTT
TAAGCTTCTTTTATATGTAATCTCACCTGTATTACGAATATTGTTGTTGGATGCACTAATGCCTTGTTCCCT
CCCACAGGGATGCTGAAACTGTTGTGGATGCTGTAGAGTTTGTTCTCCAAAATTTCACGGAAATGAACAAAC
TCTGGGTTAGAATGCAACATCAGGTTGGTTGAAACATCTGTGGATGCTATAACATGCTCTCATGCTTTGACA
TGCATAGTACCACAATGCTTGCATGTCATGAAGGTAAATGGAAATCATGAGGGCAGAATTCGTGGTCATGCA
GGTGTTTTAATGCTTGTGAATGATTCATACTCTTTGCTGATCATGAGTTGAGGCTAGCATCGGGCTTTCTCA
TCTGCAGGGACCTGCTCGCGAAAAGGAGAAACGAGAAAAGAAAGGAGCGAGCTTCGTGATCTCGTATGAGC
TGTTACTTCATCATGTTTACTAGCACCCAAATAAGCAATGGAAGTGCACACTCATGCGAGGATTTTCCTTTT
```

Figure 46C

```
TGCTTTTACTTTTGGTAGGTTGGGAAGAACCTGCATGTTCTCAGTCAAATAGAAGGAATCGACCTGGAGATG
TACAAAGAGACTGTGCTTCCAAGAATTTTAGAGCAGGTGATTGGTCTAGGAATGTAGTGGCCTTTCAATAAC
TTTTTATGGTTTGTTTAAGCCATATGTGAACTATTTTCTGACTCAAAATGCGTACCTCATGGTTGTGTTTAG
GTTGTCAACTGTAAAGATGAGATTGCACAGGGCTATTTGATGGATTGCATAATTCAAGTCTTCCCTGATGAA
TATCACTTACAAACTCTTGAAACATTATTGGGTGCTTGTCCCCAGCTTCAGGTGTGTTATTTTGCTGTTTTG
TATCACTAGCTTTTCATTAAATAGACCAAAAGTGTAGAAGGAAAAATGTCATACCTGGTAGGATCCGAGGAG
TGGGATTGGTTTAATATCTGCAACAATGTAATATAATATGTTGGCTATATCAGATGAAAGATTTGGTTGTGA
AGATTTATAAGAGTATTGTTTGTTTACAGCGTTTCCACCTTATACTGAAGTTCATTATCTTTTTTTATTGG
CTTCTGATAAAATCTTTGATAATTTTGTCACCATTGATAAAGTCATACTGGTGATGCAAATTTGTACATTCA
TTTTCTTTGTACTGTCTGTGACAGTTCTAAGTATCTGCCATTAAATGCTTAACGTCTATGAGAATTTGAACT
TCTGAACACCATTTCCTATGTCATTATTTCAGCCATCTGTTGATATCAAGATGGTGCTTGCTCGGCTGATGG
AAAGGCTCTCAAACTATGCTGCTTTAAGTACAGATGTAAGTATTACATTATAAACTTTCTGTAATCGGATTT
TTTACATGTAGTCTCTAAATGATTTGTTACTGCAGGTTTTACCAGAGTTTTTCCAAGTGGAAGCTTTTGCAA
AACTAAATAATGCCATAGGGAAGGTAAACGAGATAACTACCCTTGACTAAAATGCAATTCTTGTTTATGAAG
GCGTACTTAAAGAAAATATTCCCAGGCGTGGATTTTCTACCTCCAACATGTGAATATTAAGTGGAACTCACT
GAACTTTAAAAGCTAGAATCAATTATCTGACTAATTCAAAAATTAATAAGCCAAGAAATAGAAATTGATCAT
AGATCTGTGGATGTCACTGGAAAGTTAATTCATGGAGACCGTGCTTGTCACAACAATAGAGTGGTAATCTTT
AGATTTATGAATGCACAGATTCTGATTTTCTTCCAATTTTTGCCTCCCCAAACTTATGCGCTTTCCATGAAG
AGGCCACCAAACCTTCCATGACATTCTTTCAACTTATTTCCTGTTTTCTGACTGGAGGGATTCTGCATACAT
CTTTTTTCCAATATCAATGGTGGCTTTGGCTTTTCAAGTAGTTCGGATATCATGCCCGTATCTCTGTTGTGC
AGGTGATAGAAGCACAAGAAGACATGCCTATTGCTGGAGTTGTGACTTTATATTCATCTCTTCTAACTTTTA
CTCTTCATGTACACCCTGATCGTCTTGATTATGTGGATCAGATCTTGGTAGGTCAACTCTTATTCTTTCCCT
TTTTCTTTTTATCTATATTAAAATAGTTTTTGATAAGGTTGTTTATGTCATTTATGTTTGTTCTTATTCCAG
AATGAAGATTGCGTGTGAAACAGTTTAACATTAAATAAAAATTAAAAAAAAATAAGGGAAGAAACAAATAGA
AACAACAGAAGGTTGACTAGAAGCTGTGAGCATTTAGATAACTTGCTTGCCTGCCTTGTGCATATGAAACCT
GTAACTTACTAATGACCACTCTATTCTTATCTTTAGGGTGCATGTGTTAAGAAACTTTCTGGTAAAGGAAAG
CTCAAAGACAGTAAAGCAACAAAACAGATTGTGGCTCTTTTAAGTGCTCCCCTGGAGAAGTATAAGGATATT
GATACTGCATTAAAGCTGTCAAATTATCCTCATGTTATGGAGCACCTTGATGATGCAACTAGTAAAGAGATG
GCTAATGTTTTAGTTCAAACTATTTTAAAAAGTAAGACTTGCATTTCGACAGCTGAAAAGGTTAGTTCCTTT
TAATTTTAGTTCTTTAAATTATTCTTTATGGGTAATACTATAGCCTCTTTATTACTTCAAACTTACTGGTCT
GTCAGGTAGAGGCACTTTTTGAATTAATGAAAGGACTTATCAGGGATTTGGATGAGAATCTTCATGATGAGG
TGATTGGGGACTTCTCTGCTTATGCAATTAGATTCCTCATATCTCCCGACTTTCTTTCTGCTCTATTCTTAG
CGGCTAGGCTTTCTTAAATTTATTTTGCTTAAATCAGTATGTAATTAAGCCAAAGTTTCTTTAACCTCCCAT
TTTCAGCTTGACGAAGAAGATTTCAAGGAAGAGCAGAACTCTGTTGCACGGCTTATTCAAATGCTTCACAAT
GACGACCCTGAAGAGATGCTGAAGGTAACGAGTGTATAGTGATACCTGTTTCTAGATTCTTTGCATATTCCT
CTGAAGGCTAGCCTCTCTACTTGTTATTGCTGGAAAAGTTTGTTATATCATGTAGTTCTTATAGTTCGGGGT
TGAGCGTGGTCAACTGTGTTTTAAATCAAAACTTTAAAGATGCCTAGAATTGTTTTTCTCTGTTCCAAAGTT
GAATGCCATGGTTTCATAGGCATGACGTTGATTGAGAACTTTTTTCTTTTGTTCTTTTGGGGATTAAATGGT
GTAAAAGTAGGTTTCATATATCTTTCCAATTTCCATAATTTGGAATAATTAAACAGTAATTTTACAAATGAA
AAACATAGTATCTTTTCCAGGACATTGGCTGATACCTTCTTGGGACATCACAAAGTAAACCAGGACACTTGC
ATTTGGGATAAAGTACCTTTGTTGTCTCTGTTTCATCTCTTCTTTCTATGACATGCTTTCTCCAATATATAT
ACCCAACCAGAGGCGGATCCAGAAATTAAACTTTTTGGGTTCAATATTTAAGGTTCTTATTATTGAACCGTG
AACCCACTATATTTTAAACTTATGAGTTCATATATACTATTTTTCGCAATTCTTGTGGATGTTGCATTTAA
ATTTATGCTCCGTGTCAAAAGTTATGGACTCAATTGAACCCGTAACTTTCATCCTACATTCGCCCTGTACC
AAACTCGTGCGCACAACCGATCAGCTAAATAAGTATCTCTTATAACAGCAATCCTTGATCTTCCTAGTCAGC
TTATAATGAGAGATATAGAACGAAGATGACTCTTGACCTAAGTTGCACCTGATTGGTTGGATATGTTCTATT
GAATCCTTCTGATATTGATGTAATGAGAAGCCTTTGCTTGTGCATCTACTGTTAAAAAACATATAATGATG
AAGTATCTGCCAAAACAAGATAGCTTTTGCTTTTTGTTGGTTCTGTTCGCTTTTCATGGTTTCTTTTGTTGA
TCCTTTTCTTTTTGAAAATATGAGAGGGATAAGTTGCCATCTCAGATTCTATTCATGAGAATGCCAAAAGGC
ACTTAGGTACTTGAGTACAAGACTGAAGCACTTTACATCCGCTACTACACCACGTGATACATCTGTGCTAC
CAATGTTCTCACATTCAACTCTACACCATCCTTCAGCAATGTCGCTGTTGCTTGGTGCCTCTGCATCTATCC
GGATGGATTTTGTCACAACAAGTGGTGTAGTAGCTTGAAAGCCTTCCCTGACAAGTCTGCTACCAACAAGAG
CACGGCAAAAAAGCTAGATTTGCAATATGTATGCTCAGATCTAGGACTAGAACTGCCACCAAGGGGTAGAT
AAATTAACATAACCATGGAGATAAAGGGAAAAGAACTAAGACACAAACAGATTAGAAGCAAATGGAACTGCC
AAAGAAAGGAGTTTATAAAGACAAAACTGCTTTGAAATGGGACCACAGAGAGCAGTTGTTTTATGGGGAGAT
GGTCTCTCAAAAAATCTCCTTGCTCTTCGTAGTTAATAAGGGAAATATGAAAAAGAAATTGGGAATGAAGT
CAGTTAAATGAAGCAGTAGCTGTAGAGATTGATATGACATGATTGACGTGCCAAAGCTTCACCAGCTGTAAA
```

Figure 46D

```
TTCAATTCAAGATTGACATAAAAATTCTTGTTAAATTGAGAATGAAATTTTCATTCCTCTAGCAAGTAGAAA
AGTGTGATGTTCTTATTTTCTTTTATATGTTTGTTGGTGCAAAATAAAATGCTTCAATCCGGTGTTACATAT
CTATGTAGCCATAAGGTTTATCTCTGGCTATAGCTGTTGGCTTCTTGCTTTTCAGATTTGATATGGTTTGCT
AATTGCTGATTTGCAGATAATTTCTACTGTGAAGAAGCATATTCTGACAGGAGGACCGAAGAGGCTTCCCTT
TACTGTCCCTCCCCTTATTTTCAATTCTCTTAAGGTATGAATTGACCACTCAAGGACTACAAAAGGGGTGAA
GTGGTGATGAATGGCCCATGCTTTTTATTCTTAAAAAGAAATAATTTAAGTTACAAAATTTTTGAATGTGCA
TTTTAAGATGATCCTTTCCCAATGCAACTGCTTGTTCAAAGGATTAAATAACAGAAAAAGGAAATCAACCCC
CTCCCCCTTTTCTCAGGGAGAGAGTTTCCAGTGTCATACAGAACTGAAGTTTCTGTTGAGTTACTGATGTTG
TAAATTTCCTTCTTTTCAGTTGGTTAGGCGACTGCAGAACCAAGATGAAAATGCTCCAGAGGAAGAGGCATC
TGCTATGCCTAAGAAAATTTTTCAGATTTTAAATCTGGTAATATAGCTGAATGGGGTTATATGAGTTATTTG
GTCAAATGTGATGCATTGCATTTCAAGCTCTCGACTAAAGCTATTATGATTCTCAGTCAAAGACCAAAAAA
ATAAATCAGCTTATGTCTCTTATATCCCTTTTCTTTATTTAGCTTCTATTCCTTCATTTTCAATTGTTCTG
TGATACTCATGATTGTGCTAACTGCTGAGGCAATTGTTATTACTTATAAATTGCATATACCGTATTCCAGAT
AATTGAGGCTCTCTCAAGTGTTCCAGTACCTGAACTATCATTGAGGTTGTACTTGGAGTGTGCTGAGGTACA
TTAATTTATCCTTGGATTTGTGTAAGATTGTGGAATCACAAATTCTAAAAAATATGGGTTTACTGCCATGTG
TGTTGCTCAGGCTGCCAATGACGCTGACCTAGAGCCTGTTGCCTACGAATTTTTCACCCAAGCTTATATACT
ATACGAAGAAGAAATTTCGGTAGGATTTGCTCATTTTATCATTACTTTATCATGATTTCTATTTGCTTGACT
TCCTGGTATTTCGATATATCTACATTTATTGTGCATTTCATGCATTGCTTGATTTTCTAATTCCAGTTGAA
TGGTTTGATAGGACTCCAAAGCTCAGGTGACTGCAATACACTTAATTATAGGAACTCTTCAGAGAATGCACG
TCTTTGGTGTTGAGAACAGGGACACATTAACACACAAGGCCACGGGGTAACTATTTTACCACCTCTTATTT
TCTTATTCCTGATTTCAGCTTCGTCATTCTATGATTGTAACCATTTCCTCCTCCTTTTCTTGATATCCTCCA
GTACTCGGCAAAACTCCTGAAGAAGCCTGATCAGTGCAAGGCTGTCTACTCCTGTTCGCATCTTTTCTGGGT
TGATGATCAGGACAACATCAAGGATGGAGAGAGGTTCGTAACTCTGCCATGCACATGAGGGATGAAATTTAC
ATTTGGCCTCCCGTGCCTCTCTTATTATGAACATTTATTAGCCTGGGTTTATACCAGCATGAGATGTGATTT
ATGTATTTGTGGGTCTTCCCTGACTGAGTTTTGCCCCTTTGAGTTCCGCTCCGTGATTTCAAGCTTTTCTGT
ATCCTTTCATGTTCTTCTTATGTGGTTGTTTCTTTTTCATTGATCCAGGGTTTTGCTTTGCTTAAAACGGGC
TTTAAGAATTGCAATGCCGCTCAACAAATGTCCAATGCAACCCGAGGCAGCAGTGGATCGGTCTTGCTCTT
TATAGAAATTCTAAACAAGTAAAACTACACTATACATCATTGTTTGTTTACCTTTCTTGGCGACGGTCTCTG
TTTTGCAGGTCATTAACGATAGATACACTTAATCATTTGTATGATCTCAGGTATTTATATTTCTTTGAGAAG
GGGGTGACACAGATCACTGTTGCATCCATCCAAAGCCTAATTGAGCTAATAACAACTGAAATGCAAAGTGAA
AATACAACTTCGGATCCTGCTGCAGATGCTTTCCTTGCAAGCACATTACGATATATCCAGTTCCAGAAGGAT
AAAGGTGGAGCAGTTGGTGAGAAATATGAATCCATCAAGTCTTAGTTATAAAGACATTTTCTTGCAAGGAGT
TTGCATTCTTGATGTTACAGAAGCAGATTATTTTGTTTCCAATACAAATTCATTTTCGCCTTTTGATTTGT
CTGTTAGTGGAGATTCTGCACTTTACAGCAGGCTAGCGGAAGAAGCTGCAAATATCTGTATATCCTAACCAT
ACTTGTCATGATTTTGATTGTTGTAACAATTTTTTCTCGTAGAGATCTGACTAAATTAGAGGCTATATAATT
CAGATCAAACTTGTGATTGTGATAATAACTGGAATAAGTTTGTTTTGGAGTTG
```

Figure 47
Nitab4.5_0002978g0020.2 amino acid sequence (SEQ ID NO. 44)

```
MAEVEYSCFVGGLAWATTDRTLADAFGTYGEVLDSKIINDRETGRSRGFGFVTFKDEKCMRDAIEGMNGQEL
DGRSITVNEAQARGSGGGGGYGGGRREGGGGYGGGGGYGGRREGGGGYGGRREGGGGYGGGYGG
GGRY
```

Figure 48
Nitab4.5_0002978g0020.2 coding sequence (SEQ ID NO. 45)

```
ATGGCTGAAGTAGAATACAGTTGCTTCGTCGGTGGGCTCGCATGGGCTACCACCGATAGAACCTTAGCTGAT
GCTTTCGGTACATACGGCGAAGTTCTCGACTCGAAGATCATTAACGACAGAGAAACTGGCAGATCTAGAGGA
TTTGGCTTTGTTACCTTTAAGGATGAGAAATGCATGAGGGATGCAATCGAAGGGATGAACGGTCAGGAACTT
GACGGCCGTAGCATTACCGTTAACGAAGCTCAGGCTCGTGGAAGTGGAGGCGGCGGCGGTGGTTACGGAGGT
GGCCGACGTGAAGGAGGAGGCGGTGGTTACGGAGGTGGTGGTGGTGGCTACGGAGGTGGCCGACGTGAGGGA
GGAGGCGGTGGCTACGGAGGTGGCCGACGTGAAGGAGGAGGCGGTGGTTACGGAGGTGGCGGTTATGGCGGT
GGTGGTCGTTATTAG
```

Figure 49
Nitab4.5_0002978g0020.2 genomic sequence (SEQ ID NO. 46)

ACCCCATCTCTTCTTTCTGATATTTTCCTTTAGGGTTTATCCTCTTCTCTCTTTTCTCAGTGTAGTAAAATG
GCTGAAGTAGAATACAGTTGCTTCGTCGGTGGGCTCGCATGGGCTACCACCGATAGAACCTTAGCTGATGCT
TTCGGTACATACGGCGAAGTTCTCGACTCGAAGGTCCGTTTGTTGCGCAGAGCAGAAATCGAATCCGGGCCC
ATTTTTTGGCTTTGTTGATGACCTTCTGTTACTGATTACTGTTTATTAATCTCTGGTTTACTTGATTCATCT
GTTACTGTTACTGTTACTGTTATTACTGTTATACCCTTGAAACGGTACGTTCCGTCTTTTTTCTCTTTTTGT
CAAGAGATGAAGATAGATCGGTTAATTATTTTGCGTGTAAACGTTGTAGATCTGTTAGATCTGAGCTTAGTT
TTGTTTTACTTTTATTTTTCAGATCATTAACGACAGAGAAACTGGCAGATCTAGAGGATTTGGCTTTGTTAC
CTTTAAGGATGAGAAATGCATGAGGGATGCAATCGAAGGGATGAACGGTCAGGAACTTGACGGCCGTAGCAT
TACCGTTAACGAAGCTCAGGCTCGTGGAAGTGGAGGCGGCGGCGGTGGTTACGGAGGTGGCCGACGTGAAGG
AGGAGGCGGTGGTTACGGAGGTGGTGGTGGTGGCTACGGAGGTGGCCGACGTGAGGGAGGAGGCGGTGGCTA
CGGAGGTGGCCGACGTGAAGGAGGAGGCGGTGGTTACGGAGGTGGCGGTTATGGCGGTGGTGGTCGTTATTA
GATTAAATTTACTTAATTTTGGCCTATTGTTAAATTGGCCTTTAGATTAGTATCCATTACTGTTTAGTGTG
GTTGGTGTTATTGTCCTTTATATTTGGTTAAGATACTGTGAATCTGTATTTTACAAAGTTCCATGGAATCAA
GTAAATGATGGTTTACGAAATAACTGTGTCGGCTTCTTAGTTCATTACTAGTTGAGGAACTCTCTTATATTC
ATTACTTTTTAAATGAAGTTTAAAGGATTAAATTAATTGAGTTATTAAAGAGTGAGTACTTG

Figure 50
Nitab4.5_0005552g0010.2 amino acid sequence (SEQ ID NO. 47)

METADSTRTFVRNVKRVIVKVGTAVVTRTDGRLALGRLGALCEQIQELNSQGYEVILVTSGAVGVGRQRLRY
RKLLNSSFLDLQKPQSELDGKACAAVGQNGLMALYDSLFSQLDMTSAQLLVTDNDFRDPDFRRQLNDTVNSL
LSLKVIPIFNENDAISTRKAPYEDSSGIFWDNDSLAALLALELKADLLVLLSDVEGLYSGPPRDPDSKLIHT
YIKERHETVITFGDKSRVGRGGMTAKVKAAMYAAYAGIPVVITSGFAVDNIIKVLHGECIGTLFHRDANKWA
STGEIGAREMAVAARECSRRLQALSSQERSKILQDMADALEANEKAILAENEADVVAAQQAGYEKSLISRLA
LKPGKISNLANSVRVLANMDEPIGRILKRTEVADGFILEKSSSPLGVLLIIFESRPDALVQIASLAVRSGNG
LLLKGGKEAKRSNAILHKVITSAIPGTVGERLIGLVTSREEIPELLKHDDVIDLVIPRGSNKLVSQIKASTK
IPVLGHADGICHVYVDKSADMDMAKRVVVDAKTDYPAACNAMETLLVHKDLAQNGGLNDLIVELQTKGVSLY
GGPKASSLLKIPEARTFHHEYGSLACTVEVVEDVYAAIDHIHQHGSTHTDSIITKDQEVAEIFLRQVDSAAV
FHNASTRFSDGFRFGLAEVGISTSRIHARGPVGVEGLLTTRWLARGTGQIVDGDKAVVYTHKDLSGLEIA

Figure 51
Nitab4.5_0005552g0010.2 coding sequence (SEQ ID NO. 48)

ATGGAGACAGCTGATTCTACTCGGACATTTGTCAGGAACGTGAAACGAGTAATTGTCAAGGTTGGGACTGCA
GTTGTGACACGGACTGATGGAAGATTAGCACTTGGAAGATTGGGAGCGCTCTGTGAGCAGATTCAGGAGCTT
AACTCGCAAGGCTATGAAGTTATTTTGGTGACTTCAGGTGCTGTAGGTGTTGGTCGTCAGCGGCTTAGATAT
AGGAAGTTGCTGAATAGCAGTTTTCTTGATCTTCAAAAGCCCCAAAGTGAGCTTGATGGCAAAGCTTGTGCT
GCTGTGGGCCAGAATGGCCTTATGGCTCTGTATGATTCATTGTTCAGTCAGTTGGATATGACTTCAGCTCAG
CTTTTGGTGACTGATAATGACTTTAGGGATCCAGATTTTAGGAGACAACTCAATGACACAGTAAACTCTTTG
CTGTCTCTTAAAGTTATACCTATATTTAATGAGAATGACGCTATCAGTACGCGGAAAGCTCCTTATGAGGAC
TCTTCTGGAATATTTTGGGACAATGACAGTTTGGCAGCTCTACTAGCTTTGGAATTAAAAGCTGATCTTCTA
GTTCTGTTGAGTGACGTAGAGGGTCTTTATAGTGGCCCTCCCCGTGATCCAGATTCGAAGTTAATTCACACA
TACATTAAGGAGAGACATGAGACAGTGATTACTTTTGGAGACAAGTCCAGGGTGGGAAGAGGGGGCATGACT
GCCAAAGTAAAAGCTGCTATGTATGCTGCTTATGCTGGCATTCCTGTTGTCATAACCAGTGGCTTCGCTGTC
GATAACATCATTAAAGTGCTACATGGGGAATGTATCGGCACCCTCTTTCATCGTGATGCCAATAAATGGGCT
TCAACTGGAGAGATAGGTGCTCGTGAGATGGCAGTTGCCGCAAGGGAATGTTCCAGGCGGCTTCAGGCACTT
TCTTCCCAAGAAAGGAGTAAAATTTTGCAGGATATGGCTGATGCATTGGAAGCAAATGAAAAGGCAATCCTT
GCTGAGAATGAAGCTGATGTGGTTGCTGCTCAACAGGCTGGATATGAGAAGTCTTTGATATCTCGGCTGGCA
TTAAAGCCAGGAAAAATTTCTAATCTTGCAAATTCAGTTCGTGTGCTTGCTAACATGGATGAGCCCATTGGT
CGCATTTTAAAGAGAACGGAGGTTGCTGATGGATTCATCTTGGAGAAATCATCATCTCCATTAGGCGTTCTA
TTGATTATTTTTGAGTCACGACCGGATGCACTTGTACAGATAGCTTCTCTAGCAGTCCGAAGTGGGAACGGC
CTCTTGTTGAAAGGAGGAAAGGAGGCCAAAAGATCAAACGCTATCTTACACAAGGTGATTACCTCAGCGATT
CCTGGAACTGTTGGTGAAAGGCTTATTGGACTAGTGACTTCTAGAGAAGAGATCCCTGAATTGCTCAAGCAT
GATGATGTGATTGATCTTGTTATTCCAAGAGGTAGCAATAAACTTGTTTCTCAAATTAAGGCATCAACAAAA
ATTCCTGTTCTTGGCCATGCTGATGGAATTTGCCATGTTTATGTTGACAAGTCTGCTGACATGGATATGGCA
AAGCGGGTTGTTGTGGATGCAAAAACGGATTATCCTGCAGCCTGTAATGCGATGGAAACACTTCTTGTGCAT
AAGGATTTGGCACAAAATGGAGGTCTTAATGACCTGATTGTGGAACTTCAAACAAAGGGGTTTCTTTATAT
GGTGGACCAAAAGCAAGCTCCCTGCTCAAGATTCCAGAGGCGCGTACTTTTCATCACGAATATGGTTCACTG
GCTTGCACTGTGGAAGTTGTTGAAGATGTATATGCTGCAATAGATCATATACATCAGCATGGAAGTACCCAC
ACTGATAGCATTATTACCAAAGATCAGGAAGTTGCTGAAATATTTTACGTCAGGTTGACAGTGCTGCTGTA
TTTCATAATGCAAGCACAAGATTTAGTGATGGGTTCCGCTTTGGACTGGGTGCAGAGGTTGGGATTAGCACA
AGTCGTATTCATGCTCGTGGCCCAGTTGGAGTTGAAGGGTTGCTAACTACGAGATGGCTTGCAAGGGGAACT
GGACAAATTGTTGACGGTGATAAAGCAGTTGTCTACACTCACAAAGACCTTAGTGGGCTTGAGATTGCATAA

Figure 52A
Nitab4.5_0005552g0010.2 genomic sequence (SEQ ID NO. 49)

ATGAAAATGTGTTGGATAAAAGCAAAATAAGGTAAGGGAAAACGACTTTCCACAACAAAAACAAACAATAG
TGGAGGAAAACGTGCTGAGCAATCCCCAAGTTCCAATACACGCCCGTACAAAACCCAAAATCCCCAAATCGA
AGTCGGATTAAGTAGAACTAGAGAACTGGCTGAAGGCAGTAGACTCCACATATTCTGCTGCCGTTTTGCAG
TCTACATTTCTTTCTCTCTTCTGAGCTAAAAATGGAGACAGCTGATTCTACTCGGACATTTGTCAGGAAC
GTGAAACGAGTAATTGTCAAGGTCTCAACTTTATCCTCCTTTTTCCTCTAATTTCTTTTCCTTATTATTGC
TTAATCCCTGCATTGCATTTGGCCCTGATTTCTTTTGTAGAATAATTCTTGTCAGATTGGAAAGAGTCGTC
TGTCCTTAATGAAGATTGATTTTAGTTAGCTATCATACTTATGTTTATTGTATGTATAAGGATTTAACTTAT
ATAGTGGGACAATGAGTGTAATTTAACCTTGTTTTAACATATTTTCAGGTTACCAATCCGTACTTAACATTG
ATATTTACTTGTAATTAGTTTTAAGTGACTTGATTGTTAAGTACGTGTTTAATTAGCTATTTGACTGGGC
ACGAAATTTAAGAAAGAAATTAAATTTTTTGAAACTTGTGATTTTAAATATGCCATAATACTTGTAGGTT
ATAGAAGCTTTCCCATTAAGGTAAAATGGAAAGTTTAACTTAAATTGTTTCCAAATTCTTTTCAAAACAGAT
TAAAAAGGAAATAGGGTCATATAAGCTGGAAGAGAGGGGATAATTTTTACACTGTCAATGTACAAAAGTTAA
AATCATTGTGTATGTTGTTCCTTCTATTCCCTGTCTGTTATTTTAGTTTTTTCTTAATATATTGCTAACAAA
TTTAATTTTTGATGTCATTTTTAAAGGTTGGGACTGCAGTTGTGACACGGACTGATGGAAGATTAGCACTTG
GAAGATTGGGAGCGCTCTGTGAGCAGGTGAATCTTATACTCCCTCTGTTTCAATTTATGTGACATAATTTGA
CTTGGAATGGAGTTTAATAAAAATGGAAGACTTTTGAAACTTGTGGTCTTACTTGCCATAATATTTGGGTGT
CTATAAGACATTTGAAACTTGTGGTCTTAAACATTCCATAACATTTGTTGGCTATAAAAGCTTCTCATTAAG
GGTAAATTGGAAAGTTCAAAGTTAAGTTGTTCCCAAATAGAGAATTTTTCATTCTTTTTTGCAATAAGTAA
ATTGTGTCACATATATTGAAACAGAGGGAGAAATAGTTTGATTGTTAGTATATATCTGCATCTTCTAAAGCT
TACTGGTTTTGCTGCAAACTGCATTACAGATTCAGGAGCTTAACTCGCAAGGCTATGAAGTTATTTTGGTGA
CTTCAGGTGCTGTAGGTGTTGGTCGTCAGCGGCTTAGATATAGGAAGTTGCTGAATAGCAGGTTTCTACCAT
GTCCTTGCTGTCAAATAAGATATTTACTTAGTAAATAGGTTATATAACTAGAATTGTTAATAAACAAGTTTA

Figure 52B

```
ACTCAAATGTAACTTGACTTATTAGTAAGAGCTAACCTTGATGGTATAGTTGATATTGAATTATGCAAATGA
ACCACAAACATATCTGAAGTACTCTATCCATCCCATTTTATATGGCTATATTTGATTGTGCATCGACTTAAG
ATATTAATTAACACATTATATTAGTGATGGTAGAAGAAAACATTAAAGCAAAAGAAAAGTTAGTTTGATAG
AAAAAATATCAAGTCAGTTTAAAATTTGAATAGTTTAATGAATTTGAGTTCTGGAAAATTGTAAAAATTGTA
TAAAGATATGGTGTCAATCCTTTTGGGATCTCAAAATGGAAAGAAGGGTCATATGAACTGGGTCTTAGGTTG
TAACTCGTTCATAGATATATATATTGGTTGTACTAATGATCTGAATAATAAAGTAATGCTCTATATATATCT
CACTCTGTGAATCAGAAGTTACTTGAAAAAGAATCAATATTCTTACCTTTTGATTTGATGTAGTACTGAAAG
GGTATTAAACTCTATCTTTTATCCTCAGTGACAAGATTCCAACGATAGGATTTGAATATTCCAGTATCTGCA
ATTTACTATTAACTACCAAGTCATCATATTTGCAGTTTTCTTGATCTTCAAAAGCCCCAAAGTGAGCTTGAT
GGCAAAGCTTGTGCTGCTGTGGGCCAGAATGGCCTTATGGCTCTGTATGATTCATTGTTCAGTCAGGTTGAA
GCACAGTTCTTGGAACTTTTTGTTTGTTCTAACTCTTGATTTGTTTATCATAACCACATAACCGTCCTTAG
CTTAAAGGATTGTCTACTGACTTTTTATTCTTTGTACCATCTTTATACAGTTGGATATGACTTCAGCTCAGC
TTTTGGTGACTGATAATGACTTTAGGGATCCAGATTTTAGGAGACAACTCAATGACACAGTAAACTCTTTGC
TGTCTCTTAAAGTTATACCTATATTTAATGAGAATGACGCTATCAGTACGCGGAAAGCTCCTTATGAGGTGT
GTCTCTCTGATTTTACACTGTAGTTGCTGTCTTCTTGCCCCTTTTTGTGAAAGTGATGTACTTTTAAGGTTT
TGCACCTCTTAAGCACAAAGAAGAGAGAAAAATAAAAGCACCCCGTTAAATTTTTCAAAAAACTAGTGAAA
GCGTTCTTCAAACTCACGTAAAAAGAATGTAAGATGAAAAGAACCTTACCACTGTTCTTCTGGAGGAAGAAT
GAAATAAAAGATAAATCACGTTTTTGAAGCAAGAGCTTAGAAAAACTAATCACCAATGTTTATTTTCAGTAT
ATTGAGCCCTTTAAATAGGCCTTACAATGAGTAAAATTGATAAGGTTAAGGAAAACTAATCCTAATTAAACT
AGAATAAGAATAAGGCGAAGAAAACCTATCCTAACTAAAATAGGAAGAAGAATTCTAGTAGGAATGGACTAC
CAATTAACAATCCCACTTTGACTAGAACCATAAATATAATCCTACTAAAACAAGAATTAAGAAATCCTAATA
TTTAAGGAAAGGAAATCCTAATCTTGAATGGATTCTTGGACTTTCAATTTCTTGAGATTCTTGGGCCTCAAT
TGGACCAGGGCTAATTAGTGTAACCATTTTAAATTTGTGGCCCAATTCTCCAAATCCATTGGCACCTTCATG
AACCCAATAAGCCTCCATTGTTGTAGAAAACATGGCCTCCATGCTACTCTAACATCACGTCTTGAGCTTGTA
TGTTCATCAGAAAGTTCCTCTCATTAGTAGATAGGTCACAATGTTTCTTGCTGTAGGGCTGACCAGTTGCGT
AATGGTCAATCCATGCGTTGGAACTAGAAATCCCTTGAGTAATGTTCATGCATCTATTTCAAGTAAACTTC
ATCATGTGCTGTTATTAACTAATCAAAAATAAAGAACTCATTTGTTGATTTTACAGTCGACATATACATATA
TGGTTGTCTGATATATGCTTCTACTCATCAGTTCTCTGTTATTATTCTCATTGTTGTTTCCTGGGATTGGGA
GGGGAATGTATTAAGATAGTGCATGTGACCATGCACGGCATTTAAAGTTGGTTTCTGCCACTTTGGTCCCAA
AATTTCATCTTTGCTTTAATGAGCTTTTGTTTGGTTGAATCCTGCTGTTCTCCAAATCTGTAATATGATTTC
GAGTTCTAGCAAGTATTTCTAGATATAATATCTTATATCTTTTCATTTCCTCAGCTCATGGTTTTATTGTAA
TAATGAACACTTCTTGTAGGACTCTTCTGGAATATTTTGGGACAATGACAGTTTGGCAGCTCTACTAGCTTT
GGAATTAAAAGCTGATCTTCTAGTTCTGTTGAGTGACGTAGAGGGTCTTTATAGTGGCCCTCCCCGTGATCC
AGATTCGAAGTTAATTCACACATACATTAAGGAGAGACATGAGACAGTGATTACTTTTGGAGACAAGTCCAG
GGTGGGAAGAGGGGGCATGACTGCCAAAGTAAAAGCTGCTATGTATGCTGCTTATGCTGGCATTCCTGTTGT
CATAACCAGGTCTGATACTAGTATTTACGCAATTGGAATTCTTAATATTTATGTGCATCAGTTTTACACTTG
TTCATTTAAAATATTCAAGTGTTGTCTTCTTAGTAGAGTGGACAGGATTTGTGATACCTCTTTATATATGGG
CTTTGCCCTTTTTTGTCAATAAAAATAATATAACTGTCCAAAGAGAAGCATTTAGGATGACCTTAAAAGTGC
AAAAAAGTCTGAATTAAAAGTTGAATTTATAGCTTTGTTGGGGATGCACAAGAAAATCTGAGGTACCTGAC
TGGAGCTGAAAGGAAAATGCTGTCATTGAGTCTGTATCAAAGTTGAATTTATAGCTTACGGTAGGAAATGCA
GAAGAATCTGAGGTATTTTACTGGAGCTGAAAGAGAAAAGATGTCATTCTACTGTGATAAAACATGACAAT
TGATCTGCTGAAAGCACAAACAGGCACACAAGAAAAAAAAAGAAGAAAAAGTAAAAAAAATAAAAAGAA
GCAAAAGCAAGAACAAACATGAGGTAAAACCGATTCTGTATTGCATAGCCTGCATTATGAAGAATGCATTTT
GAGTAGTATAACCATTTCTTTAAAAAACAATTCTTGTTATCTTTGAGTGAACCGCTTGGGCGTTAATTGAGT
GGGTTGGGGCAGTTGACTTTTAGGTGAACCTGCTTCCAGAAAATTTGGCTTCTAGTTGTTGATGCTTAATTA
AGAAAAGACGCTCTTCAGCAACGAAAGTATGCCAACGGTAGAGAAGTTTGAGCTCTTTATGCTGCCATATTA
TTTGTGTAAATATTGGGTATATCAAGTGGCTAATATATGCCTGTAATATTTCATTTCAAAATTGATTGAATT
TCAGGCTAAGCAGTTTATAATTGAAAAATTAAAACGGGTAGACTTTTTATAAATCTGTCGCATATGAGACTA
CTGTATTCTATTGTTGAATAATATTATGCCGCTTGTGACCATTAATGTCCATAGATAGTGAGAAAGGCAAAT
GTAATAATTTTCTAATTATGTGTGGTTAAGGACCTAGCAAGAGTGTGTGTGTATAGGGTCTTGCTAACCTAC
TACATTGTTGTAGTAAGTTAGCATTGTATACATATTTCATTTCTCCAAAATACCCCGCGTTTTCTTTAATA
GTAAGGACATCTTTGTCTTTTAAATCTATTAGGGCAATCATCTCCATTCGGCAAACTTTCCGTCCTCGTGAA
TCTTTAATCCCGTTTTTGCTGAAAACTGGGAATTCTTTGTTATTAATGCAACAAATTTCCTTTTAGCAATTT
ATCAATGTTGGGCTTCAATTGATTTTTTGTTCTTTTCCGAAAAAAATTTGAATCAAGTTCTTAACAAAAAGA
CAGAGAAATCATTATGTTTTGATCTGTAATACTAAGCCCCATTTCGATTCAAGATCTGTTCAGATCAAAATC
CGGCTATGGTTAATCTTCAAAATGCCGGTCAAACCGACTTAGAATGTTGACGAGAAAAACAAGGAAAGAGGA
TGTAGAGCTTGCTCTGCATCACTTAATCGACCTCCCAAGGCATTGTCTTCCACTTCATCTGAGTAGAAATTG
```

Figure 52C

```
GGGAATTTGGGTGAATTCATGAATGATTAAGATTGGACTACAAATCCGATATAGAAAATTGAAGATGCAACT
TGGATTGAAAAGAGGAAGCTTAAGTAGCATTATGTTCTGGCATTGGATTCTTACTCATACTAGATTGTTCTT
TTGCCGAGTATCGATAAAATGATAAGAGGAAAAAGGTATACGGTTCCAATTTTATAAAAGTTATGAATAGGT
TAGATTTAGACATATAAAGTTCTGAAGATAAAAAAATCTCTCACAAAAACATCAGATTGCAACTCCTTCATA
GATCGGAAGAGGAAGCTAAAGAGAATGCTAGAATGAGAAAATGAGAAAAAAGGGAGAAGAATTTGGGTTTAA
GTTTTCAGTAGAAGACAAAAATGCGCTTGCCATTAATGTGTTGCTGAACCACTATTAAGGGTATTTAAGTGA
AACCAAATATGTATACAATGCTAACCTACTACAACTATGTAGTAGGTTAGCAAAACCTATATAAGGTCTTGC
TAACCTACTACATTGTTGTAGTAAGTTAGCATTGTATACATATTTCATTTCTCCAAAATACCCCCATGTTTT
CTTTAATAGTAAGGACATCTTTGTCTTTTAAATCAATTAGGGCAATCATCTCCATTCGGCAAACTTTCCGTC
CTCGTGAATCTTTAATCCCGTTTTGCTGAAAACTGGAATTCTTTGTTATTAATGCAACAAATTTCCTTTTA
GCAATTTATCAATGTTGGGCTTCAATTGATTTTTGTTCTTTTCCAAAAAAAATTGAATCAAGTTCTTAACA
AAAAGATAGAGGAATCATTATGTTTTGATATGTAATACTAAGCCCCATTTCGATTCTAGATCTGTTCAGATC
AAAATCCAGCTATGGTTAATCTTTAAAATGCTGGTCAAACCGGCTTAGAATGTTGACGAGAAAACAAGGAA
AGAGGATGTAGAGCTTGCTCTGCATCACTTCATCGACTTCCCAAGGCATTGTCTTCCACTTCATCTGTGTAG
AAATAGGGAAATTTGGGTGAAATTCATGAATGATTAAGATTGGACTACAAAACCGATATAGAAAATTGAAGA
TGCAGCTTGGACTCAAAAGAGGAAGCTTAAGTAGCATTATATTCTGGCATTGGATTCTTACTCATACGAGAT
TGTTCTTTTGCCGAGTATCCATAAAATGATAAGAGGAAAAAGGTATACGGTTCCAATTTTATAAAAGTTATG
AATAGGTTAGATTTAGACATATAAAGTTCCGAAGATAAAAAAATCTCACACAAAACATCAGATTGCAACTC
CTTCATAGATCGGAAGAGGAAGCTAACGAGAATGCTAGAATGAGAAAAAGGGGAGAAGAATTTGGGTTTAAG
TTTTCAGTAGAAGACAAAAATGCACTTGCCATTAATGTGTTGCTGAACCACTATTAAGGGTATTTAAGTGAA
ACCAAATTTGTATACAATGCTAACCTACTACAACTATGTAGTAGGTTATATATATATATATACACACACA
CACATACATACTCCCTCCGTTTCAATTTATGTGACCCTATTTGATTGAACACAGTGTTTAAGAAAAAGAGA
AGACTTTTGAACTTGTGCTGTAAAATGAAACGTATATTTTGTGTCGCTATAAATCATTGCATAAAGGTAATT
ATTTCCAAATATGAAGAGGTCATTCTTTTTGGCACGGACTAAAAAGGAAATAGGTTCACATAAATTGAAACC
AATATAATAATGAGTCTAAATCTAAATTGTATTACATATAGTTGGGTATATAGAAGGGGAGCCTTGGCGTAA
CTGGTAAAGTTGCTGCCATGTGACCAGGAGGTCACAGCTTCGAGCCGTGGAAACAGCCTCTTGCAGAAATGC
AGGGTAAGGCTGCGTACAATAGACCATTGTGGTCCGGCCCTTCCCCGGACCCCGCGCATAGCGGGAGCTTAG
TGCACCCGGTTGCCCTTATATAGTTGTTCTAAATCTAGGAACCAATATAGTAGTGAGTCTAAACCTAAATTA
GTAGTAGTTTACTTTTAATTCTAGTACTAAAATTATATTCTACTTAGAGTAGATGATAATAACCTTCGTACT
AATTATAGTTTTTTTCTATGTAAATCAAAATAATTATTTCTATTTTGTTCTAGATAAATAAAATGTATTCCC
AGATCTATTATAGAGTACAATCTTGTATCTTTATTTAACTTAAATTCTTCTAGATCTTCGCTCAGATTTTGA
GCAAATATTTCTATATTGTAGTTTGAAGCAAATATTTAGACGCAATGTAATGAAGTAATGAACTACTACAAA
AGGCTAGTCTTCTCATGGAGTTTGAGGACATAGCAAAATATGAAGAGATAGTATGGAGGCAGAAATCCAGAA
TATTATGGCTAAAGGAAAGAAACAAAAATTTAAAAGTTGCCCAAAAAATGGCAAGTTCTCATAGAAGATTCA
ACTACATAAATGATGCAAGATCAAGAAGGTCAGGAGTCCAAGAAATTCAAGAAGTCTAAGAATCCATTTAAG
ATTAGGATTTTTCTCCATAAAAATTAGGATTTCTTATTTGATGTTTCCTAGTAATTTGATTCTTGATTTAG
TAGGATTGAATTTTGTAGCTCTAGTCAAACTAGGATTGTTAGTTGGTATTCTACTCCTAATAGAATTCTTTT
TCTTTTTTAGTTAGAATATGTTTTTCTTAACCTTATTGTTATTCTGGTTTAATTATGATTAGTTTTCCTTAA
CATGATCAATTTTACTCATTGTAAGGCCTATTTAAAGGGCTTAGTATGTTGAAAATAAAGATTGGTGATTAG
TATTGTGATATCACAACGGAAGTATGCCTTATACATTCTTGAGGAGATAGGAATGCCGGGCTGTAGACCCAT
TCACACTCATGTGGATTCGAATTCTAAACTTTCGCCAGGACCCGGGGAATCACTAAACGATCTGGAAGATAT
AGGCGGCTGGTTGGTAAGTTAAATTACCTCACAGGTACTAGACTTGACAATTCTTTTCCTGTGAGTGTTGTG
AGTCAGTTTATGGATTCTCCCTGTGATAGTCATTGGAATGCAATTGTGTATATAAAATCAGCCCCAAACAAA
GGATTATTGTTCGTAGATCGAGGCCATGAGNNNNNNNNNNNNNNNNNNNNNNNTAATAAATTGAAACGGA
GGGAGTAGTTAATACATCAATCAATAATGTAATTTTCCGATTATTTTACAACAACCTTTTGGTTATCAAAA
ATGTAATTTTCCGATTATTTTCACAAGTACCAAGGGCCCAATATTATAAATATTCAGATAATCAAGGGAGT
GAAGAGGACAAAACTGATGAATACAATATCAAAGAGACAAGGAACATGCATTGGATCCACAAGTTGAGGATT
TACTACCAAAGTTTTATGATGATCCATTGGAGTATCTAGCCATGTGTGTCATTGACTTTCCGTCTTTCAGAG
ATGCTCAACACAATGTTGACTTGATTGTTGATTCTATCCATTGTAGTATCTAGCCATGTGTCATTGACTTTC
CGTCTTTCAGAGATGCTCAACACAATGTTGACTTGATTGTTGACTCTATCATTCCAAACAAGTCAGCATATT
GCGTTAATCCTAAAGTCCATAAAAATATGCATGAACAAGAGGAAGGATTACTTAAAAAATAGTGGATAATGG
AGAGTTTGAGGTATATTGGAGAAACAAGATGTCTTCACTTGATAAATATATATGGCCATCATCAAATTTTGG
TGTACAATCATTGCAATTGATGCATTCCCACGAAGAGCGCTGATCTCTATACTTAATTCAAAGCTAGACACG
GAGTTAGCTAAGTTTTATGAAGTTCTAACACCAATAACTTCTTATTGAAAGTTGAAGTTTGATAGTCAACAT
AGAAATATTACATGGAGAAGGCTTAGTAGAAAGTTGAAACTTAGAAAGTGGGATTTAGTTCGACCCAAGTGC
TAAGGTTCACTTACAACATGAAGAAGCTCCATAAATAAGCTAGCAAAATATAACTTGAAACCTAGTGAGCAC
TGGGTCCCCATTCCTTAATATAGCAAATCTTGCACCATCTATGGAAGTTGTTAGACTAGAGGACGAGTCTTT
```

Figure 52D

```
TTCAACTAGGGGAGAATGCGAAATCAAGAAGGCCAAGAATTCAGGGAATTCAAGAATCCATTCAAGATTAGA
ATTTCTCCATCAAGATTAGGATTTCTTATTTCCTGTTTTCTAGTAATTTGATTCTTGATTTAGTAGGCTTAT
ATTTTTGTAGTCCTAGTCAAACCAGAATTGTTAGTTGGTATTCTATTCCTACTAGAATTCTTTTTTCTTTTT
TAGTTAGGATATATTTTTCTTAACCTTATTCTTATTCTAGTTTAATTAGGATTAATTTTCCTTAACATCATC
AATTTTACTCATTGTAAGCACTATTTAAATGGCTCAATATGCTGAAAATAAAGATTGGTAATTAATTTTTCT
ATGATCTTGCTTCAAAAACGTGATTTACTTTTTATTTCATTGTTCTTCGCTTATTCAACGTTTCTTGCAATC
TTGCTGGATTGCGGAACGTGTGGGTGAGGTTTCTTTTCATCTTACATTCTTCTAATATGAGTTTGAAGAACG
CTTTCACTAGTTTTGTGGAAAACTTTAGTGGGGTTTTTTTGTTTTTCTTTCTTCTTTATGTGTGAGAGGTGC
AAAACCTTGAAAGTACATCAGACATCCTATGGTTCAAGGCGAGACCATTACTAATCTAGATGATATCAAAAG
GGAGATTATAGCCTATTATCAGAATCTATATGCTGAAACAGAATCTTGGAGGCCTGATATAAAACAAAATGG
GTGGGTCAAGCATTAGAGAGGAGGAAAGGGAGTGGATGCAAAGAGACTTTGAAGAACAAGAAGTACTGGAAA
GTTTGAAATTATGTGAAGCAGACAAGATGGATACAACTTAGAGACCAATACTTCATGGAGAAAGGTAATATA
TGTGTAGTTTGACAAGATTGAATAGGGGTGCAAAAGATCTGTTAATAGTCCATATGTGGGTGGGTGTCGCAA
TTTTGGAATTCTCTTGTGGTTAACACTAGCATAAAGGTGGGTAATGGAAGACACTTTATTTTAGAGTGATAA
TTGGTTAGGACATGATCCACTTAAAGAGATGTTTCCCGAATTCTATGGTATTGCCACCATACCTGAAATTAA
AGTGGAAGAAGCCCGGGGACTGCATGGCTGGAATATCACTTTTAGAAGAGGGTTCAGTGATTGGGAAATGGG
AAGAAATGCTGACTTCTTTAAAGCTTTGGAAGTTTTCTAGGGTCTCACTGATCATGAAGATACCTTACTATG
GAACAAATGTAAGAATTGGAGCTACACTTTCAAATCTGCCTATCTTGTGCTTTCAAATAAAGGCCAGCATAG
TGAGGGATGGTCATGGAAGAATATGGAAAGCTAAAGCTCCCTTTAAGGTGGTCTATTTCTCATGGCTGGGTA
GCAAGAGAAGCATGCTTGCCTCAAGAAAAACTGAAAAGAAGGGGATTTCAGTTATGTGGTAGAGATCCGGAA
ACAAACAGCCATTTGTTCCTGCATTGTCCTATCACTAGGCAACTGTGGAAACCGTTCCTTAACATTGTGGGC
CTCAGGTGGACCATGCCTTCAACTACTGAGGAGCTTTTGAAGTCTTGGAATAACAATGGAGGTTCACTTAGA
CAGAAGGCATGGTGGAGGCTGATACCTGCTTGCATTTAGTGGACAGTATGGAAAGAGAGGAATACATGAGTT
TTTGAAGATATATATAATCCCCTCCAAAATATCAAGATGAATTGTATTCTTTTGTTTTATTTTGGTGTAAA
GAAAGTCATGTAGATAATACAGAGTCCTTGGTTGACATGTTAGGCTTTTGTAACTTCGATGGATCAGTTTT
GATTTATCCACCTTGTACATATGGTTTTCTGCATTGCCTTAGTGCGTTTTCTAATATATTGTTACAAGTCTC
AAAAAGATTAGAGGTTCTCATCTCAGACTTAACCTAGTCAGAACCCAAAAAGTATAACCAAAACAATAAATC
AGCCTACAGAGTGAATATTTTAGTCGTCGTAGGAAAAGTGCTTCTATTTATGTATGATAACACTTTGTAAAG
TTTCTCATTCTAATGCATTTTAAGCATTGATAATCCTAATGTTGTAAGTTCAATGGTTGGAAAACATAAAAA
TTTCTATTCATCCACCCAGGATTCTAAGAAGATGGGTGCACTATTACAAAGAGGTGAATCTAGAAGTTATAT
TTGTAAGTTATTACCATCTATGTTGCTCGGACTCTTCGAAGATGTGGCCGGATACGTGTCGGATCCTCCAAA
AGTAGTGCATTTTTGAAGGATCCGACACGGGTGCGGTTACATTTTGGAGAGTCCTTGCAACATAGATTACCA
TGAACCTAAAGGTTAAAGTTATAGGTTAATAGGTTAAGTTATAGGTGAATCTATTACCATTTAGAAATTATA
GCTTGAAATTAAAAATTTCGTGCAATTTTAGAGATTTTTAACATATATATACCTATACTCCATATAAAAAAT
ATTGGGTCATTGAACCGTGTTATATCATCCACTGCTATTAGTTTTAATTATTTAAAATCTTGCTATGACAAA
AGGAGATCAAGGATTTCAATGTCTTAGATATGGGGATTTTGAATGAATAAATTAAATTAAAAATGAAAGAAA
AAGAAAAGAAAATACTTAATTAAAATAAAATAGGGGACACTAGATATGCCTTCAAACTGAGATTTAAACCT
CTAGTTCACTTGGAAAGGTGCACCCAATAATCATTGTTTTAAAGGACTCTTTGAGCTGGGGTGCACACATGT
ATATTTAAGCAATTTTAAAGAAATATAACATTATTATACATGGTATAGAGAGACGAGTATGGGTTCATGTGC
CCCATGCTCCAACACATAGATACTCCCTTGCATCCACCAACAGATCTGTTAACACTTGACACATTCTGGAGA
AGACCACCTTCGAATCAATTTAGACTGTTCTCTAATCCTCAAAAACAGATTCCTGCAGGCCTCTTTTTGGT
AATTAACCTTTGTTGTATACAGTTTATCAGAAGTCCTACTACAATTGAAGATACTTTATGCTCTCTTCTATT
CCAAAAAAAAAAGTTGGGTGCATTAACTGCTAAAAGAGATTACTCTATTTCATCCTTGGACTTTTACCTTGG
AAATATAAAGTTACTGTCAAAAATGTCGACTATGGAGCTTAGCTAGAAAGAATAACTATGTTATGAAGAACT
TTTCCAAGCTGTGGCTCAGTGGATGAAGCTGGGATAAAGATCATAGGAGACCATGGTCTAAAATCCAGCAGA
GGCCAAGTGAACAAAGTTACCCTAGCCTGTATATGTATTGGTGGGAGGATGTAATTACCCGGTGGAATAGTT
GAGGTACGTGCAAGCTGGTCCAAAACACCAATAAAACACCATTGCTATTTAAAAAGAAAAGGGTGCTAGCAG
AACAAGATGGTGATAGTAAGTGGTTAGGTTGAAAACGAATGCAATAAAATAAGGCTGAAAAACGAATGCAAA
TCAGTACATGAGTAAAGCGTATTATATGTAGCAAAGCATTGTTCTTCAGATGTTCAGTGTGAAAGCTGATTT
CTCTAAGTTTCTTGCTCCCTTTACCTAAAATTTCTGCTGATTCTTTCTCTATCCGTCTGTGTGCGTTCGC
GGGGATAAGTGGCTTCGCTGTCGATAACATCATTAAAGTGCTACATGGGAATGTATCGGCACCCTCTTTCA
TCGTGATGCCAATAAATGGGCTTCAACTGGAGAGATAGGTGCTCGTGAGATGGCAGTTGCCGCAAGGGAATG
TTCCAGGCGGCTTCAGGTATATCTAGAGAGACATCTGGCTGTAACATTTGTAAACCGCATGGATGTGAATA
TTTATTCTTTGTTCCTTCACCTCCAGGCACTTTCTTCCCAAGAAAGGAGTAAAATTTTGCAGGATATGGCTG
ATGCATTGGAAGCAAATGAAAAGGCAATCCTTGCTGAGAATGAAGCTGATGTGGTTGCTGCTCAACAGGCTG
GATATGAGAAGTCTTTGATATCTCGGCTGGCATTAAAGCCAGGAAAAGTAAGAGCGTGCTCACTTTGCAACT
TAGTCTGAATGATCATGTACCTTTTTAGTATTCTTGCTGAAAGGGCTACTCCTTTGTCATAGATTTCTAATC
```

Figure 52E

```
TTGCAAATTCAGTTCGTGTGCTTGCTAACATGGATGAGCCCATTGGTCGCATTTTAAAGAGAACGGAGGTAA
GCAAATCACACCAAATATATGTGGCATGTAGTTTTTAATACATGAGGAATAGAGAACAAATTGTGAAGGAGT
CTTGTGAAGTACTTCTTTAAGAAAAAACTTCTGCACTCTCAGACGATTTAGTGGGTATTGTACAATGTCCAT
TGACAATTATATTTAATGGTATAGCCAAAGCTATTTTGTTGTTGTTTTGTTTCTTGGCCATGAAAAGAACTG
GGCTGACTTGTTGGAATATTGGGAGCAACAGAGATGTCGATTTGTAACTAGAAACCTTTATTGATCAGTGTT
CAGTTATTAGCCTTTAGTTTCAGAGTGAGATGTTGATTTAATGTCTGGAATATTGTCGTCTCGTCCAGGTTG
CTGATGGATTCATCTTGGAGAAATCATCATCTCCATTAGGCGTTCTATTGATTATTTTTGAGTCACGACCGG
ATGCACTTGTACAGGTAAGCAATGCTGGCAAAAAGAAGTTTTCCACTAGCAGGAAGGTTCTGCTGCATGTCC
AATATAAATTAGTAGGGTTCTCTTTTTAGTAGTTATGAAACACTTTTTCTTTACTAATGGCGGGGACAATGG
TGATTAACATATGTCTGTATATGTAAACTTCACGGAATTCTCTGCATGCTTGAATTGCATGTCCTTGGATTA
TTCCTTTACAGTTCACAAACTCGTTGCACTTTTTTGCATGACTAGATAGCTTCTCTAGCAGTCCAAGTGG
GAACGGCCTCTTGTTGAAAGGAGGAAAGGAGGCCAAAAGATCAAACGCTATCTTACACAAGGTTTAACTGAT
ATCTTACACGCTATCATACACTCTTCACTGAAGCTTCACGTTTCCATCATTTCATGTCCAGCTTTGTCACCT
TCTCCTCTTTTTCTTTTTCGTCTTAGGTGATTACCTCAGCGATTCCTGGAACTGTTGGTGAAAGGCTTATTG
GACTAGTGACTTCTAGAGAAGAGATCCCTGAATTGCTCAAGGTACCTGCCAAATATCTTAAATGAGAAACTT
ATATTCTCCCTCTCTTTCTTTTTAGGAAATCATGACCTACACTGGACATGAGTTTGGTTCTTAGTTTATTT
TTCTTGCATCCCGCAGCATGATGATGTGATTGATCTTGTTATTCCAAGAGGTAGCAATAAACTTGTTTCTCA
AATTAAGGCATCAACAAAAATTCCTGTTCTTGGCCATGCTGGTAATTATGTGTTACTTGAGTATTGGTTACT
TGCTAGACTCAATCTCTGCTTTGATGTCACGGATTCTTTTCCTGCGATGGTAATATTACTATGTTTGCTTCC
AGATGGAATTTGCCATGTTTATGTTGACAAGTCTGCTGACATGGATATGGCAAAGCGGGTTGTTGTGGATGC
AAAAACGGATTATCCTGCAGCCTGTAATGCGATGGTAGTTTGTTATACTTTTTCATAAAACAGTGTCCAGTT
TTAACCAGGTAGTTTATTGATTTCTTTTCTTTTTTGGTTTTTTTGCAATAAAATTGTTTCATTGCTTTCCCT
GGTAGGAAACACTTCTTGTGCATAAGGATTTGGCACAAAATGGAGGTCTTAATGACCTGATTGTGGAACTTC
AAACAAAAGGTAGAACTTCTTTTTTCAAATTCTTTGTGTAATTAAAGCTTCTATATGATTACTGTGGAGTCTT
GACTTGAAAGTAGGGAAAATAGAATCTGAGGGTATTTCTGATAGCAAAATCTGCTTTGTAATGATTATTTTT
GTTAATCTCAGTTTAGCGTTGAGTTGCATCACCCATGAAAACACTCTTGTTGTTGAGTCTCATCTATAATGA
ACAGCTATGTTGCACGGACTCTCCAAAATGCTGCCTAATAGTTTTCACACAGTTTTGCGTACTAACCATTCT
GTCCTAATAGTTTTAGAATATGGTAAATGCTGTCTTTCCTCAACTTTCTTTTTTTGTTGAGAAAAGTGACCG
ACTATCCTCACATTCCTTGGCCCTGAAAATAAAGTTTAATTGGATTGAAGAAATGTGAACTGATGTTTGCAT
TTGTGGCAGGGGTTTCTTTATATGGTGGACCAAAAGCAAGCTCCCTGCTCAAGATTCCAGAGGCGCGTACTT
TTCATCACGAATATGGTTCACTGGCTTGCACTGTGGAAGTTGTTGAAGATGTATATGCTGCAATAGATCATA
TACATCAGCATGGAAGGTGTTATGTTTGCCTAACTTTTATCTTTTACAAGGCTGCATTATGATTCTTTTCTT
TTTCAAATTATTTCATATTGGAGCTCTTATACTATGCAAACTTTTGCAATCCTTATTTTTATACACAACTCA
TTGGCAGTACCCACACTGATAGCATTATTACCAAAGATCAGGAAGTTGCTGAAATATTTTTACGTCAGGTTG
ACAGGTACATTCTCATGTTTTCAACTTCATCTTTCGTCATGACTGATGAGTAGTTTCTTCAATCTGATATAC
TAAGACCTCTGGAATTTCATTAATTTCTGATAGTAAGTTTTGCCCATTATTGTTAATCATTTAATTGGGGA
ACTACTACTACCATCCCTGCTTAAACATGTTTGATCTTCACTTTTCAGTGCTGCTGTATTTCATAATGCAAG
CACAAGATTTAGTGATGGGTTCCGCTTTGGACTGGGTGCAGAGGTATATAATCTATCAGTGGTTCCAAATTG
TCTTTTGGTATCATAATTTCATATTTGTAAGTATCTTGATTGCTTTTGGTTGAATAGGTTGGGATTAGCACA
AGTCGTATTCATGCTCGTGGCCCAGTTGGAGTTGAAGGGTTGCTAACTACGAGATGGTATATCTGTTGTCAA
CTCTCTTTTGATTTCAATCCCTGTTTTCTACATCATTCTGGCTTTAAGTCCTATCTGGAAAACTACCACTCT
TGAGAGATTGCCCTCGGAACAAGAGACTTCTCAAATCTCTGGCAATTCACGTATCCCTTATGATAAAAGAGA
AAATAGAAGTAAAGAAGATGACGTTGTCAGTTAAATCTCTTTATGTTAGTCGAAAATGAAGTCTCTCAGCTT
GACCTAGATCCCATGGGTTCCCTATAAGACATGTCCTCCAGCTTTATTGCATTTGCTACAACTTCTTGTTTA
TCTTTGTCTGTTTGCTGCATGAACTTGGTTATTACTTCATTACAGGATCACATCTGACTGAACTGGCCCCAA
TTTAGTTTTTTCTTGACCAAACCAGTCTTTTATATCAAGTGTAGCCAGATCTCTGTGCATAATTGCATAT
CCAGCCTGCAGTCCGTTGCCCGGTAGTTTTCCTACTTGGCAAGATTTGGATGTGGTAGGCCAAAGGACATAC
ATCACAAAACTCCTTAGCTAGTTCATATTGTTTAAGTAAAAAGTCCAAAAAGAGTTGGAACTTTTAAGTTCT
TGAGCACGGCTGTCGAGTAAAGTCAAAGAATTACTATATTTCCCTCGATCAGAAAGAGGTATTACATTTCTG
CTTATACATTGAACGTGTGTGTGTGTGTGTGTGTGTGTGTATACCCTTCTTTGTTTGTGCCTTCTTCT
ATTAGACGCATGCTTTTATTGCATGTTGCACATAAAGCCCGGCAGACGCTTGACTTTTTTTCTTTCTTTTTG
CTTGGAAAATACTGGAAAATCACACGAAAATGGATGCGCAAATGATCATCTCTGACTAAATTGGAGATGGAG
ACCTAATCTCAAGAATCTACTCTATAGTTGCTGTATGTCCTTTTTGCCATGAGCTCTTGATTCTTATCAGA
AATCTTTCTTGACTCTCTTCTTTAGCAGTGTTATGAAATAGTCTGGTAAGACAAATTTCACTTAGATTGACT
GCTGTTCAAGATGCATGAATGCTTTATCCCCAAAGTGGAAAAAGAGAGATCAGAGGCATGAATTTGCGGTGG
TTTTACTGGGTGTATGGCATGTGTAAGAGGAAGAGTTTAGTAGCTGTACAAAATTTAGGCCAAATACATAAG
TGGCCACCTAAAATTGCCACGATTTTTCATGCACTTCAACTAAGGCTTTCCTATTAGTCACTTAAAGTATAT
```

Figure 52F

CTAAAATGTGTCTATTGAGCACTTCATTGATCATGTATGAATGGGATGAAGACATGTGTTATTTCGACCAAA
AATAATCCCACTATAAACAGCTTCTACAACCAGAGAAAAACCAACAGTATCTGAGCAAACAACAACCAAAAA
ATATCCGACCAGCAGCGGCCATCGAAAAAAACTCGAGCCTGGTCCAAAAATTAATTCTCCGGCGAACCTGTA
CAACGAGCCGACCCTTTGTCTCCTTTTGTTCTATTCTCTCCTCATTTCAGATGCACATTAAAAAATCCTTGC
ACCTTCAAAATAATATAAGAGAACCATTGAGTTTGACCGGATATCTATTCCAGTTCTCTCAATGACAACGAG
AGCTTTGACGGCGCTGATGATGAAGAAGATTTTGAGAATAAGCTGAAGGAGATTTTTAGGAAATAAGGAAT
GATTCTTTGTTGTTCTCCTCGGTCTTGTGTAATAAATGAAATTGGAGATAAAGATTAGAGGATGGTGAAAAT
GATCTCAAAATAAAATTTCTCTGAGAATGGTTGCTGGTGGAATTGGAAAGTTTGTAAGGAATGATTCTTTGT
TTTGGTGCTTAGGTGGTACTGCTGGCCGGTCATCGACGATCCTAAGTTGAGTGGCCGATGGGTTATTGTGG
TGTTCTGGTGAAGAAACTAAAAAAATAAAATTTTAATTACAAATAAAAATATTAGGCTCATCACGCAAAGAG
AACTGTTATTCACATAACATGACATGTCATCATTTTGTGTTTAATAGCACACATTTATTGAAGTTGGGACTG
CCTAATAGGAAAGAGCCTAAGTTGAAGTGCTAAAATGAAAAATCGCGGCAATATGTATTTGGCCTGAAATAT
ATGCTAAGTTTTGGATTCCAGTACCTACTTTTACCTCTGCTTTTTCAGCCGTTTCTTTCTTGATTTCTTATA
AAGGAATTTGTCTTTGTTAAAGTTTTCTTAAGGTCGTTTAGTTAGTTTCCTTGGGCATAACACACTTATATT
CATTCTGCATTTTGAACATGAATTTTGTTCAAATTATTTGGCCAATGCTGCAATTTTCTGTAGGCTTGCAAG
GGGAACTGGACAAATTGTTGACGGTGATAAAGCAGTTGTCTACACTCACAAAGACCTTAGTGGGCTTGAGAT
TGCATAATTGAAAGCATTGGTTGTCCCAGTTATGTTTTACGAAGATCTTCTGTTGTACTATTGGATGTGGGT
AAAGCAGGTTTGATGCTTACTCTCTGTACGTTCCAGTCATGGATTGACTTATGATCATTTGCATACTACAGG
TCAAAAATTATTTTGTATAACAAAGTTTCACTGCTGCATAGGTTATAACTTGTAGCATTATAAACTCGCAGT
CTATTTTGTCTGGCAAAGGTTTCCAATTATGATAAAATAGGAATGTGTTCCAAAGAATTTTTTTTCATAGA
AAAGAATTTGAGTT

Figure 53
Nitab4.5_0003679g0060.2 amino acid sequence (SEQ ID NO. 50)

MAIEDNESCGSRVVDSATTSGRHQRKKLEVYNEVLRRLKESNNVEALEPGFDDELWAHFNRLPTRYAIDVNV
ERAEDVLTHKRLLHLAHVPANRPAFDVRLVQVASVPDGNLRDSFHSSFAKKEVSRSVHPPPAFGSSPNLEAL
ACEAIKSEVQDEDTAAPCANFSRPMHEITFSTDDKPKLLSQLTSLLAELGLNIQEAHAFSTVDGYSLDVFVV
DGWPYEEVVRLRTALEREILRNEKSWPSPSQSFIKQEQDLIKREFDHLTIPFDGIDVWEIDHQLLKFEYKIA
SGSYGDLYKGTYCSQDVAIKILKSERLNTELQTEFAQEVYIMRKVRHKNVVQFIGACTRPPNLCIVTEYMSG
GSVYDYLHKRKGSFKLPTLLKVAIDVAKGMNYLHQNNIIHRDLKAANLLMDENEVIKVADFGVARVKAQTGV
MTAETGTYRWMAPEVIEHKPYDHKADVFSFGVVLWELLTGKLPYEYLTPLQAAIGVVQKGLRPTIPKHTPPR
LAELLETCWQQDPTSRPDFSEIVDILQQIAKEVGDERADRCKEKSAGGFFSALRRGHH

Figure 54
Nitab4.5_0003679g0060.2 coding sequence (SEQ ID NO. 51)

ATGGCGATAGAGGATAACGAGAGTTGTGGGAGTAGAGTGGTGGATTCGGCGACTACCAGTGGTCGTCATCAG
AGAAAAAAATTGGAGGTCTACAATGAGGTTTTACGGAGGCTTAAGGAATCAAACAACGTCGAGGCTTTAGAA
CCTGGATTTGACGATGAACTTTGGGCTCACTTCAATCGTCTACCTACTCGGTACGCAATAGATGTGAATGTC
GAAAGGGCAGAAGATGTACTCACACACAAGCGATTGCTACATCTTGCACATGTTCCAGCTAATAGACCTGCC
TTTGATGTCCGGTTGGTGCAGGTTGCTTCGGTTCCTGATGGAAACTTAAGAGATTCTTTTCATTCGAGCTTT
GCAAAGAAGGAAGTTAGCAGAAGTGTCCATCCTCCACCTGCCTTTGGTTCTTCTCCTAATCTCGAAGCCCTT
GCTTGTGAAGCAATCAAATCTGAAGTTCAAGACGAAGATACTGCTGCTCCTTGTGCAAATTTTCGCGGCCC
ATGCATGAAATTACATTTTCAACAGATGACAAGCCAAAGCTTCTTAGCCAGTTAACTTCATTACTAGCTGAG
CTTGGGCTGAACATCCAGGAAGCGCATGCCTTTTCCACTGTGGATGGCTACTCCCTAGATGTCTTTGTTGTT
GATGGTTGGCCCTATGAGGAAGTTGTGCGACTTCGAACTGCATTGGAGAGGGAAATCTTGAGAAATGAGAAA
TCATGGCCAAGCCCGTCACAATCGTTCATAAAGCAGGAGCAAGACTTGATCAAACGTGAATTTGACCATTTG
ACAATACCTTTTGATGGCATTGACGTCTGGGAAATTGATCATCAGCTTTTAAAATTTGAATACAAGATTGCA
TCTGGTTCATATGGTGACTTATACAAAGGTACATACTGCAGTCAGGATGTAGCTATCAAAATCCTAAAATCT
GAGCGCTTGAACACAGAATTGCAGACGGAGTTTGCCCAAGAAGTGTATATCATGAGAAAGTTCGTCACAAA
AATGTTGTCCAATTCATAGGGGCTTGTACCAGGCCTCCCAACTTGTGTATAGTAACAGAGTACATGTCTGGG
GGAAGCGTATATGACTATTTACACAAACGAAAGGGCAGTTTTAAACTACCTACCCTGCTTAAAGTAGCGATT
GATGTAGCTAAAGGGATGAACTACCTGCATCAAAATAATATTATACATAGGGACTTGAAGGCTGCCAATCTA
CTGATGGATGAAAATGAAGTCATTAAAGTGGCTGATTTGGTGTTGCCAGAGTGAAGGCACAAACAGGTGTA
ATGACGGCAGAAACCGGGACTTATAGATGGATGGCCCCGGAGGTAATAGAACACAAGCCCTACGATCACAAA
GCAGATGTATTCAGTTTTGGGGTTGTGCTATGGGAGTTGCTGACAGGGAAGCTTCCATATGAGTACTTGACC
CCATTGCAAGCTGCTATTGGAGTGGTCCAGAAGGGTTTGCGACCAACTATACCCAAGCACACTCCTCCCAGA
CTTGCTGAGCTGCTAGAGACATGCTGGCAACAAGACCCGACATCCAGGCCTGACTTTTCTGAAATAGTAGAT
ATTTTGCAGCAAATAGCAAAAGAGGTTGGAGATGAAAGAGCAGATCGTTGCAAGGAGAAGTCAGCTGGAGGA
TTCTTTTCAGCCCTTAGACGTGGACATCATTGA

Figure 55A
Nitab4.5_0003679g0060.2 genomic sequence (SEQ ID NO. 52)

ATTCATCACCTAAATTTTGCCAAAGCTAAGAATATTAAGCAAAGCAAAAAAAAAGGGGAATGTAATTAGCA
CGCAAAAAAGCAGATCGAAGATAAGCAGATCCACGTCAACTTGACTGTGCCAATTAAAATCCCACCTTTAC
CCCGAGTCAAAAAGGGTTATACAATACATACATACATGATTCATTTCATGTACCCACCCCCCCACACACA
GAGAGAGGGAAAAACGATATGACCAATGGGAATGAAACCTTCCTCAAAACCACTCCCCCCACCGCCATTTGT
TTCTTAATAATTCTTCTCAGTTTTCTTTCACAAATTAAACATGCATCTTTGATATAAAGTAGAATTTGAATT
CTGTAATTTTCCATCTCCATAACGAAGATTCACTTTACGTAAACTGCACCGCGGCCATTATTTTTCATTCCG
GAGGAATTTAAGACTAGTGAGAGAGGTGAAATGGCGATAGAGGATAACGAGAGTTGTGGGAGTAGAGTGGTG
GATTCGGCGACTACCAGTGGTCGTCATCAGAGAAAAAAATTGGAGGTCTACAATGAGGTTTTACGGAGGCTT
AAGGAATCAAACAACGTCGAGGCTTTAGAACCTGGATTTGACGATGAACTTTGGGCTCACTTCAATCGTCTA
CCTACTCGGTAACTTTACCTTTCTACCTCTCTATGTATTAATCCGTACAATTATATACGTTTTATGCGGT
TTTCTATAGACGATAATATATGACTACTGACATATGATCTCAAATGTACCGTTGTCGTTCGCATTTGTTGTG
CCTTTGGGAGATTGGATTATTTTGGTCGACAGTTTCAATCTTCTTATCAAGTTAGAAGTCGATAATGCCAG
TTATCGTTTCCAGCTTCCTCTTCTGGTCTTAAATTTTTAGGTTTTACTTGCCGAAAAGTTTGCTATCTTAGC
TTGTTAAAATTTCGATGAACCAGTTGAATTTGCTAAGCAGTTCACATTTGTGCAGATGTATTAATGTGCGTG
TTTTAGATGCACGACGTTGCGAAACGCTGAATACTTTTTTTTTTGGAGAAGTGCATACTTATGTGCCGCCA
AAATTGATTGATCAATAAACGAATACCTTATTTTTGCATTTAAGGTACGCAATAGATGTGAATGTCGAAAGG
GCAGAAGATGTACTCACACACAAGCGATTGCTACATCTTGCACATGTTCCAGCTAATAGACCTGCCTTTGAT
GTCCGGTTGGTGCAGGTAATTAAACTACTCTTGCAAGATAACACCTTTTAGTTGCTTTGCTCTTGATATCGC
ATACATTTAAATCAAGCATGCCTTTTCTGGAGTTAAGGAGGATATTTAGATGTTCGTTCACTCTGACTAG
CTAGTTCAATAGACCAACACATCTCCGTGTAATCTTGGTCCTTTGTATTTTTGTTATTGTTGCTTGTCCA
GTACCTAATTATTCCCAGTATATGCTAGTTATGGATTGAATCAAACTTGGCATTGTGCAGGTTGCTTCGGTT
CCTGATGGAAACTTAAGAGATTCTTTTCATTCGAGCTTTGCAAAGAAGGAAGTTAGCAGAAGGTATCACCTT
CGTGACATTCTACCTGAAAACGATTTCCCATAGGACGCTGTATTTCTTTGGTTACTTAGTGATTCATTGAAG
CCTTTTTCTGTTGTTTAATATAATCTTGAATTCTTACTTGTCATTGACTGTGCTAAATAACCGCTTCCATTT
TGATACATAGTGTCCATCCTCCACCTGCCTTTGGTTCTTCTCCTAATCTCGAAGCCCTTGCTTGTGAAGCAA
TCAAATCTGAAGTTCAAGACGAAGATACTGCTGCTCCTTGTGCAAATTTTCGCGGTATAGAATTTTTTTTC
TTTTTGTGCATTCCGCTTCGACGAGTATATATTATGAAGCATAAAATTGTAAATAATTTTGCAGGCCCATGC
ATGAAATTACATTTTCAACAGATGACAAGCCAAAGCTTCTTAGCCAGGTAATTGATGTGCTTATTATTCAA

Figure 55B

```
TACACTATCTGCTTGATAGAAATGTACTCTATCTGTTGGCAGAGGTGGGATGTGGTAAGCTTTTTATTTGAC
ATTGAAAAAATGTCCATTTATTATTGAAACCAATTGTTGACCCATGAACATGTATAATATTTAATTCTTTAT
GTAGAAATGTAATTCAGGGACCTTGATGTATGAAGGGCTGAGGCTTTTGTCTGTTCCTTTGTTTCATGAAAG
AACACAACTCTCATCTTGCTGCAGATTTCAAATGATGCATGATTTGGAATGTGCAAGTAAAACAGACATAA
TTGTATTTGGTGACACCAAAATTGATAAATATTGCCTGCCTACTTGGCATTGTGATGCAGTGAGAAAGGATT
GTGTATTGCAAGAAAGAAGTAGTTCTTTATATCAGTTTATATCTCATGATAAGGAAATCTGAGACAATAAT
GAACCTTTGAATATGACAGTTAACTTCATTACTAGCTGAGCTTGGGCTGAACATCCAGGAAGCGCATGCCTT
TTCCACTGTGGATGGCTACTCCCTAGATGTCTTTGTTGTTGATGGTTGGCCCTATGAGGTACATCTCTGACG
TTATATCCTCACTTTGATCTGGGTTCGCTTAGGTGCCTGTTATATTTTGTGACCTAACATCAAGAAGTGACA
GATAATGTATGCATGGTTTAAAGTTCTGTATTATGGTCGCTTTCAGCTCAACTAAAAATTGAGTAACCACTT
TTAAACTATGTAAAGTTTATGAGAATTTCATCAAATTATTTAGGCTACATAATTTAAAAGGAATTTGATAAT
TCTGATTAAAAAATAATATAAAGGATTTGTACTTGTACATCTAGAAAATTCAGTTATAAATACTTTTAACAT
TAAGATTTCAATAAATCAAAGTGCATAAAGGTTTACGTATGACAATCGACTATGATAAAACATATTGGAGTA
TAACTATGTTGAATTCAATGAGAGTATATCATACACTTTCATTTAACTATTATTATGTCATTAGGTTTTTGT
TTTGTTTTTTGTTATTTCGTAAGAAAAAATGTGACATAAATTTAATAAGAGTGTCCCGCTTTCAGCTTACC
TTGGGAAATGATTATGTCTTGCTTTCTTGATTATTACTTTGTATATATCACAGTCATGATTCTCTACTTCAC
TTATTAGGAAATGAGTTTTAAAAGGTCTACAGTAAAATAATCTTTTTGAAGTGTTGGTTCGCCAATTAACTT
TTTCCGGCATAGGAATCCTTTCTGTAGTTGGCTTGTTGAGTTCTAGGCTACACTGTTGCACCTCTAAATTCA
GTGCATAAACTGGGAGTATTTTACATTTCAAACAGAAGTGAATGAAATTCTGTGCTCCAATGCTTCATATTT
GTAGCACCAATTCCAGCATTCAGTGTGAGCCCCATGGTAGGTGCCAATTTTTATTTTTTTTCTAATTGAAA
AAGTAAAATCACTCTGTTATGGTTTCTCGGTCATGGTCGGGGTTGTCTATTATATTCCTTCTGATGTCATGT
GTCCAATGGAACATTTATTTCTGTTTCTTATCAGGAAGTTGTGCGACTTCGAACTGCATTGGAGAGGGAAAT
CTTGAGAAATGAGGTACTTTCCTGTTATTTTGTTCTATATAATGACATTTGATATTCTGCCGAGATTTCTGG
ATATGTTTTTTCTGCACTAGTTAAATCCCAACTAATGTACAAAGGACTTTGGTAAGAACAGATTTCTGGTCG
TTTTCTGAATGATTATACTTTTGGAGTTACTAGGATTAGTCATTTCCTTGTTCTCCTCGACGAGCAATATAA
GATTTAGCCAGTTGTCTGTAAGTTTTGTGTACTTATCATTTAACGAGGTGTAGCTCCATTCAGAAATCATGG
CCAAGCCCGTCACAATCGTTCATAAAGCAGGAGCAAGACTTGATCAAACGTGAATTTGACCATTTGACAATA
CCTTTTGATGGCATTGACGTCTGGGAAATTGATCATCAGCTTTTAAAATTTGAATACAAGATTGCATCTGGT
TCATATGGTGACTTGTAAGTTTGTTATGAGCTATATCATTCCTCTGACCATTTTAGTTTCCTGGAGACTTAA
TTAATTAGGTAATTGTTTCAGATACAAAGGTACATACTGCAGTCAGGATGTAGCTATCAAAATCCTAAAATC
TGAGCGCTTGAACACAGAATTGCAGACGGAGTTTGCCCAAGAAGTGTATATCATGAGGTCTGTCTGGTTATA
CCTCCCTATGAAGCTTATGGCTATTATCTTTGATTTCTTTCTCTATGCTTAAAATATGTTCAGACAATATAT
GGTATTATTGTCACATTGCTATATCCTTTACTTTTCAGGACAAGTATAAGATTACACACCATGTCAAGTCGT
TATCTTTCCTCTGATACTGTATTTCTTTTGTACTTGCAGAAAAGTTCGTCACAAAAATGTTGTCCAATTCAT
AGGGGCTTGTACCAGGCCTCCCAACTTGTGTATAGTAACAGGTAGTAAATGTCGTATTCAGATCACCCAACT
TGCAGAATTGTTTCAAAATCGCCGACTATCACTGTTTTCAAAACCATTTCCTGTATCAGTTTCAGTAGGAGT
TCACTTAATGTTTATTTATCTTTCATTTCTTTGACTGTAGAGTACATGTCTGGGGGAAGCGTATATGACTAT
TTACACAAACGAAAGGGCAGTTTTAAACTACCTACCCTGCTTAAAGTAGCGATTGATGTAGCTAAAGGGATG
AACTACCTGCATCAAAATAATATTATACATAGGGACTTGAAGGCTGCCAATCTACTGATGGATGAAAATGAA
GTAAGACGCAATTTTCAGTAAGGCTGAAAATCTTATACTTTGTGTGCTGTCTTATTGCTAGATGTTTTAGT
CGCTGATGTTACGTATATTGATGATTGATCAACTTTCTAGAGTAATTTTATCATGTCCAACTAACTATGCT
TGTAAATATTGATTTCCCATTTTCATTTGCAAATGTAGAACCATTAGCTAGTACACAAGGCCCTACCACATG
AAAGAGGTTTATTTCTGAACGACTATAGGGAAGTTATTGGAGATGCCACCACAGGATACGGAGCGCTGCGTA
TTTTATATACCACTGATAACATTTGTTATCACTCTTTTGCTTAGCGATAATGGGCTGCTTGAACTTTGGGA
CATTTTCCAAAGTTTTTATTATCAGCCTATAGGAAATCTGCTAAAGGCAAATCATTGTGGTTGCATTAGATC
TATGAAATAGGATATGACTGTGTTTTATTTCGAGTCCGTGAAAAACATATTGCTTTTCTTGAAAATATTGAG
AACACAAGCAGGTTGAAACACACTGACGATCTGTCCTCATCGTGGTCTTTTAGTGATAGAACCAGGATGGAA
AGAACTGAGAGGCACTTAAGGCTATTTTGTATAAAGATAGGAAAGAATTAAATGCTAAAGCGGAAGTAACA
AAACATTAGCAAGTCCAAAGCCTCCTTGACTGAAAAACAGTGTCTAAAAGGCAGACATGATGTAATTCAATT
TGTAGTTTCTGTTACCTCCGTGTCTGAGATTGTAGAACGACTCCACTTCTCCCTTACAGCCAGATTCTAATA
TTGGTGACCAAATTGCGCGAAATGCATTAATGATGCAATTGCCATCTTTTATCCCAAAATTTCATTGTTGTA
GCTTTCAATTAAGCTTCAGCTTGAAATTCAGTTCATAACAGTGGAGTTCAAAGTGTGCCAAATTAAGGGTGT
AATCTTTCATTCATCCCATGTTCTTTCAATTGTACTCTAGTTTTCAACTAAGTTTCACTTTGAAATCCCTTT
TAATTTGACTTAAATCATTTGGTTAGTGTACTTAGACATAATAAAATATGTGTTGTAGGCATGTGTGGGTTC
ATTAGTCCTTCATCCACCTTATGTTCTGAATCAGTTAGTGGTAAATTTTGAGTCTAAAATTAGTTTTCAGCT
GTTTGTAATCAATAGTTTGCTATAATTTTCTCGCAGAATATATCGATCATGTTATTTTTTCAACTGAGAATT
ACTCATTGATGCTTCACTATGGGTTAAATTACCCAATACACCTTTTTATCCGCTTTTATTTTCTTAAGTGGG
```

Figure 55C

```
TTTCAAAAATAATTATATTCAAGCTCTCTTTTGTTAGTTTAGTCTAGGCCAATCTTAACCCAAATTAGTTGG
TTGCTTATCAAGTTTTACCTAATGTCTTTTTTCAGGTCATTAAAGTGGCTGATTTTGGTGTTGCCAGAGTGA
AGGCACAAACAGGTGTAATGACGGCAGAAACCGGGACTTATAGATGGATGGCCCCGGAGGTAGGCCTATCAT
TCAAATCTTAAGATAGGAAATTTAATCCGAAATCTCCCAAACCAGGCTTAAGCCTTAAGATAGAAGTTAGTT
ATGAGTGAGCAGAATTTTGGTGCAGATCTTAAATTTAGCCATCTATATTGTTTAGGATTTAGGCGGTATTAA
TTGATTGTACACACAGTAGTGAGTAGACTGTTGAAGGTGATTTAAGAGAAGGAAGGGATGGAAGAAGAGGAA
TAGAGAGAGGGAGCAGTCCTTATGTCAAGAGGGTGGAGTCTTAACTAAGATTTGTTCATTATAAGAATTATA
TAATACAAAGACGTGTAGACTCTATTTGATCTCTCAAAGAATTCGATAGCTTGTGGTACCAATTATGAATCC
ATTCAAGGTAACAGCAGTTGTTACAATGGAGGCTGAAGGTACTAAAGTTATGTGTGAAGGCAGACCAATACG
AAAGCAATATGCGACATGGTTCCTCTAAATAGATACAGAAAGAGCTACATACATATGATAGGTGTAGTATCA
GAGGTATATGTTGCATCATATTTACCAAGAACTAGATAGCTAGTACTACCAATCATGACTTGTGTTAGGTAA
GAGAGTCTGCAATTACTGACACAAGCTTTCCTTCTGGACCTCCCCATCCAAATAACTCGCGTGAGTCCTAGA
TAATGTGCCGAGATGTTACGTTATTAAATTGCTGCATGGCAAGTCTCTAGTGATCTTGGCAAAGGATATTTT
GTTTTTTTAGTACCAGAATTGTGTGTTACTAGAATCAGAGAGCTGACTGTGGGGTACCTTACTGCACCATTT
TGGGCTGCAACTGCATAAGGGATGAGTATCAGAAAAAGTTTTGTGCTTTCTAAAGCTCTAATATCCTTTCTT
GTAGATTCTAGATACAAACTTATCAAAAATGGTTAAATTGGGAACAAAACACAGTTTATGATGGAGCATGAG
TTTTCTCATATTTCCATAACTGGAATTAGAGGCAATTGAAACTGTACCTTTTAGCTTTTTCTTGTTTGAATT
TTGTTTCATTGGAGTGTTGTGAGATACAAGCACTGATATCAACTCTCTGCCCAGTTGATTGATGCACAACAA
CAACAAACCCAGTGAAGGTGTGGGGAGGATAATGTGTACACAGACCTTACCCCTACCCCGGAAGGTCAGAGA
GGGAGAGGTTGTTTCTGATAGACCCTCGACTAGAGAGTAGATGAAATGCGCTTTATAGGAATATCACATATA
CATAAAGAAGCATAGGCCACAAGTAGTAACAACAACAGTATATTAAAAAACCAAAGCGAAAGATGCCAATCA
AACAACAAGTAAAGATAGCAGTCTATGAGTAAAAGGGATACCATACTAATACTAATGCTATAGGTCTGGAAA
AGAAAGAGCAGCGCGCTCGACTACCCACTAGCCTTCTACCCTAATACTCGACCTCCACAACCTCCTATCAAG
GGACATGTCCGCAGTAAGCTCCAGCTGCGTCATATCCTGCCTAATCACCTCTCCCCGATACTTCTTCGGCAT
GCTACTACCCTTCCTCATACCCATTGTTGCTAACCTCTCACACATCATAACTGGGGCATCAATGTTTCTCCT
TTGTCCGAACCATCTCAGACTCGCCTCCCGCATATTATCCTCCACGGAGGCCACTTTCGCCTTTTCTCAAAT
AACTCCATTCCTAATCTTATCAAATCGGGTATGCCCGCACATCCATTGCAATATTCTTATTTCAGCTACTTT
TATCTTTTGGACATGAGAGTTCTTGACTGGCCAACACTCTACTCCATACAACATAGTCGGTCTAACCACCAC
TCTATAGAACTTACCTTTAAGTTTTAATGGAATATTCTTATTACACAAGACACCGGAAGCGAACTCCATTTC
ATCCACCCTGACACGATACGATGTGTGACATCCTCATCAACCTCCCTATTTCTTTGTATTATTGACCCAAGA
TACCTAAAACTTACTCTCTTGGGGATGACTTGTGTATCAAGCCTCACCTCCATGTCCGCTTCCTGGGTTACG
TCGTTGAATTTGCACTCTAAGTATTCCGTCTTGGTCCTGCTCAACTTGAAACCTTTAGACTCCAGGGTCTCC
CTCCAAACCTACAGTCTCTTGTTAACACCTCCCAACGTCTCATCAATCAGAACTTTGTCATTAGCAAATAAC
ATACACCATGACACCTCCCTTGAATGTGTCGCGTAGGTGCGTCTATCACCAAGGAAAATAGAAACGGGCTAA
GAGCTGATCCCTGGTGCAACTCTATCACAACCAGAAAGTGTTCCGAGTCTCCTCCCGTTGTCCTAACCAGGG
TATTACCTCTATCATACATGTCCTTAATCACCCTAATATAGGCTACCGTGACCCCTTTAGCCTCCAAGCATC
TCCATAGCACCTCCCTCGGGACTTTGTCGTATACTTTTTCTAGGTCAATGAACATCATATGCAAGTCCTTTA
TCTCCCTATACCTCTCCACCAATCTCCTCACGAGGTGAGTGGCTTCCGTAGTCGAACGACCCGACATGAAAC
CGAACTGGTTCTCAAAAATAGATACAACTCTCCTCACCCTCACTTCAACCATCCTCTCCCAAACTTTCATCG
TATGGCTGGCTCTTAATATGTTGACTATAGTGGTGATATCTTGTGTTTTTGTTGTTTGGAGTGGCTTAGAAT
TGAGGTATTTCATTGGTTGTTACTGGCCAAGAGGATCCAGATGTGTTAGGTAACTCCTAGGTGTCAGTGGTG
ATTGATGAAATTTAATGAGGTTGAGCTTATTTAGTGGGTACACGCAATGCTGATCAATGATTTATGACTGC
TTGTATAAGATTTGTGTTAAAAACTCCCTGTTATTTTGTATAAGATTTGTGTCATTGTAAGCATCACTGCAG
TTGCTTGAATAGTAATTGAACTAGATGGAGCATGGGAAGGGTTATAGAAACTCGGCCAAAAACAATCAGTTA
GTTATTTGTGACAGTTACTTAAATCAGTTAATGTGCGAGTTACTTCCGTTATTTTCTCAATGAGATTTTATA
TAACTAGTTGTGCAGTTAGCATGGCTGCATTGGCTTATTTCAGATCTTTCTTCTTGAAGGTAATAGAACACA
AGCCCTACGATCACAAAGCAGATGTATTCAGTTTTGGGGTTGTGCTATGGGAGTTGCTGACAGGGAAGGTAC
TGATATGTGATTGGAAATTTTTGGGTTAGCCCGTTTTTGTTGGTTGTTTTCTTGGTATATACTTATATTCAC
TTGATTTTGTTTAACCAGCTTCCATATGAGTACTTGACCCCATTGCAAGCTGCTATTGGAGTGGTCCAGAAG
GTAATGCTTCTTTTATTTGATTTTATTTTATTTGTAATATCGTATGACCATAATGGTTGATTGCATATTGCG
CGCTCATCACATGCATGCGGGCGCACATAGAAAAGATATGCACAAATGATTTGATATTAATTTTCTAATTGC
TGCCAGGGTTTGCGACCAACTATACCCAAGCACACTCCTCCCAGACTTGCTGAGCTGCTAGAGACATGCTGG
CAACAAGACCCGACATCCAGGCCTGACTTTTCTGAAATAGTAGATATTTTGCAGCAAATAGCAAAAGAGGTA
TTTGTCTCTGCTCAGGCATTGGCCAGTTAATAATTATTTTCTTGGTGATAAATGTACAGTACACGTCACAA
ATTGGATTTACTGGGATTTAAAAGGGTATTGATTTTCTTTGGCCGAACATCTTTTGGTCACGATTTACAATT
TTCTGTCAAATTGCCACCTCATGCCGATAATATAAATTGTATTAATGGCTGGGGAAAAAAGAGTTCACTCTC
CTTGAACTTCTTAAGAGTTGGCAGTCCCTTCTTCAGCTTCCCTAGAATAATAACTATCCTCATTTGTGCTTT
```

Figure 55D

```
GCTTTTAATTTTCATAATTTCTCTGCACACAAAGATGGATTTAAATAGTACTCTCATAACATAAACTGTAAC
AAAGGAAGTAGTTTATTAACTCGGCAACACTCGACATGTGGGTCAGGTTGGAGATGAAAGAGCAGATCGTTG
CAAGGAGAAGTCAGCTGGAGGATTCTTTTCAGCCCTTAGACGTGGACATCATTGAGTAGATGCACACATACA
GAATGTTGATAAAGTTTTGATTTTTAGCCTCATTTATCCAGACTGTACAGTTTTTTTCCAGATCAATGTTCC
CATGGTCAAAGGAAGTTATTATTTCCAATTCTTTGAACAAATTCCTTTTATAAGCAACTTTCTTTTGGCAG
CTCCGTCAGAAGCTTTCGGAGTTGGATCAAATTAGATTAATATAATTTTGCGACTACTCCATCAACATCAAC
ATCCACATCCACATCATTATTCATTCCCCACGATCACGATATGTTTCGTATTCCCTGAAAGTAATGGTAGGT
TTCCCGTATATTGTTGTTTCCGCTTTCTAGTTGTTTTGCGTGTGTTTCACTGTTTATGTGATATTTGACCTT
TATATCGTGGTTTTAGGTTTATGGCATCGATTATGTGCGCTATGAAAGAAATGAATTTTAAACTT
```

METHOD FOR MODIFYING ALKALOID CONTENT IN PLANTS

CROSS REFERENCE TO RELATED APPLICATIONS

This is a U.S. National Phase application claiming priority to PCT/GB2020/051603, filed Jul. 3, 2020, the entire contents of which are hereby expressly incorporated by reference in its entirety including, without limitation, the specification, claims, and abstract, as well as any figures, tables, or drawings thereof.

FIELD OF THE INVENTION

The present invention relates to methods of modulating the alkaloid content a plant or part thereof or cell or cell culture. The invention also extends to methods of modulating the expression and/or activity of polypeptides which modulate alkaloid content within plants. Alternatively, the invention provides methods of modulating the expression and/or activity of genes which encode polypeptides which modulate alkaloid content within plants. The invention also extends to constructs, which can be used to modulate the polypeptides. The invention further relates to plant cells and plants modified to achieve a modulation in alkaloid content. The invention also relates to a processed and harvested leaf from such modulated plants and use thereof in a tobacco industry product, including combustible smoking articles.

BACKGROUND

Alkaloids are a group of naturally occurring compounds which mostly contain basic nitrogen atoms and are produced by a large variety of organisms including bacteria, fungi, plants and animals.

Alkaloids may be classified according to the similarity of the carbon skeleton e.g. indole-, isoquinoline- and pyridine-like. Pyridine derivatives are one class of monomeric alkaloids; this class includes simple derivatives of pyridine, polycyclic condensed and noncondensing pyridine derivatives and sesquiterpene pyridine derivatives. Examples are nicotine, nornicotine, pseudooxynicotine, anabasine, myosmine and anatabine.

Most of the known biological functions of alkaloids are related to protection. Neuroactive molecules, such as caffeine, cocaine, morphine, and nicotine, act as defence compounds against invading predators. The accumulation of these alkaloids is the result of signal transduction cascades that monitor gene expression, enzyme activities, and alkaloid concentrations. The fine-tuning of alkaloid content in the plant involves negative feedback loops and degradative pathways. Nicotine occurs naturally in several varieties of plants but is found at the highest level in the tobacco plant. Cultivated tobacco produces 2-4% alkaloids of total dry weight. Nicotine is produced in wild and cultivated *Nicotiana* species and plays an important role in plant defence against herbivores and insects (Voelckel et al. (2001) Oecologia 127(2): 274-280, incorporated herein by reference). It accounts for ~90% of the total alkaloid content. The remaining 10% of the alkaloid pool is mostly constituted by the structurally related compounds nornicotine, anatabine, anabasine and pseudooxynicotine (PON).

The regulation of alkaloid content in tobacco is complex. Several factors including genotype, environment, fertilization and agronomic practices (e.g. topping) affect alkaloid levels in tobacco plants. Some key regulators of nicotine biosynthesis are well characterized, for example putrescine N-methyltransferase (PMT), which plays a pivotal role in this pathway, is activated by members of the ethylene responsive factor (ERF) superfamily, the largest transcription factor family in the tobacco genome (Rushton et al. (2008) Plant Physiol. 147(1): 280-295 incorporated herein by reference). Other transcription factors that induce alkaloid biosynthesis belong to the MYC2-like basic helix-loop-helix (bHLH) family. MYC2-like bHLHs regulate alkaloid levels directly, through the Gbox-mediated binding and activation of alkaloid structural genes, and indirectly, through the activation of ERFs.

Tobacco pyridine alkaloids are precursors of tobacco-specific nitrosamines (TSNAs) that form during the post-harvest leaf curing. The four primary TSNAs found in cured tobacco leaves are N'-nitrosonornicotine (NNN), N'-nitrosoanatabine (NAT), N'-nitrosoanabasine (NAB) and 4-(methylnitrosamino)-1-(3-pyridyl)-1-butanone (NNK). During the post-harvest leaf curing, reactions between pyridine alkaloids and nitrosating species leads to the formation of tobacco-specific nitrosamines (TSNAs). PON is likely to function as the direct precursor in the synthesis of the TSNA NNK (Bush et al., 2001 incorporated herein by reference). Reducing the production and accumulation of TSNAs is of high importance. The CYP82E family of nicotine demethylase genes is one of the primary regulators of nicotine to nornicotine conversion, and altering their activity or accumulation may result in a decrease in NNN levels. However, no enzymes or genes responsible for producing PON have been identified thus far.

As described in the Examples, the inventors sought to investigate genes responsible for alkaloid and/or TSNA precursor synthesis, with the aim of modulating alkaloid content in plants, e.g. decreasing TSNA content in tobacco.

SUMMARY OF THE INVENTION

It has been surprisingly found that by modulating the activity or expression of a gene encoding an RNA binding protein the alkaloid content and/or TSNA content or precursor of TSNA content of plants can be modulated. The gene(s) as taught herein which encode RNA binding proteins, for example Nitab4.5_0013685g0010.2, are regulators of alkaloid and TSNA precursor content in cultivated tobacco. In particular the gene(s) as taught herein, for example Nitab4.5_0013685g0010.2, is a regulator of alkaloid content in cultivated tobacco. Nitab4.5_0013685g0010.2.encodes an RNA binding protein according to the present invention. Nitab4.5_0000308g0150.2, Nitab4.5_0003919g0010.2, Nitab4.5_0002978g0020.2, Nitab4.5_0001361g0220.2, Nitab4.5_0002978g0030.2, Nitab4.5_0001361g0225.2, Nitab4.5_0003978g0020.2, Nitab4.5_0000078g0240.2, Nitab4.5_0005079g0050.2, Nitab4.5_0008185g0030.2 are homologues of Nitab4.5_0013685g0010.2 according to the present invention.

RNA binding proteins according to the present invention may contain conserved domains termed an RNA binding domain (RBD) and an RGG domain.

According to the present invention, tobacco industry products with modulated alkaloid content and commercially desirable traits sought after by consumers of tobacco industry products can be produced. In some instances, consumers may desire a product with low levels of alkaloid content. In some instances, consumers may desire a product with low levels of TSNA precursors.

The present invention may be particularly useful in the field of plant molecular farming, where plants (such as tobacco and other *Nicotiana* spp.) are used for the production of proteins, peptides, and metabolites e.g. for the production of therapeutics and pharmaceuticals such as antibiotics, virus like particles, or neutraceuticals or small molecules. Tobacco has been used for the development of an HIV-neutralising antibody in an EU-funded project called PharmPlant and Medicago Inc., Canada have worked on a tobacco-based platform for the production of virus-like particles for flu vaccine manufacture.

Thus, a plant according to the present invention may be used for molecular farming to reduce or eliminate the presence of nicotinic alkaloids. The use of a low nicotine plant or rootsock is beneficial in molecular farming and would reduce downstream processing costs associated with purification.

The present inventors have surprisingly determined a method for modulating (e.g. decreasing) the alkaloid content, of a plant (e.g. a tobacco plant) by modulating (e.g. decreasing) the activity or expression of a gene encoding an RNA binding protein. The alkaloid content (e.g. the content of one or more of nornicotine, PON, anabasine, anatabine or myosmine, suitably the content of one or more of nornicotine, PON, anabasine or anatabine) of a plant (e.g. tobacco plant) may be decreased by decreasing the activity or expression of a gene encoding an RNA binding protein or may be increased by increasing the activity or expression of gene encoding an RNA binding protein. Prior to the present invention it had not been known that modulation of the activity or expression of a gene encoding an RNA binding protein as described herein could be used to modulate alkaloid content or modulate TSNA precursor content in particular, nornicotine, PON, anabasine and/or anatabine content.

In one aspect, the present invention provides a method of modulating (e.g. reducing) the alkaloid content of a tobacco plant or part thereof or tobacco cell or tobacco cell culture, the method comprising modifying said plant or part thereof or cell by decreasing the activity or expression of at least one gene encoding an RNA binding protein having an amino acid sequence shown as SEQ ID NO. 1, or a sequence which has at least 80% identity to SEQ ID NO. 1, or a homologue of SEQ ID NO. 1.

In one aspect, the present invention provides a method of modulating (e.g. reducing) the alkaloid content of a tobacco plant or part thereof or tobacco cell or tobacco cell culture, the method comprising modifying said plant or part thereof or cell by decreasing the activity or expression of at least one gene encoding an RNA binding protein having an amino acid sequence shown as SEQ ID NO. 1, 4, 7, 10, 13, 16, 19, 22, 25, 28 or 31, or a sequence which has at least 80% identity to SEQ ID NO. 1, 4, 7, 10, 13, 16, 19, 22, 25, 28 or 31.

In another aspect, the present invention provides a method of reducing the content of a tobacco-specific nitrosamine (TSNA) precursor in a tobacco plant or part thereof or tobacco cell or tobacco cell culture, the method comprising modifying said plant or part thereof or cell by decreasing the activity or expression of at least one gene encoding an RNA binding protein having an amino acid sequence shown as SEQ ID NO. 1, or a sequence which has at least 80% identity to SEQ ID NO. 1, or a homologue of SEQ ID NO. 1.

In one aspect, the present invention provides a method of reducing the content of a tobacco-specific nitrosamine (TSNA) precursor in a tobacco plant or part thereof or tobacco cell or tobacco cell culture, the method comprising modifying said plant or part thereof or cell by decreasing the activity or expression of at least one gene encoding an RNA binding protein having an amino acid sequence shown as SEQ ID NO. 1, 4, 7, 10, 13, 16, 19, 22, 25, 28 or 31, or a sequence which has at least 80% identity to SEQ ID NO. 1, 4, 7, 10, 13, 16, 19, 22, 25, 28 or 31.

In another aspect, the present invention provides the use of at least one gene encoding an RNA binding protein having an amino acid sequence shown as SEQ ID NO. 1, 4, 7, 10, 13, 16, 19, 22, 25, 28 or 31, or a sequence which has at least 80% identity to SEQ ID NO. 1, 4, 7, 10, 13, 16, 19, 22, 25, 28 or 31, for modulating (e.g. decreasing) alkaloid content or reducing TSNA precursor content in a tobacco cell or tobacco plant or part thereof or a tobacco cell culture.

In a further aspect, there is provided a method for producing a plant or part thereof, a tobacco cell or tobacco cell culture, a plant propagation material, a leaf, a cut harvested leaf, a processed leaf or a cut and processed leaf which has modulated (e.g. decreased) alkaloid content or reduced TSNA precursor content, the method comprising modifying said plant or part thereof or cell or cell culture or plant propagation material to decrease the activity or expression of at least one gene encoding an RNA binding protein having an amino acid sequence shown as SEQ ID NO. 1, 4, 7, 10, 13, 16, 19, 22, 25, 28 or 31, or a sequence which has at least 80% identity to SEQ ID NO. 1, 4, 7, 10, 13, 16, 19, 22, 25, 28 or 31.

Suitably, the alkaloid content or TSNA precursor content may be reduced in comparison to a plant or part thereof or cell or cell culture or plant propagation material or leaf which has not been modified to decrease the activity or expression of the at least one gene encoding said RNA binding protein having an amino acid sequence shown as SEQ ID NO. 1, 4, 7, 10, 13, 16, 19, 22, 25, 28 or 31, or a sequence which has at least 80% identity to SEQ ID NO. 1, 4, 7, 10, 13, 16, 19, 22, 25, 28 or 31.

In another aspect, the present invention provides a plant or part thereof or a cell or cell culture which has been modified to achieve a modulation (e.g. decrease) in alkaloid content or reduction in TSNA precursor content in comparison to an unmodified plant or part thereof or unmodified cell culture, wherein the modification is reduction of the activity or expression of at least one gene encoding an RNA binding-protein having an amino acid sequence shown as SEQ ID NO. 1, 4, 7, 10, 13, 16, 19, 22, 25, 28 or 31, or a sequence which has at least 80% identity to SEQ ID NO. 1, 4,7,10, 13,16, 19, 22, 25, 28 or 31.

In one aspect, the present invention provides a plant propagation material obtainable (e.g. obtained) from a plant according to the present invention, or from a plant or cell culture produced by a method according to the present invention.

Suitably, the TSNA precursor may be selected from nornicotine, PON, anabasine and anatabine. Suitably, the TSNA precursor may be nornicotine. Suitably, the TSNA precursor may be PON. Suitably, the TSNA precursor may be anabasine. Suitably, the TSNA precursor may be anatabine. In one aspect, the present invention provides the use of a plant or part thereof or cell culture according to the present invention, or of a plant produced by a method according to the present invention to breed a plant.

In another aspect, the present invention provides the use of a plant or part thereof or a cell culture according the present invention, or of a plant produced by a method according to the present invention for production of a product.

In a further aspect, the present invention provides the use of a plant or part thereof according to the present invention, or of a plant produced by a method according to the present invention to grow a crop.

In another aspect, the present invention provides the use of a plant or part thereof according to the present invention, or of a plant produced by a method according to the present invention to produce a leaf.

In a further aspect, the present invention provides a harvested leaf of a plant according to the present invention, or obtainable (e.g. obtained) from a plant propagated from a propagation material according to the present invention, or obtainable (e.g. obtained) from a plant obtained by a use according to the present invention, or obtainable (e.g. obtained) from a plant produced by a method the present invention.

Suitably, the harvested leaf of a plant may be a cut harvested leaf.

In another aspect, the present invention provides a processed leaf, preferably a processed tobacco leaf, preferably a non-viable processed tobacco leaf:
  obtainable (e.g. obtained) from a plant obtainable (e.g. obtained) from a use according to the present invention;
  obtainable (e.g. obtained) by processing a plant according to the present invention;
  obtainable (e.g. obtained) from a plant propagated from a plant propagation material according to the present invention; or
  obtainable (e.g. obtained) by processing a harvested leaf according to the present invention; or
  obtainable (e.g. obtained) from a plant produced by a method the present invention.

Suitably, the leaf may be processed by curing, fermenting, pasteurising or a combination thereof. Suitably, the content of one or more TSNAs selected from N'-nitrosonornicotine (NNN), 4-(methylnitrosamino)-1-(3-pyridyl)-1-butanone (NNK), N'-nitrosoanatabine (NAT) and N-nitrosoanabasine (NAB) may be reduced, wherein preferably the content of NNN and/or NNK is reduced, wherein more preferably at least the content of NNN is reduced.

Suitably, the processed leaf may be a cut processed leaf.

In a further aspect, the present invention provides cured tobacco material made from a plant or a part thereof according to the present invention or an extract thereof, or from a leaf according to the present invention, or an extract thereof.

In one aspect, the present invention provides a tobacco blend comprising cured tobacco material according to the present invention.

In one aspect, the present invention provides a tobacco industry product prepared from: a tobacco plant or a part thereof or a tobacco cell or cell culture according to the present invention;
  a tobacco plant or part thereof propagated from a tobacco plant propagation material according to the present invention;
  a harvested leaf of a plant according to the present invention;
  a processed leaf according to the present invention;
  a plant produced by a method the present invention;
  cured tobacco according the present invention; or
  a tobacco blend according to the present invention.

Suitably, the tobacco industry product may be a combustible smoking article.

Suitably, the tobacco industry product may be a smokeless tobacco product.

Suitably, the tobacco industry product may be a non-combustible aerosol provision system such as a tobacco heating device or an aerosol-generating device.

In another aspect, the present invention provides a combustible smoking article, non-combustible aerosol provisioning system, smokeless tobacco product or tobacco heating device comprising a plant or a part thereof according to the present invention, or a tobacco cell or cell culture according to the present invention; or a harvested leaf according to the present invention, or a processed leaf according to the present invention, or a cured tobacco material according to the present invention; or a tobacco blend according to the present invention.

In a further aspect, the present invention provides the use of a nucleotide sequence of at least one gene encoding an RNA binding protein to select a plant having modulated (e.g. decreased) alkaloid content and/or reduced content of a tobacco specific nitrosamine (TSNA) precursor, wherein the sequence of the RNA binding protein is selected from SEQ ID NO. 1, 4, 7, 10, 13, 16, 19, 22, 25, 28 or 31, or a sequence which has at least 80% identity to SEQ ID NO. 1, 4, 7, 10, 13, 16, 19, 22, 25, 28 or 31, or wherein the at least one gene encoding an RNA binding protein comprises a nucleotide sequence as set out in SEQ ID NO. 2, 3, 5, 6, 8, 9, 11, 12, 14, 15, 17, 18, 20, 21, 23, 24, 26, 27, 29, 30, 32 or 33, or a sequence which has at least 80% identity to SEQ ID NO. 2, 3, 5, 6, 8, 9, 11, 12, 14, 15, 17, 18, 20, 21, 23, 24, 26, 27, 29, 30, 32 or 33.

In another aspect, the present invention provides a mutant of a plant carrying a heritable mutation in a nucleotide sequence of at least one gene encoding an RNA binding protein wherein the gene is selected from SEQ ID NO. 2, 3, 5, 6, 8, 9, 11, 12, 14, 15, 17, 18, 20, 21, 23, 24, 26, 27, 29, 30, 32 or 33, or a sequence which has at least 80% identity to SEQ ID NO. 2, 3, 5, 6, 8, 9, 11, 12, 14, 15, 17, 18, 20, 21, 23, 24, 26, 27, 29, 30, 32 or 33, wherein said heritable mutation decreases the activity or expression of the at least one gene encoding an RNA binding protein and wherein the mutant plant has modulated (e.g. decreased) alkaloid content and/or reduced tobacco specific nitrosamine (TSNA) precursor relative to a comparable plant which does not carry said heritable mutation.

In another aspect, the present invention provides progeny or seed of a mutant plant which carries the heritable mutation according to the present invention.

In one aspect, the present invention provides a harvested leaf, a processed leaf or cured tobacco material produced from a plant comprising a modification in a nucleotide sequence of at least one gene encoding an RNA binding protein, wherein the at least one gene is selected from SEQ ID NO. 2, 3, 5, 6, 8, 9, 11, 12, 14, 15, 17, 18, 20, 21, 23, 24, 26, 27, 29, 30, 32 or 33, or a sequence which has at least 80% identity to SEQ ID NO. 2, 3, 5, 6, 8, 9, 11, 12, 14, 15, 17, 18, 20, 21, 23, 24, 26, 27, 29, 30, 32 or 33, wherein said modification decreases the activity or expression of the at least one gene encoding an RNA binding protein and wherein said plant has modulated (e.g. decreased) alkaloid content and/or reduced tobacco specific nitrosamine (TSNA) precursor content relative to a comparable plant which does not carry said modification in the at least one gene encoding said RNA binding protein.

In another aspect, the present invention provides a method, a leaf, a plant, a plant propagation material, a harvested leaf, a processed tobacco, a tobacco product, a use or a combination thereof as described herein with reference to the description and drawings.

BRIEF DESCRIPTION OF THE DRAWINGS

Embodiments of the invention will now be described, by way of example only, with reference to the accompanying drawings, in which:

FIG. 3 shows the alkaloid content of 5-week-old tobacco leaves expressing Nitab4.5_0013685g0010.2_deltaRBD-RGG. Alkaloid content is represented relative to a control and is representative of two biological replicates analysed by one-way ANOVA and Tukey's multiple-comparison post-test. Values are shown as means±SEM. Asterisks indicate statistical significance of P value≤0.05.

FIG. 4 shows the amino acid sequence of Nitab4.5_0013685g0010.2—SEQ ID NO. 1—a protein from *Nicotiana tabacum* according to the present invention.

FIG. 5 shows the coding sequence of Nitab4.5_0013685g0010.2—SEQ ID NO. 2—encoding a protein from *Nicotiana tabacum* according to the present invention.

FIG. 6 shows the genomic sequence of Nitab4.5_0013685g0010.2—SEQ ID NO. 3—encoding a protein from *Nicotiana tabacum* according to the present invention.

FIG. 7 shows the amino acid sequence of Nitab4.5_0000308g0150.2—SEQ ID NO. 4—a protein from *Nicotiana tabacum* according to the present invention.

FIG. 8 shows the coding sequence of Nitab4.5_0000308g0150.2—SEQ ID NO. 5—encoding a protein from *Nicotiana tabacum* according to the present invention.

FIG. 9 shows the genomic sequence of Nitab4.5_0000308g0150.2—SEQ ID NO. 6—encoding a protein from *Nicotiana tabacum* according to the present invention.

FIG. 10 shows the amino acid sequence of Nitab4.5_0003919g0010.2—SEQ ID NO. 7—a protein from *Nicotiana tabacum* according to the present invention.

FIG. 11 shows the coding sequence of Nitab4.5_0003919g0010.2—SEQ ID NO. 8—encoding a protein from *Nicotiana tabacum* according to the present invention.

FIG. 12 shows the genomic sequence of Nitab4.5_0003919g0010.2—SEQ ID NO. 9—encoding a protein from *Nicotiana tabacum* according to the present invention.

FIG. 13 shows the amino acid sequence of Nitab4.5_0002978g0020.2—SEQ ID NO. 10—a protein from *Nicotiana tabacum* according to the present invention.

FIG. 14 shows the coding sequence of Nitab4.5_0002978g0020.2—SEQ ID NO. 11—encoding a protein from *Nicotiana tabacum* according to the present invention.

FIG. 15 shows the genomic sequence of Nitab4.5_0002978g0020.2—SEQ ID NO. 12—encoding a protein from *Nicotiana tabacum* according to the present invention.

FIG. 16 shows the amino acid sequence of Nitab4.5_0001361g0220.2—SEQ ID NO. 13—a protein from *Nicotiana tabacum* according to the present invention.

FIG. 17 shows the coding sequence of Nitab4.5_0001361g0220.2—SEQ ID NO. 14—encoding protein from *Nicotiana tabacum* according to the present invention.

FIG. 18 shows the genomic sequence of Nitab4.5_0001361g0220.2—SEQ ID NO. 15—encoding a protein from *Nicotiana tabacum* according to the present invention.

FIG. 19 shows the amino acid sequence of Nitab4.5_0002978g0030.2—SEQ ID NO. 16—protein from *Nicotiana tabacum* according to the present invention.

FIG. 20 shows the coding sequence of Nitab4.5_0002978g0030.2—SEQ ID NO. 17—encoding a protein from *Nicotiana tabacum* according to the present invention.

FIG. 21 shows the genomic sequence of Nitab4.5_0002978g0030.2—SEQ ID NO. 18—encoding a protein from *Nicotiana tabacum* according to the present invention.

FIG. 22 shows the amino acid sequence of Nitab4.5_0001361g0225.2—SEQ ID NO. 19—a protein from *Nicotiana tabacum* according to the present invention.

FIG. 23 shows the coding sequence of Nitab4.5_0001361g0225.2.—SEQ ID NO. 20—encoding a protein from *Nicotiana tabacum* according to the present invention.

FIG. 24 shows the genomic sequence of Nitab4.5_0001361g0225.2.—SEQ ID NO. 21—encoding a protein from *Nicotiana tabacum* according to the present invention.

FIG. 25 shows the amino acid sequence of Nitab4.5_0003978g0020.2—SEQ ID NO. 22—a protein from *Nicotiana tabacum* according to the present invention.

FIG. 26 shows the coding sequence of Nitab4.5_0003978g0020.2—SEQ ID NO. 23—encoding a protein from *Nicotiana tabacum* according to the present invention.

FIG. 27 shows the genomic sequence of Nitab4.5_0003978g0020.2—SEQ ID NO. 24—encoding a protein from *Nicotiana tabacum* according to the present invention.

FIG. 28 shows the amino acid sequence of Nitab4.5_0000078g0240.2—SEQ ID NO. 25—a protein from *Nicotiana tabacum* according to the present invention.

FIG. 29 shows the coding sequence of Nitab4.5_0000078g0240.2—SEQ ID NO. 26—encoding a protein from *Nicotiana tabacum* according to the present invention.

FIG. 30 shows the genomic sequence of Nitab4.5_0000078g0240.2—SEQ ID NO. 27—encoding a protein from *Nicotiana tabacum* according to the present invention.

FIG. 31 shows the amino acid sequence of Nitab4.5_0005079g0050.2—SEQ ID NO. 28—a protein from *Nicotiana tabacum* according to the present invention.

FIG. 32 shows the coding sequence of Nitab4.5_0005079g0050.2—SEQ ID NO. 29—encoding a protein from *Nicotiana tabacum* according to the present invention.

FIG. 33 shows the genomic sequence of Nitab4.5_0005079g0050.2—SEQ ID NO. 30—encoding a protein from *Nicotiana tabacum* according to the present invention.

FIG. 34 shows the amino acid sequence of Nitab4.5_0008185g0030.2—SEQ ID NO. 31—a protein from *Nicotiana tabacum* according to the present invention.

FIG. 35 shows the coding sequence of Nitab4.5_0008185g0030.2—SEQ ID NO. 32—encoding a protein from *Nicotiana tabacum* according to the present invention.

FIG. 36 shows the genomic sequence of Nitab4.5_0008185g0030.2—SEQ ID NO. 33—encoding a protein from *Nicotiana tabacum* according to the present invention.

FIG. 37 shows SEQ ID NO. 34 which corresponds to the nucleotide sequence of Nitab4.5_0013685g0010.2_deltaRBD-RGG as described in Example 3.

FIG. 38 shows SEQ ID NO. 35 which corresponds to the amino acid sequence of Nitab4.5_0013685g0010.2_deltaRBD-RGG as described in Example 3.

FIG. 39 shows SEQ ID NO. 36 which corresponds to the amino acid sequence of an RNA-binding domain (RBD) (amino acid residues 6-84 of SEQ ID NO. 1).

FIG. 40 shows SEQ ID NO. 37 which corresponds to an RGG motif (amino acid residues 97-99 of SEQ ID NO. 1).

FIG. 41 shows SEQ ID NO. 38 which corresponds to the amino acid sequence of Nitab4.5_0005487g0030.2, an interactor of Nitab4.5_0013685g0010.2.

FIG. 42 shows SEQ ID NO. 39 which corresponds to the coding sequence of Nitab4.5_0005487g0030.2, an interactor of Nitab4.5_0013685g0010.2.

FIG. 43 shows SEQ ID NO. 40 which corresponds to the genomic acid sequence of Nitab4.5_0005487g0030.2, an interactor of Nitab4.5_0013685g0010.2.

FIG. 44 shows SEQ ID NO. 41 which corresponds to the amino acid sequence of Nitab4.5_0007831g0020.2, an interactor of Nitab4.5_0013685g0010.2.

FIG. 45 shows SEQ ID NO. 42 which corresponds to the coding sequence of Nitab4.5_0007831g0020.2, an interactor of Nitab4.5_0013685g0010.2.

FIG. 46 shows SEQ. ID NO. 43 which corresponds to the genomic sequence of Nitab4.5_0007831g0020.2, an interactor of Nitab4.5_0013685g0010.2.

FIG. 47 shows SEQ ID NO. 44 which corresponds to the amino acid sequence of Nitab4.5_0002978g0020.2, an interactor of Nitab4.5_0013685g0010.2.

FIG. 48 shows SEQ ID NO. 45 which corresponds to the coding sequence of Nitab4.5_0002978g0020.2, an interactor of Nitab4.5_0013685g0010.2.

FIG. 49 shows SEQ ID NO. 46 which corresponds to the genomic sequence of Nitab4.5_0002978g0020.2, an interactor of Nitab4.5_0013685g0010.2.

FIG. 50 shows SEQ ID NO. 47 which corresponds to the amino acid sequence of Nitab4.5_0005552g0010.2, an interactor of Nitab4.5_0013685g0010.2.

FIG. 51 shows SEQ ID NO. 48 which corresponds to the coding sequence of Nitab4.5_0005552g0010.2, an interactor of Nitab4.5_0013685g0010.2.

FIG. 52 shows SEQ ID NO. 49, which corresponds to the genomic sequence of Nitab4.5_0005552g0010.2, an interactor of Nitab4.5_0013685g0010.2.

FIG. 53 shows SEQ ID NO. 50, which corresponds to the amino acid sequence of Nitab4.5_0003679g0060.2, an interactor of Nitab4.5_0013685g0010.2.

FIG. 54 shows SEQ ID NO. 51, which corresponds to the coding sequence of Nitab4.5_0003679g0060.2, an interactor of Nitab4.5_0013685g0010.2.

FIG. 55 shows SEQ ID NO. 52, which corresponds to the genomic sequence of Nitab4.5_0003679g0060.2, an interactor of Nitab4.5_0013685g0010.2.

SEQUENCE LISTING

Figure 1:
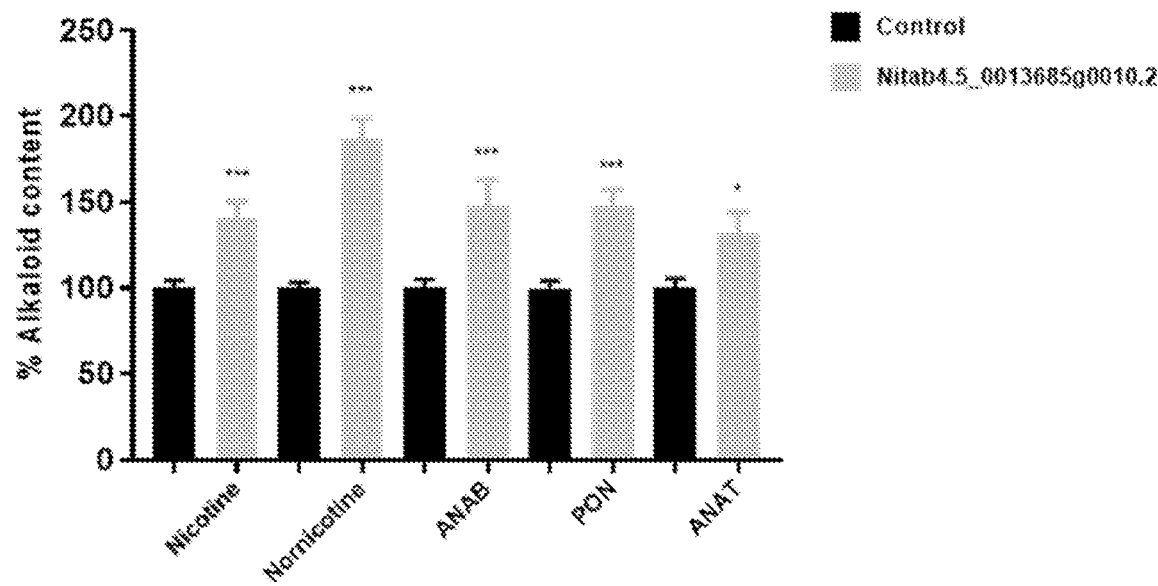
FIG. 1 shows the alkaloid content of 5-week-old tobacco leaves overexpressing Nitab4.5_0013685g0010.2. Alkaloid content is represented relative to a control and is representative of two biological replicates analysed by one-way ANOVA and Tukey's multiple-comparison post-test. Values are shown as means±SEM. Asterisks indicate statistical significance of P value≤0.01.

A summary of sequence identifiers used throughout the subject specification and the corresponding sequence listing is provided wherein:

SEQ ID NO. 1 corresponds to the amino acid sequence of Nitab4.5_0013685g0010.2.

SEQ ID NO. 2 corresponds to the coding sequence of Nitab4.5_0013685g0010.2.

SEQ ID NO. 3 corresponds to the genomic sequence of Nitab4.5_0013685g0010.2.

SEQ ID NO. 4 corresponds to the amino acid sequence of Nitab4.5_0000308g0150.2.

SEQ ID NO. 5 corresponds to the coding sequence of Nitab4.5_0000308g0150.2.

SEQ ID NO. 6 corresponds to the genomic sequence of Nitab4.5_0000308g0150.2.

SEQ ID NO. 7 corresponds to the amino acid sequence of Nitab4.5_0003919g0010.2.

SEQ ID NO. 8 corresponds to the coding sequence of Nitab4.5_0003919g0010.2.

SEQ ID NO. 9 corresponds to the genomic sequence of Nitab4.5_0003919g0010.2.

SEQ ID NO. 10 corresponds to the amino acid sequence of Nitab4.5_0002978g0020.2.

SEQ ID NO. 11 corresponds to the coding sequence of Nitab4.5_0002978g0020.2.

SEQ ID NO. 12 corresponds to the genomic sequence of Nitab4.5_0002978g0020.2.

SEQ ID NO. 13 corresponds to the amino acid sequence of Nitab4.5_0001361g0220.2.

SEQ ID NO. 14 corresponds to the coding sequence of Nitab4.5_0001361g0220.2.

SEQ ID NO. 15 corresponds to the genomic sequence of Nitab4.5_0001361g0220.2.

SEQ ID NO. 16 corresponds to the amino acid sequence of Nitab4.5_0002978g0030.2.

SEQ ID NO. 17 corresponds to the coding sequence of Nitab4.5_0002978g0030.2.

SEQ ID NO. 18 corresponds to the genomic sequence of Nitab4.5_0002978g0030.2.

SEQ ID NO. 19 corresponds to the amino acid sequence of Nitab4.5_0001361g0225.2.

SEQ ID NO. 20 corresponds to the coding sequence of Nitab4.5_0001361g0225.2.

SEQ ID NO. 21 corresponds to the genomic sequence of Nitab4.5_0001361g0225.2.

SEQ ID NO. 22 corresponds to the amino acid sequence of Nitab4.5_0003978g0020.2.

SEQ ID NO. 23 corresponds to the coding sequence of Nitab4.5_0003978g0020.2.

SEQ ID NO. 24 corresponds to the genomic sequence of Nitab4.5_0003978g0020.2.

SEQ ID NO. 25 corresponds to the amino acid sequence of Nitab4.5_0000078g0240.2.

SEQ ID NO. 26 corresponds to the coding sequence of Nitab4.5_0000078g0240.2.

SEQ ID NO. 27 corresponds to the genomic sequence of Nitab4.5_0000078g0240.2.

SEQ ID NO. 28 corresponds to the amino acid sequence of Nitab4.5_0005079g0050.2.

SEQ ID NO. 29 corresponds to the coding sequence of Nitab4.5_0005079g0050.2.

SEQ ID NO. 30 corresponds to the genomic sequence of Nitab4.5_0005079g0050.2.

SEQ ID NO. 31 corresponds to the amino acid sequence of Nitab4.5_0008185g0030.2.

SEQ ID NO. 32 corresponds to the coding sequence of Nitab4.5_0008185g0030.2.

SEQ ID NO. 33 corresponds to the genomic sequence of Nitab4.5_0008185g0030.2.

SEQ ID NO. 34 corresponds to the nucleotide sequence of Nitab4.5_0013685g0010.2_deltaRBD-RGG as described in Example 3.

SEQ ID NO. 35 corresponds to the amino acid sequence of Nitab4.5_0013685g0010.2_deltaRBD-RGG as described in Example 3.

SEQ ID NO. 36 corresponds to the amino acid sequence of an RNA-binding domain (RBD) (amino acid residues 6-84 of SEQ ID NO. 1).

SEQ ID NO. 37 corresponds to an RGG motif (amino acid residues 97-99 of SEQ ID NO. 1).

SEQ ID NO. 38 corresponds to the amino acid sequence of Nitab4.5_0005487g0030.2, an interactor of Nitab4.5_0013685g0010.2.

SEQ ID NO. 39 corresponds to the coding sequence of Nitab4.5_0005487g0030.2, an interactor of Nitab4.5_0013685g0010.2.

SEQ ID NO. 40 corresponds to the genomic sequence of Nitab4.5_0005487g0030.2, an interactor of Nitab4.5_0013685g0010.2.

SEQ ID NO. 41 corresponds to the amino acid sequence of Nitab4.5_0007831g0020.2, an interactor of Nitab4.5_0013685g0010.2.

SEQ ID NO. 42 corresponds to the coding sequence of Nitab4.5_0007831g0020.2, an interactor of Nitab4.5_0013685g0010.2.

SEQ ID NO. 43 corresponds to the genomic sequence of Nitab4.5_0007831g0020.2, an interactor of Nitab4.5_0013685g0010.2.

SEQ ID NO. 44 corresponds to the amino acid sequence of Nitab4.5_0002978g0020.2, an interactor of Nitab4.5_0013685g0010.2.

SEQ ID NO. 45 corresponds to the coding sequence of Nitab4.5_0002978g0020.2, an interactor of Nitab4.5_0013685g0010.2.

SEQ ID NO. 46 corresponds to the genomic sequence of Nitab4.5_0002978g0020.2, an interactor of Nitab4.5_0013685g0010.2.

SEQ ID NO. 47 corresponds to the amino acid sequence of Nitab4.5_0005552g0010.2, an interactor of Nitab4.5_0013685g0010.2.

SEQ ID NO. 48 corresponds to the coding sequence of Nitab4.5_0005552g0010.2, an interactor of Nitab4.5_0013685g0010.2.

SEQ ID NO. 49 corresponds to the genomic sequence of Nitab4.5_0005552g0010.2, an interactor of Nitab4.5_0013685g0010.2.

SEQ ID NO. 50 corresponds to the amino acid sequence of Nitab4.5_0003679g0060.2, an interactor of Nitab4.5_0013685g0010.2.

SEQ ID NO. 51 corresponds to the coding sequence of Nitab4.5_0003679g0060.2, an interactor of Nitab4.5_0013685g0010.2.

SEQ ID NO. 52 corresponds to the genomic sequence of Nitab4.5_0003679g0060.2, an interactor of Nitab4.5_0013685g0010.2.

Some sequences disclosed herein contain "X" or "N" in nucleotide sequences. "X" or "N" can be any nucleotide or a deletion or insertion of one or more nucleotides. For example, in some cases a string of "X"s or "N"s are shown. The number of "X"s or "N"s does not necessarily correlate with the actual number of nucleotides at that position. There may be more or fewer nucleotides than shown as "X" or "N" in the sequence.

DETAILED DESCRIPTION

For the first time the present inventors have shown that by modulating the activity or expression of at least one gene encoding an RNA binding protein in a plant (e.g. a tobacco plant) or a cell (e.g. tobacco cell), the alkaloid and/or TSNA precursor content of the plant (or processed plant) or cell can be modulated.

The present invention provides a method of modulating (e.g. decreasing) the alkaloid content of a plant or a part thereof, the method comprising modifying said plant by modulating (e.g. decreasing) the activity or expression of at least one gene encoding an RNA binding protein.

Also provided is a method of modulating (e.g. decreasing) the content of a tobacco specific nitrosamine (TSNA) precursor in a tobacco plant or plant part thereof, the method comprising modifying said plant by modulating (e.g. decreasing) the activity or expression of at least one gene encoding an RNA binding.

The at least one gene encoding an RNA binding protein may be selected from at least one gene encoding an amino acid sequence as set out in SEQ ID NO. 1, 4, 7, 10, 13, 16, 19, 22, 25 or 28, or a functional variant or functional fragment or orthologue thereof, or a sequence which has at least 80% identity to SEQ ID NO. 1, 4, 7, 10, 13, 16, 19, 22, 25 or 28; or wherein the at least one gene encoding an RNA bindingprotein may comprise a nucleotide sequence as set out in SEQ ID NO. 2, 3, 5, 6, 8, 9, 11, 12, 14, 15, 17, 18, 20, 21, 23, 24, 27 or 30 or a functional variant or functional fragment or orthologue of SEQ ID NO. 2, 3, 5, 6, 8, 9, 11, 12, 14, 15, 17, 18, 20, 21, 23, 24, 27 or 30 or a nucleic acid sequence which has at least 80% identity to SEQ ID NO. 2, 3, 5, 6, 8, 9, 11, 12, 14, 15, 17, 18, 20, 21, 23, 24, 27 or 30.

Suitably, the protein may comprise an RNA binding domain and/or an RGG domain. Suitably, the protein may comprise an RNA binding domain and an RGG domain. In one embodiment at least two genes encoding RNA binding proteins are modified selected from the group of: genes which encode polypeptides comprising an amino acid sequence as set out in SEQ ID NO. 1, 4, 7, 10, 13, 16, 19, 22, 25 or 28 or a functional variant or functional fragment or orthologue thereof, or a sequence which has at least 80% identity to SEQ ID NO. 1, 4, 7, 10, 13, 16, 19, 22, 25 or 28; or genes encoding an RNA binding protein comprising a nucleotide sequence as set out in SEQ ID NO. 2, 3, 5, 6, 8, 9, 11, 12, 14, 15, 17, 18, 20, 21, 23, 24, 27 or 30 or a functional variant or functional fragment or orthologue of SEQ ID NO. 2, 3, 5, 6, 8, 9, 11, 12, 14, 15, 17, 18, 20, 21, 23, 24, 27 or 30 or a nucleic acid sequence which has at least 80% identity to SEQ ID NO. 2, 3, 5, 6, 8, 9, 11, 12, 14, 15, 17, 18, 20, 21, 23, 24, 27 or 30.

In one embodiment at least three, such as at least four, such as at least five, such as at least six, such as at least seven, such as at least eight, such as at least nine, such as ten genes encoding RNA binding proteins are modulated, wherein the genes are selected from those which encode polypeptides comprising an amino acid sequence as set out in SEQ ID NO. 1, 4, 7, 10, 13, 16, 19, 22, 25 or 28 or a functional variant or functional fragment or orthologue thereof, or a sequence which has at least 80% identity to SEQ ID NO. 1, 4, 7, 10, 13, 16, 19, 22, 25 or 28; or wherein the at least one gene encoding an RNA binding protein comprises a nucleotide sequence as set out in SEQ ID NO. 2, 3, 5, 6, 8, 9, 11, 12, 14, 15, 17, 18, 20, 21, 23, 24, 27 or 30 or a functional variant or functional fragment or orthologue of SEQ ID NO. 2, 3, 5, 6, 8, 9, 11, 12, 14, 15, 17, 18, 20, 21, 23, 24, 27 or 30 or a nucleic acid sequence which has at least 80% identity to SEQ ID NO. 2, 3, 5, 6, 8, 9, 11, 12, 14, 15, 17, 18, 20, 21, 23, 24, 27 or 30. Suitably, the protein may comprise an RNA binding protein and/or an RGG domain. Suitably, the protein may comprise an RNA binding domain and an RGG domain. In one aspect, the at least one gene encoding an RNA binding protein encodes a polypeptide which comprises an amino acid sequence as set out in: SEQ ID NO. 1 or a functional variant or functional fragment or orthologue thereof, or a sequence which has at least 80% identity to SEQ ID NO. 1; or wherein the at least one gene encoding an RNA binding protein comprises a nucleotide sequence as set out in SEQ ID NO. 2 or 3 or a functional variant or functional fragment or orthologue of SEQ ID NO. 2 or 3; or a nucleic acid sequence which has at least 80% identity to SEQ ID NO. 2 or 3. Suitably, the protein may comprise an RNA binding domain and/or an RGG domain. Suitably, the protein may comprise an RNA binding domain and an RGG domain.

In one aspect, the activity or expression of at least one further gene is modulated. Suitably, at least two (or at least three or at least four or at least five or at least six or at least seven or at least eight or at least nine) additional genes selected from SEQ ID NO. 2, 3, 5, 6, 8, 9, 11, 12, 14, 15, 17, 18, 20, 21, 23, 24, 27 or 30 or a functional variant or functional fragment or orthologue of SEQ ID NO. 2, 3, 5, 6, 8, 9, 11, 12, 14, 15, 17, 18, 20, 21, 23, 24, 27 or 30 or a nucleic acid sequence which has at least 80% identity to SEQ ID NO. 2, 3, 5, 6, 8, 9, 11, 12, 14, 15, 17, 18, 20, 21, 23, 24, 27 or 30 may also be modulated. Suitably, the protein may comprise an RNA binding domain and/or an RGG domain. Suitably, the protein may comprise an RNA binding domain and an RGG domain.

The "expression" of a gene encoding an RNA binding protein may refer to the level of transcription, translation i.e. protein expression.

Measurement of the level or amount of a gene product may be carried out by any suitable method, for example comparison of mRNA transcript levels, protein or peptide levels, and/or phenotype of a plant, between a modified plant and comparable plant which has not been modified according to the present invention.

The term "a comparable product" as defined herein would be one derived from a plant (e.g. a tobacco plant) which had not been modified according to the present invention, but in which all other relevant features were the same (e.g. plant species, growing conditions, method of processing the plant, e.g. tobacco, etc.). The comparable product according to the present invention may mean a plant (e.g. a tobacco plant) or a part thereof, such as a leaf (e.g. a tobacco leaf), a harvested leaf (e.g. a harvested tobacco leaf), a cut harvested leaf (e.g. a cut harvested tobacco leaf), a processed leaf (e.g. a processed tobacco leaf) or plant propagation material (e.g. tobacco plant propagation material), or a product comprising said plant or part therefore, e.g. a tobacco industry product or combinations thereof obtainable or obtained from a plant which has not been modified in accordance with the present invention, e.g. to modulate the activity or expression of gene encoding an RNA binding protein. In one embodiment a comparable product is one which does not comprise gene encoding an RNA binding protein whose activity or expression has been modulated.

The term "modifying" or "modified" as used herein means a plant (e.g. a tobacco plant) or nucleic acid sequence that has been altered or changed. The present invention comprises the modification of plants using techniques for genetic modification of plants or non-genetic modification of plants. Such methods are well known in the art and examples of genetic modification techniques include transformation, transgenics, cisgenics, and gene editing methods. Examples of non-genetic modification techniques include fast-neutron mutagenesis, chemical mutagenesis e.g. ethyl methanesulfonate (EMS) mutagenesis and modern population analysis approaches.

In one embodiment a natural variant which has a modified gene encoding an RNA binding protein is selected and that trait or gene is bred into a second plant which may have commercially desirable traits.

In one embodiment the plant according to the present invention is a transgenic plant. In one embodiment the plant according to the invention is a non-transgenic plant.

The term "unmodified plant" as defined herein would be a plant (e.g. a tobacco plant) which had not been modified according to the present invention, e.g. to modulate the activity or expression of a gene encoding an RNA binding protein or to modify the nucleic acid sequence of at least one gene encoding an RNA binding protein; and in which all other relevant features were the same (e.g. plant species, growing conditions, method of processing tobacco, etc.). In one embodiment an unmodified plant is one which does not comprise a gene encoding an RNA binding protein whose activity or expression has been modulated. In one embodiment, an unmodified plant is one which does not comprise a modified nucleic acid sequence which encodes at least one gene encoding an RNA binding protein.

RNA Binding Protein

An "RNA binding protein" as used herein has its usual meaning in the art and refers to a protein which is capable of binding RNA. Methods for measuring binding between proteins and RNA are known in the art and include, for example electrophoretic mobility shift assays.

An illustrative sequence of an RNA binding protein from tobacco is shown in SEQ ID NO. 1.

An "RNA binding domain" as used herein has its usual meaning in the art and refers to the common protein structural domain which binds single stranded RNA.

The RNA binding domain contributes to RNA binding.

An illustrative sequence of an RNA binding domain is set forth at amino acids 6-84 of SEQ ID NO. 1 and is also presented as SEQ ID NO. 35.

An RNA binding domain may be identified by comparing the protein in question to SEQ ID NO. 35 and/or SEQ ID NO. 1.

Suitably, an RNA binding. domain as used herein may refer to a sequence set forth in SEQ ID NO. 35 or a sequence which has at least 80% identity thereto. Suitably, an RNA binding domain as used herein may refer to a sequence which corresponds to amino acids 6-84 of SEQ ID NO. 1 when aligned with SEQ ID NO. 1.

An "RGG domain" or "RGG motif" as used herein has its usual meaning in the art and refers to an RGG sequence (SEQ ID NO. 36). The RGG domain or motif is a common feature in numerous RNA binding proteins.

An illustrative sequence of an RGG domain is set forth at amino acids 97-99 of SEQ ID NO. 1 and is also presented as SEQ ID NO. 36.

An RGG domain may be identified by comparing the protein in question to SEQ ID NO. 36 and/or SEQ ID NO. 1.

Domains within the amino acid sequence of a protein may be identified using domain prediction software known in the art. Domains are also described in protein databases such as UniprotKB. Without wishing to be bound by theory, it is hypothesized that modulating content of an RNA binding protein in a plant cell or modulating activity, such as RNA binding activity, of an RNA binding protein in a plant would alter the metabolic pathways producing alkaloids and TSNA precursors such as nornicotine and/or PON, resulting in modulated alkaloid and/or TSNA precursor content.

In one embodiment an RNA binding protein comprises an amino acid sequence shown as SEQ ID NO. 1 or a sequence which has at least 80% identity thereto, or a homologue thereof. The protein comprises an RNA binding domain and an RGG domain. Suitably, a homologue of SEQ ID NO. 1 may be selected from the group comprising: SEQ ID NO. 4, 7, 10, 13, 16, 19, 22 25 or 28, or a sequence which has at least 80% identity thereto. Suitably, a homologue of SEQ ID NO. 1 may be selected from the group comprising: SEQ ID NO. 4, 7, 10, 13, 16, 19, 22, 25 or 28, wherein said sequence comprises an RNA binding domain and an RGG domain, or a sequence which has at least 80% identity to SEQ ID NO. 4, 7, 10, 13, 16, 19, 22, 25 or 28 and comprises an RNA binding domain and an RGG domain.

In one embodiment an RNA binding protein comprises an amino acid sequence shown as SEQ ID NO. 1, 4, 7, 10, 13, 16, 19, 22 25 or 28, or a sequence which has at least 80% identity thereto (preferably at least 85%, at least 90%, at least 95%, at least 96%, at least 97%, at least 98%, or at least 99% identity thereto). In one embodiment an RNA binding protein comprises an amino acid sequence shown as SEQ ID NO. 1, 4, 7, 10, 13, 16, 19, 22 25 or 28, or a sequence which has at least 80% identity thereto (preferably at least 85%, at least 90%, at least 95%, at least 96%, at least 97%, at least 98%, or at least 99% identity thereto) and comprises an RNA binding domain and an RGG domain.

Suitably, an RNA binding protein according to the present invention may comprise an amino acid sequence shown as SEQ ID NO. 1, or a sequence which has at least 80% identity thereto (preferably at least 85%, preferably at least 90%, preferably at least 93%, preferably at least 95%, at least 96%, at least 97%, at least 98%, or at least 99% identity thereto). Suitably, the protein may comprise an RNA binding domain and/or an RGG domain. Suitably, the protein may comprise an RNA binding domain and an RGG domain.

Suitably, an RNA binding protein according to the present invention may comprise an amino acid sequence shown as SEQ ID NO. 4, or a sequence which has at least 80% identity thereto (preferably at least 85%, preferably at least 90%, preferably at least 93%, preferably at least 95%, at least 96%, at least 97%, at least 98%, or at least 99% identity thereto). Suitably, the protein may comprise an RNA binding domain and/or an RGG domain. Suitably, the protein may comprise an RNA binding domain and an RGG domain.

Suitably, an RNA binding protein according to the present invention may comprise an amino acid sequence shown as SEQ ID NO. 7, or a sequence which has at least 80% identity thereto (preferably at least 85%, preferably at least 90%, preferably at least 93%, preferably at least 95%, at least 96%, at least 97%, at least 98%, or at least 99% identity thereto). Suitably, the protein may comprise an RNA binding domain and/or an RGG domain. Suitably, the protein may comprise an RNA binding domain and an RGG domain.

Suitably, an RNA binding protein according to the present invention may comprise an amino acid sequence shown as SEQ ID NO. 10, or a sequence which has at least 80% identity thereto (preferably at least 85%, preferably at least 90%, preferably at least 93%, preferably at least 95%, at least 96%, at least 97%, at least 98%, or at least 99% identity thereto). Suitably, the protein may comprise an RNA binding domain and/or an RGG domain. Suitably, the protein may comprise an RNA binding domain and an RGG domain.

Suitably, an RNA binding protein according to the present invention may comprise an amino acid sequence shown as SEQ ID NO. 13, or a sequence which has at least 80% identity thereto (preferably at least 85%, preferably at least 90%, preferably at least 93%, preferably at least 95%, at least 96%, at least 97%, at least 98%, or at least 99% identity thereto). Suitably, the protein may comprise an RNA binding domain and/or an RGG domain. Suitably, the protein may comprise an RNA binding domain and an RGG domain.

Suitably, an RNA binding protein according to the present invention may comprise an amino acid sequence shown as SEQ ID NO. 16, or a sequence which has at least 80% identity thereto (preferably at least 85%, preferably at least 90%, preferably at least 93%, preferably at least 95%, at least 96%, at least 97%, at least 98%, or at least 99% identity thereto). Suitably, the protein may comprise an RNA binding domain and/or an RGG domain. Suitably, the protein may comprise an RNA binding domain and an RGG domain.

Suitably, an RNA binding protein according to the present invention may comprise an amino acid sequence shown as SEQ ID NO. 19, or a sequence which has at least 80% identity thereto (preferably at least 85%, preferably at least 90%, preferably at least 93%, preferably at least 95%, at least 96%, at least 97%, at least 98%, or at least 99% identity thereto). Suitably, the protein may comprise an RNA binding domain and/or an RGG domain. Suitably, the protein may comprise an RNA binding domain and an RGG domain.

Suitably, an RNA binding protein according to the present invention may comprise an amino acid sequence shown as SEQ ID NO. 22, or a sequence which has at least 80% identity thereto (preferably at least 85%, preferably at least 90%, preferably at least 93%, preferably at least 95%, at least 96%, at least 97%, at least 98%, or at least 99% identity thereto). Suitably, the protein may comprise an RNA binding domain and/or an RGG domain. Suitably, the protein may comprise an RNA binding domain and an RGG domain.

Suitably, an RNA binding protein according to the present invention may comprise an amino acid sequence shown as SEQ ID NO. 25, or a sequence which has at least 80% identity thereto (preferably at least 85%, preferably at least 90%, preferably at least 93%, preferably at least 95%, at least 96%, at least 97%, at least 98%, or at least 99% identity thereto). Suitably, the protein may comprise an RNA binding domain and/or an RGG domain. Suitably, the protein may comprise an, RNA binding domain and an RGG domain.

Suitably, an RNA binding protein according to the present invention may comprise an amino acid sequence shown as SEQ ID NO. 28, or a sequence which has at least 80% identity thereto (preferably at least 85%, preferably at least 90%, preferably at least 93%, preferably at least 95%, at least 96%, at least 97%, at least 98%, or at least 99% identity thereto). Suitably, the protein may comprise an RNA binding domain and/or an RGG domain. Suitably, the protein may comprise an RNA binding domain and an RGG domain.

In one embodiment the RNA binding protein according to the present invention comprises or consists of an amino acid sequence selected from: SEQ ID NO. 1, 4, 7, 10, 13, 16, 19, 22, 25 or 28.

Suitably, the protein may be from *Nicotiana tabacum*.

In one embodiment the at least one RNA binding protein is encoded by a polynucleotide sequence wherein the gene (prior to mutation) comprises the sequence shown as SEQ ID NO. 2, 3, 5, 6, 8, 9, 11, 12, 14, 15, 17, 18, 20, 21, 23, 24, 26, 27, 29 or 30; or a sequence which has at least 80% sequence identity thereto. Suitably, the protein may comprise an RNA binding domain and/or an RGG domain. Suitably, the protein may comprise an RNA binding domain and an RGG domain. Suitably, the RNA binding protein for use according to the present invention may be encoded by a polynucleotide sequence wherein the gene (prior to mutation) comprises the sequence shown as SEQ ID NO. 2, or a sequence which has at least 80% sequence identity thereto (preferably at least 85%, preferably at least 90%, preferably at least 93%, preferably at least 95%, at least, 96%, at least 97%, at least 98%, or at least 99% identity thereto). Suitably, the protein may comprise an RNA binding domain and/or an RGG domain. Suitably, the protein may comprise an RNA binding domain and an RGG domain.

Suitably, the RNA binding protein for use according to the present invention may be encoded by a polynucleotide sequence wherein the gene (prior to mutation) comprises the sequence shown as SEQ ID NO. 3, or a sequence which has at least 80% sequence identity thereto (preferably at least 85%, preferably at least 90%, preferably at least 93%, preferably at least 95%, at least, 96%, at least 97%, at least 98%, or at least 99% identity thereto). Suitably, the protein may comprise an RNA binding domain and/or an RGG domain. Suitably, the protein may comprise an RNA binding domain and an RGG domain.

Suitably, the RNA binding protein for use according to the present invention may be encoded by a polynucleotide sequence wherein the gene (prior to mutation) comprises the sequence shown as SEQ ID NO. 5, or a sequence which has at least 80% sequence identity thereto (preferably at least 85%, preferably at least 90%, preferably at least 93%, preferably at least 95%, at least, 96%, at least 97%, at least 98%, or at least 99% identity thereto). Suitably, the protein may comprise an RNA binding domain and/or an RGG domain. Suitably, the protein may comprise an RNA binding domain and an RGG domain.

Suitably, the RNA binding protein for use according to the present invention may be encoded by a polynucleotide sequence wherein the gene (prior to mutation) comprises the sequence shown as SEQ ID NO. 6, or a sequence which has at least 80% sequence identity thereto (preferably at least 85%, preferably at least 90%, preferably at least 93%, preferably at least 95%, at least, 96%, at least 97%, at least 98%, or at least 99% identity thereto). Suitably, the protein may comprise an RNA binding domain and/or an RGG domain. Suitably, the protein may comprise an RNA binding domain and an RGG domain.

Suitably, the RNA binding protein for use according to the present invention may be encoded by a polynucleotide sequence wherein the gene (prior to mutation) comprises the sequence shown as SEQ ID NO. 8, or a sequence which has at least 80% sequence identity thereto (preferably at least 85%, preferably at least 90%, preferably at least 93%, preferably at least 95%, at least, 96%, at least 97%, at least 98%, or at least 99% identity thereto). Suitably, the protein may comprise an RNA binding domain and/or an RGG domain. Suitably, the protein may comprise an RNA binding domain and an RGG domain.

Suitably, the RNA binding protein for use according to the present invention may be encoded by a polynucleotide sequence wherein the gene (prior to mutation) comprises the sequence shown as SEQ ID NO. 9, or a sequence which has at least 80% sequence identity thereto (preferably at least 85%, preferably at least 90%, preferably at least 93%, preferably at least 95%, at least, 96%, at least 97%, at least 98%, or at least 99% identity thereto). Suitably, the protein may comprise an RNA binding domain and/or an RGG domain. Suitably, the protein may comprise an RNA binding domain and an RGG domain.

Suitably, the RNA binding protein for use according to the present invention may be encoded by a polynucleotide sequence wherein the gene (prior to mutation) comprises the sequence shown as SEQ ID NO. 11, or a sequence which has at least 80% sequence identity thereto (preferably at least 85%, preferably at least 90%, preferably at least 93%, preferably at least 95%, at least, 96%, at least 97%, at least 98%, or at least 99% identity thereto). Suitably, the protein may comprise an RNA binding domain and/or an RGG domain. Suitably, the protein may comprise an RNA binding domain and an RGG domain.

Suitably, the RNA binding protein for use according to the present invention may be encoded by a polynucleotide sequence wherein the gene (prior to mutation) comprises the sequence shown as SEQ ID NO. 12, or a sequence which has at least 80% sequence identity thereto (preferably at least 85%, preferably at least 90%, preferably at least 93%, preferably at least 95%, at least, 96%, at least 97%, at least 98%, or at least 99% identity thereto). Suitably, the protein may comprise an RNA binding domain and/or an RGG domain. Suitably, the protein may comprise an RNA binding domain and an RGG domain.

Suitably, the RNA binding protein for use according to the present invention may be encoded by a polynucleotide sequence wherein the gene (prior to mutation) comprises the sequence shown as SEQ ID NO. 14, or a sequence which has at least 80% sequence identity thereto (preferably at least 85%, preferably at least 90%, preferably at least 93%, preferably at least 95%, at least, 96%, at least 97%, at least 98%, or at least 99% identity thereto). Suitably, the protein may comprise an RNA binding domain and/or an RGG domain. Suitably, the protein may comprise an RNA binding domain and an RGG domain.

Suitably, the RNA binding protein for use according to the present invention may be encoded by a polynucleotide sequence wherein the gene (prior to mutation) comprises the sequence shown as SEQ ID NO. 15, or a sequence which has at least 80% sequence identity thereto (preferably at least 85%, preferably at least 90%, preferably at least 93%, preferably at least 95%, at least, 96%, at least 97%, at least 98%, or at least 99% identity thereto). Suitably, the protein may comprise an RNA binding domain and/or an RGG domain. Suitably, the protein may comprise an RNA binding domain and an RGG domain.

Suitably, the RNA binding protein for use according to the present invention may be encoded by a polynucleotide sequence wherein the gene (prior to mutation) comprises the sequence shown as SEQ ID NO. 17, or a sequence which has at least 80% sequence identity thereto (preferably at least 85%, preferably at least 90%, preferably at least 93%, preferably at least 95%, at least, 96%, at least 97%, at least 98%, or at least 99% identity thereto). Suitably, the protein may comprise an RNA binding domain and/or an RGG domain. Suitably, the protein may comprise an RNA binding domain and an RGG domain.

Suitably, the RNA binding protein for use according to the present invention may be encoded by a polynucleotide sequence wherein the gene (prior to mutation) comprises the sequence shown as SEQ ID NO. 18, or a sequence which has at least 80% sequence identity thereto (preferably at least 85%, preferably at least 90%, preferably at least 93%, preferably at least 95%, at least, 96%, at least 97%, at least 98%, or at least 99% identity thereto). Suitably, the protein may comprise an RNA binding domain and/or an RGG domain. Suitably, the protein may comprise an RNA binding domain and an RGG domain.

Suitably, the RNA binding protein for use according to the present invention may be encoded by a polynucleotide sequence wherein the gene (prior to mutation) comprises the sequence shown as SEQ ID NO. 20, or a sequence which has at least 80% sequence identity thereto (preferably at least 85%, preferably at least 90%, preferably at least 93%, preferably at least 95%, at least, 96%, at least 97%, at least 98%, or at least 99% identity thereto). Suitably, the protein may comprise an RNA binding domain and/or an RGG domain. Suitably, the protein may comprise an RNA binding domain and an RGG domain.

Suitably, the RNA binding protein for use according to the present invention may be encoded by a polynucleotide sequence wherein the gene (prior to mutation) comprises the sequence shown as SEQ ID NO. 21, or a sequence which has at least 80% sequence identity thereto (preferably at least 85%, preferably at least 90%, preferably at least 93%, preferably at least 95%, at least, 96%, at least 97%, at least 98%, or at least 99% identity thereto). Suitably, the protein may comprise an RNA binding domain and/or an RGG domain. Suitably, the protein may comprise an RNA binding domain and an RGG domain.

Suitably, the RNA binding for use according to the present invention may be encoded by a polynucleotide sequence wherein the gene (prior to mutation) comprises the sequence shown as SEQ ID NO. 23, or a sequence which has at least 80% sequence identity thereto (preferably at least 85%, preferably at least 90%, preferably at least 93%, preferably at least 95%, at least, 96%, at least 97%, at least 98%, or at least 99% identity thereto). Suitably, the protein may comprise an RNA binding domain and/or an RGG domain. Suitably, the protein may comprise an RNA binding domain and an RGG domain.

Suitably, the RNA binding for use according to the present invention may be encoded by a polynucleotide sequence wherein the gene (prior to mutation) comprises the sequence shown as SEQ ID NO. 24, or a sequence which has at least 80% sequence identity thereto (preferably at least 85%, preferably at least 90%, preferably at least 93%, preferably at least 95%, at least, 96%, at least 97%, at least 98%, or at least 99% identity thereto). Suitably, the protein may comprise an RNA binding domain and/or an RGG domain. Suitably, the protein may comprise an RNA binding domain and an RGG domain.

Suitably, the RNA binding protein for use according to the present invention may be encoded by a polynucleotide sequence wherein the gene (prior to mutation) comprises the sequence shown as SEQ ID NO. 26, or a sequence which has at least 80% sequence identity thereto (preferably at least 85%, preferably at least 90%, preferably at least 93%, preferably at least 95%, at least, 96%, at least 97%, at least 98%, or at least 99% identity thereto). Suitably, the protein may comprise an RNA binding domain and/or an RGG domain. Suitably, the protein may comprise an RNA binding domain and an RGG domain.

Suitably, the RNA binding protein for use according to the present invention may be encoded by a polynucleotide sequence wherein the gene (prior to mutation) comprises the sequence shown as SEQ ID NO. 27, or a sequence which has at least 80% sequence identity thereto (preferably at least 85%, preferably at least 90%, preferably at least 93%, preferably at least 95%, at least, 96%, at least 97%, at least 98%, or at least 99% identity thereto). Suitably, the protein may comprise an RNA binding domain and/or an RGG domain. Suitably, the protein may comprise an RNA binding domain and an RGG domain.

Suitably, the RNA binding protein for use according to the present invention may be encoded by a polynucleotide sequence wherein the gene (prior to mutation) comprises the sequence shown as SEQ ID NO. 29, or a sequence which has at least 80% sequence identity thereto (preferably at least 85%, preferably at least 90%, preferably at least 93%, preferably at least 95%, at least, 96%, at least 97%, at least 98%, or at least 99% identity thereto). Suitably, the protein may comprise an RNA binding domain and/or an RGG domain. Suitably, the protein may comprise an RNA binding domain and an RGG domain.

Suitably, the RNA binding protein for use according to the present invention may be encoded by a polynucleotide sequence wherein the gene (prior to mutation) comprises the sequence shown as SEQ ID NO. 30, or a sequence which has at least 80% sequence identity thereto (preferably at least 85%, preferably at least 90%, preferably at least 93%, preferably at least 95%, at least, 96%, at least 97%, at least 98%, or at least 99% identity thereto). Suitably, the protein may comprise an RNA binding domain and/or an RGG domain. Suitably, the protein may comprise an RNA binding domain and an RGG domain.

In one embodiment the at least RNA binding protein is encoded by a polynucleotide sequence wherein the gene (prior to mutation) is selected from: SEQ ID NO. 2, 3, 5, 6, 8, 9, 11, 12, 14, 15, 17, 18, 20, 21, 23, 24, 26, 27, 29 or 30.

Suitably, the protein for use according to the present invention may be encoded by a polynucleotide sequence from *Nicotiana tabacum*.

In one aspect the present invention provides a method of decreasing the alkaloid content of a plant or part thereof or cell (e.g. plant cell), the method comprising modifying said plant by decreasing or inhibiting the activity or expression of at least one gene encoding an RNA binding protein.

In one aspect the present invention provides a method of decreasing the alkaloid content of a plant or part thereof or plant cell, the method comprising modifying said plant by decreasing or inhibiting the activity or expression of at least one gene encoding an RNA binding protein comprising the amino acid sequence shown as SEQ ID NO. 1, 4, 7, 10, 13, 16, 19, 22, 25 or 28, or a sequence which has at least 80% identity thereto or wherein the at least one gene encoding an RNA binding protein comprises a nucleotide sequence as set out in SEQ ID NO. 2, 3, 5, 6, 8, 9, 11, 12, 14, 15, 17, 18, 20, 21, 23, 24, 26, 27, 29 or 30, or a functional variant or functional fragment or orthologue of SEQ ID NO. 2, 3, 5, 6, 8, 9, 11, 12, 14, 15, 17, 18, 20, 21, 23, 24, 26, 27, 29 or 30, or a nucleic acid sequence which has at least 80% identity to SEQ ID NO. 2, 3, 5, 6, 8, 9, 11, 12, 14, 15, 17, 18, 20, 21, 23, 24, 26, 27, 29 or 30. Suitably, the protein may comprise an RNA binding domain and/or an RGG domain. Suitably, the protein may comprise an RNA binding domain and an RGG domain.

In one aspect the present invention provides a method of decreasing the content of a tobacco specific nitrosamine (TSNA) precursor in a plant or part thereof (e.g. leaf), the method comprising modifying said plant by decreasing or inhibiting the activity or expression of at least one gene encoding an RNA binding protein.

In one aspect the present invention provides a method of decreasing the content of a tobacco specific nitrosamine (TSNA) precursor in a plant or part thereof (e.g. leaf), the method comprising modifying said plant by decreasing or inhibiting the activity or expression of at least one gene encoding an RNA binding protein comprising the amino acid sequence shown as SEQ ID NO. 2, 3, 5, 6, 8, 9, 11, 12, 14, 15, 17, 18, 20, 21, 23, 24, 26, 27, 29 or 30, or a sequence which has at least 80% identity thereto, or wherein the at least one gene encoding an RNA binding protein comprises a nucleotide sequence as set out in SEQ ID NO. 2, 3, 5, 6, 8, 9, 11, 12, 14, 15, 17, 18, 20, 21, 23, 24, 26, 27, 29 or 30, or a functional variant or functional fragment or orthologue of SEQ ID NO. 2, 3, 5, 6, 8, 9, 11, 12, 14, 15, 17, 18, 20, 21, 23, 24, 26, 27, 29 or 30, or a nucleic acid sequence which has at least 80% identity to SEQ ID NO. 2, 3, 5, 6, 8, 9, 11, 12, 14, 15, 17, 18, 20, 21, 23, 24, 26, 27, 29 or 30. Suitably, the protein may comprise an RNA binding domain and/or an RGG domain. Suitably, the protein may comprise an RNA binding domain and an RGG domain.

In one aspect the present invention provides a method of decreasing the content of a TSNA in a processed leaf, such as a cured leaf, the method comprising:
  modifying a plant by decreasing or inhibiting the activity or expression of at least one gene encoding an RNA binding protein;
  harvesting a leaf from said plant;
  and processing e.g. curing said harvested leaf.

Suitably, the method of decreasing the content of a TSNA in a processed leaf may comprise: modifying said plant by decreasing or inhibiting the activity or expression of at least one gene encoding an RNA binding protein comprising the amino acid sequence shown as SEQ ID NO. 2, 3, 5, 6, 8, 9, 11, 12, 14, 15, 17, 18, 20, 21, 23, 24, 26, 27, 29 or 30, or a sequence which has at least 80% identity thereto, or wherein the at least one gene encoding an RNA binding protein comprises a nucleotide sequence as set out in SEQ ID NO. 2, 3, 5, 6, 8, 9, 11, 12, 14, 15, 17, 18, 20, 21, 23, 24, 26, 27, 29 or 30, or a functional variant or functional fragment or orthologue of SEQ ID NO. 2, 3, 5, 6, 8, 9, 11, 12, 14, 15, 17, 18, 20, 21, 23, 24, 26, 27, 29 or 30, or a nucleic acid sequence which has at least 80% identity to SEQ ID NO. 2, 3, 5, 6, 8, 9, 11, 12, 14, 15, 17, 18, 20, 21, 23, 24, 26, 27, 29 or 30. Suitably, the protein may comprise an RNA binding domain and/or an RGG domain. Suitably, the protein may comprise an RNA binding domain and an RGG domain.

The term "decreasing" or "inhibiting" (e.g. inhibiting the activity or expression of gene encoding an RNA binding protein) as used herein means that the activity or expression of the gene encoding the RNA binding protein is lower or decreased compared with the activity or expression of the gene in a comparable product.

In one aspect the present invention provides a method of increasing the alkaloid content of a plant or part thereof or cell (e.g. plant cell), the method comprising modifying said plant by increasing or enhancing the activity or expression of at least one gene encoding an RNA binding protein.

In one aspect the present invention provides a method of increasing the alkaloid content of a plant or part thereof or plant cell, the method comprising modifying said plant by increasing or enhancing the activity or expression of at least one gene encoding an RNA binding protein comprising the amino acid sequence shown as SEQ ID NO. 1, 4, 7, 10, 13, 16, 19, 22, 25 or 28, or a sequence which has at least 80% identity thereto or wherein the at least one gene encoding an RNA binding protein comprises a nucleotide sequence as set out in SEQ ID NO. 2, 3, 5, 6, 8, 9, 11, 12, 14, 15, 17, 18, 20, 21, 23, 24, 26, 27, 29 or 30, or a functional variant or functional fragment or orthologue of SEQ ID NO. 2, 3, 5, 6, 8, 9, 11, 12, 14, 15, 17, 18, 20, 21, 23, 24, 26, 27, 29 or 30, or a nucleic acid sequence which has at least 80% identity to SEQ ID NO. 2, 3, 5, 6, 8, 9, 11, 12, 14, 15, 17, 18, 20, 21, 23, 24, 26, 27, 29 or 30. Suitably, the protein may comprise an RNA binding domain and/or an RGG domain. Suitably, the protein may comprise an RNA binding domain and an RGG domain In one aspect the present invention provides a method of increasing the content of a tobacco specific nitrosamine (TSNA) precursor in a plant or part thereof (e.g. leaf), the method comprising modifying said plant by increasing or enhancing the activity or expression of at least one gene encoding an RNA binding protein.

In one aspect the present invention provides a method of increasing the content of a tobacco specific nitrosamine (TSNA) precursor in a plant or part thereof (e.g. leaf), the method comprising modifying said plant by increasing or enhancing the activity or expression of at least one gene encoding an RNA binding protein comprising the amino acid sequence shown as SEQ ID NO. 2, 3, 5, 6, 8, 9, 11, 12, 14, 15, 17, 18, 20, 21, 23, 24, 26, 27, 29 or 30, or a sequence which has at least 80% identity thereto, or wherein the at least one gene encoding an RNA binding comprises a nucleotide sequence as set out in SEQ ID NO. 2, 3, 5, 6, 8, 9, 11, 12, 14, 15, 17, 18, 20, 21, 23, 24, 26, 27, 29 or 30, or a functional variant or functional fragment or orthologue of SEQ ID NO. 2, 3, 5, 6, 8, 9, 11, 12, 14, 15, 17, 18, 20, 21, 23, 24, 26, 27, 29 or 30, or a nucleic acid sequence which has at least 80% identity to SEQ ID NO. 2, 3, 5, 6, 8, 9, 11, 12, 14, 15, 17, 18, 20, 21, 23, 24, 26, 27, 29 or 30.

The term "increasing" or "enhancing" (e.g. increasing the activity or expression of gene encoding an RNA binding protein) as used herein means that the activity or expression of the gene encoding the RNA binding protein is higher or increased compared with the activity or expression of the gene in a comparable product.

According to the present invention, the activity or expression of a gene encoding an RNA binding protein is modulated.

In one aspect the present invention provides a method of modulating (i.e. increasing or decreasing) the alkaloid content of a plant or part thereof or cell (e.g. plant cell), the method comprising modifying said plant by modulating (i.e. increasing or decreasing) the activity of at least one gene encoding an RNA binding protein.

The term "activity" refers to any functionality of the RNA binding protein encoded by the at least one gene. Examples of activity include the formation of protein:protein interactions, enzymatic activity or localization of the RNA binding protein.

Suitably, the activity may be the ability of the RNA binding protein to interact with another molecule or molecules. In some embodiments the invention provides a method of modulating (i.e. increasing or decreasing) the alkaloid content of a plant or part thereof or cell (e.g. plant cell), the method comprising modifying said plant by modulating (i.e. increasing or decreasing) the ability of an RNA binding protein to interact with another molecule.

Suitably, the ability of the RNA binding protein to interact with the other molecule may be the ability to bind the other molecule. The other molecule may be a protein, such as another RNA binding protein. Suitably, the other molecule may be more than one molecule, such as one or more molecules, such as two or more molecules, such as three or more molecules. Where the other molecule is more than one molecule, the other molecules may be the same molecule or may be different molecules. Suitably, the other molecule may be RNA.

Suitably, the activity may be the ability of the RNA binding protein to bind RNA. In some embodiments the invention provides a method of modulating (i.e. increasing or decreasing) the alkaloid content of a plant or part thereof or cell (e.g. plant cell), the method comprising modifying said plant by modulating (i.e. increasing or decreasing) the ability of an RNA binding protein to bind RNA.

Modulation of the activity of a gene encoding an RNA binding protein may entail increasing or decreasing the activity of the RNA binding protein.

Increasing the activity of a RNA binding protein refers to enhancing or improving the ability of the RNA binding protein to carry out a particular function in comparison to RNA binding protein in a plant that has not been modified in accordance with the invention.

Decreasing the activity of a RNA binding domain-containing protein refers to reducing, inhibiting or disrupting the ability of the RNA binding protein to carry out a particular function in comparison to a RNA binding protein in a plant that has not been modified in accordance with the invention.

The activity of a RNA binding domain-containing protein may be reduced to such an extent that the activity is prevented or eliminated.

In some embodiments the activity of a RNA binding protein may be modulated (i.e. increased or decreased) by at least about 10% 20% 30%, or 40%, suitably at least about 50%, 60%, 70%, more suitably at least about 80%, 90%, 95% or 100% in comparison to the activity of a gene encoding an RNA binding protein in a plant (e.g. a tobacco plant) which has not been modified in accordance with the present invention.

In some embodiments the modulated RNA binding protein exhibits increased or decreased activity compared to an unmodified RNA binding protein. The modulated RNA binding protein may exhibit at least about 1%, at least about 3%, at least about 5%, at least about 10%, at least about 20%, at least about 30%, at least about 40%, at least about 50%, at least about 60%, at least about 70%, at least about 80% or at least about 90% increased or decreased activity compared to an unmodified RNA binding protein.

Techniques are known in the art for measuring protein activities. For example, assays are known for measuring the enzymatic activity of a protein and the localization of a protein can be identified using microscopy techniques.

In particular, the ability of an RNA binding protein to bind another molecule may be measured using techniques known in the art. Examples of such techniques include immunoprecipitation, isothermal calorimetry, surface plasmon resonance and microscale thermophoresis. For example, the ability of a modulated or mutated RNA binding protein to bind other molecules may be determined for example by performing co-immunoprecipitation experiments using a modulated or mutated RNA binding protein and a corresponding unmodified or unmutated RNA binding protein. If the modulation or mutation in the RNA binding protein reduces, inhibits or eliminates the ability of the RNA binding protein to bind other molecules, the co-immunoprecipitation will show that the modulated or mutated RNA binding protein binds fewer other molecules.

The ability of an RNA binding protein to bind RNA may be measured using techniques known in the art. Examples of such techniques include techniques such as a bandshift assay (e.g. RNA—electrophoretic mobility shift assay), RNA pull down assay using affinity tags, RNA immunoprecipitation followed by RT-PCR or a non-specific assay such as a poly(A) northern or oligonucleotide-targeted RNase H protection assays.

In one aspect the present invention provides a method of modulating (i.e. increasing or decreasing) the alkaloid content of a plant or part thereof or cell (e.g. plant cell), the method comprising modifying said plant by modulating (i.e. increasing or decreasing) the expression of at least one gene encoding an RNA binding protein.

The "expression" of a gene refers to the degree to which the information encoded in the gene is converted to a functionality. The level of expression of a gene may be equated with the amount of the product of that gene present in a cell or organism. A modification that modulates (i.e. increases or decreases) the expression of a gene is one that increases the amount of the product of that gene in a plant or cell in comparison to an unmodified plant or cell.

In some embodiments the expression of an RNA binding protein is modulated (i.e. increased or decreased) in comparison to the expression of a gene encoding an RNA binding protein in a plant (e.g. a tobacco plant) which has not been modified in accordance with the present invention.

In some embodiments the expression of an RNA binding protein may be modulated (i.e. increased or decreased) by at least about 10% 20% 30%, or 40%, suitably at least about 50%, 60%, 70%, more suitably at least about 80%, 90%, 95% or 100% in comparison to the expression of a gene encoding an RNA binding protein in a plant (e.g. a tobacco plant) which has not been modified in accordance with the present invention.

In some embodiments the modulated RNA binding protein exhibits increased or decreased expression compared to an unmodified RNA binding protein. The modulated RNA binding protein may exhibit at least about 1%, at least about 3%, at least about 5%, at least about 10%, at least about 20%, at least about 30%, at least about 40%, at least about 50%, at least about 60%, at least about 70%, at least about 80% or at least about 90% increased or decreased expression compared to an unmodified RNA binding protein.

Typically, genes are transcribed to mRNA, which is translated to protein, the final gene product. Proteins may be sequestered in cellular stores and/or degraded. The expression of a gene may be modulated by modulating any or all of these steps. Accordingly, in some embodiments the modification modulates expression of at least one gene encoding an RNA binding protein in one of the following ways:

modulating transcription from the at least one gene encoding an RNA binding protein;

modulating translation of the mRNA from the at least one gene encoding an RNA binding protein;

modulating release of the RNA binding protein from intracellular stores; and/or modulating the rate of degradation of the RNA binding protein.

The expression of specific genes encoding RNA binding proteins can be measured by measuring transcription and/or translation of the gene. Methods for measuring transcription are well known in the art and include, amongst others, northern blot, RNA-Seq, in situ hybridization, DNA microarrays and RT-PCR. Alternatively, the expression of a gene may be measured indirectly by measuring the level of the gene product for example the protein encoded by said gene. For example, the expression of an RNA binding protein may be determined by measuring the presence of the protein using an antibody specific for the RNA binding protein (for example antibodies specific for an RNA binding domain) by western blot.

Modifying

The plant or cell may be modified in any way that modulates activity or expression of at least one gene encoding an RNA binding protein. Types of modifications to plants and cells that modulate activity or expression of genes, as well as techniques to achieve those modifications, are known in the art.

In some embodiments the present invention provides a method of decreasing the alkaloid content of a plant or part thereof or cell (e.g. plant cell), the method comprising modifying said plant by decreasing or inhibiting the activity or expression of at least one gene encoding an RNA binding protein as described herein.

In some embodiments the present invention provides a method of decreasing the content of a tobacco specific nitrosamine (TSNA) or a precursor of a TSNA in a tobacco plant or plant part thereof, the method comprising modifying said plant or a cell culture by decreasing the activity or expression of at least one gene encoding an RNA binding protein as described herein.

Any method known in the art for decreasing or inhibiting the activity or expression of a gene may be used in the methods according to the present invention.

Suitably, the activity or expression of the gene encoding an RNA binding protein may be reduced, partly inactivated, inhibited, eliminated, knocked out or lost such that the protein activity, expression or function of the gene encoding an RNA binding protein may not be detectable.

In one aspect, the at least one gene encoding an RNA binding protein is knocked out. In other words, the gene encoding an RNA binding protein has been rendered completely inoperative.

By way of example, the present method may comprise:
providing a mutation in a nucleic acid sequence which encodes a protein comprising the amino acid sequence shown as SEQ ID NO. 1, 4, 7, 10, 13, 16, 19, 22, 25 or 28, or an amino acid sequence which has at least 80% sequence identity thereto;
providing a mutation in a regulatory region (e.g. a promoter or an enhancer) which contributes to controlling the expression of a protein comprising the amino acid sequence shown as SEQ ID NO. 1, 4, 7, 10, 13, 16, 19, 22, 25 or 28, or an amino acid sequence which has at least 80% sequence identity thereto;
providing an antisense RNA, siRNA or miRNA which reduces the level of nucleic acid sequence encoding a protein comprising the amino acid sequence shown as SEQ ID NO. 1, 4, 7, 10, 13, 16, 19, 22, 25 or 28, or an amino acid sequence which has at least 80% sequence identity thereto.

Each of the above approaches results in the reduction or prevention of activity or expression of a protein comprising the amino acid sequence shown as SEQ ID NO. 1, 4, 7, 10, 13, 16, 19, 22, 25 or 28, or an amino acid sequence which has at least 80% sequence identity thereto or wherein the at least one gene encoding an RNA binding protein comprises a nucleotide sequence as set out in SEQ ID NO. 2, 3, 5, 6, 8, 9, 11, 12, 14, 15, 17, 18, 20, 21, 23, 24, 26, 27, 29 or 30, or a functional variant or functional fragment or orthologue of SEQ ID NO. 2, 3, 5, 6, 8, 9, 11, 12, 14, 15, 17, 18, 20, 21, 23, 24, 26, 27, 29 or 30, or a nucleic acid sequence which has at least 80% identity to SEQ ID NO. 2, 3, 5, 6, 8, 9, 11, 12, 14, 15, 17, 18, 20, 21, 23, 24, 26, 27, 29 or 30. As used herein, the term "mutation" encompasses a natural genetic variant or an engineered variant. In particular, the term "mutation" refers to a variation in the nucleotide sequence encoding the amino acid sequence or in the amino acid sequence compared to the sequence shown as SEQ ID NO. 1, 4, 7, 10, 13, 16, 19, 22, 25 or 28, or an amino acid sequence which has at least 80% (preferably at least 85%, preferably at least 90%, preferably at least 93%, preferably at least 95%, preferably at least 98%, preferably at least 99%) sequence identity thereto.

In one embodiment the mutation decreases the alkaloid content of a plant. In another embodiment, the mutation decreases the content of at least one TSNA precursor in a plant or part thereof, or leaf such as a harvested or processed leaf. In one embodiment the mutation decreases the content of one or more TSNAs selected from NNN, NNK, NAT, NAB, preferably NNN and/or NNK content is decreased in a processed leaf. Suitably, the TSNA content is reduced in relation to a comparable product.

In one embodiment, a method according to the present invention may comprise providing a nucleic acid sequence to a plant or part thereof or plant cell, wherein said nucleic acid results in the reduction or elimination of the activity or expression of at least one gene encoding an RNA binding protein.

In one embodiment, a method according to the present invention may comprise providing a nucleic acid sequence to a plant or part thereof or plant cell, wherein said nucleic acid results in the modification of the nucleic acid sequence of at least one gene encoding an RNA binding protein.

Suitably said nucleic acid sequence may be introduced to the plant or part thereof or cell. Suitably an endogenous nucleic acid sequence in the plant or part thereof or cell may be modified to encode the polypeptide according to the present invention (e.g. by gene editing). For example, an endogenous nucleotide sequence may be modified to decrease the activity or expression of at least one gene encoding an RNA binding protein.

In a preferred embodiment, each copy of a nucleic acid sequence encoding a protein comprising a sequence shown as SEQ ID NO. 1, 4, 7, 10, 13, 16, 19, 22, 25 or 28, or a sequence which has at least 80% sequence identity thereto or wherein the at least one gene encoding an RNA binding protein comprises a nucleotide sequence as set out in SEQ ID NO. 2, 3, 5, 6, 8, 9, 11, 12, 14, 15, 17, 18, 20, 21, 23, 24, 26, 27, 29 or 30 or a functional variant or functional fragment or orthologue of SEQ ID NO. 2, 3, 5, 6, 8, 9, 11, 12, 14, 15, 17, 18, 20, 21, 23, 24, 26, 27, 29 or 30 or a nucleic acid sequence which has at least 80% identity to SEQ ID NO. 2, 3, 5, 6, 8, 9, 11, 12, 14, 15, 17, 18, 20, 21, 23, 24, 26, 27, 29 or 30 which is present in the plant is modified e.g. mutated as defined herein (e.g. each genomic copy of a gene encoding said protein in a plant is mutated). For example, each copy of the gene in the allotetraploid genome of *Nicotiana tabacum* may be mutated.

In a preferred embodiment, some or all of the homologues of the RNA binding protein described herein are modified e.g. inhibited or mutated. Suitably, some or all of SEQ ID NO. 1, 4, 7, 10, 13, 16, 19, 22, 25 or 28, or corresponding sequences which have at least 80% sequence identity thereto are modified e.g. inhibited or mutated.

In some embodiments the plant or plant cell according to the present invention is homozygous. Suitably, the plant or plant cell may be homozygous for the modification e.g. inhibition or mutation. In some embodiments the plant or plant cell according to the present invention expresses only the modified e.g. mutated nucleic acid encoding the RNA binding protein. In other words, in some embodiments no endogenous (or endogenous and functional protein) is present in the plant according to the present invention. In other words, if any endogenous protein is present it is preferably in an inactive form.

In one embodiment the present method may comprise providing a mutation in the nucleic acid sequence shown as SEQ ID NO. 2, 3, 5, 6, 8, 9, 11, 12, 14, 15, 17, 18, 20, 21, 23, 24, 26, 27, 29 or 30, or a nucleic acid sequence which has at least 80% identity thereto.

The mutation may alter the plant genome such that a nucleic acid sequence encoding a protein comprising the amino acid sequence shown as SEQ ID NO. 1, 4, 7, 10, 13, 16, 19, 22, 25 or 28, or an amino acid sequence which has at least 80% sequence identity thereto is completely or partially deleted or otherwise modified to inhibit or eliminate the ability of the RNA binding protein to bind RNA. In some embodiments the mutation does not alter the level or expression of the protein but reduces inhibits or eliminates the ability of the RNA binding protein to bind RNA.

Suitably, the mutation may be in an RNA binding domain of the RNA binding protein. Suitably, the mutation may be in an RGG domain of the RNA binding protein. Suitably, the RNA binding protein may comprise multiple mutations, each in a different domains for example, at least one mutation in an RNA binding domain and at least one mutation in an RGG domain. In some embodiments, the mutation i modifies the ability of the RNA binding protein to bind RNA. Suitably, the mutation may prevent or reduce RNA binding Suitably, the mutation may prevents or reduces RNA binding and reduce the activity of the RNA binding protein.

The mutation may be in one or more domains of the RNA binding protein, such as in an RNA binding domain and/or an RGG domain. In some embodiments, one or more domains of the RNA binding protein, such as an RNA binding domain and/or an RGG domain, may be mutated thereby modifying the ability of the protein to bind RNA. In some embodiments, one or more domains, such as an RNA binding domain and/or an RGG domain are deleted from the RNA binding protein.

The mutation may interrupt the nucleic acid sequence which encodes a protein comprising the amino acid sequence shown as SEQ ID NO. 1, 4, 7, 10, 13, 16, 19, 22, 25 or 28, or an amino acid sequence which has at least 80% sequence identity thereto.

The interruption may cause the nucleic acid sequence to not be transcribed and/or translated.

The nucleic acid sequence may be interrupted, for example, by deleting or otherwise modifying the ATG start codon of the nucleic acid sequence such that translation of the protein is reduced or prevented.

The nucleic acid sequence may comprise one or more nucleotide change(s) that reduce or prevent expression of the protein or affect protein trafficking. For example, expression of the protein may be reduced or prevented by introduction of one or more pre-mature stop codons, a frame shift, a splice mutation or a non-tolerated amino acid substitution in the open reading frame. A premature stop codon refers to a mutation which introduces a stop codon into the open reading frame and prevents translation of the entire amino acid sequence. The premature stop codon may be a TAG ("amber"), TAA ("ochre"), or TGA ("opal" or "umber") codon.

A frame-shift mutation (also called a framing error or a reading frame shift) is a mutation caused by indels (insertions or deletions) of a number of nucleotides in a nucleic acid sequence that is not divisible by three. Due to the triplet nature of gene expression by codons, the insertion or deletion can change the reading frame, resulting in a completely different translation from the original. A frameshift mutation will often cause the reading of the codons after the mutation to code for different amino acids. The frameshift mutation will commonly result in the introduction of a premature stop codon.

A splice mutation inserts, deletes or changes a number of nucleotides in the specific site at which splicing takes place during the processing of precursor messenger RNA into mature messenger RNA. The deletion of the splicing site results in one or more introns remaining in mature mRNA and may lead to the production of abnormal proteins.

A non-tolerated amino acid substitution refers to a mutation which causes a non-synonymous amino acid substitution in the protein which results in reduced or ablated function of the protein.

Any method known in the art for providing a mutation in a nucleic acid sequence may be used in the method according to the present invention. For example, homologous recombination may be used, in which a vector is created in which the relevant nucleic acid sequence(s) are mutated and used to transform plants or plant cells. Recombinant plants or plant cells expressing the mutated sequence may then be selected.

In one embodiment the mutation introduces a non-tolerated amino acid substitution in a protein comprising an amino acid sequence shown as SEQ ID NO. 1, 4, 7, 10, 13, 16, 19, 22, 25 or 28, or a sequence which has at least 80% sequence identity thereto.

In some embodiments, the RNA binding domain may contain a mutation which decreases the expression of the at least one gene encoding an RNA binding protein.

In some embodiments, the RGG domain may contain a mutation which decreases the expression of the at least one gene encoding an RNA binding protein.

The mutation may be a deletion, a splice mutant or codon encoding a non-tolerated amino acid substitution.

In one embodiment, the nucleic acid sequence encoding the RNA binding protein may be wholly or partially deleted. The deletion may be continuous, or may comprise a plurality of sections of sequence. The deletion preferably removes a sufficient amount of nucleotide sequence such that the nucleic acid sequence no longer encodes a functional RNA binding protein. The deletion may be total, in which case 100% of the coding portion of the nucleic acid sequence is absent, when compared to the corresponding genome of a comparable unmodified plant. The deletion may, for example, remove at least 50, 60, 70, 80 or 90% of the coding portion of the nucleic acid sequence. Suitably, at least part of the protein may be deleted. The deletion may, for example, remove at least 10, 20, 30, 40, 50, 60, 70, 80 or 90% of the coding portion of the protein.

The deletion may remove at least 10 amino acids (such as at least 20, at least 30, at least 40, at least 50, at least 60, at least 70, at least 80, at least 90 amino acids) from the C terminal of the RNA binding protein. Suitably, the deletion may remove at least 10 amino acids (such as at least 20, at least 30, at least 40, at least 50, at least 60, at least 70, at least 80, at least 90 amino acids) which correspond to the C terminus of the RNA binding protein wherein the sequence of the RNA binding protein is aligned with SEQ ID NO. 1. Suitably, the deletion may remove at least 10 amino acids (such as at least 20, at least 30, at least 40, at least 50, at least 60, at least 70, at least 80, at least 90 amino acids) from the C terminus of the RNA binding protein wherein the RNA binding protein prior to deletion comprises an amino acid sequence set forth in SEQ ID NO. 1, 4, 7, 10, 13, 16, 19, 22, 25 or 28, or a sequence which has at least 80% sequence identity thereto. Suitably, the deletion may remove at least 10 amino acids (such as at least 20, at least 30, at least 40, at least 50, at least 60, at least 70, at least 80, at least 90 amino acids) from the C terminus of the RNA binding protein wherein the RNA binding protein prior to deletion comprises an amino acid sequence set forth in SEQ ID NO. 1, or a sequence which has at least 80% sequence identity thereto.

Suitably, the protein for use according to the present invention may comprise a truncated RNA binding protein. Suitably, the truncated protein may be a truncated version of an amino acid sequence set forth in SEQ ID NO. 1, 4, 7, 10, 13, 16, 19, 22, 25 or 28, or a sequence which has at least 80% sequence identity thereto. Suitably, the truncated protein lacks at least 10 amino acids (such as at least 20, at least 30, at least 40, at least 50, at least 60, at least 70, at least 80, at least 90 amino acids) from the C terminus of the RNA binding protein.

The deletion may remove at least part of an RNA binding domain. The deletion may, for example, remove at least 10, 20, 30, 40, 50, 60, 70, 80 or 90% of an RNA binding domain. Suitably, the deletion may remove at least 5 amino acids, at least 10 amino acids, at least 15, at least 20, at least 25, at least 30 amino acids, at least 40 amino acids, at least 50 amino acids, at least 60 amino acids, at least 70 amino acids, at least 80 amino acids of an RNA binding domain. Suitably, the deletion may remove 5 amino acids, 10 amino acids, 15, 20 amino acids, 25 amino acids, 30 amino acids, 40 amino acids, 50 amino acids, 60 amino acids, 70 amino acids, 80 amino acids of an RNA binding domain.

The deletion may remove at least part of an RGG motif. The deletion may, for example, remove at least one or at least two amino acids from an RGG domain. Suitably, the RGG domain may be completely deleted.

In one embodiment, the RNA binding protein is encoded by a nucleotide sequence which comprises or consists of the sequence set forth in SEQ ID NO. 34 or a sequence with at least 80% identity thereto (such as at least 85%, 90%, 95% identity).

In one embodiment, the RNA binding protein comprises or consists of a sequence as set forth in SEQ ID NO. 35, or a sequence with at least 80% identity thereto (such as at least 85%, 90%, 95% identity).

Methods for deletion of nucleic acid sequences in plants are known in the art. For example, homologous recombination may be used, in which a vector is created in which the relevant nucleic acid sequence(s) are missing and used to transform plants or plant cells. Recombinant plants or plant cells expressing the new portion of sequence may then be selected.

Plant cells transformed with a vector as described herein may be grown and maintained in accordance with well-known tissue culturing methods such as by culturing the cells in a suitable culture medium supplied with the necessary growth factors such as amino acids, plant hormones, vitamins, etc.

Modification of the nucleic acid sequence may be performed using targeted mutagenesis methods (also referred to as targeted nucleotide exchange (TNE) or oligo-directed mutagenesis (ODM)). Targeted mutagenesis methods include, without limitation, those employing zinc finger nucleases, TALENs (see WO2011/072246 and WO2010/079430), Cas9-like, Cas9/crRNA/tracrRNA, Cas9/gRNA, or other CRISPR systems (see WO 2014/071006 and WO2014/093622), meganucleases (see WO2007/047859 and WO2009/059195), or targeted mutagenesis methods employing mutagenic oligonucleotides, possibly containing chemically modified nucleotides for enhancing mutagenesis with sequence complementarity to the gene, into plant protoplasts (e.g., KeyBase® or TALENs).

Alternatively, mutagenesis systems such as TILLING (Targeting Induced Local Lesions IN Genomics; McCallum et al. (2000) Nat. Biotech. 18:455, and McCallum et al. (2000) Plant Physiol. 123, 439-442, both incorporated herein by reference) may be used to generate plant lines which comprise a gene encoding a protein having a mutation. TILLING uses traditional chemical mutagenesis (e.g. ethyl methanesulfonate (EMS) mutagenesis, which produces random mutations) followed by high-throughput screening for mutations. Thus, plants, seeds, cells and tissues comprising a gene having the desired mutation may be obtained.

The method may comprise the steps of mutagenizing plant seeds (e.g. EMS mutagenesis), pooling of plant individuals or DNA, PCR amplification of a region of interest, heteroduplex formation and high-throughput detection, identification of the mutant plant, sequencing of the mutant PCR product. It is understood that other mutagenesis and selection methods may equally be used to generate such modified plants. Seeds may, for example, be radiated or chemically treated and the plants may be screened for a modified phenotype.

Fast neutron deletion mutagenesis may be used in a reverse genetics sense (i.e. with PCR) to identify plant lines carrying a deletion in the endogenous gene. See for example Ohshima et al. (1998) Virology 213:472-481; Okubara et al. (1994) Genetics 137:867-874; and Quesada et al. (2000) Genetics 154:421-4315 which are incorporated herein by reference.

In another approach, dominant mutants may be used to trigger RNA silencing due to gene inversion and recombination of a duplicated gene locus. See for example Kusaba et al. (2003) Plant Cell 15:1455-1467 (incorporated herein by reference).

Modified plants may be distinguished from non-modified plants, i.e., wild type plants, by molecular methods, such as the mutation(s) present in the DNA, and by the modified phenotypic characteristics. The modified plants may be homozygous or heterozygous for the modification. Preferably modified plants are homozygous for the modification.

In one embodiment the method of reducing or preventing the activity or expression of a protein comprising the amino acid sequence shown as SEQ ID NO. 1, 4, 7, 10, 13, 16, 19, 22, 25 or 28, or an amino acid sequence which has at least 80% sequence identity thereto does not comprise treating the plant with a chemical (e.g. an agrochemical).

Other ways of reducing or preventing the expression will be apparent to one skilled in the art and include the use of virus-induced gene silencing (VIGs), micro RNA silencing, RNAi, antisense, tDNA insertions, or dominant negative constructs (or antimorphic mutations).

In one embodiment the expression of a gene encoding a protein comprising the amino acid sequence shown as SEQ ID NO. 1, 4, 7, 10, 13, 16, 19, 22, 25 or 28, or an amino acid sequence which has at least 80% sequence identity thereto may be reduced or eliminated by virus-induced gene silencing.

In one embodiment the expression of a gene encoding a protein comprising the amino acid sequence shown as SEQ ID NO. 1, 4, 7, 10, 13, 16, 19, 22, 25 or 28, or an amino acid sequence which has at least 80% sequence identity thereto may be reduced or eliminated by microRNAs.

In one embodiment the expression of a gene encoding a protein comprising the amino acid sequence shown as SEQ ID NO. 1, 4, 7, 10, 13, 16, 19, 22, 25 or 28, or an amino acid sequence which has at least 80% sequence identity thereto may be reduced or eliminated by RNAi.

In one embodiment the expression of a gene encoding a protein comprising the amino acid sequence shown as SEQ ID NO. 1, 4, 7, 10, 13, 16, 19, 22, 25 or 28, or an amino acid sequence which has at least 80% sequence identity thereto may be reduced or eliminated by antisense suppression.

In one embodiment the expression of a gene encoding a protein comprising the amino acid sequence shown as SEQ ID NO. 1, 4, 7, 10, 13, 16, 19, 22, 25 or 28, or an amino acid sequence which has at least 80% sequence identity thereto may be reduced or eliminated by sense suppression.

In one embodiment the expression of a gene encoding a protein comprising the amino acid sequence shown as SEQ ID NO. 1, 4, 7, 10, 13, 16, 19, 22, 25 or 28, or an amino acid sequence which has at least 80% sequence identity thereto may be reduced or eliminated by tDNA insertions.

In one embodiment the expression of a gene encoding a protein comprising the amino acid sequence shown as SEQ ID NO. 1, 4, 7, 10, 13, 16, 19, 22, 25 or 28, or an amino acid sequence which has at least 80% sequence identity thereto may be reduced or eliminated by dominant negative constructs (or antimorphic mutations).

In one embodiment the expression of a gene encoding a protein comprising the amino acid sequence shown as SEQ ID NO. 1, 4, 7, 10, 13, 16, 19, 22, 25 or 28, or an amino acid sequence which has at least 80% sequence identity thereto may be reduced or eliminated by a targeted mutagenesis based system.

In one embodiment the expression of a gene encoding a protein comprising the amino acid sequence shown as SEQ ID NO. 1, 4, 7, 10, 13, 16, 19, 22, 25 or 28, or an amino acid sequence which has at least 80% sequence identity thereto may be reduced or eliminated by a gene editing e.g. CRISPR based system.

In one embodiment the expression of a gene encoding a protein comprising the amino acid sequence shown as SEQ ID NO. 1, 4, 7, 10, 13, 16, 19, 22, 25 or 28, or an amino acid sequence which has at least 80% sequence identity thereto may be reduced or eliminated by zinc finger nuclease, TALENs, meganucleases, mutagenic oligonucleotides or TILLING.

In some embodiments the present invention provides a method of increasing the alkaloid content of a plant or part thereof or cell (e.g. plant cell), the method comprising modifying said plant by increasing or enhancing the activity or expression of at least one gene encoding an RNA binding protein.

Any method known in the art for increasing or enhancing the activity or expression of a gene may be used in the methods according to the present invention.

In some embodiments the method may comprise overexpressing at least one gene encoding an RNA binding protein. Suitably the method may comprise expressing one or more additional copies of the at least one gene encoding an RNA binding protein in the plant or cell. Suitably the method may comprise modifying the endogenous copy of the at least one gene encoding an RNA binding protein such that its expression is increased. The method may comprise mutating the coding sequence of the at least one gene encoding an RNA binding protein. The method may comprise mutating a regulatory sequence that regulates expression of the at least one gene encoding an RNA binding protein.

Suitably the method may comprise transforming a cell of a plant (e.g. a tobacco plant) with a genetic construct which encodes at least one RNA binding protein comprising an amino acid sequence as set out in SEQ ID NO. 1, 4, 7, 10, 13, 16, 19, 22, 25 or 28, or a functional variant or functional fragment or orthologue thereof, or a sequence which has at least 80% identity to SEQ ID. NO. 1, 4, 7, 10, 13, 16, 19, 22, 25 or 28; or wherein the at least one gene encoding an RNA binding protein comprises a nucleotide sequence as set out in SEQ ID NO. 2, 3, 5, 6, 8, 9, 11, 12, 14, 15, 17, 18, 20, 21, 23, 24, 26, 27, 29 or 30 or a functional variant or functional fragment or orthologue of SEQ ID NO. 2, 3, 5, 6, 8, 9, 11, 12, 14, 15, 17, 18, 20, 21, 23, 24, 26, 27, 29 or 30 or a nucleic acid sequence which has at least 80% identity to SEQ ID NO. 2, 3, 5, 6, 8, 9, 11, 12, 14, 15, 17, 18, 20, 21, 23, 24, 26, 27, 29 or 30; or which comprises a nucleotide sequence which encodes a protein which is capable of promoting or augmenting at least one endogenous RNA binding protein. It will be appreciated that each of these options would result in an increased activity and expression of the polypeptide encoded by the at least one RNA binding protein. The method may comprise regenerating the plant from the transformed cell. There is provided use of genetic construct which is capable of increasing the activity and/or expression of a polypeptide encoded by at least one gene encoding an RNA binding protein for increasing the alkaloid content (e.g. nicotine content) in a plant or part there of or cell transformed with the construct.

The genetic construct may encode a polypeptide comprising the amino acid SEQ ID NO. 1, 4, 7, 10, 13, 16, 19, 22, 25 or 28, or a functional variant or functional fragment or orthologue thereof, or a sequence which has at least 80% identity to SEQ ID NO. 1, 4, 7, 10, 13, 16, 19, 22, 25 or 28; or wherein the at least one gene encoding an RNA binding protein comprises a nucleotide sequence as set out in SEQ ID NO. 2, 3, 5, 6, 8, 9, 11, 12, 14, 15, 17, 18, 20, 21, 23, 24, 26, 27, 29 or 30, or a functional variant or functional fragment or orthologue of SEQ ID NO. 2, 3, 5, 6, 8, 9, 11, 12, 14, 15, 17, 18, 20, 21, 23, 24, 26, 27, 29 or 30, or a nucleic acid sequence which has at least 80% identity to SEQ ID NO. 2, 3, 5, 6, 8, 9, 11, 12, 14, 15, 17, 18, 20, 21, 23, 24, 26, 27, 29 or 30.

In another embodiment, the invention relates to a method of increasing the alkaloid content of a plant or part thereof or a cell, comprising modifying said plant or cell by increasing the activity of at least one gene encoding an RNA binding protein.

In one embodiment the activity of at least one gene encoding an RNA binding protein may be increased by introducing (or providing) a mutation to at least one gene encoding an RNA binding protein.

Suitably, the activity of at least one gene encoding an RNA binding protein may be increased by introducing a mutation to at least one gene encoding an RNA binding protein which comprises an amino acid sequence as set out in SEQ ID NO.1, 4, 7, 10, 13, 16, 19, 22, 25 or 28; or a functional variant or functional fragment or orthologue thereof, or a sequence which has at least 80% identity to SEQ ID NO. 1, 4, 7, 10, 13, 16, 19, 22, 25 or 28; or wherein the at least one gene encoding an RNA binding protein comprises a nucleotide sequence as set out in SEQ ID NO. 2, 3, 5, 6, 8, 9, 11, 12, 14, 15, 17, 18, 20, 21, 23, 24, 26, 27, 29 or 30, or a functional variant or functional fragment or orthologue of SEQ ID NO. 2, 3, 5, 6, 8, 9, 11, 12, 14, 15, 17, 18, 20, 21, 23, 24, 26, 27, 29 or 30, or a nucleic acid sequence which has at least 80% identity to SEQ ID NO. 2, 3, 5, 6, 8, 9, 11, 12, 14, 15, 17, 18, 20, 21, 23, 24, 26, 27, 29 or 30.

In some embodiments a modification which increases the activity or expression of at least one gene encoding an RNA binding protein and thereby increases alkaloid content by one of the following:

modulating transcription from the at least one gene encoding an RNA binding protein;

modulating translation of the mRNA from the at least one gene encoding an RNA binding protein;

modulating release of the RNA binding protein from intracellular stores; and/or modulating the rate of degradation of the RNA binding protein.

In one aspect, the activity and or expression of an RNA binding protein as defined herein may be modulated e.g. decreased by modifying the activity or expression of an interactor protein.

Without wishing to be bound by theory, in one aspect the interactor protein may reduce or block the activity and/or expression of said RNA binding protein. For example the interactor protein may bind to and/or sequester the RNA binding protein; thus increasing the activity and/or expression of the interactor protein may reduce the activity and/or expression of the RNA binding protein.

In an alternative aspect, the interactor protein may increase or enhance the activity and/or expression of an RNA binding protein as defined herein. For example the interactor protein may act as a co-factor to the RNA binding protein; thus decreasing the activity and/or expression of the interactor protein may reduce the activity and/or expression of the RNA binding protein.

In one aspect, the activity and/or expression of an RNA binding protein may be modulated (e.g. reduced) by modifying the activity and/or expression of an interactor protein.

Suitably the interactor protein may be selected from SEQ ID NO. 38, SEQ ID NO. 41. SEQ ID NO. 44, SEQ ID NO. 47, SEQ ID NO. 50 or variants thereof having at least 80% identity thereto (such as at least 85% identity, at least 90% identity, at least 95% identity, at least 97% identity, at least 98% identity).

Suitably the interactor protein may have a coding sequence be selected from SEQ ID NO. 39, SEQ ID NO. 42. SEQ ID NO. 45, SEQ ID NO. 48, SEQ ID NO. 51 or variants thereof having at least 80% identity thereto (such as at least 85% identity, at least 90% identity, at least 95%, at least 97% identity, at least 98% identity).

Suitably the interactor protein may be encoded by a nucleotide sequence selected from SEQ ID NO. 40, SEQ ID NO. 43. SEQ ID NO. 46, SEQ ID NO. 49, SEQ ID NO. 52 or variants thereof having at least 80% identity thereto (such as at least 85% identity, at least 90% identity, at least 95%, at least 97% identity, at least 98% identity).

Alkaloid Content

In one embodiment the present invention provides a method of modulating the alkaloid content of a plant (e.g. a tobacco plant) or a part thereof, the method comprising modifying said plant by modulating the activity or expression of at least one gene encoding an RNA binding protein.

The term "modulating" is used herein to mean either increasing or decreasing.

The term "increasing alkaloid content" is used herein to mean that the alkaloid content in the product of the present invention (e.g. plant, part thereof (e.g. leaf), processed leaf or a product made from the plant (e.g. a tobacco industry product)) is higher compared with a comparable product which has not been modified in accordance with the present invention.

The term "decreasing alkaloid content" is used herein to mean that alkaloid content in the product of the present invention (e.g. plant, part thereof (e.g. leaf), processed leaf or a product made from the plant (e.g. a tobacco industry product)) is lower compared with a comparable product which has not be modified in accordance with the present invention.

In some embodiments, the modulation of alkaloid content refers to an increase in alkaloid content wherein the activity or expression of at least one gene encoding an RNA binding proteindomain-containing protein is increased (or in other words the protein is overexpressed).

In some embodiments, the modulation of alkaloid content refers to a decrease in alkaloid content wherein the expression of at least one gene encoding an RNA binding protein is decreased or inhibited or eliminated.

In a further aspect, the alkaloid content is measured from leaves. In one aspect the alkaloid content is measured from green leaves. In a further aspect, the alkaloid content is measured from cured leaves, e.g. air-cured, flue-cured, fire-cured or sun-cured leaves. In a further aspect, the alkaloid content is measured from flue-cured leaves. In a further aspect, the alkaloid content is measured from air-cured leaves.

The term "alkaloid content" is used herein to mean the concentration and/or total amount of the entire group of compounds classified as alkaloids or the concentration and/or total amount of one or more compounds classified as alkaloids. Alkaloids typically present in tobacco include nornicotine, PON, anatabine, anabasine, nicotine, and myosmine. In some embodiments the content of one or more alkaloids, such as two or more alkaloids, such as three or more alkaloids, such as four or more alkaloids, such as five or more alkaloids, such as all six alkaloids, selected from nicotine, nornicotine, PON, anatabine, anabasine and myosmine is modulated. In some embodiments the content of one or more alkaloids, such as two or more alkaloids, such as three or more alkaloids, such as four or more alkaloids, such as five or more alkaloids, such as all six alkaloids, selected from nicotine, nornicotine, PON, anatabine, anabasine and myosmine is increased. In some embodiments the content of one or more alkaloids, such as two or more alkaloids, such as three or more alkaloids, such as four or more alkaloids, such as five or more alkaloids, such as all six alkaloids, selected from nicotine, nornicotine, PON, anatabine, anabasine and myosmine is decreased. In some embodiments the total alkaloid content of the plant or cell is modulated. In some embodiments the total alkaloid content is increased. In some embodiments the total alkaloid content is increased.

Any method known in the art for determining the concentration and/or total content of alkaloids may be used. One preferred method for analysing alkaloid content involves the analysis by gas chromatography-flame ionization detection method (GC-FID) or by reversed phase high performance liquid chromatography with tandem mass spectrometry (LC-MS/MS).

In one embodiment there is provided a method for producing a plant (e.g. a tobacco plant) or part thereof, a plant propagation material (e.g. a tobacco plant propagation material), a cell (e.g. a tobacco cell), a leaf (e.g. a tobacco leaf), a harvested leaf (e.g. a harvested tobacco leaf), a cut harvested leaf (e.g. a cut harvested tobacco leaf), a processed leaf (e.g. a processed tobacco leaf), a cut and processed leaf (e.g. a cut and processed tobacco leaf), a product comprising said plant or part thereof (e.g. a tobacco industry product) or combinations thereof obtainable or obtained by a plant of the invention which has modulated alkaloid content, the method comprising modifying said plant to modulate the activity or expression of a gene encoding an RNA binding protein. The modulated alkaloid content may be determined by comparing the alkaloid content in the plant (e.g. tobacco plant) or part thereof, plant propagation material (e.g. tobacco plant propagation material), a cell (e.g. a tobacco cell), leaf (e.g. tobacco leaf), harvested leaf (e.g. a harvested tobacco leaf), cut harvested leaf (e.g. a cut harvested tobacco leaf), processed leaf (e.g. processed tobacco leaf), cut and processed leaf (e.g. cut and processed tobacco leaf), a product comprising a plant or part thereof of the present invention, e.g. a tobacco industry product, or combinations thereof with a comparable product.

Suitably the alkaloid content may be modulated in a plant, e.g. a tobacco plant e.g. modified tobacco plant. Suitably the alkaloid content may be modulated in a leaf (e.g. a tobacco leaf e.g. a tobacco leaf from a modified tobacco plant). Suitably the alkaloid content may be modulated in a harvested leaf (e.g. a harvested tobacco leaf from a modified tobacco plant). Suitably the alkaloid content may be modulated in a cut harvested leaf (e.g. a cut harvested tobacco leaf from a modified tobacco plant). Suitably the alkaloid content may be modulated in a processed leaf (e.g. a processed tobacco leaf e.g. a processed tobacco leaf from a modified tobacco plant). Suitably the alkaloid content may be modulated in a cut and processed leaf (e.g. a cut and processed tobacco leaf e.g. a cut and processed tobacco leaf from a modified tobacco plant). Suitably the alkaloid content may be modulated in a cured leaf (e.g. cured a tobacco leaf from a modified tobacco plant). Suitably the alkaloid content may be modulated in an extract of a green leaf (e.g. a green tobacco leaf from a modified tobacco plant). Suitably the alkaloid content may be modulated in a product comprising the plant of the present invention or part thereof (e.g. a tobacco industry product, for example a tobacco industry product produced from a modified tobacco plant or part thereof). Suitably the alkaloid content may be modulated in any one of the above products or combinations thereof. Suitably the modulation of alkaloid content described above may be an increase in alkaloid content. Suitably the modulation of alkaloid content described above may be a decrease in alkaloid content (e.g. a decrease in nornicotine and/or PON content).

In one embodiment the content of one or more alkaloids selected from nornicotine, PON, anatabine and anabasine is decreased. In one embodiment the content of nornicotine is decreased. In one embodiment the content of PON is decreased. In one embodiment the content of anatabine is decreased. In one embodiment the content of anabasine is decreased.

In one embodiment the nicotine content of a modified plant (e.g. tobacco plant), plant propagation material (e.g. tobacco plant propagation material), leaf (e.g. tobacco leaf), harvested leaf (e.g. harvested tobacco leaf), cut harvested leaf (e.g. cut harvested tobacco leaf), processed leaf (e.g. processed tobacco leaf), cut and processed leaf (e.g. cut and processed tobacco leaf) or tobacco industry product from a modified tobacco plant is not substantially decreased. Suitably, the nicotine content is at least 85% (such as at least 90%, such as at least 95%, such as at least 98%, such as at least 99%) of the nicotine content of a comparable product.

In one embodiment the alkaloid content of a plant (e.g. tobacco plant) or part thereof may be modulated by at least 0.5, 1.5, 2, 3 or 4 fold when compared to the alkaloid content of a plant (e.g. tobacco plant) or part thereof, respectively, which has not been modified to modulate the activity or expression of at least one gene encoding an RNA binding protein and which has been grown under similar growth conditions. Suitably the alkaloid content may be modulated by about 0.5 fold to about 4 fold. Suitably the alkaloid content may be modulated by about 4 fold. Suitably the modification may be an increase or a decrease in alkaloid content. Suitably the modulation may be of one or more alkaloids selected from nicotine, nornicotine, PON, anatabine, anabasine and myosmine. Suitably the modulation may be of one or more alkaloids selected from nicotine, nornicotine, PON, anatabine and anabasine. Suitably, the nornicotine content may be reduced. Suitably, the PON content may be reduced. Suitably, the anatabine content may be reduced. Suitably, the anabasine content may be reduced.

In one embodiment of the invention the alkaloid content of a plant (e.g. a tobacco plant) or part thereof may be modulated by at least 1%, 2%, 5%, 8%, 10%, 12%, 15%, 20%, 25%, 30%, 40%, 50%, 60%, 70%, 80%, 90% or 100% in comparison to a plant (e.g. a tobacco plant) or part thereof which has not been modified according to the present invention. In one embodiment the alkaloid content may be modulated by at least 30% in comparison to an unmodified plant or part thereof. In one embodiment the alkaloid content may be modulated by at least 40% in comparison to an unmodified plant or part thereof. In one embodiment the alkaloid content may be modulated by at least 50% in comparison to an unmodified plant or part thereof. In one embodiment the alkaloid content may be modulated by at least 60% in comparison to an unmodified plant or part thereof. The modulation may be an increase or a decrease in alkaloid content when compared to an unmodified plant (e.g. a tobacco plant) or part thereof.

Suitably the modulation may be of total alkaloid content. Suitably the modulation may be of one or more alkaloids selected from nicotine, nornicotine, PON, anatabine, anabasine and myosmine. Suitably the modulation may be of one or more alkaloids selected from nornicotine, nicotine, PON, anatabine and anabasine. Suitably the modulation may be of nornicotine content, such as decrease in nornicotine content. Suitably the modulation may be of anabasine content, such as decrease in anabasine content. Suitably the modulation may be of PON content, such as decrease in PON content. Suitably the modulation may be of anatabine content, such as decrease in anatabine content.

Suitably the modulation may be of more than one alkaloid, such as two or more alkaloids, such as three or more alkaloids, such as four or more alkaloids, such as five or more alkaloids, such as all six alkaloids, selected from nicotine, nornicotine, PON, anatabine, anabasine and myosmine.

In some embodiments the alkaloid content of the plant may be modulated by between about 5% and about 100%, by between about 10% and about 90%, by between about 20% and about 80%, by between about 30% and about 70%, by between about 40% and 60%, by between about 40% and 50%, or by between about 50% and 60%.

Tobacco-Specific Nitrosamine (TSNA) Content

In one embodiment the present invention provides a method of decreasing the content of at least one tobacco-specific nitrosamine (TSNA) precursor in a plant (e.g. a tobacco plant) or a part thereof or in a tobacco cell. Suitably, the method may comprise modifying said plant by modulating the activity or expression of at least one gene encoding an RNA binding protein. In one embodiment, the present invention provides a method of producing a processed leaf with decreased TSNA content (e.g. relative to a comparable product). The method of producing a processed leaf with decreased TSNA content may comprise:

modifying a plant by decreasing or inhibiting the activity or expression of at least one gene encoding an RNA binding protein;

harvesting a leaf from said plant;

and processing e.g. curing said harvested leaf.

The TSNA may be measured in a processed tobacco, e.g. cured tobacco or reconstituted tobacco. In one embodiment the TSNA content is measured and/or modified (e.g. reduced) in a cured tobacco plant or part thereof (e.g. in cured tobacco leaf).

The term "tobacco-specific nitrosamine" or "TSNA" as used herein has its usual meaning in the art, namely a nitrosamine which is found only in tobacco industry products or other nicotine-containing products. Suitably the at least one tobacco-specific nitrosamine may be N'-nitrosonornicotine (NNN), 4-(methylnitrosamino)-1-(3-pyridyl)-1-butanone (NNK), N'-nitrosoanatabine (NAT) or N-nitrosoanabasine (NAB).

The term "precursor thereto" when used in relation to at least one tobacco-specific nitrosamine refers to one or more chemicals or compounds of a tobacco plant that give rise to the formation of a tobacco-specific nitrosamine or are involved in the nitrosation reaction leading to tobacco-specific nitrosamine production.

In one embodiment the TSNA may be one or more of group selected from: N'-nitrosonornicotine (NNN), 4-(methyl nitrosamino)-1-(3-pyridyl)-1-butanone (NNK), N'nitrosoanatabine (NAT) and N'-nitrosoanabasine (NAB). Suitably the at least one tobacco-specific nitrosamine may be NNK or NNN. In one embodiment the tobacco-specific nitrosamine is NNN. In another embodiment the tobacco-specific nitrosamine is NNK.

In one embodiment the precursor of the TSNA is one or more of the group selected from nornicotine, anabasine, anatabine, and an oxidised derivative of nicotine such as pseudooxynicotine (PON).

In one embodiment the TSNA is N'nitrosonornicotine (NNN) and/or the precursor is nornicotine. In one embodiment the content of NNN is decreased. In one embodiment the content of nornicotine is decreased. In one embodiment the content of NNN and nornicotine is decreased.

In one embodiment the TSNA is 4-(methylnitrosamino)-1-(3-pyridyl)-1-butanone (NNK) and/or the precursor is PON. In one embodiment the content of NNK is decreased. In one embodiment the content of PON is decreased. In one embodiment the content of NNK and PON is decreased.

In one embodiment the TSNA is N'nitrosoanatabine (NAT) and/or the precursor is anatabine. In one embodiment the content of NAT is decreased. In one embodiment the content of anatabine is decreased. In one embodiment the content of NAT and anatabine is decreased.

In one embodiment the TSNA is N'-nitrosoanabasine (NAB) and/or the precursor is anabasine.

In one embodiment the content of NAB is decreased. In one embodiment the content of nornicotine is decreased. In one embodiment the content of NAB and anabasine is decreased.

The precursor of the TSNA (e.g. NNK, NNN, NAB and/or NAT) may be measured in green tobacco leaf, e.g. prior to processing, e.g. prior to curing. In one embodiment the precursor of the TSNA (e.g. NNK, NNN, NAB and/or NAT) is measured and/or modified (e.g. reduced) in a green tobacco leaf, e.g. prior to processing, e.g. prior to curing.

In one embodiment carrying out a method and or use of the invention results in a reduction of at least one TSNA or a precursor thereto in the modified tobacco plant (or part thereof) when compared to a tobacco plant (or part thereof) which has not been modified in accordance with the present invention.

The terms "reducing at least one TSNA or precursor thereto" or "reduction of at least one TSNA or precursor thereto" are used herein to mean that the concentration and/or total content of the at least one TSNA or precursor thereto in the product, method or use of the invention is lower in relation to a comparable product, method or use. For example, a comparable tobacco industry product would be derived from a tobacco plant which had not been modified according to the present invention, but in which all other relevant features were the same (e.g. plant species, growing conditions, method of processing tobacco, etc.).

Any method known in the art for determining the concentration and/or levels of at least one TSNA or precursor thereto may be used. In particular a method such may comprise the addition of deuterium labelled internal standard, an aqueous extraction and filtration, followed by analysis using reversed phase high performance liquid chromatography with tandem mass spectrometry (LC-MS/MS) may be used. Other examples for determining the concentration and/or level of a precursor to a tobacco-specific nitrosamine include a method such as the one detailed in CORESTA recommended method CRM-72: Determination of Tobacco Specific Nitrosamines in Tobacco and Tobacco Products by LC-MS/MS; CRM being developed into ISO/DIS 21766 or Wagner et al. (2005) Analytical Chemistry 77(4), 1001-1006 all of which are incorporated herein by reference.

Suitably the concentration and/or total content of the at least one tobacco-specific nitrosamine or precursor thereto may be reduced by carrying out a method and/or use of the present invention. Suitably the concentration and/or level of the at least one tobacco-specific nitrosamine or precursor thereto may be reduced in a tobacco plant of the invention (e.g. obtainable or obtained by a method and/or use of the invention) when compared to the concentration and/or level of the at least one tobacco-specific nitrosamine(s) or precursor thereto in a tobacco plant which has not been modified in accordance with present invention.

The concentration and/or total content of the at least one tobacco-specific nitrosamine(s) or precursor thereto may be reduced in a tobacco leaf, harvested leaf, processed tobacco leaf, tobacco industry product or combinations thereof obtainable or obtained from a tobacco plant (or part of a tobacco plant or a tobacco cell culture) of the invention when compared with a tobacco leaf, harvested leaf, processed tobacco leaf, tobacco industry product or combinations thereof obtainable or obtained from a tobacco plant (or part of a tobacco plant or a tobacco cell culture) which has not been modified in accordance with the present invention.

Suitably the concentration and/or total content of the at least one tobacco-specific nitrosamine or precursor thereto may be reduced in a processed tobacco leaf.

Suitably the concentration and/or level of the at least one tobacco-specific nitrosamine or precursor thereto may be reduced in a tobacco industry product.

In one embodiment the at least one tobacco-specific nitrosamine or precursor thereto may be reduced by at least about 1%, at least about 3%, at least about 5%, at least about 10%, at least about 20%, at least about 30%, at least about 40% or at least about 50%. In some embodiments the at least one tobacco-specific nitrosamine or precursor thereto may be reduced by between about 5% and about 50%, by between about 10% and about 50%, by between about 20% and about 50%, by between about 30% and about 50%, or by between about 40% and 50%.

In relation to processed (e.g. cured) tobacco leaf (e.g. cured or reconstituted), the at least one tobacco-specific nitrosamine or precursor thereto may be reduced by between about 5000 ng/g and about 50 ng/g, by between about 4000 ng/g and about 100 ng/g, by between about 3000 ng/g and 500 ng/g or by between 2000 ng/g and 1000 ng/g. In some embodiments the at least one tobacco-specific nitrosamine or precursor thereto may be reduced by at least about 5000 ng/g, at least about 4000 ng/g, at least about 3000 ng/g, at least about 2000 ng/g, at least about 1000 ng/g, at least about 500 ng/g, at least about 100 ng/g or at least about 50 ng/g.

Biomass Production

In some instances, it may be desirable to produce plants or biomass with high alkaloid levels e.g. high levels of nicotine content so that nicotine may be purified to produce a pure nicotine product for example for use in devices which utilize liquid containing nicotine (e.g. e-cigarettes) or within tobacco heating devices. For example, the production of nicotine in this way could reduce costs of nicotine extraction for the production of e-liquids for e-cigarettes.

In one aspect, the present invention provides a method of producing a biomass comprising: growing a cell which has been engineered to modulate (e.g. increase) the activity or expression of a gene encoding an RNA binding protein under conditions to produce a biomass. Suitably, the activity or expression of an RNA binding protein may be increased in order to increase the concentration and/or total nicotine content.

In one embodiment, the present invention provides a method of producing a biomass having modified (e.g. increased) concentration and/or total content of nicotine, comprising growing a cell which has been engineered to increase the activity or expression of at least one gene encoding an RNA binding protein comprising an amino acid sequence as set out in SEQ ID NO. 1, 4, 7, 10, 13, 16, 19, 22, 25 or 28, or a functional variant or functional fragment or orthologue thereof, or a sequence which has at least 80% identity to SEQ ID NO. 1, 4, 7, 10, 13, 16, 19, 22, 25 or 28; or wherein the at least one gene encoding an RNA binding protein comprises a nucleotide sequence as set out in SEQ ID NO. 2, 3, 5, 6, 8, 9, 11, 12, 14, 15, 17, 18, 20, 21, 23, 24, 26, 27, 29 or 30, or a functional variant or functional fragment or orthologue of SEQ ID NO. 2, 3, 5, 6, 8, 9, 11, 12, 14, 15, 17, 18, 20, 21, 23, 24, 26, 27, 29 or 30 or a nucleic acid sequence which has at least 80% identity to SEQ ID NO. 2, 3, 5, 6, 8, 9, 11, 12, 14, 15, 17, 18, 20, 21, 23, 24, 26, 27, 29 or 30.

The cell may be engineered by any method known in the art to modify the activity or expression of at least one gene encoding an RNA binding protein. Suitably, the cell may be engineered to express an exogenous gene encoding an RNA binding protein. Suitably, the cell may be engineered to overexpress a gene encoding an RNA binding protein.

Suitably, the biomass may contain a higher concentration and/or total content of nicotine compared with the biomass produced by a comparable cell which has not been modified in accordance with the present invention.

Suitably the cell for use in biomass production may be a plant cell, such as a tobacco cell.

Suitably the cell for use in biomass production may be a yeast cell.

In one embodiment the cell (e.g. yeast cell) may be further modified to comprise one or more sequences that increases nicotinic alkaloid biosynthesis. Suitably these one or more sequences may be incorporated into a nucleic acid construct that is suitable for cell (e.g. yeast cell) transformation. The one or more sequences may be overexpressed in the cell (e.g. yeast cell). The sequences may be selected from one or more of the following genes: MPO (or Methylputrescine Oxidase or MPO1 or MPO2); A622 (or Isoflavone reductase-like protein or Isoflavone reductase homolog or Isoflavone reductase-like protein); BBL (or Berberine bridge enzyme or Berberine bridge enzyme-like or BBE or NBB1); PMT (or Putrescine N-Methyltransferase or putrescine methyltransferase or S-adenosyl-L-methionine: putrescine N-methyltransferase or PMT or PMT1 or PMT2 or PMT3 or PMT4) and QPT (or quinolinate phosphoribosyltransferase). In one embodiment the sequences may be selected from one or more of the following genes: BBL, A622, PMT and MPO (MPO1 or MPO2). Genes suitable for modification in this way may be taught in US2016032299 for example, which is incorporated herein by reference.

Commercially Desirable Traits

In one embodiment the plants of the present invention have modified (i.e. increased or decreased) total alkaloid content and/or modified (i.e. increased or decreased) content of one or more alkaloids, whilst the flavour characteristics and/or other commercially desirable traits are at least maintained. Suitably, the plants of the present invention may have decreased total alkaloid content and/or decreased content of one or more alkaloids, whilst the flavour characteristics and/or other commercially desirable traits are at least maintained.

In one embodiment the plants of the present invention produce leaves of a similar grade and/or quality to plants which have not been modified according to the invention.

In one embodiment the plants of the present invention have reduced nornicotine and/or PON and/or anabasine and/or anatabine content without a significant change in the flavour characteristics of the plant (e.g. compared with the same plant which has not been modified in accordance with the present invention).

In one embodiment the plants of the present invention have decreased TSNA precursor content without a significant change (e.g. decrease) in other commercially desirable traits of the plant (e.g. compared with the same plant which has not been modified in accordance with the present invention). In particular the yield of the modified plant is preferably not reduced compared with the same plant which has not been modified in accordance with the present invention.

Therefore in one embodiment the methods and uses of the present invention relate to decreasing TSNA precursor content whilst maintaining the flavour characteristics and/or other commercially desirable traits (e.g. yield).

The term "commercially desirable traits" as used herein will include traits such as yield, mature plant height, harvestable leaf number, average node length, cutter leaf length, cutter leaf width, quality (e.g. leaf quality, suitably cured leaf quality), abiotic (for instance drought) stress tolerance, herbicide tolerance and/or biotic (for instance insect, bacteria or fungus) stress tolerance.

Leaf quality may be measured based on colour, texture and aroma of the cured leaf, for example according to United States Department of Agriculture (USDA) grades and standards.

Tobacco grades are evaluated based on factors including, but not limited to, the leaf stalk position, leaf size, leaf colour, leaf uniformity and integrity, ripeness, texture, elasticity, sheen (related with the intensity and the depth of coloration of the leaf as well as the shine), hygroscopicity (the faculty of the tobacco leaves to absorb and to retain the ambient moisture), and green nuance or cast.

Leaf grade can be determined using standard methods known in the art, for example, using an Official Standard Grade published by the Agricultural Marketing Service of the US Department of Agriculture (7 U.S.C. § 511). See, e.g., Official Standard Grades for Burley Tobacco (U.S. Type 31 and Foreign Type 93), effective Nov. 5, 1990 (55 F. R. 40645); Official Standard Grades for Flue-Cured Tobacco (U.S. Types 11, 12, 13, 14 and Foreign Type 92), effective Mar. 27, 1989 (54 F. R. 7925); Official Standard Grades for Pennsylvania Seedleaf Tobacco (U.S. Type 41), effective Jan. 8, 1965 (29 F. R. 16854); Official Standard Grades for Ohio Cigar-Leaf Tobacco (U.S. Types 42, 43, and 44), effective Dec. 8, 1963 (28 F. R. 11719 and 28 F. R. 11926); Official Standard Grades for Wisconsin Cigar-Binder Tobacco (U.S. Types 54 and 55), effective Nov. 20, 1969 (34 F. R. 17061); Official Standard Grades for Wisconsin Cigar-Binder Tobacco (U.S. Types 54 and 55), effective Nov. 20, 1969 (34 F. R. 17061); Official Standard Grades for Georgia and Florida ShadeGrown Cigar-Wrapper Tobacco (U.S. Type 62), Effective April 1971. A USDA grade index value can be determined according to an industry accepted grade index. See e.g. Bowman et al. (1988) Tobacco Science, 32:39-40; Legacy Tobacco Document Library (Bates Document #523267826-523267833, Jul. 1, 1988, Memorandum on the Proposed Burley Tobacco Grade Index); and Miller et al. (1990) Tobacco Intern., 192:55-57 (all foregoing references are incorporated herein in their entirety).

In one aspect, a USDA grade index is a 0-100 numerical representation of federal grade received and is a weighted average of all stalk positions. A higher grade index indicates higher quality. Alternatively, leaf grade may be determined via hyper-spectral imaging. See e.g. WO 2011/027315 (which is incorporated herein by reference).

In one embodiment, a tobacco plant of the present invention provides tobacco of commercially acceptable grade.

Suitably, the tobacco plant of the present invention provides cured tobacco of commercially acceptable grade.

In one embodiment, a tobacco plant of the present invention is capable of producing leaves having a USDA grade index value of at least about 70% of the USDA grade index value of leaves of a comparable plant when grown in similar growth conditions. Suitably, tobacco plants disclosed herein may be capable of producing leaves having a USDA grade index value of at least about 65%, at least about 70%, at least about 75%, at least about 80%, at least about 85%, at least about 90%, at least about 95%, or at least about 98% of the USDA grade index value of a control plant when grown in similar growth conditions. Suitably, tobacco plants disclosed herein may be capable of producing leaves having a USDA grade index value of between 65% and 130%, between 70% and 130%, between 75% and 130%, between 80% and 130%, between 85% and 130%, between 90% and 130%, between 95% and 130%, between 100% and 130%, between 105% and 130%, between 110% and 130%, between 115% and 130%, or between 120% and 130% of the USDA grade index value of a comparable plant.

In one aspect, the tobacco plant of the present invention is capable of producing leaves having a USDA grade index value of at least 50. Suitably, tobacco plants disclosed herein may be capable of producing leaves having a USDA grade index value of 55 or more, 60 or more, 65 or more, 70 or more, 75 or more, 80 or more, 85 or more, 90 or more, and 95 or more.

Unless specified otherwise, used herein, tobacco yield refers to cured leaf yield which is calculated based on the weight of cured tobacco leaves per acre under standard field conditions following standard agronomic and curing practice.

In one aspect, a plant (e.g. a tobacco plant) of the present invention has a yield between 50% and 150%, between 55% and 145%, between 60% and 140%, between 65% and 135%, between 70% and 130%, between 75% and 125%, between 80% and 120%, between 85% and 115%, between 90% and 110%, between 95% and 105%, between 50% and 100%, between 55% and 100%, between 60% and 100%, between 65% and 100%, between 70% and 100%, between 75% and 100%, between 80% and 100%, between 85% and 100%, between 90% and 100%, between 95% and 100%, between 100% and 150%, between 105% and 150%, between 110% and 150%, between 115% and 150%, between 120% and 150%, between 125% and 150%, between 130% and 150%, between 135% and 150%, between 140% and 150%, or between 145% and 150% of the yield of a comparable plant when grown in similar field conditions.

In another aspect, the plant (e.g. a tobacco plant) yield of the present invention is approximately 1.5, 1.6, 1.7, 1.8, 1.9, 2.0, 2.1, 2.2, 2.3, 2.4, 2.5, 2.6, 2.7, 2.8, 2.9, or 3.0 times of the yield of a comparable plant when grown in similar field conditions.

In another aspect, the yield of a tobacco plant of the present invention is comparable to the yield of the flue cured comparable plant when grown in similar field conditions.

In one aspect, a tobacco plant of the present invention provides a yield selected from the group consisting of about between 1200 and 3500, between 1300 and 3400, between 1400 and 3300, between 1500 and 3200, between 1600 and 3100, between 1700 and 3000, between 1800 and 2900, between 1900 and 2800, between 2000 and 2700, between 2100 and 2600, between 2200 and 2500, and between 2300 and 2400 lbs/acre.

In another aspect, a tobacco plant of the present invention provides a yield selected from the group consisting of about between 1200 and 3500, between 1300 and 3500, between 1400 and 3500, between 1500 and 3500, between 1600 and 3500, between 1700 and 3500, between 1800 and 3500, between 1900 and 3500, between 2000 and 3500, between 2100 and 3500, between 2200 and 3500, between 2300 and 3500, between 2400 and 3500, between 2500 and 3500, between 2600 and 3500, between 2700 and 3500, between 2800 and 3500, between 2900 and 3500, between 3000 and 3500, and between 3100 and 3500 lbs/acre.

In a further aspect, a tobacco plant of the present invention provides a yield selected from the group consisting of about between 1200 and 3500, between 1200 and 3400, between 1200 and 3300, between 1200 and 3200, between 1200 and 3100, between 1200 and 3000, between 1200 and 2900, between 1200 and 2800, between 1200 and 2700, between 1200 and 2600, between 1200 and 2500, between 1200 and 2400, between 1200 and 2300, between 1200 and 2200, between 1200 and 2100, between 1200 and 2000, between 1200 and 1900, between 1200 and 1800, between 1200 and 1700, between 1200 and 1600, between 1200 and 1500, and between 1200 and 1400 lbs/acre.

Plant Breeding

In one embodiment the present invention provides a method of producing a plant having a modified alkaloid content and/or modified content of a tobacco specific nitrosamine (TSNA) precursor comprising:
  a. crossing a donor plant having modified nicotine content and/or modified content of a tobacco specific nitrosamine (TSNA) precursor and wherein the activity or expression of at least one gene encoding an RNA binding protein according to the present invention has been modulated in the donor plant in accordance with the present invention with a recipient tobacco plant that does not have modified nicotine content or modified content of a tobacco specific nitrosamine (TSNA) precursor and possesses commercially desirable traits;
  b. isolating genetic material from a progeny of said donor plant crossed with said recipient plant; and
  c. performing molecular marker-assisted selection with a molecular marker comprising:
    i. identifying an introgressed region comprising a mutation in a polynucleotide sequence encoding a protein defined in a.

Suitably, the activity or expression of a protein comprising an amino acid sequence as set out in SEQ ID NO. 1, 4, 7, 10, 13, 16, 19, 22, 25 or 28, or a functional variant or functional fragment or orthologue thereof, or a sequence which has at least 80% identity to SEQ ID NO. 2, 3, 5, 6, 8, 9, 11, 12, 14, 15, 17, 18, 20, 21, 23, 24, 26, 27, 29 or 30; or a protein encoded by a nucleotide sequence as set out in SEQ ID NO. 2, 3, 5, 6, 8, 9, 11, 12, 14, 15, 17, 18, 20, 21, 23, 24, 26, 27, 29 or 30 or a functional variant or functional fragment or orthologue of SEQ ID NO. 2, 3, 5, 6, 8, 9, 11, 12, 14, 15, 17, 18, 20, 21, 23, 24, 26, 27, 29 or 30 or a nucleic acid sequence which has at least 80% identity to SEQ ID NO. 2, 3, 5, 6, 8, 9, 11, 12, 14, 15, 17, 18, 20, 21, 23, 24, 26, 27, 29 or 30 is modulated in the donor plant when compared to a comparable plant. Suitably, the alkaloid content and/or TSNA precursor content is decreased by said method. Suitably, the alkaloid content and/or TSNA precursor content is decreased and the activity or expression of said RNA binding protein is decreased or inhibited.

The molecular marker assisted selection may comprise performing PCR to identify an introgressed nucleic acid sequence comprising a mutation which modulates the activity or expression of a protein comprising the amino acid sequence shown as SEQ ID NO. 1, 4, 7, 10, 13, 16, 19, 22, 25 or 28 or an amino acid sequence which has at least 80% identity thereto.

Plants

In one embodiment, the present invention relates to methods of modulating (e.g. decreasing) alkaloid content in plants, or parts thereof or plant cells.

Suitable plants according to the invention include the Solanaceae family of plants which include, for example jimson weed, eggplant, mandrake, deadly nightshade (*Belladonna*), *Capsicum* (paprika, chilli pepper), potato and tobacco.

In one embodiment a suitable genus of Solanaceae is *Nicotiana*, e.g. *Nicotiana tabacum* or *Nicotiana rustica*.

A suitable species of *Nicotiana* may be *Nicotiana tabacum*. Species of *Nicotiana* may be referred to herein as a tobacco plant, or simply tobacco.

Tobacco Plants

The present invention provides methods, uses directed to plants (e.g. tobacco plants) as well as a cell (e.g. a tobacco cell), a plant (e.g. a tobacco plant) and a plant propagation material.

The term "tobacco plant" as used herein refers to a plant in the genus *Nicotiana* that is used in the production of tobacco industry products. Non-limiting examples of suitable "tobacco" plants include *N. tabacum* and *N. rustica* (for example, *N. tabacum* L., LA B21, LN KY171, TI 1406, Basma, Galpao, Perique, Beinhart 1000-1, and Petico).

In one aspect, the tobacco plant according to the present invention is a non-naturally occurring tobacco plant. Suitably, the tobacco plant may be a mutant, non-naturally occurring tobacco plant. Suitably, the tobacco plant may be a transgenic tobacco plant.

In one aspect, the tobacco plant according to the present invention comprises a non-naturally occurring mutation which modulates (e.g. decreases) the activity or expression of at least one RNA binding protein as defined herein. Suitably, the tobacco plant may comprise a mutation which has been introduced.

The tobacco material can be derived or obtained from varieties of *Nicotiana tabacum* types, commonly known as Burley varieties, flue or bright varieties and dark varieties. In some embodiments, the tobacco material is derived from a Burley, Virginia or a dark tobacco plant. The tobacco plant may be selected from Burley tobacco, rare tobacco, speciality tobacco, expanded tobacco or the like.

The use of tobacco cultivars and elite tobacco cultivars is also contemplated herein. The tobacco plant for use herein may therefore be a tobacco variety or elite tobacco cultivar. Particularly useful *Nicotiana tabacum* varieties include Flue-cured Virginia type, Burley type, and Oriental type.

In some embodiments, the tobacco plant may be, for example, selected from one or more of the following varieties: L. cultivar T. I. 1068, AA 37-1, B 13P, Xanthi (Mitchell-Mor), KT D #3 Hybrid 107, Bel-W3, 79-615, Samsun Holmes NN, F4 from cross BU21×Hoja Parado, line 97, KTRDC #2 Hybrid 49, KTRDC #4 Hybrid 1 10, Burley 21, PM016, KTRDC #5 KY 160 SI, KTRDC #7 FCA, KTRDC #6 TN 86 SI, PM021, K 149, K 326, K 346, K 358, K 394, K 399, K 730, KY 10, KY 14, KY 160, KY 17, KY 8959, KY 9, KY 907, MD 609, McNair 373, NC 2000, PG 01, PG 04, P01, P02, P03, RG 11, RG 17, RG 8, Speight G-28, TN 86, TN 90, VA 509, AS44, Banket A1, Basma Drama B84/31, Basma I Zichna ZP4/B, BasmaXanthi BX 2A, Batek, Besuki Jember, C104, Coker 319, Coker 347, Criollo Misionero, PM092, Delcrest, Djebel 81, DVH 405, Galpao Comum, HB04P, Hicks Broadleaf, Kabakulak Elassona, PM102, Kutsage E1, KY 14×L8, KY 171, LA BU 21, McNair 944, NC 2326, NC 71, NC 297, NC 3, PVH 03, PVH 09, PVH 19, PVH 21 10, Red Russian, Samsun, Saplak, Simmaba, Talgar 28, PM132, Wislica, Yayaldag, NC 4, TR Madole, Prilep HC-72, Prilep P23, Prilep PB 156/1, Prilep P12-2/1, Yaka JK-48, Yaka JB 125/3, T1-1068, KDH-960, TI-1070, TW136, PM204, PM205, Basma, TKF 4028, L8, TKF 2002, TN 90, GR141, Basma xanthi, GR149, GR153, and Petit Havana.

Non-limiting examples of varieties or cultivars are: BD 64, CC 101, CC 200, CC 27, CC 301, CC 400, CC 500, CC 600, CC 700, CC 800, CC 900, Coker 176, Coker 319, Coker 371 Gold, Coker 48, CD 263, DF91 1, DT 538 LC, Galpao tobacco, GL 26H, GL 350, GL 600, GL 737, GL 939, GL 973, HB 04P, HB 04P LC, HB3307PLC, Hybrid 403LC, Hybrid 404LC, Hybrid 501 LC, K 149, K 326, K 346, K 358, K394, K 399, K 730, KDH 959, KT 200, KT204LC, KY10, KY14, KY 160, KY 17, KY 171, KY 907, KY907LC, KTY14×L8 LC, Little Crittenden, McNair 373, McNair 944, msKY 14×L8, Narrow Leaf Madole, Narrow Leaf Madole LC, NBH 98, N-126, N-777LC, N-7371 LC, NC 100, NC 102, NC 2000, NC 291, NC 297, NC 299, NC 3, NC 4, NC 5, NC 6, NC7, NC 606, NC 71, NC 72, NC 810, NC BH 129, NC 2002, Neal Smith Madole, OXFORD 207, PD 7302 LC, PD 7309 LC, PD 7312 LC 'Periq'e' tobacco, PVH03, PVH09, PVH19, PVH50, PVH51, R 610, R 630, R 7-1 1, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight NF3, TI 1406, TI 1269, TN 86, TN86LC, TN 90, TN 97, TN97LC, TN D94, TN D950, TR (Tom Rosson) Madole, VA 309, VA359, AA 37-1, B 13P, Xanthi (Mitchell-Mor), Bel-W3, 79-615, Samsun Holmes NN, KTRDC number 2 Hybrid 49, Burley 21, KY 8959, KY 9, MD 609, PG 01, PG 04, P01, P02, P03, RG 1 1, RG 8, VA 509, AS44, Banket A1, Basma Drama B84/31, Basma I Zichna ZP4/B, Basma Xanthi BX 2A, Batek, Besuki Jember, C104, Coker 347, Criollo Misionero, Delcrest, Djebel 81, DVH 405, Galpao Comum, HB04P, Hicks Broadleaf, Kabakulak Elassona, Kutsage E1, LA BU 21, NC 2326, NC 297, PVH 21 10, Red Russian, Samsun, Saplak, Simmaba, Talgar 28, Wislica, Yayaldag, Prilep HC-72, Prilep P23, Prilep PB 156/1, Prilep P12-2/1, Yaka JK-48, Yaka JB 125/3, TI-1068, KDH-960, TI-1070, TW136, Basma, TKF 4028, L8, TKF 2002, GR141, Basma xanthi, GR149, GR153, Petit Havana. Low converter subvarieties of the above, even if not specifically identified herein, are also contemplated.

The tobacco plant may be a Burley, Flue-cured Virginia, or Oriental.

In one embodiment the plant propagation material may be obtainable from a plant (e.g. a tobacco plant) of the invention.

A "plant propagation material" as used herein refers to any plant matter taken from a plant from which further plants may be produced. Suitably, a plant propagation material may be selected from a seed, plant calli and plant clumps. Suitably the plant propagation material may be a seed. Suitably, the plant propagation material may be plant calli. Suitably the plant propagation material may be plant clumps.

In one embodiment the cell (e.g. tobacco cell), tobacco plant and/or plant propagation material may be obtainable (e.g. obtained) by a method according to the invention.

Suitably a tobacco plant according to the present invention may have modulated (e.g. decreased) nicotine content when compared to an unmodified tobacco plant, wherein the tobacco plant has been modified to modulate (e.g. decrease) the activity or expression of at least on one gene encoding an RNA binding protein. Suitably a tobacco plant according to the present invention may have decreased nicotine content when compared to an unmodified tobacco plant, wherein the tobacco plant has been modified to decrease or inhibit the activity or expression of at least on one gene encoding an RNA binding protein.

Suitably a tobacco plant according to the present invention may have modulated (e.g. reduced) content of a tobacco specific nitrosamine (TSNA) precursor when compared to an unmodified tobacco plant, wherein the tobacco plant has been modified to modulate (e.g. increase) the activity or expression of at least on one gene encoding an RNA binding protein.

Suitably a tobacco plant according to the present invention may have decreased tobacco specific nitrosamine (TSNA) precursor content when compared to an unmodified tobacco plant, wherein the tobacco plant has been modified to decrease or inhibit the activity or expression of at least on one gene encoding an RNA binding protein.

In one embodiment the tobacco plant in accordance with the present invention comprises a tobacco cell of the invention.

In another embodiment the plant propagation material may be obtainable (e.g. obtained) from a tobacco plant of the invention.

In one embodiment there is provided the use of a tobacco plant as described herein to breed a tobacco plant.

The present invention also provides in another embodiment the use of a tobacco plant of the foregoing embodiments for the production of a tobacco industry product.

In another embodiment there is provided the use of a tobacco plant of the invention to grow a crop.

In one embodiment there is provided a cell such as a plant cell, such as a tobacco plant cell having modulated activity or expression of at least one gene encoding an RNA binding protein as defined herein. Suitably, the cell may be a non-naturally occurring cell. Suitably, the cell may be a mutant cell. Suitably, the cell may be a non-naturally occurring mutant cell. For example the cell may comprise a non-naturally occurring mutation which modulates (e.g. decreases) activity or expression of at least one gene encoding an RNA binding protein as defined herein.

In one embodiment there is provided the use of a cell as provided for in the foregoing embodiments for production of a tobacco industry product.

In one embodiment the present invention provides a cell culture (e.g. in in vitro culture).

The tobacco cell culture may be a cell suspension culture. These cells cultured in vitro may be incorporated into a tobacco industry product, e.g. as a substitute for conventional tobacco particles, shreds, fine cut or long cut tobacco lamina, as an additive ingredient or as both a substitute and an additive. Suitably, the cell culture may produce nicotine.

In one embodiment there is provided the use of a cell culture, e.g. a harvested and/or processed cell culture according to the present invention for the production of a tobacco industry product.

The tobacco cells harvested from an in vitro culture may be dried, e.g. freeze-dried, for example to produce a powder.

In one embodiment, the cell culture is a tobacco cell culture. The skilled person will be aware of known methods for establishing in vitro cultures of tobacco cells. By way of example only, the following method may be used: collecting seeds form a tobacco plant of interest and sterilising their exterior to eliminate unwanted organisms, planting said seeds to grown a tobacco plant of interest, removing tissue from the tobacco plant (for example, from the tobacco stem) for use as an explant, establishing a callus culture form the tobacco explant, establishing a cell suspension culture from the callus culture, and harvesting culture material (e.g. including tobacco cells) to produce a tobacco cell culture.

The tobacco cells can be harvested by various methods, including filtration, e.g. vacuum filtration. The sample may be washed in the filter by adding water and the remaining liquid removed with the filtration, e.g. vacuum filtration.

The harvested tobacco cell culture may be further processed, e.g. dried, such as air-dried and/or freeze-dried. The harvested tobacco cell culture or dried harvested tobacco cell culture or an extract therefrom may be incorporated into tobacco industry products according to the present invention.

In one embodiment, the present invention provides a plant (e.g. tobacco plant) or part thereof for use in molecular farming. Suitably, a plant or part thereof modified in accordance with the present invention may be used in the manufacture of proteins such as therapeutics e.g. antibiotics, virus like particles, neutraceuticals or small molecules.

In one embodiment, the present invention provides a method for the production of proteins (e.g. therapeutic proteins), the method comprising modifying a plant or part thereof capable of producing said protein (e.g. therapeutic protein) by modulating the activity or expression of at least one gene encoding an RNA binding protein having an amino acid sequence as set out in SEQ ID NO. 1, 4, 7, 10, 13, 16, 19, 22, 25 or 28 or a functional variant or functional fragment or orthologue thereof, or a sequence which has at least 80% identity to SEQ ID NO. 1, 4, 7, 10, 13, 16, 19, 22, 25 or 28; or wherein the at least one gene encoding an RNA binding protein comprises a nucleotide sequence as set out in SEQ ID NO. 2, 3, 5, 6, 8, 9, 11, 12, 14, 15, 17, 18, 20, 21, 23, 24, 26, 27, 29 or 30 or a functional variant or functional fragment or orthologue of SEQ ID NO. 2, 3, 5; 6, 8, 9, 11, 12, 14, 15, 17, 18, 20, 21, 23, 24, 26, 27, 29 or 30 or a nucleic acid sequence which has at least 80% identity to SEQ ID NO. 2, 3, 5, 6, 8, 9, 11, 12, 14, 15, 17, 18, 20, 21, 23, 24, 26, 27, 29 or 30; and culturing the plant under conditions sufficient to allow the production of said protein (e.g. therapeutic protein).

Products

The present invention also provides for products obtainable or obtained from plants according to the present invention. Products are provided which are obtainable or obtained from a plant in which the activity or expression of gene encoding an RNA binding protein has been modulated.

In one embodiment, the product may comprise a construct of the invention which modulates the activity or expression of at least one gene encoding an RNA binding protein as defined herein. In one embodiment, the product may comprise a construct of the invention which modifies the nucleic acid sequence of at least one gene encoding an RNA binding protein as defined herein.

The present invention also provides for products obtainable or obtained from tobacco according to the present invention.

In one embodiment there is provided the use of a tobacco plant of the invention to produce a tobacco leaf.

Suitably the tobacco leaf may be subjected to downstream applications such as processing.

Thus in one embodiment the use of the foregoing embodiment may provide a processed tobacco leaf. Suitably the tobacco leaf may be subjected to curing, fermenting, pasteurising or combinations thereof. In another embodiment the tobacco leaf may be cut. In some embodiments the tobacco leaf may be cut before or after being subjected to curing, fermenting, pasteurising or combinations thereof.

In one embodiment the present invention provides a harvested leaf of a tobacco plant of the invention.

In a further embodiment the harvested leaf may be obtainable (e.g. obtained) from a tobacco plant propagated from a propagation material of the present invention.

In another embodiment there is provided a harvest leaf obtainable from a method or use of the present invention.

Suitably the harvested leaf may be a cut harvested leaf.

In some embodiments the harvested leaf may comprise viable tobacco cells. In other embodiments the harvested leaf may be subjected to further processing.

There is also provided a processed tobacco leaf.

The processed tobacco leaf may be obtainable from a tobacco plant of the invention. Suitably the processed tobacco leaf may be obtainable from a tobacco plant obtained in accordance with any of the methods and/or uses of the present invention.

Suitably, the processed leaf may comprise reduced content of one or more TSNAs selected from NNN, NNK, NAT and NAB. Suitably, the content of NNN may be reduced. Preferably, the content of NNK may be reduced. Suitably, the content of NAT may be reduced. Suitably, the content of NAB may be reduced. Suitably, the reduction in TSNA content is in relation to a comparable product which has not been modified according to the present invention.

In another embodiment the processed tobacco leaf may be obtainable (e.g. obtained) from a tobacco plant propagated form a tobacco plant propagation material according to the present invention.

The processed tobacco leaf of the present invention may be obtainable (e.g. obtained) by processing a harvested leaf of the invention.

The term "processed tobacco leaf" as used herein refers to a tobacco leaf that has undergone one or more processing steps to which tobacco is subjected to in the art. A "processed tobacco leaf" comprises no or substantially no viable cells.

The term "viable cells" refers to cells which are able to grow and/or are metabolically active. Thus, if a cell is said to not be viable, also referred to as "non-viable" then a cell does not display the characteristics of a viable cell.

The term "substantially no viable cells" means that less than about 5% of the total cells are viable. Preferably, less than about 3%, more preferably less than about 1%, even more preferably less than about 0.1% of the total cells are viable.

In one embodiment the processed tobacco leaf may be processed by one or more of: curing, fermenting and/or pasteurising.

Suitably the processed tobacco leaf may be processed by curing.

Tobacco leaf may be cured by any method known in the art. In one embodiment tobacco leaf may be cured by one or more of the curing methods selected from the group consisting of: air curing, fire curing, flue curing and sun curing.

Suitably the tobacco leaf may be air cured.

Typically air curing is achieved by hanging tobacco leaf in well-ventilated barns and allowing to dry. This is usually carried out over a period of four to eight weeks. Air curing is especially suitable for burley tobacco.

Suitably the tobacco leaf may be fire cured. Fire curing is typically achieved by hanging tobacco leaf in large barns where fires of hardwoods are kept on continuous or intermittent low smoulder and usually takes between three days and ten weeks, depending on the process and the tobacco. In another embodiment the tobacco leaf may be flue cured. Flue curing may comprise stringing tobacco leaves onto tobacco sticks and hanging them from tier-poles in curing barns. The barns usually have a flue which runs from externally fed fire boxes. Typically this results in tobacco that has been heat-cured without being exposed to smoke. Usually the temperature will be raised slowly over the course of the curing with the whole process taking approximately 1 week.

Suitably the tobacco leaf may be sun cured. This method typically involves exposure of uncovered tobacco to the sun.

Suitably the processed tobacco leaf may be processed by fermenting.

Fermentation can be carried out in any manner known in the art. Typically during fermentation, the tobacco leaves are piled into stacks (a bulk) of cured tobacco covered in e.g. burlap to retain moisture. The combination of the remaining water inside the leaf and the weight of the tobacco generates a natural heat which ripens the tobacco. The temperature in the centre of the bulk is monitored daily. In some methods every week, the entire bulk is opened. The leaves are then removed to be shaken and moistened and the bulk is rotated so that the inside leaves go outside and the bottom leaves are placed on the top of the bulk. This ensures even fermentation throughout the bulk. The additional moisture on the leaves, plus the actual rotation of the leaves themselves, generates heat, releasing the tobacco's natural ammonia and reducing nicotine, while also deepening the colour and improving the tobacco's aroma. Typically the fermentation process continues for up to 6 months, depending on the variety of tobacco, stalk position on the leaf, thickness and intended use of leaf.

Suitably the processed tobacco leaf may be processed by pasteurising. Pasteurising may be particularly preferred when the tobacco leaf will be used to make a smokeless tobacco industry product, most preferably snus.

Tobacco leaf pasteurisation may be carried out by any method known in the art. For example pasteurisation may be carried out as detailed in J Foulds, L Ramstrom, M Burke, K Fagerstrom. Effect of smokeless tobacco (snus) on smoking and public health in Sweden Tobacco Control (2003) 12: 349-359, the teaching of which is incorporated herein by reference.

During the production of snus, pasteurisation is typically carried out by a process in which the tobacco is heat treated with steam for 24-36 hours (reaching temperatures of approximately 100° C.). This results in an almost sterile product and without wishing to be bound by theory one of the consequences of this is believed to be a limitation of further TSNA formation.

In one embodiment the pasteurisation may be steam pasteurisation.

In some embodiments the processed tobacco leaf may be cut. The processed tobacco leaf may be cut before or after processing. Suitably, the processed tobacco leaf may be cut after processing.

In one embodiment, the use of the foregoing embodiment may provide reconstituted tobacco. In one embodiment, there is provided reconstituted tobacco.

"Reconstituted" as used herein may also be referred to as recon, recycled or homogenized sheet tobacco and refers to tobacco material generated from remnants of tobacco leaf after processing. Reconstituted tobacco allows the production of a consistent, high quality blend and allows the adjustment of the ratio of individual components.

Reconstituted tobacco may be nano fibre recon (nanofibers can be extracted in solid or liquid form), paper making recon (which uses stems, scraps, and midribs, etc. as the raw material) or slurry type recon (which uses a mixture of fines and tobacco stems, ground to power, mixed with water and vegetable binding agent; the soluble residue is formed to sheets by extracting the water).

Any method known in the art may be used for making reconstituted tobacco, for example see CORESTA Congress, Sapporo, 2012, Smoke Science/Product Technology Groups, SSPT 12 (incorporated herein by reference).

In some embodiments the tobacco plant, harvested leaf of a tobacco plant and/or processed tobacco leaf may be used to extract nicotine. The extraction of nicotine can be achieved using any method known in the art. For example a method for extracting nicotine from tobacco is taught in U.S. Pat. No. 2,162,738 which is incorporated herein by reference.

In one aspect, the present invention provides cured tobacco material made from a tobacco plant or part thereof according to the invention.

Suitably, the cured tobacco may comprise a reduced content of one or more TSNAs selected from NNK, NNN, NAT and NAB. Suitably, the content of NNN may be reduced. Preferably, the content of NNK may be reduced. Suitably, the content of NAT may be reduced. Suitably, the content of NAB may be reduced. Suitably, the reduction in TSNA content is in relation to a comparable product which has not been modified according to the present invention.

In another aspect, the present invention provides a tobacco blend comprising tobacco material made from a tobacco plant or part thereof according to the present invention, or from a tobacco cell culture according to the present invention. In one aspect, the present invention provides a tobacco blend comprising cured tobacco material according to the present invention.

Suitably, the tobacco blend according to the present invention may comprise approximately 10%, 20%, 30%, 40%, 50%, 60%, 70%, 80% or 90% tobacco from a tobacco plant or part thereof according to the present invention, or from a tobacco cell culture according to the present invention. Suitably, the tobacco blend may comprise approximately 10% tobacco from a tobacco plant or part thereof according to the present invention, or from a tobacco cell culture according to the present invention. Suitably, the tobacco blend may comprise approximately 20% tobacco from a tobacco plant or part thereof according to the present invention, or from a tobacco cell culture according to the present invention. Suitably, the tobacco blend may comprise approximately 30% tobacco from a tobacco plant or part thereof according to the present invention, or from a tobacco cell culture according to the present invention. Suitably, the tobacco blend may comprise approximately 40% tobacco from a tobacco plant or part thereof according to the present invention, or from a tobacco cell culture according to the present invention. Suitably, the tobacco blend may comprise approximately 50% tobacco from a tobacco plant or part thereof according to the present invention, or from a tobacco cell culture according to the present invention. Suitably, the tobacco blend may comprise approximately 60% tobacco from a tobacco plant or part thereof according to the present invention, or from a tobacco cell culture according to the present invention. Suitably, the tobacco blend may comprise approximately 70% tobacco from a tobacco plant or part thereof according to the present invention, or from a tobacco cell culture according to the present invention. Suitably, the tobacco blend may comprise approximately 80% tobacco from a tobacco plant or part thereof according to the present invention, or from a tobacco cell culture according to the present invention. Suitably, the tobacco blend may comprise approximately 90% tobacco from a tobacco plant or part thereof according to the present invention, or from a tobacco cell culture according to the present invention.

In one aspect, a tobacco blend product of the present invention comprises at least about 5, 10, 20, 30, 40, 50, 60, 70, 80, 90, or 95 percent by dry weight of tobacco cured from a tobacco plant or part thereof according to the present invention, or a tobacco cell culture according to the present invention.

Suitably, the cured tobacco material may be air cured. Suitably, the cured tobacco material may be flue cured. Suitably, the cured tobacco material may be sun cured. Suitably, the cured tobacco material may be fire cured.

A tobacco industry product or smoking article according to the present invention may comprise the tobacco material (e.g. cured tobacco material or reconstituted tobacco material) according to the present invention.

In another aspect the present invention provides a tobacco industry product.

In one embodiment the tobacco industry product according to the present invention may be a blended tobacco industry product. Suitably, the tobacco blend may comprise cured tobacco material according to the present invention.

In one embodiment the tobacco industry product may be prepared from a tobacco plant of the invention or a part thereof.

Suitably the tobacco plant or part thereof may be propagated from a tobacco plant propagation material according to the present invention.

The term "part thereof" as used herein in the context of a tobacco plant refers to a portion of the tobacco plant. Suitably, the "part thereof" may be a leaf, root or stem of a tobacco plant or the flowers. Suitably, the "part thereof" may be a leaf, root or stem of a tobacco plant.

Delivery System

As used herein, the term "delivery system" is intended to encompass systems that deliver at least one substance to a user, and includes:

combustible aerosol provision systems, such as cigarettes, cigarillos, cigars, and tobacco for pipes or for roll-your-own or for make-your-own cigarettes (whether based on tobacco, tobacco derivatives, expanded tobacco, reconstituted tobacco, tobacco substitutes or other smokable material);

non-combustible aerosol provision systems that release compounds from an aerosol-generating material without combusting the aerosol-generating material, such as electronic cigarettes, tobacco heating products, and hybrid systems to generate aerosol using a combination of aerosol-generating materials; and aerosol-free delivery systems that deliver the at least one substance to a user orally, nasally, transdermally or in another way without forming an aerosol, including but not limited to, lozenges, gums, patches, articles comprising inhalable powders, and oral products such as oral tobacco which includes snus or moist snuff, wherein the at least one substance may or may not comprise nicotine.

According to the present disclosure, a "combustible" aerosol provision system is one where a constituent aerosol-generating material of the aerosol provision system (or component thereof) is combusted or burned during use in order to facilitate delivery of at least one substance to a user.

In some embodiments, the delivery system is a combustible aerosol provision system, such as a system selected from the group consisting of a cigarette, a cigarillo and a cigar.

In some embodiments, the disclosure relates to a component for use in a combustible aerosol provision system, such as a filter, a filter rod, a filter segment, a tobacco rod, a spill, an aerosol-modifying agent release component such as a capsule, a thread, or a bead, or a paper such as a plug wrap, a tipping paper or a cigarette paper.

According to the present disclosure, a "non-combustible" aerosol provision system is one where a constituent aerosol-generating material of the aerosol provision system (or component thereof) is not combusted or burned in order to facilitate delivery of at least one substance to a user.

In some embodiments, the delivery system is a non-combustible aerosol provision system, such as a powered non-combustible aerosol provision system.

In some embodiments, the non-combustible aerosol provision system is an electronic cigarette, also known as a vaping device or electronic nicotine delivery system (END), although it is noted that the presence of nicotine in the aerosol-generating material is not a requirement.

In some embodiments, the non-combustible aerosol provision system is an aerosol-generating material heating system, also known as a heat-not-burn system. An example of such a system is a tobacco heating system.

In some embodiments, the non-combustible aerosol provision system is a hybrid system to generate aerosol using a combination of aerosol-generating materials, one or a plurality of which may be heated. Each of the aerosol-generating materials may be, for example, in the form of a solid, liquid or gel and may or may not contain nicotine. In some embodiments, the hybrid system comprises a liquid or gel aerosol-generating material and a solid aerosol-generating material. The solid aerosol-generating material may comprise, for example, tobacco or a non-tobacco product.

Typically, the non-combustible aerosol provision system may comprise a non-combustible aerosol provision device and a consumable for use with the non-combustible aerosol provision device.

In some embodiments, the disclosure relates to consumables comprising aerosol-generating material and configured to be used with non-combustible aerosol provision devices. These consumables are sometimes referred to as articles throughout the disclosure.

In some embodiments, the non-combustible aerosol provision system, such as a non-combustible aerosol provision device thereof, may comprise a power source and a controller. The power source may, for example, be an electric power source or an exothermic power source. In some embodiments, the exothermic power source comprises a carbon substrate which may be energised so as to distribute power in the form of heat to an aerosol-generating material or to a heat transfer material in proximity to the exothermic power source.

In some embodiments, the non-combustible aerosol provision system may comprise an area for receiving the consumable, an aerosol generator, an aerosol generation area, a housing, a mouthpiece, a filter and/or an aerosol-modifying agent.

In some embodiments, the consumable for use with the non-combustible aerosol provision device may comprise aerosol-generating material, an aerosol-generating material storage area, an aerosol-generating material transfer component, an aerosol generator, an aerosol generation area, a housing, a wrapper, a filter, a mouthpiece, and/or an aerosol-modifying agent.

Suitably, the delivery system may be prepared from (e.g. may comprise) a tobacco plant or a part thereof according to the present invention.

Suitably, the delivery system may be prepared from a tobacco cell culture according to the present invention.

Suitably, the delivery system may be prepared from (e.g. may comprise) a tobacco plant or part thereof propagated from a tobacco plant propagation material according to the present invention.

Suitably, the delivery system may be prepared from (e.g. may comprise) a harvested leaf of a tobacco plant according to the present invention.

Suitably, the delivery system may be prepared from (e.g. may comprise) a processed tobacco leaf according to the present invention.

Suitably, the delivery system may be prepared from (e.g. may comprise) a cured tobacco material according to the present invention.

Suitably, the delivery system may be prepared from (e.g. may comprise) a tobacco blend according to the present invention.

In one embodiment, the delivery system is a combustible smoking article, selected from the group consisting of a cigarette, a cigarillo and a cigar.

In one embodiment, the delivery system comprises one or more components of a combustible smoking article, such as a filter, a filter rod, a filter rod segments, tobacco, a tobacco rod, a tobacco rod segment, a spill, an additive release component such as a capsule, a thread, beads, a paper such as a plug wrap, a tipping paper or a cigarette paper.

In one embodiment, the delivery system is a non-combustible aerosol provision system.

In one embodiment, the delivery system comprises one or more components of a non-combustible aerosol provision system, such as a heater and an aerosolizable substrate.

In one embodiment, the aerosol provision system is an electronic cigarette also known as a vaping device.

In one embodiment the electronic cigarette comprises a heater, a power supply capable of supplying power to the heater, an aerosolizable substrate such as a liquid or gel, a housing and optionally a mouthpiece.

In one embodiment the aerosolizable substrate is contained in a substrate container. In one embodiment the substrate container is combined with or comprises the heater.

In one embodiment, the delivery system is a heating product which releases one or more compounds by heating, but not burning, a substrate material. The substrate material is an aerosolizable material which may be for example tobacco or other non-delivery systems, which may or may not contain nicotine. In one embodiment, the heating product is a tobacco heating product.

In one embodiment, the heating product is an electronic device.

In one embodiment, the tobacco heating product comprises a heater, a power supply capable of supplying power to the heater, an aerosolizable substrate such as a solid or gel material.

In one embodiment the heating product is a non-electronic article.

In one embodiment the heating product comprises an aerosolizable substrate such as a solid or gel material and a heat source which is capable of supplying heat energy to the aerosolizable substrate without any electronic means, such as by burning a combustion material, such as charcoal.

In one embodiment the heating product also comprises a filter capable of filtering the aerosol generated by heating the aerosolizable substrate.

In some embodiments the aerosolizable substrate material may comprise a vapour or aerosol generating agent or a humectant, such as glycerol, propylene glycol, triacetin or diethylene glycol.

In one embodiment, the delivery system is a hybrid system to generate aerosol by heating, but not burning, a combination of substrate materials. The substrate materials may comprise for example solid, liquid or gel which may or may not contain nicotine. In one embodiment, the hybrid system comprises a liquid or gel substrate and a solid substrate. The solid substrate may be for example tobacco or other non-delivery systems, which may or may not contain nicotine. In one embodiment, the hybrid system comprises a liquid or gel substrate and tobacco.

In another embodiment, the product may comprise a construct of the invention which modulates activity or expression of at least one RNA binding domain containing protein and thereby decreases alkaloid content when expressed in a plant (e.g. tobacco plant).

Tobacco Industry Product

As used herein, the term "tobacco industry product" is intended to include combustible smoking articles such as cigarettes, cigarillos, cigars, tobacco for pipes or for roll-your-own cigarettes, (whether based on tobacco, tobacco derivatives, expanded tobacco, reconstituted tobacco, tobacco substitutes or other smokable material), non-combustible aerosol provision systems such as heating products that release compounds from substrate materials without burning such as electronic cigarettes, tobacco heating products, and hybrid systems to generate aerosol from a combination of substrate materials, for example hybrid systems containing a liquid or gel or solid substrate, as well as aerosolizable substrate materials used within these aerosol provision systems; and aerosol-free delivery articles such as lozenges, gums, patches, articles comprising breathable powders and smokeless tobacco industry products such as snus and snuff, which aerosol-free delivery articles may or may not deliver nicotine.

In one embodiment the tobacco industry product may be prepared from (e.g. may comprise) a tobacco plant of the invention or a part thereof.

Suitably the tobacco plant or part thereof may be propagated from a tobacco plant propagation material according to the present invention.

The term "part thereof" as used herein in the context of a tobacco plant refers to a portion of the tobacco plant. Preferably the "part thereof" is a leaf of a tobacco plant.

In another embodiment the tobacco industry product may be prepared from a harvested leaf of the invention.

In a further embodiment the tobacco industry product may be prepared from a processed tobacco leaf of the invention.

Suitably the tobacco industry product may be prepared from a tobacco leaf processed by one or more of: curing, fermenting and/or pasteurising.

Suitably the tobacco industry product may comprise a cut tobacco leaf, optionally processed as per the foregoing embodiment.

In another embodiment, the tobacco industry product may be prepared from a tobacco cell culture according to the present invention.

In another embodiment, the tobacco industry product may be prepared from (e.g. may comprise) a cured tobacco material according to the present invention.

In another embodiment, the tobacco industry product may be prepared from (e.g. may comprise) a tobacco blend according to the present invention.

In one embodiment the tobacco industry product may be a smoking article.

As used herein, the term "smoking article" can include smokeable products, such as rolling tobacco, cigarettes, cigars and cigarillos whether based on tobacco, tobacco derivatives, expanded tobacco, reconstituted tobacco or tobacco substitutes.

In another embodiment the tobacco industry product may be a smokeless tobacco industry product.

The term "smokeless tobacco industry product" as used herein refers to a tobacco industry product that is not intended to be smoked and/or subjected to combustion.

Smokeless tobacco industry products (including heat-not-burn materials) may contain tobacco in any form, including dried particles, shreds, granules, powders, or slurry, deposited on, mixed in, surrounded by, or combined with other ingredients in any format, such as flakes, films, tabs, foams, or beads.

In one embodiment a smokeless tobacco industry product may include snus, snuff, chewing tobacco or the like.

In one embodiment, the tobacco industry product is a combustible smoking article, selected from the group consisting of a cigarette, a cigarillo and a cigar.

In one embodiment, the tobacco industry product comprises one or more components of a combustible smoking article, such as a filter, a filter rod, a filter rod segments, tobacco, a tobacco rod, a tobacco rod segment, a spill, an additive release component such as a capsule, a thread, beads, a paper such as a plug wrap, a tipping paper or a cigarette paper.

In one embodiment, the tobacco industry product is a non-combustible aerosol provision system. In one embodiment, the tobacco industry product comprises one or more components of a non-combustible aerosol provision system, such as a heater and an aerosolizable substrate.

In one embodiment, the aerosol provision system is an electronic cigarette also known as a vaping device.

In one embodiment the electronic cigarette comprises a heater, a power supply capable of supplying power to the heater, an aerosolizable substrate such as a liquid or gel, a housing and optionally a mouthpiece.

In one embodiment the aerosolizable substrate is contained in a substrate container. In one embodiment the substrate container is combined with or comprises the heater.

In one embodiment, the tobacco industry product is a heating product which releases one or more compounds by heating, but not burning, a substrate material. The substrate material is an aerosolizable material which may be for example tobacco or other non-tobacco products, which may or may not contain nicotine. In one embodiment, the heating product is a tobacco heating product.

In one embodiment, the heating product is an electronic device.

In one embodiment, the tobacco heating product comprises a heater, a power supply capable of supplying power to the heater, an aerosolizable substrate such as a solid or gel material.

In one embodiment the heating product is a non-electronic article.

In one embodiment the heating product comprises an aerosolizable substrate such as a solid or gel material and a heat source which is capable of supplying heat energy to the aerosolizable substrate without any electronic means, such as by burning a combustion material, such as charcoal.

In one embodiment the heating product also comprises a filter capable of filtering the aerosol generated by heating the aerosolizable substrate.

In some embodiments the aerosolizable substrate material may comprise a vapour or aerosol generating agent or a humectant, such as glycerol, propylene glycol, triacetin or diethylene glycol.

In one embodiment, the tobacco industry product is a hybrid system to generate aerosol by heating, but not burning, a combination of substrate materials. The substrate materials may comprise for example solid, liquid or gel which may or may not contain nicotine. In one embodiment, the hybrid system comprises a liquid or gel substrate and a solid substrate. The solid substrate may be for example tobacco or other non-tobacco products, which may or may not contain nicotine. In one embodiment, the hybrid system comprises a liquid or gel substrate and tobacco.

In a further embodiment the tobacco industry product may be a tobacco heating device or hybrid device or e-cigarette or the like.

Typically in tobacco heating devices or hybrid devices, an aerosol is generated by the transfer of heat from a heat source to a physically separate aerosol-forming substrate or material, which may be located within, around or downstream of the heat source. During smoking, volatile compounds are released from the aerosol-forming substrate by heat transfer from the heat source and entrained in air drawn through the smoking article. As the released compounds cool, they condense to form an aerosol that is inhaled by the user.

Aerosol-generating articles and devices for consuming or smoking tobacco heating devices are known in the art. They can include, for example, electrically heated aerosol-generating devices in which an aerosol is generated by the transfer of heat from one or more electrical heating elements of the aerosol-generating device to the aerosol-forming substrate of a tobacco heating device.

Suitably the tobacco heating device may be an aerosol-generating device.

Preferably the tobacco heating device may be a heat-not-burn device. Heat-not-burn devices are known in the art and release compounds by heating, but not burning, tobacco.

An example of a suitable, heat-not-burn device may be one taught in WO2013/034459 or GB2515502 which are incorporated herein by reference.

In one embodiment the aerosol-forming substrate of a tobacco heating device may be a tobacco industry product in accordance with the present invention.

In one embodiment the tobacco heating device may be a hybrid device.

Polynucleotides/Polypeptides/Constructs

In certain embodiments of the present invention, constructs which modulate activity or expression at least gene encoding an RNA binding protein as described herein may be transformed into plant cells, suitably under the direction of a promoter.

In certain embodiments of the present invention, constructs which decrease (i.e. inhibit) the activity or expression of at least one gene encoding an RNA binding protein as described herein may be transformed into plant cells under the direction of a promoter. For example, the genetic construct may be a gene editing construct or may comprise an RNAi molecule, which may comprise a small interfering RNA (siRNA) molecule, or a short hairpin loop (shRNA) molecule.

In certain embodiments of the present invention, constructs which increase activity or expression of gene encoding an RNA binding protein as described herein may be transformed into plant cells, suitably under the direction of a promoter e.g. constructs which encode a gene encoding an RNA binding protein such as an endogenous RNA binding protein.

Constructs may be introduced into plants according to the present invention by means of suitable vector, e.g. plant transformation vectors. A plant transformation vector may comprise an expression cassette comprising 5'-3' in the direction of transcription, a promoter sequence, a construct sequence targeting gene encoding an RNA binding protein as described herein and, optionally a 3' untranslated, terminator sequence including a stop signal for RNA polymerase and a polyadenylation signal for polyadenylase. The promoter sequence may be present in one or more copies, and such copies may be identical or variants of a promoter sequence as described above. The terminator sequence may be obtained from plant, bacterial or viral genes. Suitable terminator sequences are the pea rbcS E9 terminator sequence, the nos terminator sequence derived from the nopaline synthase gene of *Agrobacterium tumefaciens* and the 35S terminator sequence from cauliflower mosaic virus, for example. A person skilled in the art will be readily aware of other suitable terminator sequences.

The construct of the present invention may also comprise a gene expression enhancing mechanism to increase the strength of the promoter. An example of such an enhancer element is one derived from a portion of the promoter of the pea plastocyanin gene, and which is the subject of International Patent Application NO. WO 97/20056 which is incorporated herein by reference. Suitable enhancer elements may be the nos enhancer element derived from the nopaline synthase gene of *Agrobacterium tumefaciens* and the 35S enhancer element from cauliflower mosaic virus, for example.

These regulatory regions may be derived from the same gene as the promoter DNA sequence or may be derived from different genes, from *Nicotiana tabacum* or other organisms, for example from a plant of the family Solanaceae, or from the subfamily Cestroideae. All of the regulatory regions should be capable of operating in cells of the tissue to be transformed.

The promoter DNA sequence may be derived from the same gene as the gene of interest, e.g. the gene the promoter is going to direct, for instance a gene encoding an RNA binding protein according to the invention, a coding sequence used in the present invention or may be derived from a different gene, from *Nicotiana tabacum*, or another organism, for example from a plant of the family Solanaceae, or from the subfamily Cestroideae.

The expression cassette may be incorporated into a basic plant transformation vector, such as pBIN 19 Plus, pBI 101, pKYLX71:35S2, pCAMBIA2300 or other suitable plant transformation vectors known in the art. In addition to the expression cassette, the plant transformation vector will contain such sequences as are necessary for the transformation process. These may include the *Agrobacterium* vir genes, one or more T-DNA border sequences, and a selectable marker or other means of identifying transgenic plant cells.

The term "expression vector or plant transformation vector" means a construct capable of in vivo or in vitro expression. Preferably, the expression vector is incorporated in the genome of the organism. In one embodiment the vector of the present invention expresses a protein e.g. an RNA binding protein as described herein. The term "incorporated" preferably covers stable incorporation into the genome.

Techniques for transforming plants are well known within the art and include *Agrobacterium*-mediated transformation, for example. The basic principle in the construction of genetically modified plants is to insert genetic information in the plant genome so as to obtain a stable maintenance of the inserted genetic material. A review of the general techniques may be found in articles by Potrykus (*Annu Rev Plant Physiol Plant Mol Biol* [1991] 42:205-225) and Christon (AgroFood-Industry Hi-Tech March/April 1994 17-27), which are incorporated herein by reference. Typically, in *Agrobacterium*-mediated transformation a binary vector carrying a foreign DNA of interest, i.e. a construct according to the present invention, is transferred from an appropriate *Agrobacterium* strain to a target plant by the co-cultivation of the *Agrobacterium* with explants from the target plant. Transformed plant tissue is then regenerated on selection media, which selection media comprises a selectable marker and plant growth hormones. An alternative is the floral dip method (Clough & Bent, 1998 Plant J. 1998 December; 16(6):735-43, which is incorporated herein by reference) whereby floral buds of an intact plant are brought into contact with a suspension of the *Agrobacterium* strain containing the chimeric gene, and following seed set, transformed individuals are germinated and identified by growth on selective media. Direct infection of plant tissues by *Agrobacterium* is a simple technique which has been widely employed and which is described in Butcher et al. (1980) *Tissue Culture Methods for Plant Pathologists*, eds.: D. S. Ingrams and J. P. Helgeson, 203-208 which is incorporated herein by reference.

Further suitable transformation methods include direct gene transfer into protoplasts using polyethylene glycol or electroporation techniques, particle bombardment, microinjection and the use of silicon carbide fibres for example. Transforming plants using ballistic transformation and production of fertile transgenic maize plants by silicon carbide whisker-mediated transformation is taught in Frame et al. (1994) The Plant Journal 6(6): 941-948, which is incorporated herein by reference, and viral transformation techniques is taught in, for example, Meyer et al. (1992) Mol. Gen. Genet. 231(3): 345-352, which is incorporated herein by reference. The use of cassava mosaic virus as a vector system for plants is taught in Meyer et al. (1992) Gene 110: 213-217, which is incorporated herein by reference. Further teachings on plant transformation may be found in EP-A-0449375, incorporated herein by reference.

In a further aspect, the present invention relates to a vector system which carries a construct and introducing it into the genome of an organism, such as a plant, suitably a tobacco plant. The vector system may comprise one vector, but it may comprise two vectors. In the case of two vectors, the vector system is normally referred to as a binary vector system. Binary vector systems are described in further detail in Gynheung et al. (1980) Binary Vectors, Plant Molecular Biology Manual A3, 1-19, which is incorporated herein by reference.

One extensively employed system for transformation of plant cells uses the Ti plasmid from *Agrobacterium tumefaciens* or a Ri plasmid from *Agrobacterium rhizogenes* described by An et al. (1986) Plant Physiol. 81, 301-305 and Butcher et al. (1980) *Tissue Culture Methods for Plant Pathologists* eds.: D. S. Ingrams and J. P. Helgeson, 203-208 which are incorporated herein by reference. After each introduction method of the desired exogenous gene according to the present invention in the plants, the presence and/or insertion of further DNA sequences may be necessary. The use of T-DNA for the transformation of plant cells has been intensively studied and is described in EP-A-120516; Hoekema (1985) The Binary Plant Vector System, Offset-drukkerij Kanters B. B., Amsterdam Chapter V; Fraley et al. Crit. Rev. Plant Sci. 4:1-46; and An et al. (1985) EMBO J 4: 277-284, all incorporated herein by reference.

Plant cells transformed with construct(s) which modulate the activity or expression of at least one gene encoding an RNA binding protein may be grown and maintained in accordance with well-known tissue culturing methods such as by culturing the cells in a suitable culture medium supplied with the necessary growth factors such as amino acids, plant hormones, vitamins, etc.

The term "transgenic plant" in relation to the present invention includes any plant that comprises a construct which modulates the activity or expression of at least one gene encoding an RNA binding protein according to the invention. Accordingly a transgenic plant is a plant which has been transformed with a construct according to the invention. Preferably the transgenic plant exhibits modulated (e.g. reduced) alkaloid content and/or modulated (e.g. reduced) TSNA precursor content according to the present invention. The term "transgenic plant" does not cover native nucleotide coding sequences in their natural environment when they are under the control of their native promoter which is also in its natural environment.

In one aspect, a gene encoding an RNA binding protein, a construct, a plant transformation vector or a plant cell according to the present invention is in an isolated form. The term "isolated" means that the sequence is at least substantially free from at least one other component with which the sequence is naturally associated in nature and as found in nature.

In one aspect, a gene encoding an RNA binding protein, a construct, plant transformation vector or a plant cell according to the invention is in a purified form. The term "purified" means in a relatively pure state, e.g. at least about 90% pure, or at least about 95% pure or at least about 98% pure.

The term "nucleotide sequence" as used herein refers to an oligonucleotide sequence or polynucleotide sequence, and variant, homologues, fragments and derivatives thereof (such as portions thereof). The nucleotide sequence may be of genomic or synthetic or recombinant origin, which may be double-stranded or single-stranded whether representing the sense or anti-sense strand.

The term "nucleotide sequence" in relation to the present invention includes genomic DNA, cDNA, synthetic DNA, and RNA. Preferably it means DNA, more preferably cDNA sequence coding for the present invention.

In a preferred embodiment, the nucleotide sequence when relating to and when encompassed by the per se scope of the present invention, i.e. the gene encoding an RNA binding protein according to the present invention, includes the native nucleotide sequence when in its natural environment and when it is linked to its naturally associated sequence(s) that is/are also in its/their natural environment. For ease of reference, we shall call this preferred embodiment the "native nucleotide sequence". In this regard, the term "native nucleotide sequence" means an entire nucleotide sequence that is in its native environment and when operatively linked to an entire promoter with which it is naturally associated, which promoter is also in its native environment.

The nucleotide sequence for use in the present invention may be present in a vector in which the nucleotide sequence is operably linked to regulatory sequences capable of providing for the expression of the nucleotide sequence by a suitable host organism. The constructs for use in the present invention may be transformed into a suitable host cell as described herein to provide for expression of a polypeptide of the present invention. The choice of vector e.g. a plasmid, cosmid, or phage vector will often depend on the host cell into which it is to be introduced. Vectors may be used in vitro, for example for the production of RNA or used to transfect, transform, transduce or infect a host cell.

In some applications, the nucleotide sequence for use in the present invention is operably linked to a regulatory sequence which is capable of providing for the expression of the nucleotide sequence, such as by the chosen host cell. By way of example, the present invention covers a vector comprising the nucleotide sequence of gene encoding an RNA binding protein as described herein operably linked to such a regulatory sequence, i.e. the vector is an expression vector.

The term "operably linked" refers to a juxtaposition wherein the components described are in a relationship permitting them to function in their intended manner. A regulatory sequence "operably linked" to a coding sequence is ligated in such a way that expression of the coding sequence is achieved under conditions compatible with the control sequences.

The term "regulatory sequences" includes promoters and enhancers and other expression regulation signals. The term "promoter" is used in the normal sense of the art, e.g. an RNA polymerase binding site. The nucleotide sequence within a construct which encodes gene encoding an RNA binding protein may be operably linked to at least a promoter.

The term "construct"—which is synonymous with terms such as "cassette" or "vector"—includes a nucleotide sequence for use according to the present invention directly or indirectly attached to a promoter.

An example of an indirect attachment is the provision of a suitable spacer group such as an intron sequence, such as the Sh1-intron or the ADH intron, intermediate the promoter and the nucleotide sequence of the present invention. The same is true for the term "fused" in relation to the present invention which includes direct or indirect attachment. In some cases, the terms do not cover the natural combination of the nucleotide sequence coding for the protein ordinarily associated with the wild type gene promoter and when they are both in their natural environment. The construct may even contain or express a marker, which allows for the selection of the genetic construct.

In some embodiments, a promoter may be operably linked to nucleotide sequence in a construct or vector which is used to modulate the concentration and/or total content of nicotine in a cell or cell culture or tobacco plant or part thereof.

In some embodiments the promoter may be selected from the group consisting of: a constitutive promoter, a tissue-specific promoter, a developmentally-regulated promoter and an inducible promoter.

In one embodiment the promoter may be a constitutive promoter.

A constitutive promoter directs the expression of a gene throughout the various parts of a plant continuously during plant development, although the gene may not be expressed at the same level in all cell types. Examples of known constitutive promoters include those associated with the cauliflower mosaic virus 35S transcript (Odell J T, Nagy F, Chua N H. (1985). Identification of DNA sequences required for activity of the cauliflower mosaic virus 35S promoter. Nature. 313 810-2), the rice actin 1 gene (Zhang W, McElroy D, Wu R. (1991). Analysis of rice Act1 5' region activity in transgenic rice plants. Plant Cell 3 1155-65) and the maize ubiquitin 1 gene (Cornejo M J, Luth D, Blankenship K M, Anderson O D, Blechl A E. (1993). Activity of a maize ubiquitin promoter in transgenic rice. Plant Molec. Biol. 23 567-81). Constitutive promoters such as the Carnation Etched Ring Virus (CERV) promoter (Hull R, Sadler J, Longstaff M (1986) (CaMV/35S), figwort mosaic virus 35S promoter. The sequence of carnation etched ring virus DNA: comparison with cauliflower mosaic virus and retroviruses. EMBO Journal, 5(2):3083-3090).

The constitutive promoter may be selected from a: a carnation etched ring virus (CERV) promoter, a cauliflower mosaic virus (CaMV 35S promoter), a promoter from the rice actin 1 gene or the maize ubiquitin 1 gene.

The promoter may be a tissue specific promoter. A tissue-specific promoter is one which directs the expression of a gene in one (or a few) parts of a plant, usually throughout the lifetime of those plant parts. The category of tissue-specific promoter commonly also includes promoters whose specificity is not absolute, i.e. they may also direct expression at a lower level in tissues other than the preferred tissue. Tissue specific promoters include the phaseolin-promoter, legumin b4-promoter, usp-promoter, sbp-promoter, ST-LS1 promoter, B33 (patatin class I promoter).

In another embodiment the promoter may be a developmentally-regulated promoter.

A developmentally-regulated promoter directs a change in the expression of a gene in one or more parts of a plant at a specific time during plant development. The gene may be expressed in that plant part at other times at a different (usually lower) level, and may also be expressed in other plant parts.

In one embodiment the promoter may be an inducible promoter.

An inducible promoter is capable of directing the expression of a gene in response to an inducer.

In the absence of the inducer the gene will not be expressed. The inducer may act directly upon the promoter sequence, or may act by counteracting the effect of a repressor molecule. The inducer may be a chemical agent such as a metabolite, a protein, a growth regulator (such as auxin and salicylic acid which activate the OCS promoter), or a toxic element, a physiological stress such as heat, light (such as the soybean SSU promoter), wounding (e.g. the nos, nopaline synthase promoter), or osmotic pressure, or an indirect consequence of the action of a pathogen or pest. A developmentally-regulated promoter might be described as a specific type of inducible promoter responding to an endogenous inducer produced by the plant or to an environmental stimulus at a particular point in the life cycle of the plant. Examples of known inducible promoters include those associated with wound response, such as described by Warner S A, Scott R, Draper J. ((1993) Plant J. 3 191-201), temperature response as disclosed by Benfey & Chua (1989) (Benfey, P. N., and Chua, N-H. ((1989) Science 244 174-181), and chemically induced, as described by Gatz ((1995) Methods in Cell Biol. 50 411-424).

A nucleotide sequence encoding either a protein which has the specific properties as gene encoding an RNA binding protein as defined herein or a protein which is suitable for modification may be identified and/or isolated and/or purified from any cell or organism producing said protein. Various methods are well known within the art for the identification and/or isolation and/or purification of nucleotide sequences. By way of example, PCR amplification techniques to prepare more of a sequence may be used once a suitable sequence has been identified and/or isolated and/or purified.

In a yet further alternative, the nucleotide sequence encoding the RNA binding protein may be prepared synthetically by established standard methods, e.g. the phosphoroamidite method described by Beucage et al. (1981) Tetrahedron Letters 22, 1859-1869 which is incorporated herein by reference, or the method described by Matthes et al. (1984) EMBO J. 3, 801-805 which is incorporated herein by reference. In the phosphoroamidite method, oligonucleotides are synthesised, e.g. in an automatic DNA synthesiser, purified, annealed, ligated and cloned in appropriate vectors.

As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme".

The present invention also encompasses the use of sequences having a degree of sequence identity or sequence homology with amino acid sequence(s) of a polypeptide having the specific properties defined herein or of any nucleotide sequence i.e. a gene encoding an RNA binding protein (hereinafter referred to as a "homologous sequence(s)"). Here, the term "homologue" means an entity having a certain homology with the subject amino acid sequences and the subject nucleotide sequences. Here, the term "homology" can be equated with "identity".

The homologous amino acid sequence and/or nucleotide sequence and/or fragments should provide and/or encode a polypeptide which retains the functional activity and/or enhances the activity of the RNA binding protein. Typically, the homologous sequences will comprise the same active sites etc. as the subject amino acid sequence for instance or will encode the same active sites. Although homology can also be considered in terms of similarity (i.e. amino acid residues having similar chemical properties/functions), in the context of the present invention it is preferred to express homology in terms of sequence identity. Homologous sequences typically retain functional domains or motifs.

In one embodiment, a homologous sequence is taken to include an amino acid sequence or nucleotide sequence which has one, two or several additions, deletions and/or substitutions compared with the subject sequence.

Sequence Identity

Sequence identity comparisons can be conducted by eye, or more usually, with the aid of readily available sequence comparison programs. These commercially available computer programs can calculate % homology between two or more sequences. % homology or % identity may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue, in the gap. This is the most commonly used gap scoring system. High gap penalties will of course produce optimised alignments with fewer gaps. Most alignment programs allow the gap penalties to be modified. However, it is preferred to use the default values when using such software for sequence comparisons.

Calculation of maximum % homology therefore firstly requires the production of an optimal alignment, taking into consideration gap penalties. A suitable computer program for carrying out such an alignment is the Vector NTI (Invitrogen Corp.). Examples of software that can perform sequence comparisons include, but are not limited to, the BLAST package (see Ausubel et al. (1999) Short Protocols in Molecular Biology, 4th Ed—Chapter 18), BLAST 2 (see FEMS Microbiol Left 1999 174(2): 247-50; FEMS Microbiol Lett 1999 177(1): 187-8 and tatiana@ncbi.nlm.nih.gov), FASTA (Altschul et al. 1990 J. Mol. Biol. 403-410) and AlignX for example. At least BLAST, BLAST 2 and FASTA are available for offline and online searching (see Ausubel et al. 1999, pages 7-58 to 7-60).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. Vector NTI programs generally use either the public default values or a custom symbol comparison table if supplied (see user manual for further details). For some applications, it is preferred to use the default values for the Vector NTI package.

Alternatively, percentage homologies may be calculated using the multiple alignment feature in Vector NTI (Invitrogen Corp.), based on an algorithm, analogous to CLUSTAL (Higgins D G & Sharp P M (1988), Gene 73(1), 237-244). Once the software has produced an optimal alignment, it is possible to calculate % homology, preferably % sequence identity. The software typically does this as part of the sequence comparison and generates a numerical result.

Should gap penalties be used when determining sequence identity, then preferably the following parameters are used for pairwise alignment:

| FOR BLAST | | | |
|---|---|---|---|
| GAP OPEN | | 0 | |
| GAP EXTENSION | | 0 | |
| FOR CLUSTAL | DNA | PROTEIN | |
| WORD SIZE | 2 | 1 | K triple |
| GAP PENALTY | 15 | 10 | |
| GAP EXTENSION | 6.66 | 0.1 | |

In one embodiment, CLUSTAL may be used with the gap penalty and gap extension set as defined above. In some embodiments the gap penalties used for BLAST or CLUSTAL alignment may be different to those detailed above. The skilled person will appreciate that the standard parameters for performing BLAST and CLUSTAL alignments may change periodically and will be able to select appropriate parameters based on the standard parameters detailed for BLAST or CLUSTAL alignment algorithms at the time.

Suitably, the degree of identity with regard to a nucleotide sequence is determined over at least 50 contiguous nucleotides, preferably over at least 60 contiguous nucleotides, preferably over at least 70 contiguous nucleotides, preferably over at least 80 contiguous nucleotides, preferably over at least 90 contiguous nucleotides, preferably over at least 100 contiguous nucleotides, preferably over at least 150 contiguous nucleotides, preferably over at least 200 contiguous nucleotides, preferably over at least 250 contiguous nucleotides, preferably over at least 300 contiguous nucleotides, preferably over at least 350 contiguous nucleotides, preferably over at least 400 contiguous nucleotides, preferably over at least 450 contiguous nucleotides, preferably over at least 500 contiguous nucleotides, preferably over at least 550 contiguous nucleotides, preferably over at least 600 contiguous nucleotides, preferably over at least 650 contiguous nucleotides, or preferably over at least 700 contiguous nucleotides.

Suitably, the degree of identity with regard to a nucleotide, cDNA, cds or amino acid sequence may be determined over the whole sequence.

The sequences may also have deletions, insertions or substitutions of amino acid residues which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in Ae n the third column may be substituted for each other:

| ALIPHATIC | Non-polar | G A P |
| | | I L V |
| | Polar-uncharged | C S T M |
| | | N Q |
| | Polar-charged | D E |
| | | K R |
| AROMATIC | | H F W Y |

The present invention also encompasses homologous substitution (substitution and replacement are both used herein to mean the interchange of an existing amino acid residue, with an alternative residue) that may occur i.e. like-for-like substitution such as basic for basic, acidic for acidic, polar for polar etc. Non-homologous substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Replacements may also be made by unnatural amino acids include; alpha* and alpha-disubstituted* amino acids, N-alkyl amino acids*, lactic acid*, halide derivatives of natural amino acids such as trifluorotyrosine*, p-Cl-phenylalanine*, p-Br-phenylalanine*, p-I-phenylalanine*, L-allyl-glycine*, β-alanine*, L-α-amino butyric acid*, L-γ-amino butyric acid*, L-α-amino isobutyric acid*, L-ε-amino caproic acid #, 7-amino heptanoic acid*, L-methionine sulfone#*. L-norleucine*, L-norvaline*, p-nitro-L-phenylalanine*, L-hydroxyproline#, L-thioproline*, methyl derivatives of phenylalanine (Phe) such as 4-methyl-Phe*, pentamethyl-Phe*, L-Phe (4-amino)#, L-Tyr (methyl)*, L-Phe (4-isopropyl)*, L-Tic (1,2,3,4-tetrahydroisoquinoline-3-carboxyl acid)*, L-diaminopropionic acid# and L-Phe (4-benzyl)*. The notation * has been utilised for the purpose of the discussion above (relating to homologous or non-homologous substitution), to indicate the hydrophobic nature of the derivative whereas # has been utilised to indicate the hydrophilic nature of the derivative, #* indicates amphipathic characteristics.

Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, involves the presence of one or more amino acid residues in peptoid form, which will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon et al. (1992) PNAS 89(20), 9367-9371 and Horwell (1995) Trends Biotechnol. 13(4), 132-134.

The nucleotide sequences for use in the present invention may include within them synthetic or modified nucleotides. A number of different types of modification to oligonucleotides are known in the art. These include methylphosphonate and phosphorothioate backbones and/or the addition of acridine or polylysine chains at the 3' and/or 5' ends of the molecule. For the purposes of the present invention, it is to be understood that the nucleotide sequences described herein may be modified by any method available in the art. Such modifications may be carried out in order to enhance the in vivo activity or life span of nucleotide sequences of the present invention. The present invention also encompasses sequences that are complementary to the nucleic acid sequences of the present invention or sequences that are capable of hybridising either to the sequences of the present invention or to sequences that are complementary thereto. The term "hybridisation" as used herein shall include "the process by which a strand of nucleic acid joins with a complementary strand through base pairing" as well as the process of amplification as carried out in polymerase chain reaction (PCR) technologies.

The present invention also relates to nucleotide sequences that can hybridise to the nucleotide sequences of the present invention (including complementary sequences of those presented herein). Preferably, hybridisation is determined under stringency conditions (e.g. 50° C. and 0.2×SSC {1×SSC=0.15 M NaCl, 0.015 M Na$_3$citrate pH 7.0}). More preferably, hybridisation is determined under high stringency conditions (e.g. 65° C. and 0.1×SSC {1×SSC=0.15 M NaCl, 0.015 M Na$_3$citrate pH 7.0}).

A review of the general techniques used for transforming plants may be found in articles such as Potrykus et al. (1991) Annu Rev Plant Physiol. Plant Mol. Biol. 42:205-225 and Christou et al. (1994) Agro-Food-Industry Hi-Tech March/April 17-27, which are incorporated herein by reference. Further teachings on plant transformation may be found in EP-A-0449375, incorporated herein by reference.

Unless defined otherwise, all technical and scientific terms used herein have the same meaning as commonly understood by one of ordinary skill in the art to which this disclosure belongs.

Singleton, et al., DICTIONARY OF MICROBIOLOGY AND MOLECULAR BIOLOGY, 20 ED., John Wiley and Sons, New York (1994), and Hale & Marham, THE HARPER COLLINS DICTIONARY OF BIOLOGY, Harper Perennial, NY (1991) provide one of skill with a general dictionary of many of the terms used in this disclosure.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range. Unless otherwise indicated, any nucleic acid sequences are written left to right in 5' to 3' orientation; amino acid sequences are written left to right in amino to carboxy orientation, respectively.

The headings provided herein are not limitations of the various aspects or embodiments of this disclosure which can be had by reference to the specification as a whole. Accordingly, the terms defined immediately below are more fully defined by reference to the specification as a whole.

Amino acids are referred to herein using the name of the amino acid, the three letter abbreviation or the single letter abbreviation. The term "protein", as used herein, includes proteins, polypeptides, and peptides. As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme".

In the present disclosure and claims, the conventional one-letter and three-letter codes for amino acid residues may be used. The 3-letter code for amino acids as defined in conformity with the IUPACIUB Joint Commission on Biochemical Nomenclature (JCBN). It is also understood that a polypeptide may be coded for by more than one nucleotide sequence due to the degeneracy of the genetic code.

Other definitions of terms may appear throughout the specification. Before the exemplary embodiments are described in more detail, it is to understand that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure.

It must be noted that as used herein and in the appended claims, the singular forms "a", "an", and "the" include plural referents unless the context clearly dictates otherwise. Thus, for example, reference to "an enzyme" or "a nitrate reductase" includes a plurality of such candidate agents and equivalents thereof known to those skilled in the art, and so forth.

Advantages

It has been surprisingly found that by modulating the activity or expression of at least one gene encoding an RNA binding protein as taught herein which acts as a positive regulator of alkaloid content in tobacco, the alkaloid and/or TSNA precursor content of plants can be modulated. Thereby tobacco industry products with modulated (e.g. reduced) alkaloid content) and/or reduced TSNA precursor content and commercially desirable traits sought after by consumers of tobacco industry products can be produced.

The present inventors have surprisingly determined a method for modulating the alkaloid content and/or TSNA precursor content of a plant (e.g. tobacco plant) by modulating the activity or expression of a gene encoding an RNA binding protein. Alkaloid or TSNA precursor content of a plant (e.g. tobacco plant) may be decreased by decreasing or inhibiting the activity or expression of a gene encoding an RNA binding protein as described herein. Prior to the present invention it had not been known that modulation of the activity or expression of a gene encoding an RNA binding protein as described herein could be used to modulate alkaloid (and/or TSNA precursor content of a plant (e.g. a tobacco plant).

The publications discussed herein are provided solely for their disclosure prior to the filing date of the present application. Nothing herein is to be construed as an admission that such publications constitute prior art to the claims appended hereto.

EXAMPLES

Example 1—Transient Overexpression of Gene Encoding an RNA Binding Protein Increases Alkaloid Content in Leaves Methods and Materials Cloning an RNA Binding Protein Expression Vector The Nitab4.5_0013685g0010.2 gene sequence (SEQ ID NO. 3) encoding an RNA binding protein according to the invention was amplified from a Gateway™ (cloning platform) compatible cDNA library using primers located outside restriction sites flanking the gene sequence.

The resulting plasmid was sequenced and transformed into *Agrobacterium tumefaciens* GV3101pMP90 by heat shock and transiently expressed in tobacco leaves.

Transient Gene Expression

*Agrobacterium tumefaciens* GV3101 strains carrying the construct of interest were grown overnight in Luria-Bertani (LB) medium supplemented with appropriate antibiotics. Cultures were spun down and re-suspended in buffer containing 10 mM $MgCl_2$, 10 mM MES pH 5.6 and 100 μM acetosyringone to OD600=0.6 and incubated for one hour at room temperature. Infiltration was performed with a needleless syringe into tobacco leaves. Samples are taken 5 days post-infiltration.

Tests were performed in two biological replicates.

Alkaloid Measurement

Relative content of pyridine alkaloids was determined by reversed phase high performance liquid chromatography with tandem mass spectrometry (LC-MS/MS). Chromatographic separation was achieved using a Gemini-NX column (100 mm×3.0 mm, particle size 3 μm, Phenomenex) and gradient chromatographic separation using 6.5 mM ammonium acetate buffer (aq) (pH10) and Methanol.

Mass Spectrometer operates in electrospray (ESI) positive mode using scheduled MRM data acquisition. Two MRM transitions were monitored for each analyte and one for the isotope labelled internal standard.

| Analyte | Precursor Ion | Daughter Ion (quant/confirm) |
|---|---|---|
| Nicotine | 163.1 | 130/106 |
| Nicotine d4 | 167.1 | 134.1 |
| Anabasine | 163.1 | 80/120 |
| Anatabine | 161.1 | 144/80 |
| Nornicotine | 149.1 | 80/130 |

-continued

| Analyte | Precursor Ion | Daughter Ion (quant/confirm) |
|---|---|---|
| Nornicotine d4 | 153.1 | 84.1 |
| PON | 176.1 | 106.0/148 |
| PON d4 | 183.1 | 110.0 |

Results

Alkaloid content of 5-week-old tobacco leaves expressing the Nitab4.5_0013685g0010.2 construct is shown in FIG. 1. Alkaloid content is represented relative to control and comprises two biological replicates analysed by one-way t-test. Values are shown as means±SEM. Asterisks indicate statistical significance of P value≤0.01.

Overexpression of Nitab4.5_0013685g0010.2 leads to a significant increase in alkaloid content in leaves.

Conclusions

Nitab4.5_0013685g0010.2 is a positive regulator of alkaloid content, and is a regulator of pyridine alkaloids in tobacco.

Example 2—Transient Expression of Antisense RNA Targeting Nitab4.5 0013685q0010.2 Decreases Alkaloid Content in Leaves Materials and Methods The Nitab4.5_0013685g0010.2 coding sequence was cloned in reverse orientation into a plant expression vector driven by the CERV promoter.

Results

Figure 2:
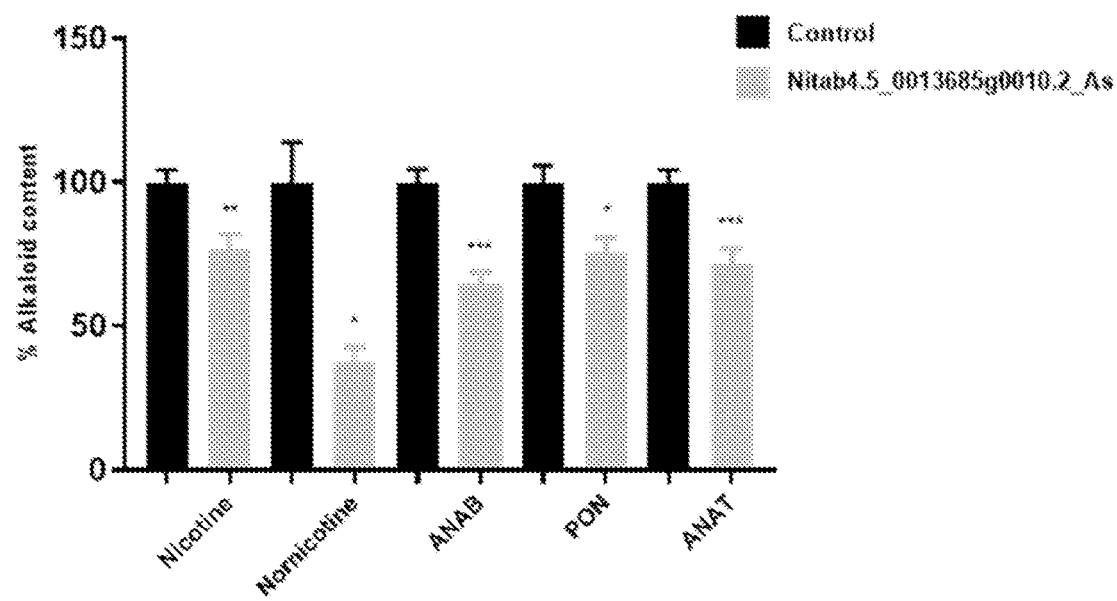
FIG. 2 shows the alkaloid content of 5-week-old tobacco leaves expressing an artificial miRNA targeting Nitab4.5_0013685g0010.2. Alkaloid content is represented relative to control and comprises two biological replicates analysed by one-way ANOVA and Tukey's multiple-comparison post-test. Values are shown as means±SEM. Asterisks indicate statistical significance of P value≤0.01.

Alkaloid content of 5-week-old tobacco leaves expressing Nitab4.5_0013685g0010.2antisense RNA is shown in FIG. 2. Alkaloid content is represented relative to control and comprises two biological replicates analysed by t-test. Values are shown as means±SEM. Asterisks indicate statistical significance of P value≤0.01

Suppressing Nitab4.5_0013685g0010.2 expression using antisense RNA leads to a decrease in alkaloid content in leaves, in particular a decrease in nornicotine, PON, nicotine, anabasine and anatabine content.

Conclusions

Nitab4.5_0013685g0010.2 is a positive regulator of alkaloid content, in particular alkaloid content in leaves and is a regulator of pyridine alkaloids in tobacco.

Example 3—Transient Expression of Nitab4.5 0013685g0010.2 deltaRBD-RGG Leads to a Significant Reduction in Alkaloids Materials and Methods The Nitab4.5_0013685g0010.2_deltaRBD-RGG coding sequence (SEQ ID NO: 34) was cloned into an expression vector as described in Example 1.

Results

Alkaloid content of 5-week-old tobacco leaves expressing Nitab4.5_0013685g0010.2_deltaRBD-RGG is shown in FIG. 3. Alkaloid content is represented relative to control and comprises two biological replicates analysed by t-test. Values are shown as means±SEM. Asterisks indicate statistical significance of P value≤0.05.

Conclusions

Disruption of the RBD-RGG domain in RNA binding proteins modulates alkaloid content in tobacco leaves.

Example 4—Homoloaue Testing

The effects of the homologues of SEQ ID NO. 3, namely SEQ ID NOs 6, 9, 12, 15, 18, 21, 24, 27 and 30, are tested in assays as described in the above examples.

Example 5—Interactome Study of Nitab4.5 0013685q0010.2

Method

Triplicate co-immunoprecipitation samples of Nitab4.5_0013685g0010.2 were submitted to mass spectrometry analysis. Samples were digested with trypsin and analysed on a mass spectrometer (e.g. Thermo Scientific™ Orbitrap Fusion™). Data was analysed with Proteome Discoverer 2.1 against the BAT tobacco proteome database and common contaminant databases, using a 5% false discovery rate. Proteins were sorted based on: identification in all replicates of the candidate sample; the number of peptides identified, in the candidate sample; and not present in control (GFP) or the other candidate samples. Using these criteria a list of candidate interactors for Nitab4.5_0013685g0010.2 was generated.

Results and Conclusion

Mass spectrometry analysis of the triplicate samples identified the bait protein correctly in each sample. In addition, other proteins were also identified in each sample which enable the characterisation of Nitab4.5_0013685g0010.2 proteome (data not shown). Several interactors are RNA binding proteins. This class of glycine-rich RNA binding proteins are known to bind RNA and inter

The invention claimed is:

1. A method of decreasing or increasing the nicotine nornicotine, pseudoxynicotine (PON), anabasine and/or anatabine content of a tobacco plant or part thereof or tobacco cell or tobacco cell culture, wherein:
(A): the method of decreasing the nicotine, nornicotine, PON, anabasine and/or anatabine content comprises modifying said plant or part thereof or cell by decreasing the activity or expression of a gene encoding an RNA binding protein; and
(B): the method of increasing the nicotine, nornicotine, PON, anabasine and/or anatabine content comprises modifying said plant or part thereof or cell by increasing the activity or expression of a gene encoding an RNA binding protein,
wherein the RNA binding protein has an amino acid sequence comprising SEQ ID NO: 1 or a sequence which has at least 95% identity to SEQ ID NO: 1.

2. The method according to claim 1, wherein the nicotine, nornicotine, PON, anabasine and/or anatabine content is reduced in comparison to a plant or part thereof or cell or cell culture or plant propagation material or leaf which has not been modified to decrease the activity or expression of the gene encoding said RNA binding protein having an amino acid sequence comprising SEQ ID NO: 1 or a sequence which has at least 95% identity to SEQ ID NO: 1.

3. A *Nicotiana* plant or part thereof or a *Nicotiana* cell or cell culture which has been modified to achieve a decrease or increase in nicotine, nornicotine, pseudoxynicotine (PON), anabasine and/or anatabine content in comparison to an unmodified plant or part thereof or unmodified cell culture, wherein:
(A): the modification to decrease the nicotine, nornicotine, PON, anabasine and/or anatabine content reduces the activity or expression of a gene encoding an RNA binding protein; and
(B): the modification to increase the nicotine, nornicotine, PON, anabasine and/or anatabine content increases the activity or expression of a gene encoding an RNA binding protein,
wherein the RNA binding protein has an amino acid sequence comprising SEQ ID NO: 1 or a sequence which has at least 95% identity to SEQ ID NO: 1.

4. A *Nicotiana* plant propagation material obtained from the *Nicotiana* plant or part thereof or the *Nicotiana* cell or cell culture according to claim 3, wherein the plant propagation material is heterozygous or homozygous for the modification.

5. The *Nicotiana* plant or part thereof or the *Nicotiana* cell or cell culture according to claim 3, or a *Nicotiana* plant propagation material obtained therefrom which is heterozygous or homozygous for the modification, wherein the nornicotine content is decreased.

6. A harvested leaf or a cut harvested leaf of the plant according to claim 3, or a plant propagated from a plant propagation material obtained therefrom, wherein the plant propagated from the propagation material is heterozygous or homozygous for the modification.

7. A processed leaf obtained by processing the plant according to claim 3, or a plant propagated from a plant propagation material obtained therefrom, wherein the plant propagated from the propagation material is heterozygous or homozygous for the modification.

8. The processed leaf according to claim 7, wherein the leaf is processed by curing, fermenting, pasteurising or a combination thereof.

9. The processed leaf according to claim 7, wherein the content of one or more TSNAs selected from N'-nitrosonornicotine (NNN), 4-(methylnitrosamino)-1-(3-pyridyl)-1-butanone (NNK), N'-nitrosoanatabine (NAT) and N-nitrosoanabasine (NAB) is reduced.

10. The processed leaf according to claim 7, wherein the processed leaf is a cut processed leaf.

11. A cured tobacco material made from the plant or part thereof according to claim 3, or a plant propagated from a plant propagation material obtained therefrom, wherein the plant propagated from the propagation material is heterozygous or homozygous for the modification.

12. A tobacco blend comprising said cured tobacco material of claim 11.

13. A mutant of a *Nicotiana* plant carrying a heritable mutation in a nucleotide sequence of a gene encoding an RNA binding protein wherein the gene is selected from SEQ ID NO: 2 or 3 or a sequence which has at least 95% identity to SEQ ID NO: 2 or 3, wherein said heritable mutation decreases the activity or expression of the gene encoding an RNA binding protein and wherein the mutant plant has decreased nicotine, nornicotine, PON, anabasine and/or anatabine relative to a comparable plant which does not carry said heritable mutation.

14. Progeny or seed of the mutant plant which carries the heritable mutation according to claim 13.

15. A harvested leaf, a processed leaf or cured tobacco material produced from the plant according to claim 13, wherein the harvested leaf, processed leaf or cured tobacco material carries the heritable mutation.

16. The processed leaf according to claim 7, wherein the leaf is a flue-cured, air-cured, fire-cured, or sun-cured processed tobacco leaf.

17. The processed leaf according to claim 9, wherein the content of NNN and/or NNK is reduced.

18. The processed leaf according to claim 9, wherein the content of NNN is reduced.

* * * * *

```
                          SEQUENCE LISTING

<160> NUMBER OF SEQ ID NOS: 52

<210> SEQ ID NO 1
<211> LENGTH: 156
<212> TYPE: PRT
<213> ORGANISM: Artificial Sequence
<220> FEATURE:
<223> OTHER INFORMATION: Nitab4.5_0013685g0010.2 amino acid sequence

<400> SEQUENCE: 1

Met Ala Glu Val Glu Tyr Arg Cys Phe Val Gly Gly Leu Ala Trp Ala
1               5                   10                  15

Thr Thr Asp Gln Thr Leu Gly Glu Ala Phe Ser Gln Phe Gly Glu Ile
            20                  25                  30

Leu Asp Ser Lys Ile Ile Asn Asp Arg Glu Thr Gly Arg Ser Arg Gly
        35                  40                  45

Phe Gly Phe Val Thr Phe Lys Asp Glu Lys Ala Met Arg Asp Ala Ile
    50                  55                  60

Glu Gly Met Asn Gly Gln Asp Leu Asp Gly Arg Asn Ile Thr Val Asn
65                  70                  75                  80

Glu Ala Gln Ser Arg Gly Ser Gly Gly Gly Gly Gly Gly Gly Gly Tyr
                85                  90                  95

Arg Gly Gly Ser Gly Gly Gly Tyr Gly Gly Gly Gly Arg Arg Glu Gly
            100                 105                 110

Gly Tyr Gly Gly Gly Gly Gly Tyr Gly Gly Gly Arg Arg Glu Gly Gly
        115                 120                 125

Tyr Gly Gly Gly Gly Gly Gly Tyr Gly Gly Gly Arg Arg Glu Gly
    130                 135                 140

Gly Tyr Gly Gly Gly Ser Glu Gly Asn Trp Arg Ser
145                 150                 155

<210> SEQ ID NO 2
<211> LENGTH: 471
<212> TYPE: DNA
<213> ORGANISM: Artificial Sequence
<220> FEATURE:
<223> OTHER INFORMATION: Nitab4.5_0013685g0010.2 coding sequence

<400> SEQUENCE: 2
```

```
atggcagaag ttgaatacag gtgcttcgtc ggtgggctag catgggctac caccgaccaa    60
acacttgggg aggcttttt tcagttcggc gaaattctcg actcgaagat tatcaatgac   120
agagaaactg gtagatctag aggatttgga tttgttacct tcaaggatga aaagccatg   180 agggacgcta ttgaagggat gaacggccag gaccttgacg tcgtaacat caccgtcaac   240 gaagctcagt ctcgcggaag cggcggaggt ggaggcggtg gcggttaccg tggtggtagc   300
ggtggaggct acgaggtgg tggccgtcgt gaaggtggat acggtggtgg cggcggttac   360
ggaggtggcc gccgtgaagg tggttatggt ggtggtggcg gcggcggtta tggaggtggc   420
cgtcgtgaag gtggttacgg tggtggctct gaaggaaact ggaggagtta g           471

<210> SEQ ID NO 3
<211> LENGTH: 1132
<212> TYPE: DNA
<213> ORGANISM: Artificial Sequence
<220> FEATURE:
<223> OTHER INFORMATION: Nitab4.5_0013685g0010.2 genomic sequence

<400> SEQUENCE: 3
acagctctct ctctttactt cattttagg gtttcttctt attaatcaga aaaaaaatg     60 gcagaagttg aatacaggtg cttcgtcggt gggctagcat gggctaccac cgaccaaaca   120 cttgggagg ctttttctca gttcggcgaa attctcgact cgaaggtctg ttgcaaaaca   180
gagcagagat cggattcgag ccgatttgaa tcggcttcgt tgaccctctg ttactggaaa   240
aattgatctg ttactactct ctctgttact gttactgtta ctactctctg gtttatctgt   300
tactgttact gtttgttact attattccac tttccccgaa acggtacgtt ccgtcttcct   360
ctgtttatac aagagatgaa gatagatcga ttttaatgtt tctcccctat ttttttttatt   420 ttatatttta tggatttacc tatttttgga tgttatgttg tagatctggt tagatctgat   480
gtgttttttt aatgatattt gaattttca gattatcaat gacagagaaa ctggtagatc   540
tagaggattt ggatttgtta ccttcaagga tgagaaagcc atgagggacg ctattgaagg   600
gatgaacggc caggaccttg acggtcgtaa catcaccgtc aacgaagctc agtctcgcgg   660
aagcggcgga ggtggaggcg gtggcggtta ccgtggtggt agcggtggag gctacggagg   720
tggtggccgt cgtgaaggtg gatacggtgg tggcggcggt tacggaggtg gccgccgtga   780
aggtggttat ggtggtggtg gcggcggcgg ttatggaggt ggccgtcgtg aaggtggtta   840
cggtggtggc tctgaaggaa actggaggag ttagatttc cgttgccttt agatttattt   900
ttttggtttg aaatttatgg ttctaagttt ggttgaagtt ccgttatggt ttactgtggt   960
tcctgctact gtcctcgttt tgaccgtga gattgttacc gtgatgttac gttgtggatc   1020
tgtatttaca aagttctctg gaatgaagtg aatgaagatt taccgtttac aattaacaat   1080
tcatgtgtgt gttattattt agtttagtaa atggagatat atcccttat gt           1132

<210> SEQ ID NO 4
<211> LENGTH: 157
<212> TYPE: PRT
<213> ORGANISM: Artificial Sequence
<220> FEATURE:
<223> OTHER INFORMATION: Nitab4.5_0000308g0150.2 amino acid sequence

<400> SEQUENCE: 4

Met Ala Asp Ala Glu Tyr Arg Cys Phe Val Gly Gly Leu Ala Trp Ala
1               5                   10                  15

Thr Thr Asp Gln Thr Leu Gly Asp Ala Phe Ser Gln Tyr Gly Glu Ile
```

```
                    20                   25                  30
Val Asp Ser Lys Ile Ile Asn Asp Arg Glu Thr Gly Arg Ser Arg Gly
             35                   40                  45

Phe Gly Phe Val Thr Phe Lys Asp Glu Gln Ala Met Arg Asp Ala Ile
         50                   55                  60

Glu Gly Met Asn Gly Gln Asp Leu Asp Gly Arg Asn Ile Thr Val Asn
 65                  70                  75                  80

Glu Ala Gln Ser Arg Gly Ser Gly Gly Gly Arg Gly Gly
                 85                  90                  95

Gly Gly Gly Tyr Gly Gly Gly Gly Tyr Gly Gly Gly Arg Arg
                100                 105                 110

Glu Gly Tyr Gly Gly Gly Gly Gly Tyr Gly Gly Arg Arg
            115                 120                 125

Asp Gly Gly Tyr Gly Gly Gly Gly Tyr Gly Gly Arg Arg Glu
            130                 135                 140

Gly Gly Tyr Gly Gly Gly Ser Glu Gly Ser Trp Arg Ser
145                 150                 155
```

<210> SEQ ID NO 5
<211> LENGTH: 474
<212> TYPE: DNA
<213> ORGANISM: Artificial Sequence
<220> FEATURE:
<223> OTHER INFORMATION: Nitab4.5_0000308g0150.2 coding sequence

<400> SEQUENCE: 5

```
atggcagatg ctgaatacag gtgcttcgtc ggtgggctag catgggctac caccgaccaa      60
acacttgggg atgcttttc tcagtacggt gaaattgtcg actcgaagat tatcaatgac     120
agagaaactg gtagatctag aggatttgga tttgttacct tcaaggatga gcaagctatg     180
agggacgcta ttgaagggat gaacggtcag gaccttgacg gtcgtaacat caccgtcaac     240
gaagcccagt ctcgcggaag cggcggaggc ggcggtcgcg gtggtggcgg tggaggctac     300
ggaggtggtg gaggctacgg aggtggtggc cgccgtgaag gtggatacgg tggcggcggt     360
ggcggttacg gaggtggccg ccgtgatggt ggttacggtg gtggtggagg ttatggaggt     420
ggccgtcgtg aaggtggtta cggtggtggc tctgaaggaa gctggaggag ttaa           474
```

<210> SEQ ID NO 6
<211> LENGTH: 1273
<212> TYPE: DNA
<213> ORGANISM: Artificial Sequence
<220> FEATURE:
<223> OTHER INFORMATION: Nitab4.5_0000308g0150.2 genomic sequence

<400> SEQUENCE: 6

```
cggagttttc tcagtaacca aacggacaat tttttaacc agaccctaa acccgagttg       60
cattgaagtt aggaaaagaa ccgccgtgca cgattaactt aaccagccct agactcaacc    120
ctaggctcct caaccagcct ataaaaaccg gcgttttcta ctctcgtatc cacagctctc    180
tcttcacttt gttttaggt attcttctta ttattaatcg ggaaataatg gcagatgctg    240
aatacaggtg cttcgtcggt gggctagcat gggctaccac cgaccaaaca cttgggatg    300
ctttttctca gtacggtgaa attgtcgact cgaaggtctg ttggaaaaca gagcagagat    360
cggattcgag ccgatttgaa tcggcttcgt tgaccctctg ttactggaaa aattgatctg    420
ttactactct ctctgttact gttactgtta ctgttactac tctctggttt atctgttact    480
gttactattt gttactgtta ttccactttc cccgaaacgg tacgttccgt cttcctctgt    540
```

```
ttatacaaga gatgaagata gatcgctttt aatgtttctc ccctattttt tttgatttt    600 gattttatgg ttttaccttt tttggatttt atgttgtaga tctggttaga tctgatgttt    660 ttttttttt tatgatttgg actttttcag attatcaatg acagagaaac tggtagatct    720
agaggatttg gatttgttac cttcaaggat gagcaagcta tgaggacgc tattgaaggg    780 atgaacggtc aggaccttga cggtcgtaac atcaccgtca acgaagccca gtctcgcgga    840
agcggcggag gcggcggtcg cggtggtggc ggtggaggct acgaggtgg tggaggctac    900 ggaggtggtg gccgccgtga aggtggatac ggtggcggcg gtggcggtta cggaggtggc    960
cgccgtgatg gtggttacgg tggtggtgga ggttatggag gtggccgtcg tgaaggtggt   1020
tacggtggtg gctctgaagg aagctggagg agttaaattt tccgttgcct tcagatcttt   1080
tgtttgaaat ttatggttct aagttttgtt gaagttccgt tatggtttac tgttgttcct   1140
gttactgtcc tcgtttttga ccgcgagatt gttaccgtga tgttaccttt gtggatctgt   1200
atttacgaag ttatctggaa ttaagtgaat ttagatttac agtctacaat tgcatacctg   1260
ttaactcttg cgc                                                      1273

<210> SEQ ID NO 7
<211> LENGTH: 165
<212> TYPE: PRT
<213> ORGANISM: Artificial Sequence
<220> FEATURE:
<223> OTHER INFORMATION: Nitab4.5_0003919g0010.2 amino acid sequence

<400> SEQUENCE: 7

Met Ala Glu Val Glu Tyr Arg Cys Phe Val Gly Gly Leu Ala Trp Ala
1               5                   10                  15

Thr Thr Asp Arg Thr Leu Gly Glu Ala Phe Ser Gln Tyr Gly Glu Val
                20                  25                  30

Leu Glu Ser Lys Ile Ile Asn Asp Arg Glu Thr Gly Arg Ser Arg Gly
            35                  40                  45

Phe Gly Phe Val Thr Phe Gly Asp Glu Lys Ser Met Arg Asp Ala Ile
        50                  55                  60

Glu Gly Met Asn Gly Gln Asp Leu Asp Gly Arg Asn Ile Thr Val Asn
65                  70                  75                  80

Glu Ala Gln Ser Arg Gly Ser Gly Gly Gly Gly Gly Gly Gly Gly Phe
                85                  90                  95

Arg Gly Gly Arg Arg Glu Gly Gly Gly Tyr Gly Gly Gly Tyr
                100                 105                 110

Gly Gly Gly Arg Arg Glu Gly Gly Gly Tyr Gly Gly Gly Gly
            115                 120                 125

Tyr Gly Gly Gly Arg Asp Arg Gly Tyr Gly Gly Asp Arg Gly Tyr
        130                 135                 140

Gly Gly Asp Gly Gly Ser Arg Tyr Ser Arg Gly Gly Asp Ser Asp
145                 150                 155                 160

Gly Asn Trp Arg Asn
                165

<210> SEQ ID NO 8
<211> LENGTH: 498
<212> TYPE: DNA
<213> ORGANISM: Artificial Sequence
<220> FEATURE:
<223> OTHER INFORMATION: Nitab4.5_0003919g0010.2 coding sequence

<400> SEQUENCE: 8
```

```
atggctgaag ttgaataccg gtgcttcgtc ggtgggctcg catgggctac cactgatcga      60
accctaggtg aagctttctc tcagtacggc gaggttcttg aatcgaagat aatcaatgac     120
cgtgaaaccg gtagatctag aggatttggc tttgttacct tcggtgatga gaaatccatg     180
agggacgcta tcgaagggat gaacggccaa gaccttgacg tcgtaacat caccgttaac      240 gaagctcaat cacgcggaag cggcggcggc ggcggcggcg tggtttccg cggtggacgt      300 cgtgaaggag gcggcggata cggaggtgga ggatatggag gtgaagacg cgagggcggc      360 ggtggtggtt acggcggcgg cggttatggt ggtggccgtg accgtggata tggcggtggt     420
gaccgtggat acggtggtga tggcggatca cgctactcaa ggggtggtgg tgactctgat     480
ggaaactgga ggaattag                                                    498

<210> SEQ ID NO 9
<211> LENGTH: 1333
<212> TYPE: DNA
<213> ORGANISM: Artificial Sequence
<220> FEATURE:
<223> OTHER INFORMATION: Nitab4.5_0003919g0010.2 genomic sequence

<400> SEQUENCE: 9
aaaaattttc ccaacgcgtg aaaaaagagt ttctcaagtc tcaacgcgtc ttcaacgacg      60
gcaaagaaaa agaaatcgcg ttgaataact tttacttttg caagaaattc ggaaaaaaca     120
agagccgaaa ccagacctct aacccaagtt gaatagagtc ctaaattaac tcaaccgccc     180
tgcttaaccc tagcatcctc ctcctcccta taaatatata gcctttcctc atattttcc      240 tcatcccttt ctcctccgtt gtcatctctc tctataattt aaaaaaaaat caatggctga     300
agttgaatac cggtgcttcg tcggtgggct cgcatgggct accactgatc gaaccctagg     360
tgaagctttc tctcagtacg gcgaggttct tgaatcgaag gtccgtttgt cggtcgcaga     420
gcagagatcg gaatccgagc cgtgatttgg cttcgtttac ccctctgtta ctgttgattc     480
atctgttact gttactatgt ctctctctgt tactgttgct tcatctgtta ctgttactat     540
ttgatactat tattcgttct ctcttaacgg tacgttccgt cttacttctc ttcttaaaaa     600
agagatgaag atagatcggt tatttctatt ttttggtcca gtttgattgg aatgaatgtt     660
agtttccgag caagctcgga catagtcctt ttgctttgtt ttttcctgtg acaagtgtgg     720
atctggcaga tctgatgttt tgttgtgga ttttgatttt acagataatc aatgaccgtg      780
aaaccggtag atctagagga tttggctttg ttaccttcgg tgatgagaaa tccatgaggg     840
acgctatcga agggatgaac ggccaagacc ttgacggtcg taacatcacc gttaacgaag     900
ctcaatcacg cggaagcggc ggcggcggcg gcggcggtgg tttccgcggt ggacgtcgtg     960
aaggaggcgc ggatacgga ggtggaggat atggaggtgg aagacgcgag gcggcggtg     1020 gtggttacgg cggcggcggt tatggtggtg gccgtgaccg tggatatggc ggtggtgacc     1080
gtggatacgg tggtgatggc ggatcacgct actcaagggg tggtggtgac tctgatggaa     1140
actggaggaa ttagataatt gagaagatgt ggattttagt tattttgatc gcatttaag    1200 ttgggtatat cttaatgtta agtgtgactg tcttttttga ccgttattgg ctcgttactt     1260
tactgtgttt ttctgtttac agagttctta tggaatgaat aaatgaagt ctacaaatta     1320 aatctttctt ttg                                                       1333

<210> SEQ ID NO 10
<211> LENGTH: 148
<212> TYPE: PRT
```

<213> ORGANISM: Artificial Sequence
<220> FEATURE:
<223> OTHER INFORMATION: Nitab4.5_0002978g0020.2 amino acid sequence

<400> SEQUENCE: 10

```
Met Ala Glu Val Glu Tyr Ser Cys Phe Val Gly Gly Leu Ala Trp Ala
1               5                   10                  15

Thr Thr Asp Arg Thr Leu Ala Asp Ala Phe Gly Thr Tyr Gly Glu Val
            20                  25                  30

Leu Asp Ser Lys Ile Ile Asn Asp Arg Glu Thr Gly Arg Ser Arg Gly
        35                  40                  45

Phe Gly Phe Val Thr Phe Lys Asp Glu Lys Cys Met Arg Asp Ala Ile
    50                  55                  60

Glu Gly Met Asn Gly Gln Glu Leu Asp Gly Arg Ser Ile Thr Val Asn
65                  70                  75                  80

Glu Ala Gln Ala Arg Gly Ser Gly Gly Gly Gly Tyr Gly Gly
                85                  90                  95

Gly Arg Arg Glu Gly Gly Gly Gly Tyr Gly Gly Gly Gly
            100                 105                 110

Tyr Gly Gly Gly Arg Arg Glu Gly Gly Gly Tyr Gly Gly Gly
        115                 120                 125

Arg Arg Glu Gly Gly Gly Gly Tyr Gly Gly Gly Tyr Gly Gly
    130                 135                 140

Gly Gly Arg Tyr
145
```

<210> SEQ ID NO 11
<211> LENGTH: 447
<212> TYPE: DNA
<213> ORGANISM: Artificial Sequence
<220> FEATURE:
<223> OTHER INFORMATION: Nitab4.5_0002978g0020.2 coding sequence

<400> SEQUENCE: 11

```
atggctgaag tagaatacag ttgcttcgtc ggtgggctcg catgggctac caccgataga    60
accttagctg atgctttcgg tacatacggc gaagttctcg actcgaagat cattaacgac   120
agagaaactg gcagatctag aggatttggc tttgttacct taaggatga gaaatgcatg    180 agggatgcaa tcgaagggat gaacggtcag gaacttgacg gccgtagcat taccgttaac   240
gaagctcagg ctcgtggaag tggaggcggc ggcggtggtt acggaggtgg ccgacgtgaa   300
ggaggaggcg gtggttacgg aggtggtggt ggtggctacg gaggtggccg acgtgaggga   360
ggaggcggtg gctacggagg tggccgacgt gaaggaggag gcggtggtta cggaggtggc   420
ggttatggcg gtggtggtcg ttattag                                       447
```

<210> SEQ ID NO 12
<211> LENGTH: 1070
<212> TYPE: DNA
<213> ORGANISM: Artificial Sequence
<220> FEATURE:
<223> OTHER INFORMATION: Nitab4.5_0002978g0020.2 genomic sequence

<400> SEQUENCE: 12

```
acccatctc ttctttctga tattttcctt tagggttat cctcttctct cttttctcag    60
tgtagtaaaa tggctgaagt agaatacagt tgcttcgtcg gtgggctcgc atgggctacc   120
accgatagaa ccttagctga tgctttcggt acatacggcg aagttctcga ctcgaaggtc   180
cgtttgttgc gcagagcaga aatcgaatcc gggcccattt tttggctttg ttgatgacct   240
```

```
tctgttactg attactgttt attaatctct ggtttacttg attcatctgt tactgttact    300
gttactgtta ttactgttat acccttgaaa cggtacgttc cgtctttttt ctcttttgt     360 caagagatga agatagatcg gttaattatt ttgcgtgtaa acgttgtaga tctgttagat    420
ctgagcttag ttttgtttta cttttatttt tcagatcatt aacgacagag aaactggcag    480
atctagagga tttggctttg ttacctttaa ggatgagaaa tgcatgaggg atgcaatcga    540
agggatgaac ggtcaggaac ttgacggccg tagcattacc gttaacgaag ctcaggctcg    600
tggaagtgga ggcggcggcg gtggttacgg aggtggccga cgtgaaggag gaggcggtgg    660
ttacggaggt ggtggtggtg gctacggagg tggccgacgt gagggaggag gcggtggcta    720
cggaggtggc cgacgtgaag gaggaggcgg tggttacgga ggtggcggtt atggcggtgg    780
tggtcgttat tagattaaat ttacttaatt ttggcctatt gttaaattgg ccttttagatt   840 agtatccatt actgttttag tgtggttggt gttattgtcc tttatatttg gttaagatac    900
tgtgaatctg tattttacaa agttccatgg aatcaagtaa atgatggttt acgaaataac    960
tgtgtcggct tcttagttca ttactagttg aggaactctc ttatattcat tactttttaa   1020
atgaagttta aaggattaaa ttaattgagt tattaaagag tgagtacttg               1070
```

<210> SEQ ID NO 13
<211> LENGTH: 147
<212> TYPE: PRT
<213> ORGANISM: Artificial Sequence
<220> FEATURE:
<223> OTHER INFORMATION: Nitab4.5_0001361g0220.2 amino acid sequence

<400> SEQUENCE: 13

```
Met Ala Ala Glu Val Glu Tyr Ser Cys Phe Val Gly Gly Leu Ala Trp
1               5                   10                  15

Ala Thr Thr Asp Arg Thr Leu Ala Asp Ala Phe Gly Thr Tyr Gly Glu
            20                  25                  30

Val Leu Asp Ser Lys Ile Ile Asn Asp Arg Glu Thr Gly Arg Ser Arg
        35                  40                  45

Gly Phe Gly Phe Val Thr Phe Lys Asp Glu Lys Cys Met Arg Asp Ala
    50                  55                  60

Ile Glu Gly Met Asn Gly Gln Glu Leu Asp Gly Arg Asn Ile Thr Val
65                  70                  75                  80

Asn Glu Ala Gln Ala Arg Gly Ser Gly Gly Gly Gly Gly Gly Tyr Gly
                85                  90                  95

Gly Gly Arg Arg Glu Gly Gly Gly Gly Tyr Gly Gly Gly Tyr
            100                 105                 110

Gly Gly Gly Arg Arg Glu Gly Gly Gly Gly Tyr Gly Gly Gly Arg
        115                 120                 125

Arg Glu Gly Gly Gly Gly Tyr Gly Gly Gly Tyr Gly Gly Gly
    130                 135                 140

Gly Arg Tyr
145
```

<210> SEQ ID NO 14
<211> LENGTH: 444
<212> TYPE: DNA
<213> ORGANISM: Artificial Sequence
<220> FEATURE:
<223> OTHER INFORMATION: Nitab4.5_0001361g0220.2 coding sequence

<400> SEQUENCE: 14

| | |
|---|---|
| atggctgctg aagtagaata cagttgcttc gtcggtgggc tcgcatgggc taccaccgat | 60 |
| agaaccttag ctgacgcttt tggtacatac ggcgaagttc tcgactcgaa gatcattaac | 120 |
| gacagagaaa ctggcagatc tagaggattt ggctttgtta cctttaagga tgagaaatgc | 180 |
| atgagggatg caatcgaagg gatgaacggt caggaacttg acggccgtaa cattactgtt | 240 |
| aacgaagctc aggctcgtgg aagtggaggc ggcggcggtg gttacggagg tggccgtcgt | 300 |
| gaaggggag gcgtggtta cggtggtggt ggatacggag gtggccgacg tgagggaggc | 360 |
| ggcggcggtt acggaggtgg tcgacgtgaa ggaggaggcg gtggttacgg aggtggtggt | 420 |
| tatggcggtg gtgggcgtta ttag | 444 |

<210> SEQ ID NO 15
<211> LENGTH: 1188
<212> TYPE: DNA
<213> ORGANISM: Artificial Sequence
<220> FEATURE:
<223> OTHER INFORMATION: Nitab4.5_0001361g0220.2 genomic sequence

<400> SEQUENCE: 15

| | |
|---|---|
| accccatctc ttctttctga tatattttc atttaggt tatcttagtc tctcgtttca | 60 |
| cagtatagta aatggctgct gaagtagaat acagttgctt cgtcggtggg ctcgcatggg | 120 |
| ctaccaccga tagaacctta gctgacgctt ttggtacata cggcgaagtt ctcgactcga | 180 |
| aggtccgttt gttgcgcaga gcagaaatcg aatccgagcc catttttgg cttcgttgat | 240 |
| gaccttctgt tactgattac tgttattact ctctggttta cttgattcat ctgttactgt | 300 |
| tactgttatt actattatac ccttgaaacg gtacgttcca tcttttctct ttttgtcaag | 360 |
| agatgaagat agatcggtta attatttagc ttgtaaacgt tggagatctg ttagatctga | 420 |
| gcatagttttt gtttttgttt tatttttca gatcattaac gacagagaaa ctggcagatc | 480 |
| tagaggattt ggctttgtta cctttaagga tgagaaatgc atgagggatg caatcgaagg | 540 |
| gatgaacggt caggaacttg acggccgtaa cattactgtt aacgaagctc aggctcgtgg | 600 |
| aagtggaggc ggcggcggtg gttacggagg tggccgtcgt gaaggggag gcggtggtta | 660 |
| cggtggtggt ggatacggag gtggccgacg tgagggaggc ggcggcggtt acggaggtgg | 720 |
| tcgacgtgaa ggaggaggcg gtggttacgg aggtggtggt tatggcggtg gtgggcgtta | 780 |
| ttagatttaa tgtacttaat tttggcctaa tgtttaattg gccttagat tagtattcat | 840 |
| tactgttttt agtgtggttg gtgtgattgt cctttataat ttggttgtta aagttactgt | 900 |
| gaatctgtat tttacaaagt tccgtggaat caagtaaatg atggtttacg aataactgt | 960 |
| gtcgacttcc ttttgtatcc cagttattta gcctccaagg tagtttagga atctcttagg | 1020 |
| gttcgttttg gcacgaggat aatttagttc gcatatcaaa tgtttcctta gcttattagt | 1080 |
| ttttaaatga agtttcaaca attaaattaa ttgtattatt aaagagtgag tacatgatac | 1140 |
| tatgatagta ttagtagatg ataatttatt gggttttat taaaatat | 1188 |

<210> SEQ ID NO 16
<211> LENGTH: 169
<212> TYPE: PRT
<213> ORGANISM: Artificial Sequence
<220> FEATURE:
<223> OTHER INFORMATION: Nitab4.5_0002978g0030.2 amino acid sequence

<400> SEQUENCE: 16

Met Ala Ala Glu Val Glu Tyr Arg Cys Phe Val Gly Gly Leu Ala Trp
1               5                   10                  15

Ala Thr Thr Asp Arg Thr Leu Gly Asp Ala Phe Ala His Tyr Gly Glu
            20                  25                  30

Val Val Asp Ser Lys Ile Ile Asn Asp Arg Glu Thr Gly Arg Ser Arg
            35                  40                  45

Gly Phe Gly Phe Val Thr Phe Asn Asp Glu Lys Ala Met Arg Asp Ala
            50                  55                  60

Ile Glu Gly Met Asn Gly Gln Asn Leu Asp Gly Arg Asn Ile Thr Val
65                  70                  75                  80

Asn Glu Ala Gln Ser Arg Gly Ser Gly Gly Gly Gly Gly Phe Gly
                85                  90                  95

Gly Gly Arg Arg Arg Glu Gly Gly Tyr Ser Gly Gly Gly Tyr Gly
            100                 105                 110

Gly Gly Gly Gly Tyr Gly Gly Gly Arg Arg Glu Gly Gly Tyr Ser Gly
            115                 120                 125

Gly Gly Tyr Gly Gly Ser Tyr Gly Gly Gly Arg Asp Arg Gly Tyr Gly
            130                 135                 140

Gly Gly Tyr Gly Gly Gly Asp Gly Gly Ser Arg Tyr Ser Arg Gly Gly
145                 150                 155                 160

Gly Ala Ser Glu Gly Ser Trp Arg Asn
                165

<210> SEQ ID NO 17
<211> LENGTH: 510
<212> TYPE: DNA
<213> ORGANISM: Artificial Sequence
<220> FEATURE:
<223> OTHER INFORMATION: Nitab4.5_0002978g0030.2 coding sequence

<400> SEQUENCE: 17
atggcagctg aggttgagta caggtgcttt gtaggtgggc tggcatgggc taccaccgat      60
agaactttag gagatgcttt tgctcactac ggcgaagttg tcgactcgaa gatcattaac     120
gatcgtgaaa ctggaagatc aaggggattt ggctttgtta ccttcaatga tgagaaagct     180
atgagggacg caattgaagg aatgaacggc cagaaccttg acggtcgtaa catcaccgtt     240
aatgaagctc aatcacgcgg aagcggcggc ggtggcggtg gttttggagg tggcagacgc     300
cgtgagggtg gatacagtgg tggtggcgga tacggtggcg gcggcggcta tggaggtggc     360
agacgtgagg gtggctacag cggtggtggc tacggtggta gttatggagg tggccgtgac     420
cgtggatatg gtggaggtta tggcggtggt gatggtgggt cccgctactc aagaggtggt     480
ggtgcgtccg agggaagctg gaggaattaa                                     510

<210> SEQ ID NO 18
<211> LENGTH: 1580
<212> TYPE: DNA
<213> ORGANISM: Artificial Sequence
<220> FEATURE:
<223> OTHER INFORMATION: Nitab4.5_0002978g0030.2 genomic sequence

<400> SEQUENCE: 18
ccacatcgta accattgtta gctaccgcct accagtggtt atccattacc gtcgcaatcg      60
gtaacgaccc ccttcccggt taaaattaac cgccatagca taaactttcg cctataaaag     120
ccagcatttg ctacccataa aattcacatc agctcttctc ttctattaat tgtttacatt     180
catattctct cttaagaaaa acaatggcag ctgaggttga gtacaggtgc tttgtaggtg     240
ggctggcatg ggctaccacc gatagaactt taggagatgc ttttgctcac tacggcgaag     300
ttgtcgactc gaaggtccgt tgttgcact gcagagctga gatcggatcc gagccgatct     360

```
gatcattgat ctctctgtta ctgttactgt tactttcact ctctggttta cttgattcac    420
tctgttacta tgttactatt tgttactgtt acgttattcc gttcccttat acggtacgtt    480
ccgatcttcc atagatttga acattgatcg cttttatata tatatggaaa attcgtattt    540
taattcacga aaattagatg aattgttcac ttgtttccta ttttcagtga cataattttat   600 tcttgtaacg gatggagtat tatttctata taccatgcat gtttaaatct gtttgttttt    660
ttgttgtaat tcatgtagat ctgtttagat ctgatctttt acggattttg atttcagatc    720
attaacgatc gtgaaactgg aagatcaagg ggatttggct ttgttacctt caatgatgag    780
aaagctatga gggacgcaat tgaaggaatg aacggccaga accttgacgg tcgtaacatc    840
accgttaatg aagctcaatc acgcggaagc ggcggcggtg gcggtggttt tggaggtggc    900
agacgccgtg agggtggata cagtggtggt ggcggatacg gtggcggcgg cggctatgga    960
ggtggcagac gtgagggtgg ctacagcggt ggtggctacg gtggtagtta tggaggtggc   1020
cgtgaccgtg gatatggtgg aggttatggc ggtggtgatg tgggtcccg ctactcaaga    1080 ggtggtggtg cgtccgaggg aagctggagg aattaataag attctgaaac tgggtttgat   1140
tgtgtcaaat atatgtcctc ctttagatag tttttttttt aaaaaataaa aataaaaatt   1200
tggtgattat gtttctgggt tgggtaagag tctattttg atactgtatt tcgtgttact    1260
gttctggttt ctcgctatcg gttctcgtta tgttactgtg tggatctgta cttacaaggt   1320
taaatgaaag ttaccaatga tcactcattt gtaagtgcct aagtatttaa atgcttttt    1380 aattactcga tgatttttta tgtaattcct tcaaccgaag agtttatgt acttcctact    1440 tgaatcaaag actagtcact cggttgttat tagcttataa tgatcatttc cacctccagg   1500
agggatttgg acaatgttgg aagaacaatt gaaattttat tataaataga ctttttattta  1560 aagtttttt tataaataaa                                                1580
```

<210> SEQ ID NO 19
<211> LENGTH: 171
<212> TYPE: PRT
<213> ORGANISM: Artificial Sequence
<220> FEATURE:
<223> OTHER INFORMATION: Nitab4.5_0001361g0225.2 amino acid sequence

<400> SEQUENCE: 19

```
Met Ala Ala Glu Val Glu Tyr Arg Cys Phe Val Gly Gly Leu Ala Trp
1               5                   10                  15

Ala Thr Thr Asp Arg Thr Leu Gly Asp Ala Phe Ala His Tyr Gly Glu
            20                  25                  30

Val Val Asp Ser Lys Ile Ile Asn Asp Arg Glu Thr Gly Arg Ser Arg
        35                  40                  45

Gly Phe Gly Phe Val Thr Phe Ser Asp Glu Lys Ala Met Arg Asp Ala
    50                  55                  60

Ile Glu Gly Met Asn Gly Gln Asn Leu Asp Gly Arg Asn Ile Thr Val
65                  70                  75                  80

Asn Glu Ala Gln Ser Arg Gly Ser Gly Gly Gly Gly Gly Phe Gly
                85                  90                  95

Gly Gly Arg Arg Arg Glu Gly Gly Tyr Ser Gly Gly Gly Tyr Gly
            100                 105                 110

Gly Gly Gly Ser Tyr Gly Gly Gly Arg Arg Glu Gly Tyr Ser Gly
        115                 120                 125

Gly Gly Gly Gly Tyr Gly Gly Gly Tyr Gly Gly Gly Arg Asp Arg Gly
    130                 135                 140
```

Tyr Gly Gly Gly Tyr Gly Gly Asp Gly Gly Ser Arg Tyr Ser Arg
145                 150                 155                 160

Gly Gly Gly Ala Ser Glu Gly Ser Trp Arg Asn
            165                 170

<210> SEQ ID NO 20
<211> LENGTH: 516
<212> TYPE: DNA
<213> ORGANISM: Artificial Sequence
<220> FEATURE:
<223> OTHER INFORMATION: Nitab4.5_0001361g0225.2 amino acid sequence

<400> SEQUENCE: 20

```
atggcagctg aggttgagta caggtgcttc gtcggtgggc tggcatgggc taccaccgat      60
agaacgttag gagatgcttt tgctcactac ggcgaagtgg tcgactcgaa gatcatcaac     120
gatcgtgaaa ctggtagatc aaggggattt ggctttgtta ccttcagtga tgagaaagca     180
atgagggatc gattgaagg aatgaacggc cagaaccttg acggccgtaa catcaccgtt      240
aatgaagctc aatcacgcgg cagcggtggt ggtggcggtg gtttcggagg tggcagacgc     300
cgtgagggtg gatacagtgg aggtggcgga tacggtggtg gtggtagtta cggaggtggc     360
agacgcgagg gtggctacag tggcggcggt ggtggctatg gtggtggtta cggaggtggc     420
cgtgaccgtg gatatggtgg cggttatggt ggtggtgatg gtgggtcccg ctactcaaga     480
ggtggaggtg catccgaggg aagctggagg aattag                               516
```

<210> SEQ ID NO 21
<211> LENGTH: 1786
<212> TYPE: DNA
<213> ORGANISM: Artificial Sequence
<220> FEATURE:
<223> OTHER INFORMATION: Nitab4.5_0001361g0225.2 genomic sequence

<400> SEQUENCE: 21

```
gcattaatca ccacattta accatagtta gctaccgcct accagtggtt atccattacc     60
gtcgcaatcg gtaaccaccc cttccggtta aaattaaccg caatagcaaa aatttagtcc    120
cctcacgcct ataaaagcca gcgtttgcta cccacaaaat tcacatcagc tcttctcttc    180
tattatatta attctctctt gtatgtttac attcatattc tcttcaaaaa aagaaaaaca    240
atggcagctg aggttgagta caggtgcttc gtcggtgggc tggcatgggc taccaccgat    300
agaacgttag gagatgcttt tgctcactac ggcgaagtgg tcgactcgaa ggtccgtttg    360
ttgcactgca gagcagagat cggatccgag ccgatctgat cattgatctc tctgttactg    420
ttactgttac tgttactgtt acttcactct ggtttacttg attcactctg ttactatgtt    480
actatttgtt actgttacgt tattccattc ccttatacgg tacgttccga tcttccatag    540
atttgaacaa ttgatggctt ttatgattct cttccttttt tttactttca ctgttttaat    600
ttatggagga attttgattg ctgttgtatt acgattttc aaaattgttg ttattactag     660
tttttaacgg atggactgtt attttagca tgcatgtgca aaatctgttt gttttagct      720
tataattcat gtagatctgt ttagatctaa atttttttt atggatttg atttcagatc       780
atcaacgatc gtgaaactgg tagatcaagg ggatttggct tgttacctt cagtgatgag      840
aaagcaatga gggatgcgat tgaaggaatg aacggccaga accttgacgg ccgtaacatc    900
accgttaatg aagctcaatc acgcggcagc ggtggtggtg gcggtggttt cggaggtggc    960
agacgccgtg agggtggata cagtggaggt ggcggatacg gtggtggtgg tagttacgga  1020
```

```
ggtggcagac gcgagggtgg ctacagtggc ggcggtggtg gctatggtgg tggttacgga    1080
ggtggccgtg accgtggata tggtggcggt tatggtggtg gtgatggtgg gtcccgctac    1140
tcaagaggtg gaggtgcatc cgagggaagc tggaggaatt agatttaaga ttctgaaact    1200
gggtttaatt aattgtgtct aatatatgtc ctcctttaga tagttttaa atttggtgac     1260 tatatttctg ggttgggtaa aagtctatt ttgttatagt ttttaaattt ggtgactata     1320
tttctgtgtt gggtaaaagt ctattttgt tactgtggct cgtgttactg ttctggtttc    1380
tcgttattgg ttctcgttat gttactgtgt ggatctgtac ttacaagttt aaacgaaggt    1440
taccaatgat cactcatttt taagtgccta tatattggat ggaatttgat gtaattgctt    1500
cactgaagag ttttatgtat tttctacttg aatcaagact agtaatcaat tgttattagc    1560
ttatagggat aatttccacc tccaaaagga atttggaaaa ctggaagaac aaattgaaat    1620
ttctatatat tttaaatcat ttttggcaaa acattactgg aaaaggtagt acttctcttt    1680
ttgtattcat acgcgttcat tcaacaaatt tactaaaact tactcgtgta tagtggatat    1740
ggatataaat cgacagattt ttatataaat ttataaccgt atcgat                   1786
```

<210> SEQ ID NO 22
<211> LENGTH: 108
<212> TYPE: PRT
<213> ORGANISM: Artificial Sequence
<220> FEATURE:
<223> OTHER INFORMATION: Nitab4.5_0003978g0020.2 amino acid sequence

<400> SEQUENCE: 22

```
Met Ala Ala Glu Val Glu Tyr Ser Cys Phe Val Gly Gly Leu Ala Trp
1               5                   10                  15

Ala Thr Thr Asp Arg Thr Leu Ala Asp Ala Phe Gly Thr Tyr Gly Lys
            20                  25                  30

Val Leu Asp Ser Lys Ile Ile Asn Asp Arg Glu Thr Gly Arg Ser Arg
        35                  40                  45

Gly Phe Gly Phe Val Thr Phe Lys Asp Glu Lys Cys Met Arg Asp Ala
    50                  55                  60

Ile Val Arg Met Asn Gly Gln Glu Leu Asp Asp Arg Asn Ile Thr Val
65                  70                  75                  80

Asn Glu Ala Gln Ala Arg Gly Ser Gly Gly Ser Gly Gly Gly Tyr Gly
                85                  90                  95

Gly Gly Arg Arg Glu Gly Gly Gly Cys Cys Lys Phe
            100                 105
```

<210> SEQ ID NO 23
<211> LENGTH: 327
<212> TYPE: DNA
<213> ORGANISM: Artificial Sequence
<220> FEATURE:
<223> OTHER INFORMATION: Nitab4.5_0003978g0020.2 coding sequence

<400> SEQUENCE: 23

```
atggctgcag aagtagaata cagttgcttc gtcggtgggc tcgcatgggc taccaccgat     60
agaaccttag ccgatgcttt cggtacatac ggcaaagttc tcgactcgaa gatcattaac    120
gatagagaaa ctggcagatc tagaggattt ggctttgtta cctttaagga tgagaaatgc    180
atgagggatg caatcgtaag gatgaacggt caggaacttg acgaccgtaa cattaccgtt    240
aacgaagctc aggctcgtgg aagtggaggc agcggtggtg gttacggagg tggccgacgt    300
gaaggaggag gatgctgcaa gttctga                                        327
```

<210> SEQ ID NO 24
<211> LENGTH: 336
<212> TYPE: DNA
<213> ORGANISM: Artificial Sequence
<220> FEATURE:
<223> OTHER INFORMATION: Nitab4.5_0003978g0020.2 genomic sequence

<400> SEQUENCE: 24

```
aaatggctgc agaagtagaa tacagttgct tcgtcggtgg gctcgcatgg gctaccaccg      60
atagaacctt agccgatgct ttcggtacat acggcaaagt tctcgactcg aagatcatta     120
acgatagaga aactggcaga tctagaggat ttggctttgt tacctttaag gatgagaaat     180
gcatgaggga tgcaatcgta aggatgaacg gtcaggaact tgacgaccgt aacattaccg     240
ttaacgaagc tcaggctcgt ggaagtggag gcagcggtgg tggttacgga ggtggccgac     300
gtgaaggagg aggatgctgc aagttctgaa gcaatt                              336
```

<210> SEQ ID NO 25
<211> LENGTH: 204
<212> TYPE: PRT
<213> ORGANISM: Artificial Sequence
<220> FEATURE:
<223> OTHER INFORMATION: Nitab4.5_0000078g0240.2 amino acid sequence

<400> SEQUENCE: 25

```
Met Gly Glu Asp Ala Glu Tyr Arg Cys Phe Ile Gly Asn Leu Ser Trp
1               5                   10                  15

Ser Thr Ser Asp Arg Gly Leu Lys Asp Ala Phe Arg Lys Phe Gly Asn
            20                  25                  30

Leu Leu Asp Ala Lys Ile Val Val Asp Lys Phe Ser Gly Arg Ser Lys
        35                  40                  45

Gly Phe Gly Phe Val Thr Phe Asp Glu Lys Lys Ala Met Glu Glu Ala
    50                  55                  60

Ile Glu Glu Met Asn Gly Met Asp Leu Asp Gly Arg Ala Ile Thr Val
65                  70                  75                  80

Asp Lys Ala Gln Pro Gln Gln Gly Ser Gly Arg Glu Tyr Asp Ser Asp
                85                  90                  95

Arg Pro Arg Asp Arg Asp Arg Gly Arg Asp His Gly Arg Ser Asn Arg
            100                 105                 110

Glu Tyr Gly Gly Arg Gly Ser Gly Gly Glu Cys Phe Lys Cys
        115                 120                 125

Gly Lys Pro Gly His Phe Ala Arg Glu Cys Pro Ser Glu Gly Gly Arg
    130                 135                 140

Gly Gly Arg Tyr Gly Gly Arg Asp Asp Arg Tyr Gly Gly Gly Gly
145                 150                 155                 160

Gly Gly Arg Ser Ser Gly His Tyr Gly Pro Arg Asn Gly Asp Arg
                165                 170                 175

Phe Gly Ser Arg Ser Ser Arg Asp Gly Gly His Gly Gly Glu Arg
            180                 185                 190

Tyr Asn Arg Asp Arg Ser Gly Pro Tyr Asp Arg Arg
        195                 200
```

<210> SEQ ID NO 26
<211> LENGTH: 615
<212> TYPE: DNA
<213> ORGANISM: Artificial Sequence
<220> FEATURE:
<223> OTHER INFORMATION: Nitab4.5_0000078g0240.2 coding sequence

<400> SEQUENCE: 26

```
atgggggagg atgctgagta ccgctgtttc attggaaact tatcatggtc aacatctgat      60
cgaggactaa aagacgcatt taggaagttt ggaaatcttc ttgatgcaaa gattgtagtt     120
gacaagttct caggccgatc taaggatttt ggttttgtta catttgatga aagaaagca     180
atggaagaag ccattgaaga aatgaatggg atggatttgg atggccgtgc tattactgtg     240
gacaaagccc agccccaaca aggttcaggt agagaatatg atagtgatcg cccccgtgac     300
cgagatcgag gtcgtgatca cggtcgcagt aatcgtgaat atggaggtgg acgtggatct     360
ggtggtggag agtgctttaa gtgtggcaag ccaggacact tgccagaga atgcccaagt      420
gaaggaggtc gaggtggtcg gtatgcggc agagatgata ggtatggcgg cggaggtggt      480
ggtggtagat caagtggcca ttatggacct gatagaaatg gagatcgttt tggaagccgc     540
agcagcaggg atggtggtgg acatggggga gaacgatata ccgtgatcg ttctggtcca     600
tacgatcgtc gttaa                                                      615
```

<210> SEQ ID NO 27
<211> LENGTH: 4915
<212> TYPE: DNA
<213> ORGANISM: Artificial Sequence
<220> FEATURE:
<223> OTHER INFORMATION: Nitab4.5_0000078g0240.2 genomic sequence

<400> SEQUENCE: 27

```
ggtcaagaag gatgactgca tcaagtcatc aactatagtg caggacaccc gccaagaaaa      60
tatatcttct tctataatac cctaatattc ccattcagat ttcagactct acaaaaacgc    120
taccttaagc ttctctctct ctcttttgcg gctcttcact cttgaaggta tcgatcaatt    180
gctaaatctt taattttcag caacagttgt atcttaattc ttgttttgcc ggcacttttc    240
tacggatcta ctttggtttt tgtcgctaat tagggcaatt cacgattttc gtattaggaa    300
agtgtagaat tgatgtacga cgtttgattc tttaatttca gaacgttttg ttttttttgtg   360
aaaaatgttt tggcatgtgt tgtctgttaa atttgtggga ctaaagata gatgcatttt     420
ttgttaatta ctaataaatg tgacaaagtg aaaaaaaagg catccatatt ccgcagttcc    480
atatcgattg ttggtgtcaa ttttgaccca ttaatgtgta aagctgtccc aatcttggat    540
agtttgggtg cgtggtgtta attagaagac taatgttggt ttcacccaga ttcaatccac    600
ccaaaagatt ggtttcaact caggctacat tacttgcatt tctttgtta attatggtgg     660
tatccgggca aagtttgtgc acctcaacta ctccaccggg accctgctat cttccatcag    720
cacaagtact ctagtactta ggcagatgag aagaaatcac atagtagtat tttcttgcct    780
ctgctgggat ttgaatctta gacttttttc ctcaccccaa aaagaagaa gaagcaaatg     840
gataagtatt tttgggctgg ccagtcctca acccttttaa ccatttcatt gaagaaacaa    900
gcatttctct cctctcattc tgattttgaa taatttacgt taatattgat aatttattgt    960
ggtgatagtt aggtgcaggc attactgggt caaccctttt tttatgttaa aagaataatg   1020
caaatctctt gttctcctag atgcttaaat ttgtagcagg ttctgcggca ggatactatt   1080
ttatttgatg aactatatgt caagaatttc aaggggaaat atcttaacat gctaggctgg   1140
tgttttatga ttcttctctt tagggagatt agggccgaca tgtcggctgt ctgcatgctt   1200
ttgagttcat ttatgtcag aatatggtta ttttgaactt aatgtaccat tctataaaga   1260
aagttatttt gaactttcta tttgggacat ttgcccatgt ttgggcttgg cacctacttt   1320
catccctttt tttatttgct catggtaatt ttcaactctc aagcatatca ttctgaactc   1380
```

```
aattgctcaa atttagattt ctagaagcta ctttgtgcaa aactcagaac ttcttaacga    1440
aaccattgac gagctactta aaggaataca ataacatgat atctatgtcc aggcacacat    1500
atatttgata agcggagaca tgatattctt tttagggata tttacacaat tagccggcca    1560
aattcactgg ttgcttttttt ttttctctag ctgatatata tagattattc actgattata    1620
tatggttata cacatatcat acatggatta tacatatatt atacataagc ggttgggtgg    1680
gcggctattt aggttaattc ttcttctttt taactagacc aaagcataag aatgtctttt    1740
tgtctctaca ttttcaaaat ttgtccaata gatcaataat taggaaacca taccgctgat    1800
gatattgaga gcacttttttg attggtccgt ttaagcttaa atgtcatact atgagacaat    1860
gggtctcata gtaaaactca tataaacaag acctgctgta acaacatttt gaaattttgt    1920
tttgctgtgt tccacctctg gatcattctt gaatttctc accccccttcc ctgtccacct    1980 ctctctcttt gtctttcctt ttcagttgca aaaagttgtg tgataaatgg gggaggatgc    2040
tgagtaccgc tgtttcattg gaaacttatc atggtcaaca tctgatcgag gactaaaaga    2100 cgcattagg aagtttggaa atcttcttga tgcaaggta aggatgagtc attctttaaa    2160
atactgtctt actattcttc tatttgtttg gcttctttca ccctccccca cctcctatgc    2220
atacccaact tgtactttg aggtgcaaat tatatctttt acagagctta tctcagtgta    2280
gtgctgtact cccttctcat gcttaaggga aaatcaaaga aaatgtgttt tctcctgtgg    2340
agtagcagaa gattttttaag atcactaaga ggcaattgag caggaaaata aatgttcaac    2400
tgcaaaaata aatgtaacta cttatctcaa cagaaaaagg ggtaaatgtg agcagctaca    2460
agagcttgat agtctattgg tacgtgagta cctgtattct ttgtgataaa acctgtgtat    2520
cccgcataca gtctgggggt tcaggaaaag catcagtttc ctttgtagac taataatgga    2580
ccaaaatatt acaaacctgt aggatcagtc atcttagcca gaaccaaaac tccaatgcct    2640
gtaggattta ttcatcatag ccataaccaa aactccagag cctttttcagt gaagaaatta    2700 ttcaatttat tttggattat gcaatttcag ccaatgcatg aaacctccac cgccacaaac    2760
atccatcagt gcgagaataa acagcaatgt gatacagtca tgttgtgagc actttactta    2820
ccaatgttgc agaatacatt ttggcttctt tgtatcatta agtctgtggc aacacttgcg    2880
tgactacttc tctgtctctt tccttttttcc ttatttttgtt tccttctttc tcatactttta    2940 tctggatata gattttaaac atgtctacgc ctctatcatt taaactcttt ccgtttggtt    3000
tagattgtag ttgacaagtt ctcaggccga tctaaaggat ttggttttgt tacatttgat    3060
gaaaagaaag caatggaaga agccattgaa gaaatgaatg ggatggattt ggatggccgt    3120
gctattactg tggacaaagc ccagccccaa caaggttcag gtagagaata tgatagtgat    3180 cggcccgtg accgagatcg aggtcgtgat cacggtcgca gtaatcgtga atatggaggt    3240
ggacgtggat ctggtggtgg agagtgcttt aagtgtggca agccaggaca ctttgccaga    3300
gaatgcccaa gtgaaggagg tcgaggtggt cggtatggcg gcagagatga taggtatggc    3360
ggcggaggtg gtggtggtag atcaagtggc cattatggac ctgatagaaa tggagatcgt    3420
tttggaagcc gcagcagcag ggatggtggt ggacatgggg gagaacgata taaccgtgat    3480
cgttctggtc catacgatcg tcgttaatgc tttaaggtgc aatagttatt ttggacttct    3540 aattttttgct gtctgatatt tgtggaatca tttcattgta gtaactgaaa ttttaacctg    3600
tctgttgcag ctaaagagtt aggcgccaac caagctggat actaagggtt tgaactttga    3660
agtatgtccg atggcatctt gtttccttgg cctgttagca gaagtggatc aatcttttga    3720
```

```
actcatgaaa catggcactt taatctactg ttctatgtcc gtaaaatgct caatagtgtg    3780
gtttgattgg gatcttatgc gtgcttaatt tacgaatttg aatatggtct cacacttttg    3840
aatgctacta tggctgctgg ttatttgctt tgttcgcttg gaaagtagaa tactgatgtt    3900
tgctgctgga atcaatggtt tcttgtgttc acaattgcac ctctaattgt ggtgatatag    3960
atgggtctga tgaattgcca gaattttgta ctggtgataa aattctgagg ctcaccagct    4020
tgtttatgtc aaattgggaa gcgagggtga attagcagtg gttttcctgt tctgttctct    4080
tagaatctct taacagttaa ttggagttaa acgggtaat ctattgcatt attcctccat    4140
ttagtcagtt cctactttgc agctttacag tattaatgat gttaaccttt tgacaggctg    4200
cctgtgttca aatgaccttt tttgggtaca tgattgggtc tctttgctag ttggtccagt    4260
taaacataat taatttgaga aagcattttg gacagcgaca atccttctgc cagtaattac    4320
accactaatt gctcttatgt tctgcaagga tttcctgagg acgagttagt ttcctcttag    4380
atgacaagtt attagttact cttgagttca gcaactgagg tccatttatt ttgttctgat    4440
tttgatgttc ctcctccatg gagaaggatc ttgttcgtcg tcgtggtttc cacatttgag    4500
accaagacga ttgtcgcttt gcttcaaagt cgggcttcat ttccatgtca gcttgtgatt    4560
cttggtatct ctccggtaat ggttctgctt tttaatttcg gctggagagc atggcctatt    4620
tgttacacaa gggttctgaa gggggatgtg gttatctgga tattcagtac ttcatctgtg    4680
tttttctcat cttgggccgg ggggggggg ggggggttgca tattcgtgca tttactcctc    4740
ttcttagaaa catcacagaa ttctatttct tgtttcgctt tattactggt aacccgtcat    4800
ccgcaggcag atcaaagata ggtgcaacct ttaaggttct taatgtggag catattgttt    4860
ttcccaaaat tatgggttca aaacttaatt ttttttgaaa ttgtagtagt ctttc         4915
```

<210> SEQ ID NO 28
<211> LENGTH: 205
<212> TYPE: PRT
<213> ORGANISM: Artificial Sequence
<220> FEATURE:
<223> OTHER INFORMATION: Nitab4.5_0005079g0050.2 amino acid sequence

<400> SEQUENCE: 28

```
Met Gly Asp Asp Ala Glu Tyr Arg Cys Phe Ile Gly Asn Leu Ser Trp
1               5                   10                  15

Ser Thr Ser Asp Arg Gly Leu Lys Asp Ala Phe Arg Lys Phe Gly Asn
            20                  25                  30

Leu Leu Asp Ala Lys Ile Val Val Asp Lys Phe Ser Gly Arg Ser Lys
        35                  40                  45

Gly Phe Gly Phe Val Thr Phe Asp Glu Lys Lys Ala Met Glu Glu Ala
    50                  55                  60

Ile Glu Glu Met Asn Gly Met Asp Leu Asp Gly Arg Ala Ile Thr Val
65                  70                  75                  80

Asp Lys Ala Gln Pro Gln Gln Gly Ser Gly Arg Glu Phe Asp Ser Asp
                85                  90                  95

Arg Pro Arg Asp Arg Asp Arg Gly Arg Asp His Gly Arg Asp Asn Arg
            100                 105                 110

Glu Tyr Gly Gly Gly Arg Gly Ser Gly Gly Glu Cys Phe Lys Cys
        115                 120                 125

Gly Lys Pro Gly His Phe Ala Arg Glu Cys Pro Ser Glu Gly Gly Arg
    130                 135                 140

Gly Gly Arg Tyr Gly Gly Arg Asp Asp Arg Tyr Gly Gly Gly Gly
145                 150                 155                 160
```

Gly Gly Gly Arg Ser Ser Gly His Tyr Gly Pro Asp Arg Asn Gly Asp
            165                 170                 175

Arg Phe Gly Ser Arg Ser Ser Arg Asp Gly Gly His Gly Gly Glu
        180                 185                 190

Arg Tyr Asn Arg Asp Arg Ser Gly Pro Tyr Asp Arg His
        195                 200                 205

<210> SEQ ID NO 29
<211> LENGTH: 618
<212> TYPE: DNA
<213> ORGANISM: Artificial Sequence
<220> FEATURE:
<223> OTHER INFORMATION: Nitab4.5_0005079g0050.2 coding sequence

<400> SEQUENCE: 29

| | | |
|---|---|---|
| atgggcgacg atgctgagta ccgctgtttc attggaaact tatcatggtc aacatctgat | 60 |
| cgaggactaa aagatgcatt taggaagttt ggcaatcttc ttgatgcaaa gattgtagtt | 120 |
| gacaagttct ctggccgatc taaaggattt ggttttgtta catttgatga aagaaagca | 180 |
| atggaagaag ccattgaaga atgaatggg atggatttgg atggccgcgc tattactgtg | 240 |
| gacaaagccc agccccaaca aggttcaggt agagaatttg atagtgatcg gccccgtgac | 300 |
| cgagatcgag gtcgtgatca cggtcgtgat aatcgtgaat atggaggtgg gcgtggatct | 360 |
| ggtggtggag agtgctttaa gtgtggcaag ccaggacact tgccagaga atgcccaagt | 420 |
| gaaggaggtc gtggtggtcg gtatggcggc agagatgata ggtatggcgg cggcggaggt | 480 |
| ggtggtggta gatcaagtgg ccattatgga cctgatagaa atggagatcg ttttggaagc | 540 |
| cgcagcagca gggatggtgg tggacatggg ggagaacgat ataatcgtga tcgttctggt | 600 |
| ccgtacgatc gtcattaa | 618 |

<210> SEQ ID NO 30
<211> LENGTH: 5375
<212> TYPE: DNA
<213> ORGANISM: Artificial Sequence
<220> FEATURE:
<223> OTHER INFORMATION: Nitab4.5_0005079g0050.2 genomic sequence
<220> FEATURE:
<221> NAME/KEY: misc_feature
<222> LOCATION: (1046)..(1070)
<223> OTHER INFORMATION: n is a, c, g, or t

<400> SEQUENCE: 30

| | | |
|---|---|---|
| ctgagcccctt aaatcttcac gacttcaccg cttggaaccg gtcattacgg gtcaagtagg | 60 |
| atgattgcat caagtcatca actatagtgc agaatatatg ctcttctata ataaccct | 120 |
| aatattcccc attcaggctc cacaaaaacg ctacctaaag ctttcggctc ttcactcttg | 180 |
| aaggtatcaa tcaatctcta attctttaat tttcagcaac agttgtatct taattcttgt | 240 |
| tttgccggta ctttttctacc gatctactta ggttttttgtc gctaattagg gcatttcacg | 300 |
| attttcgtat taggaaagtg taaaattgat gtacgacgtt tgattcttta atttcagaac | 360 |
| gttttgtttt tttttgttaa aaatgttttg gcatgtgttg tctgttaaat ttgtgggact | 420 |
| aaaagataaa tgcattttttt gttaattgct aaatatcatg tgacaaagtg aaagaaaggc | 480 |
| atccatattc cacatttcca tatcgattgt tggtgtcagt tttgacccat taatgtgtaa | 540 |
| agctgtccca atcttggatg gtttgggtgc atgatgttaa ttagaagact aatgttggtt | 600 |
| tcacccagat tcaacccacc cgaaagattg gtttcaacgc aggctacatt acttgcattt | 660 |
| tcttttgtta atgatggtgg tgtccgggca aagcttgtgc acctcaacta ttccatcggg | 720 |

| | |
|---|---|
| agcctgctat cttccattct gctatcgagt acttaggcag atgagaagaa atcacatagt | 780 |
| agtattttct tgcctctgtt gggatttgaa tcttagactt ttttcctcac acccttggct | 840 |
| acatgctaca ttaattgcct tacccatccc ataagggagt ttttaccaa tatggaaaag | 900 |
| cagtaagaca aaaagatgat tttgaacttg gggatataat tttactttct tgttggtaac | 960 |
| tcaccttttt tgcaactcaa ttatctagtt aagttaaccc ccccccaccc ccatcgcaaa | 1020 |
| aaaataaaag gaaaaaaaaa gaacgnnnnn nnnnnnnnnn nnnnnnnnnn agaagcaaag | 1080 |
| ggataagtat ttttgggctg gacggtcttc aaccctctta accatttcat tgaagaaaca | 1140 |
| agcatttctc tcctctcatt ctgattttga ataatttacg ttaatattga taatttgttg | 1200 |
| tggtgatagc tgggtgaagg cattactggg tcaacccttt tttttatgtt aaaagaataa | 1260 |
| tgcaaatctc ttgttctcct agatgcttaa atttgtagca ggttcagtgg caggatacta | 1320 |
| ttttatttga tgaactatat gtcaagggga aatatcttaa catgctaggc tggtgtttta | 1380 |
| tgattctttt cttagggag attaggaccg acatgtcggc tgtctgcagg cttttgagtt | 1440 |
| cttttatgt cagaatatgg ttattttgaa cttaatgtac cattctataa agaaagtgat | 1500 |
| tttgaatttt ctatttggga ccagtgtttt aaaaggcgtg ggcgtaaagc taggcgtttt | 1560 |
| acatatgcct cagcgagacg taagcccta ggcacgaggc atatgggtat ttaattttaa | 1620 |
| tgttttataa aataatataa ttacagtaaa tatttataaa taagtaaaat tacataaaaa | 1680 |
| ttgaaaaaaa ttataaatat gtgaaatata tatatatata gatgtgctcc atccccataa | 1740 |
| aaaactagtc gaaacaatct attatacgct acttacaagt aacttgagtc gaaaagaata | 1800 |
| aagtttctac atgaaggaac aaaaagaatg acaaatataa catgaattgc tgcgcgtacg | 1860 |
| cctcttgaga ttttcgcccg acgccatcgt atcggggcat ttttggtagg cctcgcccca | 1920 |
| gggcttgccc cgaaaacgcc ttttaaaatt agacaagata aagaattggg aaagactata | 1980 |
| aattagagct tcaatcaata aaaaaggtct ttgacttta aatttaatac atttcagttc | 2040 |
| cttttttaaa tttttgagta attacaagct gacttttgag aatttgggta ttatgtgaag | 2100 |
| gacttattca acaaattttg ttttaatttg aaaaaagtct ctggggctta cgtctcacta | 2160 |
| caaaaatgcg ccccaaacgc ccgacgtacg ccccgaacac ttgggcgtac gccccaaatt | 2220 |
| gcagggcgta cgcctcttga gactttcgcc ccacaccgcc tcgggcattt ttggtgcgcc | 2280 |
| tcgcgccttg aaaatgcttt ttaaaacact gtttgggaca attgtccatg tttgggcttg | 2340 |
| gcaccagccc ttttctgtt tgctcatggt aattttcaac tttcaagcat atcattctga | 2400 |
| actcaattac tcaaatttag atttctagaa gctactttgt gcaaaactca gatcgtttta | 2460 |
| acgaaaccaa gtaccgtagc attgacgagc tacttaaagg aatacgataa catgatattg | 2520 |
| atatctatgc tcacgcacac atatatttga taagcggaga catgatattc ttttagaga | 2580 |
| tatttacaca attagccggc caaattcact gtttgctttt ttttttttctt ctagctgata | 2640 |
| tatatataga ttattcaccg attatacatg gttatacaca tattatccat ggattataca | 2700 |
| tatattatac ataagcggtt ggatgggcga ctatttaggt taattcttct tcttttttaac | 2760 |
| taggccaaag cataagaatg tcttttagtc tctacatttt caaatttgt ccaacagatg | 2820 |
| aatagttagg aaaccatact gctgatgata ctgagagcac ttttttgattt gtctgtttaa | 2880 |
| gcttaaatgt catactatga gacaacgggt ctcatagtaa aactcacata aacaggacct | 2940 |
| gctgaaacaa cattttgaaa ttttgttttg ctgtgttcca cctctacctc tggatcattc | 3000 |
| ttgaattttc tcactccccc tccccctcca cccctctctg tctttccttt tcagttgcaa | 3060 |

```
aaagctgttt gataaatggg cgacgatgct gagtaccgct gtttcattgg aaacttatca    3120
tggtcaacat ctgatcgagg actaaaagat gcatttagga agtttggcaa tcttcttgat    3180
gcaaaggtaa ggatgagtca ttctttaaaa tactgtctta ctattcttct atttgtttgg    3240
cttcttcac ccaccccac ctcctatgca tacccaactt gtactcctga ggtgcaaatt    3300
atattttca cagagctttt ctcagtgtag tgctgtactc ccttctcatg cttaagggaa    3360
aatcaaagaa aatgtgtttt ctcctgtgga gtagcagaat ttttaagag cactaagagg    3420
caactgagca ggaaaataaa tgttcaactg cataaataaa tgtaactact tatctcaaca    3480
gaaaaagggg taaatgtgag cagctacaag tcatgttgtg agcacttac ttaccagtgt    3540
tgcagaatac attttggttt ctttgtatca ttaagtctgt ggcaacactt aagtgacgac    3600
ctttttgtct ctttccttt tccttattt gtttccttct ttctcatact ttacctggat    3660
atagagttta cacatgtcta cgccactatc atttgaactg tttttcccttt tggttcagat    3720
tgtagttgac aagttctctg gccgatctaa aggattggt tttgttacat ttgatgaaaa    3780
gaaagcaatg gaagaagcca ttgaagaaat gaatgggatg gatttggatg gccgcgctat    3840
tactgtggac aaagcccagc cccaacaagg ttcaggtaga gaatttgata gtgatcggcc    3900
ccgtgaccga gatcgaggtc gtgatcacgg tcgtgataat cgtgaatatg gaggtgggcg    3960
tggatctggt ggtggagagt gcttaagtg tggcaagcca ggacactttg ccagagaatg    4020
cccaagtgaa ggaggtcgtg gtggtcgta tggcggcaga gatgataggt atggcggcgg    4080
cggaggtggt ggtggtagat caagtggcca ttatggacct gatagaaatg gagatcgttt    4140
tggaagccgc agcagcaggg atggtggtgg acatggggga gaacgatata atcgtgatcg    4200
ttctggtccg tacgatcgtc attaatgctt taaggtgcaa tatttatttt ggacttttaa    4260
tgctgtctga tattcgtgga atcatttcat tgtagtaact gaaattttaa cctgtctgtt    4320
gcagctaaag agttaggcgc caaccaagct ggatactaag ggtttgaagt atgtccgatg    4380
gcatcttgtt tccttggcct gttagcagaa gtggatcaat cttttgaact catgaaacat    4440
ggcactttaa tctactgttc tatgtccgta aaatgttcaa tagtgtggtt tgattgggat    4500
cttatgcgtg cttaatttat gaatttgaat atggtctcac acttttgaat gctactatgg    4560
ctgctggtta tttgctttgt tcgcttggaa agtagaatac tgatgtttgc tgctggaatc    4620
aatggttct tgtgttcaca attgcacctc taattgtgtg gtgatataga tgggtctgat    4680
gaattgccag gattttgtac tgatgataaa attctgaggt tcaccagcgt gtttatgtca    4740
aattgggaag cgagggtgaa ttagcagtgg ttttcctgtt ctgttctctt agaatctctt    4800
aacagttaat gggagttaaa acgggtaatc tattgcatta ttcctccatt tagtcagttt    4860
ttactttgca gctttacagt attaatgatg ttaacctttt gacaggctgc ctgtgttcaa    4920
atgacctttt ttgggtacat gattgggtct ctttgctagt tggtccagtt aaacataatt    4980
aatttgagaa agcatttggg acagcgacaa tccttctaca agtaattaga ccactaattg    5040
ctcttatgtt ctctaaggat taccggagga cgagttagtt cctcttaga tggcaagtta    5100
ttagttactc ttgagttcag caactgaggt ccatttattt tgttctggtt ttgatgttcc    5160
tcctccatgg agaaggttct tgttcgtcgt cgtggtttcc acatttgaga cccagacgat    5220
tgtcgctttg cttcaaagtc gggcttcatt gccatctcag cttgtgattc ttggtatctc    5280
tccggtaatg gttctgcttt ctaattcggc tggaggagca tggcctattt gttacacaag    5340
ggttctgaag ggggatgtgg ttatctggat attca                              5375
```

<210> SEQ ID NO 31
<211> LENGTH: 209
<212> TYPE: PRT
<213> ORGANISM: Artificial Sequence
<220> FEATURE:
<223> OTHER INFORMATION: Amino acid sequence Nitab4.5_0008185g0030.2

<400> SEQUENCE: 31

```
Met Ala Asp Asp Glu Tyr Arg Cys Phe Ile Gly Asn Leu Ser Trp Ser
1               5                   10                  15

Thr Ser Asp Arg Gly Leu Lys Asp Ala Phe Glu Lys Phe Gly Asn Leu
            20                  25                  30

Val Asp Ala Lys Val Val Leu Asp Lys Phe Ser Gly Arg Ser Arg Gly
        35                  40                  45

Phe Gly Phe Val Thr Phe Asp Glu Lys Arg Ala Met Glu Asp Ala Ile
    50                  55                  60

Glu Ala Met Asn Gly Val Asp Leu Asp Gly Arg Asp Ile Thr Val Asp
65                  70                  75                  80

Lys Ala Gln Pro Asp Lys Gly Ser Gly Arg Asp Phe Asp Ser Asp Arg
                85                  90                  95

Pro Arg Asp Arg Glu Arg Asp Arg Gly Arg Asp Arg Asp Arg
            100                 105                 110

Gly Ser Arg Asp Tyr Gly Gly Arg Gly Ser Gly Gly Gly Asp
        115                 120                 125

Cys Phe Asn Cys Gly Lys Pro Gly His Phe Ala Arg Glu Cys Pro Ser
    130                 135                 140

Glu Gly Gly Arg Gly Gly Arg Tyr Gly Gly Gly Gly Gly Ser Arg
145                 150                 155                 160

Ser Ser Gly Tyr Gly Pro Asp Arg Asn Gly Asp Arg Tyr Gly Ser Arg
                165                 170                 175

Ser Gly Arg Asp Gly Gly Arg Gly Gly Glu Arg Phe Ser Arg
            180                 185                 190

Asp Arg Ser Gly Pro Tyr Glu Arg Ser Ser Gly Gly Ser Arg Ala
        195                 200                 205

Gly
```

<210> SEQ ID NO 32
<211> LENGTH: 630
<212> TYPE: DNA
<213> ORGANISM: Artificial Sequence
<220> FEATURE:
<223> OTHER INFORMATION: coding sequence Nitab4.5_0008185g0030.2

<400> SEQUENCE: 32

```
atggcagatg atgaatatcg ctgttttatt ggtaacttgt catggtcaac ttctgatcga     60
ggattaaaag atgcatttga aagtttggaa aatcttgttg atgcaaaggt tgtacttgac    120
aagttctctg gccgatctcg tggatttggt tttgttacat ttgatgaaaa gagagcaatg    180
gaagatgcca ttgaagcaat gaatggagtg gacttagatg gtcgtgatat tactgtagac    240
aaagcccagc ctgacaaagg ttcaggtaga gattttgata gtgatcgacc tcgtgaccgt    300
gaacgtgacc gagatcgggg tcgcgatcgc gatcgtggta ccgtgattaa tggaggtgga    360
cggggatctg gtggtggtgg agactgcttt aactgtggta agccaggaca ctttgccaga    420
gaatgcccta gtgaaggggg tagaggtggt cggtatggtg gcggtggcgg aggtagtaga    480
agcagtggct atggacccga taggaacgga gatcgatatg gaagccgcag cggcagagat    540
ggtggtggtc gtggaggagg tgaacggttt agccgtgatc gttccggacc atacgaacgt    600
```

```
cgcagttctg gaggctctcg agctggctga                                     630
```

<210> SEQ ID NO 33
<211> LENGTH: 3577
<212> TYPE: DNA
<213> ORGANISM: Artificial Sequence
<220> FEATURE:
<223> OTHER INFORMATION: Nitab4.5_0008185g0030.2 genomic sequence

<400> SEQUENCE: 33

```
gattggcatt tcttctttgg agtaaacgct actaaacttt tctgcatctc ttcgtatcgc      60
cgccgccctc tcatctccga atcttcatta ttttcaaagg taacatttat ttctagtatc     120
tacaactttt gtttcttgct atctactttt tgcatagatt gtctcgaaga tctaattcgt     180
ttgcgaattc tgaagctttg atggcttatt tggggcaatt gatgatttgg gttttcatga     240
aaatgttaaa ttgacagacc catgttcctt tatatatata tatatcttga agcaattttc     300
tgtactgtta tgtttcagtt tgtacttat gagttgataa aagataatga atttctctta      360
ttaatcattg aataaagtat ccaactcatg cttaatgttg aagaatgtct caaataaatt     420
tgttctttta atgttatatg tttttggcta tttttgtgct gtgcataatt taatttggtg     480
aaagtatact aaacagttaa aatagttaaa tggggatggg gtattttta ctgaattggg      540
gtgattgatt ggttgggctt ctggattctt ttcatgtttg catatgatta ttctgtacat     600
atttagaaaa attcattcat gtttcatgct taggaagggg tcaatttgtt tcttggtgtc     660
tgacaaaaag taggttttac agtatgattt tgttggttga tgagctttct gcttagattg     720
ttgaattata ttgttgaatt cacaattaga acacataagc taattgactg catagaggag     780
tatggtgaag tgatattcct ttttgataaa acctaaaata gtagtaaaaa tagtgtgatt     840
ttgtatttgt taagtggaac tgtatttga atcatatatg gttgatgatt attttgagtg      900
cttggcttgt ttgtctaatg ctattgttgt ctgggggcag agaaaatgga tctaatagta     960
taatccacat aagcaggccc tattatcata actgaattaa tcttttggtg cacttttga     1020
ctcttggctt gattttgcac cccccccct cccaaatcta tctcgttctg tcttcttttt     1080
cagtagcagc agtctgtttc agaaatggca gatgatgaat atcgctgttt tattggtaac    1140
ttgtcatggt caacttctga tcgaggatta aaagatgcat ttgagaagtt tggaaatctt    1200
gttgatgcaa aggtaaggat ggtttatttt ttaggttttc gaattggtta atttgtcaat    1260
gatctctttt tttttttgct tctctttttt ttcttcttta ttgttttcg agtattgttg     1320
ctgggtggat tatttatgcg aaggagtttg cctcatcctt tagactagga ttagaccatt    1380
catacctgca aacctccttc cctttcaagt gacggtcagg ttttgacca ctttagtgca     1440
atctcccttc tacttatctc tcaatgcacc tattttaac ctctttacgt gaacaattca     1500
aatcttttga gtaattttct tattcttgct ctttgaatgc tacaacatct gcactttcat    1560
tgatatcatt ttaatcctca gtcctgacct cactcccaac ttctaatgag gaatatgaag    1620
gtaaatcagt atcttttttcc cctggatgcg cacatacatc atcagggat tctgaaaatt     1680
catgaaaatg tagcttaagg tactacatca aacaagtatt accaccaaac tttatcaagg    1740
tgcatgcgag attagacaaa attgtgaatt cttcctgtca aacttcacca cagaacctca    1800
ttagaaggtt tctttgtgtt gtgaagtcta tgacaagagt tagaattgca actgtctacc    1860
tccgtttcct ctctttttct tatgtcattc ccactctatt tttttctttt tgtggatgtt    1920
aaatttcaat atttcaatgc ctctatcctt tttggcttag gttgtacttg acaagttctc    1980
```

```
tggccgatct cgtggatttg gttttgttac atttgatgaa agagagcaa tggaagatgc    2040 cattgaagca atgaatggag tggacttaga tggtcgtgat attactgtag acaaagccca    2100
gcctgacaaa ggttcaggta gagattttga tagtgatcga cctcgtgacc gtgaacgtga    2160
ccgagatcgg ggtcgcgatc gcgatcgtgg tagccgtgat tatggaggtg acggggatc     2220 tggtggtggt ggagactgct ttaactgtgg taagccagga cactttgcca gagaatgccc    2280
tagtgaaggg ggtagaggtg gtcggtatgg tggcggtggc ggaggtagta aagcagtgg     2340 ctatggaccc gataggaacg gagatcgata tggaagccgc agcggcagag atggtggtgg    2400
tcgtggagga ggtgaacggt ttagccgtga tcgttccgga ccatacgaac gtcgcagttc    2460
tggaggctct cgagctggct gatgctttaa gttgtggtaa gttttaggct atttgatttt    2520
caattatcca atattcaggg tattatttac ttttgagctg attaaatttt gattctttct    2580
gatgcagctg aagagttaga agtcctacaa gctggatgca agtgatttga tgtatgtcta    2640
cttggtgctg tttccctggc ctgagccaac aaaatggatg aatcgtttga gctcatgaaa    2700
cctggctctt ataaactact gttctatgtc cgtaaatgtt cgataataca gtttgattgg    2760
gattttatgc ttgcttaatt tgcaaatttg aatatggcct tacactttga atgccactat    2820
ggttgctggt tatttgctta cttggttgg aaatttggaa accattgtgt ggtgctggat     2880
ttataatgct tccttgcatg gcaatcgcac ctctgaaact ttgccttgtg attgatgggt    2940
ctgatgaatt gcctgaattt agtactggtg ataaaaaatc tgggccagca ggtgttcatg    3000
tctaattgga ttgtagaact ggattaggag tggcctttgt tgtgttcttg taaaatctct    3060
ttaacagtta atgggagtga accgggtaat ttattccgtt ttaccctcta ttggtccatt    3120
ctaagttctc aactgttatg atattaatgt tgttaacctt ttggcaggct attttgttcc    3180
tttgtccttt tctgggtaca tgattggctc tcttgctagt tttggtgcgc atttaaattt    3240
atagagcgag aatgcttctg catggaaaga tcgttggtgg aagagttagt tttcctgtta    3300
gatggtgaca tgtttagata ctcttggagg gttcagcaat atggctccac taatttgttc    3360
tgctttggtg tttctatttc gcggggacgg ttcttgttct tttcttgtag tcctggtgtc    3420
tgttttcaag atccaaatga gtgcaaaacc aatacagcaa gacttcattt gccaatgagc    3480
tcctggtcct aggtatctat tctttctact tggcagatct gcttttgaac tccagttgga    3540
gacttcggcc tattttgagt cactagtgca ttgaaga                              3577
```

<210> SEQ ID NO 34
<211> LENGTH: 177
<212> TYPE: DNA
<213> ORGANISM: Artificial Sequence
<220> FEATURE:
<223> OTHER INFORMATION: nucleotide sequence of
      Nitab4.5_0013685g0010.2_deltaRBD-RGG

<400> SEQUENCE: 34

```
atgagcggtg gaggctacgg aggtggtggc cgtcgtgaag gtggatacgg tggtggcggc    60
ggttacggag gtggccgccg tgaaggtggt tatggtggtg gtggcggcgg cggttatgga    120
ggtggccgtc gtgaaggtgg ttacggtggt ggctctgaag gaaactggag gagttag      177
```

<210> SEQ ID NO 35
<211> LENGTH: 58
<212> TYPE: PRT
<213> ORGANISM: Artificial Sequence
<220> FEATURE:
<223> OTHER INFORMATION: amino acid sequence of
      Nitab4.5_0013685g0010.2_deltaRBD-RGG

<400> SEQUENCE: 35

Met Ser Gly Gly Gly Tyr Gly Gly Gly Arg Arg Glu Gly Gly Tyr
1               5                   10                  15

Gly Gly Gly Gly Gly Tyr Gly Gly Gly Arg Arg Glu Gly Gly Tyr Gly
            20                  25                  30

Gly Gly Gly Gly Gly Tyr Gly Gly Arg Arg Glu Gly Gly Tyr
        35                  40                  45

Gly Gly Gly Ser Glu Gly Asn Trp Arg Ser
        50                  55

<210> SEQ ID NO 36
<211> LENGTH: 79
<212> TYPE: PRT
<213> ORGANISM: Artificial Sequence
<220> FEATURE:
<223> OTHER INFORMATION: amino acid sequence of an RNA-binding domain
      (RBD)

<400> SEQUENCE: 36

Tyr Arg Cys Phe Val Gly Gly Leu Ala Trp Ala Thr Thr Asp Gln Thr
1               5                   10                  15

Leu Gly Glu Ala Phe Ser Gln Phe Gly Glu Ile Leu Asp Ser Lys Ile
            20                  25                  30

Ile Asn Asp Arg Glu Thr Gly Arg Ser Arg Gly Phe Gly Phe Val Thr
        35                  40                  45

Phe Lys Asp Glu Lys Ala Met Arg Asp Ala Ile Glu Gly Met Asn Gly
    50                  55                  60

Gln Asp Leu Asp Gly Arg Asn Ile Thr Val Asn Glu Ala Gln Ser
65                  70                  75

<210> SEQ ID NO 37
<211> LENGTH: 3
<212> TYPE: PRT
<213> ORGANISM: Artificial Sequence
<220> FEATURE:
<223> OTHER INFORMATION: amino acid RGG motif

<400> SEQUENCE: 37

Arg Gly Gly
1

<210> SEQ ID NO 38
<211> LENGTH: 1273
<212> TYPE: PRT
<213> ORGANISM: Artificial Sequence
<220> FEATURE:
<223> OTHER INFORMATION: interactor, Nitab4.5_0005487g0030.2 protein
      sequence

<400> SEQUENCE: 38

Met Asn Thr Gln Pro Asn Asn Leu Tyr Asp Thr Ala Ser Gln Pro Asp
1               5                   10                  15

Thr Gly Asn Asp Ala Tyr Thr Phe Leu Glu Phe Asn Thr Gln Gly Glu
            20                  25                  30

Glu Phe Asp Tyr Pro Glu Phe Gln Glu Leu Ser Gln Pro Ile Arg Ser
        35                  40                  45

Ser Ala Trp Pro Thr Pro Ser Asp Ser Leu Val Ser Glu Ala Pro Asp
    50                  55                  60

Arg Pro Pro Ser Ser Asp Ala Ser Pro Ser Lys Lys Thr Arg Gly Gly
65                  70                  75                  80

```
Ser Gly Gly Asn Val Ser Gly Gly Gly Asn Gly Asn Val Ile Gly
            85              90              95

Ser Ser Ser Asn Asn Gln Ala Ala Ser Val Val Asp Ala Leu Ala
            100             105             110

Ala Gly Met Ser Gly Leu Asn Phe Glu Glu Thr Val Asp Asp Glu Gly
            115             120             125

Phe Glu Tyr Gly Lys Gly Asp Phe Gly Val Glu His Ala Cys Lys Tyr
            130             135             140

Cys Gly Val Thr Asn Pro Ala Cys Val Val Arg Cys Asn Val Pro Ser
145             150             155             160

Cys Arg Lys Trp Phe Cys Asn Ser Arg Gly Asn Thr Ser Gly Ser His
                165             170             175

Ile Val Asn His Leu Val Arg Ala Lys His Lys Glu Val Cys Leu His
            180             185             190

Lys Asp Ser Pro Leu Gly Glu Thr Ile Leu Glu Cys Tyr Asn Cys Gly
            195             200             205

Cys Arg Asn Val Phe Leu Leu Gly Phe Ile Ser Ala Lys Ala Glu Ser
210             215             220

Val Val Val Leu Leu Cys Arg Glu Pro Cys Leu Ser Val Asn Ala Leu
225             230             235             240

Lys Asp Met Asn Trp Asp Leu Ser Gln Trp Cys Pro Leu Ile Asp Asp
                245             250             255

Arg Cys Phe Leu Gln Trp Leu Val Lys Val Pro Ser Glu Gln Glu Gln
                260             265             270

Leu Arg Ala Arg Gln Ile Ser Ala Gln Gln Ile Asn Lys Val Glu Glu
            275             280             285

Leu Trp Lys Thr Asn Pro Asp Ala Thr Leu Glu Asp Leu Glu Lys Pro
            290             295             300

Gly Val Asp Asp Glu Pro Gln Pro Val Ala Leu Lys Tyr Glu Asp Ala
305             310             315             320

Tyr Gln Tyr Gln Asn Ile Phe Ala Pro Leu Ile Lys Leu Glu Ala Asp
                325             330             335

Tyr Asp Lys Met Met Lys Glu Ser Gln Ser Lys Asp Asn Leu Thr Ile
            340             345             350

Arg Trp Asp Ile Gly Leu Asn Lys Lys Arg Val Ala Tyr Phe Val Phe
            355             360             365

Pro Lys Glu Asp Asn Glu Leu Arg Leu Val Pro Gly Asp Glu Leu Arg
            370             375             380

Leu Arg Tyr Ser Gly Asp Ala Val His Pro Ala Trp Gln Ser Val Gly
385             390             395             400

His Val Val Lys Leu Thr Ala Gln Glu Glu Val Ala Leu Glu Leu Arg
            405             410             415

Val Ser Gln Gly Val Pro Val Asp Val Thr His Gly Leu Ser Val Asp
            420             425             430

Phe Val Trp Lys Ser Thr Ser Phe Asp Arg Met Gln Ser Ala Met Lys
            435             440             445

Thr Phe Ala Val Asp Glu Thr Ser Val Ser Gly Tyr Ile Tyr His His
450             455             460

Leu Leu Gly His Glu Val Glu Met Gln Met Val Arg Asn Ala Leu Pro
465             470             475             480

Arg Arg Phe Gly Ala Pro Gly Leu Pro Glu Leu Asn Ala Ser Gln Val
                485             490             495
```

Phe Ala Val Lys Ser Val Leu Gln Lys Pro Ile Ser Leu Ile Gln Gly
                500                 505                 510

Pro Pro Gly Thr Gly Lys Thr Val Thr Ser Ala Ala Ile Val Tyr His
            515                 520                 525

Met Ala Lys Gln Gly Gln Gly Gln Val Leu Val Cys Ala Pro Ser Asn
530                 535                 540

Val Ala Val Asp Gln Leu Ala Glu Lys Ile Ser Ala Thr Gly Leu Lys
545                 550                 555                 560

Val Val Arg Leu Cys Ala Lys Ser Arg Glu Ala Val Ser Ser Pro Val
                565                 570                 575

Glu His Leu Thr Leu His Tyr Gln Val Arg His Leu Asp Thr Ser Glu
            580                 585                 590

Lys Ser Glu Leu His Lys Leu Gln Gln Leu Lys Asp Glu Gln Gly Glu
            595                 600                 605

Leu Ser Ser Ser Asp Glu Lys Lys Tyr Lys Ala Leu Lys Arg Ala Thr
610                 615                 620

Glu Arg Glu Ile Ala Gln Ser Ala Asp Val Ile Cys Cys Thr Cys Val
625                 630                 635                 640

Gly Ala Gly Asp Pro Arg Leu Ala Asn Phe Arg Phe Arg Gln Val Leu
                645                 650                 655

Ile Asp Glu Ser Thr Gln Ala Thr Glu Pro Glu Cys Leu Ile Pro Leu
            660                 665                 670

Val Leu Gly Ala Lys Gln Ala Val Leu Val Gly Asp His Cys Gln Leu
            675                 680                 685

Gly Pro Val Ile Met Cys Lys Lys Ala Ala Arg Ala Gly Leu Ala Gln
690                 695                 700

Ser Leu Phe Glu Arg Leu Val Phe Leu Gly Val Lys Pro Ile Arg Leu
705                 710                 715                 720

Gln Val Gln Tyr Arg Met His Pro Ala Leu Ser Glu Phe Pro Ser Asn
                725                 730                 735

Ser Phe Tyr Glu Gly Thr Leu Gln Asn Gly Val Thr Ile Asn Glu Arg
            740                 745                 750

Gln Ser Thr Gly Ile Asp Phe Pro Trp Pro Val Pro Asn Arg Pro Met
            755                 760                 765

Phe Phe Tyr Val Gln Met Gly Gln Glu Glu Ile Ser Ala Ser Gly Thr
770                 775                 780

Ser Tyr Leu Asn Arg Thr Glu Ala Ala Asn Val Glu Lys Ile Val Thr
785                 790                 795                 800

Thr Phe Leu Lys Gly Gly Val Val Pro Ser Gln Ile Gly Val Ile Thr
                805                 810                 815

Pro Tyr Glu Gly Gln Arg Ala Tyr Ile Val Asn Tyr Met Ala Arg Asn
            820                 825                 830

Gly Ser Leu Arg Gln Gln Leu Tyr Lys Glu Ile Glu Val Ala Ser Val
            835                 840                 845

Asp Ser Phe Gln Gly Arg Glu Lys Asp Tyr Ile Ile Leu Ser Cys Val
850                 855                 860

Arg Ser Asn Glu His Gln Gly Ile Gly Phe Leu Asn Asp Pro Arg Arg
865                 870                 875                 880

Leu Asn Val Ala Leu Thr Arg Ala Arg Tyr Gly Ile Val Ile Leu Gly
                885                 890                 895

Asn Pro Lys Val Leu Ser Lys Gln Pro Leu Trp Asn Gly Leu Leu Thr
            900                 905                 910

His Tyr Lys Glu His Glu Cys Leu Val Glu Gly Pro Leu Asn Asn Leu

```
                915                 920                 925
Lys Gln Ser Met Val Gln Phe Gln Lys Pro Lys Lys Ile Tyr Asn Glu
930                 935                 940

Arg Arg Leu Phe Phe Gly Gly Pro Gly Ile Pro Gly Asp Ser Phe
945                 950                 955                 960

Gly Ser Ala Ser Gly Pro Asn Ala Asp Arg Arg Asn Ser Arg Ser Arg
                965                 970                 975

Gly Ser Tyr Met Ala Pro Gly Val Pro Asn Gly Thr Gln Lys Pro Gly
                980                 985                 990

Leu His Pro Ala Gly Tyr Pro Met Pro Arg Val Ala Phe Pro Pro Tyr
                995                 1000                1005

His Gly Gly Pro Pro Gln Pro Tyr Ala Ile Pro Thr Arg Gly Ala
    1010                1015                1020

Val His Gly Pro Val Gly Ala Val Pro His Val Pro Gln Pro Gly
    1025                1030                1035

Ser Arg Gly Phe Gly Ala Gly Arg Gly Asn Ala Asn Ala Pro Ile
    1040                1045                1050

Gly Ser His Leu Pro His His Gln Gly Ala Gln Gln Gln Ala Gly
    1055                1060                1065

Ser Leu Gly Ser Asn Phe Asn Phe Pro Ala Leu Glu Asn Pro Asn
    1070                1075                1080

Ser Gln Pro Ser Val Gly Gly Pro Leu Ser Gln Pro Gly Tyr Ala
    1085                1090                1095

Ser Asn Ile Gly Ile Gln Gly Pro Gly Gln Thr Phe Arg Asp Gly
    1100                1105                1110

Tyr Ser Leu Gly Ser Met Ser Gln Asp Phe Val Gly Asp Asp Phe
    1115                1120                1125

Lys Ser Gln Gly Ser His Val Pro Tyr Asn Val Ala Asp Phe Ser
    1130                1135                1140

Thr Gln Ala Ser Gln Ser Gly Tyr Ala Val Asp Tyr Val Thr Gln
    1145                1150                1155

Gly Ala Gln Ala Gly Phe Pro Gly Asn Phe Leu Asn Gln Asn Ser
    1160                1165                1170

Gln Ser Gly Tyr Ser Arg Phe Gly Ser Gly Asn Glu Phe Met Ser
    1175                1180                1185

Gln Asp Tyr Met Ala His Gly Ser Gln Gly Leu Phe Thr Gln Ala
    1190                1195                1200

Gly Tyr Asn Asn Pro Ser Gln Asp Asp Gly Ser Gln Asn His Phe
    1205                1210                1215

Gly Met Ser Asn Ala Ser Leu Gln Ser Gln Ser Leu Asn Pro
    1220                1225                1230

Leu Tyr Ser Gln Pro Phe Ala His Tyr Asn Thr Gln Pro Phe Asn
    1235                1240                1245

Met Gln Ser Gln Pro Gln Gln Gln Ala Pro Gln Gly Gln Gly
    1250                1255                1260

Phe Gln Asn Gln Lys Leu His Tyr Asn Ser
    1265                1270
```

<210> SEQ ID NO 39
<211> LENGTH: 3822
<212> TYPE: DNA
<213> ORGANISM: Artificial Sequence
<220> FEATURE:
<223> OTHER INFORMATION: interactor, Nitab4.5_0005487g0030.2 coding
      sequence

<400> SEQUENCE: 39

```
atgaatactc agccgaacaa tctctacgat acggcgtcgc agccggacac cgggaacgat    60
gcatacacat tcctcgaatt caacacgcaa ggcgaagagt tcgattatcc tgaatttcaa   120
gagcttccac agccaattcg atcgtcagcg tggcctacgc cgtcggattc tctggttccc   180
gaagcacccg atcggcctcc gtcttctgac gcctctccgt ccaaaaaaac ccgcggtgga   240
agcggcggaa atgtctctgg tggaggcggg aacggaaatg ttattggtag tagtagtaat   300
aatcaggcgg catcggtggt ggtggatgca ttggcggcgg ggatgagcgg gttgaatttt   360
gaggagacgt tggatgatga gggttttgag tatggaaagg gggattttgg tgttgagcat   420
gcttgtaagt actgtggagt gacgaatcct gcttgtgtag ttaggtgcaa tgtgccgtct   480
tgccgtaagt ggttttgtaa ttcaagggggg aatacttcgg gctcacatat tgttaatcac   540
ctggtgcgag caaaacacaa ggaggtgtgc cttcataaag atagtccact tggagaaacg   600
attctagagt gctataattg tggatgccga aatgtctttc ttcttggttt catttctgct   660
aaggcagaga gtgtcgttgt tctcctctgt agggaacctt gtcttagtgt taatgcattg   720
aaggatatga actgggacct aagccagtgg tgcccgctca ttgatgacag gtgcttttg   780
cagtggcttg ttaaggtccc ctctgagcaa gaacagttga gggcgcgcca gatcagtgct   840
caacaaatca acaaagtaga agaattgtgg aagacaaatc cagatgctac cctgaagat   900
cttgagaagc ctggtgtaga tgatgagcct cagcccgttg ccttgaagta tgaagatgcc   960
tatcagtatc aaaacatatt tgcaccattg atcaagctcg aagctgacta cgacaagatg  1020
atgaaagagt ctcagagtaa agacaatctt actattcgat gggatattgg tctcaacaag  1080
aagcgcgttg cgtactttgt cttccctaag gaagataatg agttgcgtct tgtacctggt  1140
gatgagctaa ggctgcgata ttcaggggat gcagtacatc cagcttggca atccgtgggg  1200
cacgtggtaa aattaactgc tcaagaggag gttgcgcttg aacttcgtgt cagccagggg  1260
gttcctgtcg atgtgaccca tgggcttagt gttgactttg tttggaaaag cacgagcttt  1320
gatcggatgc agagtgcgat gaaaaccttt gcagtggatg agactagtgt cagtgggtat  1380
atttaccatc acctgctagg tcatgaagtt gagatgcaga tggtccgcaa tgcacttcct  1440
cgtcgttttg gtgcccctgg tcttccagag cttaatgcat ctcaggtttt tgctgtaaaa  1500
agtgttcttc aaaagcccat cagtttaatt caaggtccac ctggaacggg aaaaactgtc  1560
acctctgccg ccattgtgta tcatatggcc aaacaaggcc aaggacaggt tttggtttgt  1620
gcccccagta atgttgctgt ggaccaatta gcagagaaga taagtgctac tggtctgaag  1680
gtggtcaggc tctgtgccaa gtcaagggaa gctgtcagtt ctcctgtcga gcatttaacc  1740
cttcactatc aggttcgcca tcttgacaca tctgagaaga gtgaactgca caagttacag  1800
caactgaagg atgaacaagg agagctctcc agcagcgatg agaagaaata taagctttg  1860
aagcgggcaa cagagaggga aatagctcag agtgctgatg taatttgttg cacatgcgtt  1920
ggtgctggag accctagatt ggctaacttc agattccgcc aggtgcttat tgatgaatcc  1980
actcaggcta ctgagcctga atgtcttatt ccttttggttc ttggcgcaaa gcaggctgtt  2040
cttgtcggtg atcactgcca gcttggacca gtcattatgt gcaagaaagc agcccgtgct  2100
ggacttgctc aatctctatt tgagcgcctt gtgtttctag gagtgaagcc aattaggtta  2160
caggtacaat accgtatgca tcctgcatta tctgagtttc catcaaatag cttttatgaa  2220
ggtacactcc aaaatggtgt aaccatcaat gaaaggcaat caacaggcat tgatttccct  2280
```

```
tggcctgtgc ccaaccgtcc catgttctTT tatgttcaga tgggacaaga ggagatcagt    2340
gctagtggaa cttcctatct gaatagaact gaagctgcaa atgtggagaa gattgtgact    2400
acatttctta agggtggagt agtccctagt cagattgggg tcataacacc atatgagggt    2460
caacgagcat acattgtaaa ttacatggca agaaatggtt ccttgaggca acaactttac    2520
aaggaaattg aggttgcaag tgttgattca tttcaaggga gggaaaagga ttatattatt    2580
ttgtcatgtg tcaggagtaa tgaacatcag ggcattggat tccttaatga tccacggagg    2640
cttaatgttg cccttacacg tgctcgttat ggtattgtta tccttggaaa tcctaaagtt    2700
cttagcaaac agcctctgtg gaatggcttg ctgacacact acaaggagca tgagtgcttg    2760
gtagaaggtc ctctgaataa cttaaagcag agcatggttc aatttcagaa gcccaaaaag    2820
atctacaatg agcgcagact tttctttggt ggtggacctg gaattccagg tgacagtttt    2880
ggatctgctt caggccccaa cgctgacagg agaaatagtc gttctagggg ttcttatatg    2940
gcacctggtg tacccaacgg tactcagaaa cctggtcttc atcctgctgg ttatccaatg    3000
cctcgggttg cctttccacc ttaccatgga ggccctccac aaccgtatgc aattcctact    3060
cgtggtgctg tccatggccc tgttggagct gttcctcatg ttccacagcc aggtagccgg    3120
ggttttgggg ctggacgtgg caatgccaat gccccaattg gtagtcatct ccctcaccat    3180
caaggcgccc agcaacaggc cggaagtctt ggatctaact tcaactttcc tgcattggag    3240
aatccaaaca gccagccttc tgttggagga cctttatctc agcctggata tgcttctaat    3300
attggtatcc agggggccagg ccagacattt cgggatggat attctttggg tagcatgtca    3360
caggatttcg tgggagatga tttcaagagc caggggtctc atgttccata taacgttgct    3420
gacttctcta cacaggcttc tcaaagtgga tatgctgttg attatgtaac tcaaggagca    3480
caggctggtt ttccagggaa cttcttaaac cagaattcgc aatctggata ctcccgtttt    3540
ggttcaggaa atgaattcat gtcacaggac tacatggctc atggatccca aggtctcttt    3600
actcaagctg gatacaataa cccgtcgcaa gatgatggtt cacagaatca ttttggcatg    3660
tccaatgcat ctcttcagtc tcagagttcg cttaatccac tttactccca accatttgct    3720
cactacaaca cgcaaccatt taacatgcaa agccaacctc aacagcagca agccccacaa    3780
ggccagggct tccaaaatca gaaacttcac tacaatagtt ga                      3822
```

<210> SEQ ID NO 40
<211> LENGTH: 17511
<212> TYPE: DNA
<213> ORGANISM: Artificial Sequence
<220> FEATURE:
<223> OTHER INFORMATION: interactor, Nitab4.5_0005487g0030.2 genomic
      sequence
<220> FEATURE:
<221> NAME/KEY: misc_feature
<222> LOCATION: (5095)..(6594)
<223> OTHER INFORMATION: n is a, c, g, or t

<400> SEQUENCE: 40

```
atcatatctt tctctccccc ctctctctct tcttcgccct tttcaccgaa ccctaacttt      60 ccccttttcca aaccctaatt ctgaacacac taaaaatctc acttcgaaat cgaaaacttc    120
agcctacatt aaaattcatat catcgatttt ttgattatac gatgaatact cagccgaaca    180
atctctacga tacggcgtcg cagccggaca ccgggaacga tgcatacaca ttcctcgaat    240
tcaacacgca aggcgaagag ttcgattatc ctgaatttca agagctttca cagccaattc    300
gatcgtcagc gtggcctacg ccgtcggatt ctctggtttc cgaagcaccc gatcggcctc    360
```

```
cgtcttctga cgcctctccg tccaaaaaaa cccgcggtgg aagcggcgga aatgtctctg    420
gtggaggcgg gaacggaaat gttattggta gtagtagtaa taatcaggcg gcatcggtgg    480
tggtggatgc attggcggcg gggatgagcg ggttgaattt tgaggagacg gtggatgatg    540
agggttttga gtatgaaaag ggggattttg gtgttgagca tgcttgtaag tactgtggag    600
tgacgaatcc tgcttgtgta gttaggtgca atgtgccgtc ttgccgtaag tggttttgta    660
attcaagggg gaatacttcg ggctcacata ttgttaatca cctggtatgt aagagagatg    720 cattttttc tctcgcatat ttgattcttg ttgtgaatgc ctgttttttg tggtctatag     780
aaatgtgcag aatagatgtt atcatactac aacaacaata actatgccag tcccaaacaa    840
gttggggttg gttctatgaa tccttacaga atatgttact catataaact cattgccaat    900
atcgtacaaa ataaaaataa aaggtacaag aagtttatat tgcctattga cgtataagta    960
tctgcaaata aatttatcgt gcaacaatta tgcctcaatc tcatacaagt tggggtttgt   1020
tatgtgaatc cttattcacc atgtcactcc atataaactc atatcagccc attattatac   1080
aaaataaata taaaaagtac tactagaagt tcgttatctt gttgacatat aaatctctac   1140
aaaataggtt ttaccataaa acaactatgc ctcaatatca aacaagttgg ggccaattct   1200
cgctgatcat gttacttcat atcaacttat ctcaggccaa tattatacaa ataatttca    1260 ctcagcccct agtagttttt tatatttaaa ggaaaggttg tgccaccaac aacctttagg   1320
tgttttgcgt gacaagaatg tgccaccaaa acttaaaggt aagttctata gagcggttgt   1380
cagaccgact atgttgtatg gggttgagtg ttggccgatc aagaactcac atgtccagaa   1440
ggtgaaggta aagaaatga ggatgttgag atgaatatac aagatagata aaattaagaa    1500
tgaagatatt caggaaaagg tgggtgtggc ccatgtggag gacaagatga gagacgcgag   1560
acttacatga ttcaagcatg tgaagatgag aggcaccgat gccccagtga ggaggtgtga   1620
gaggttggcc ttgtagagcc taagaagagg tagaggtaag ccggagaagt actggggaga   1680
ggtgattaag catgacatgg cgatgctcca gcttaccgag gacatgacct ttgattggaa   1740
ggtatggagg tcgagaatta gggcagaagg ttcggtagca ttgcattttc cttgttcata   1800
ccagaagtat tagtttacta cttagtgtta gtctagtatt tttttgttct tagatttcta   1860
ttattatttg aagggagcct tggcgcaact ggtgaagttg ctgccatgtg accaggaggt   1920
cacgggttca agctgtggaa acaacctctt gcagaaatgc agggtaaggt tgcgtacgag   1980
agacccttgt ggtccggccc ttccccggac cccgcgcata gcgggagctt agtgcaccgg   2040
gttgcgcttt agatttctat tattacttgt tgtctctttc gcttcggttt tcttattggt   2100
tgttggtgtc attacttgtt gttactcctt ttattttatc tttcttgagc cgagggtcta   2160
ccgcaaaaag cctctctacc ttctcaaggt aggggtaagg tctgcttata cactaccctc   2220
cctagacccc acttgtggga ttatactggg ttttttgttg ttgtacgggt tttttatatt   2280
tcctattaat gtgtaaatgt ctgcagaata ggttttgtca taactacatt attttttgac   2340
aagtagctta ctagctttat cataatgaaa tagaaaaaac ttgtatagta gctttatggt   2400
attttctttt gtagtttatt tggatgactt gaagttgatt taccagttat aattgggatg   2460
aaaaataatt tttctgtcct cattttgcta aaggaagcag ggttttaagt ggaataccttt  2520 atacctcaca cccattactc ccctgagctt aatataggta tatatatttc aagctaaagg   2580
cagtagtgtg cagcactagc tgcagatagg gtcttgggc aggggcatgt ttatcataat    2640
gtatgtagtc tccttcctcc tgtcctccct ttctctctgg tacttgtttt aggaaaggga   2700
ataacatggt taaaaaagaa gtatggaacc agaaatacta gtatcggata gcaccagaaa   2760
```

```
agtgaactag tgaagtagat gaggcttatg catttgtctt tgacctagcg attattaatc    2820
gactaaccaa ttagtcttta ttccgtttct ttattccttt taaattcttt aaatcaagca    2880
gttattggta actgctgaga aaatctcctt cctttttct  tgtttgtgtg ttaccaataa    2940 ggttttttagc cgagtatagt tcttttgttt catctggtga ttgatggtca atgctgtgga   3000
tgtcgttggt ttttgagctc tcttttattt gcttttctc  catatttggg atgctattgc    3060
ccccagggct tcactttaac ataaaatgca acatgtgatg cgtgggttag gcacttcatg    3120
ggttcgagac ctgccgcagc caaaagcgcg agtttaagtg gaggagtata gagggacggg    3180
cccattatcc accgttttg  aaccatgcgc tactgaccct cgagtgtttc ttggtcatta    3240
gaaaaaatcg ggatgctatt actcatgcag cttctagctg ttatgccatg ggatatagat    3300
ttgctgttat accatgggat agatttgctg cgtccgttta ttctttggga aagcatattt    3360
ttgaagcaac aatggaaaat ttatttgata caaatgtata gttttgtcag ccttttttctg   3420 tagtatggtg aatgtacatt tactaggtat aatgctagat ttccacatgt ccttataagt    3480
tagtaaagca acaagttctt ttctccttt  gtaatgtata tttctagcac cctttagtgc    3540
tgggatctct tcaataaaaa gatcttttat cccaataaaa tatacatttt tgtcagattc    3600
atgcaacttc acctccacaa aattcttaat ttatgcatgt gggataagtt aaaagggaaa    3660
ttctctatat gttttttcgag gagaaaaagcc aaagcgccac cttttcttag ttactaaggg  3720
agtagattat ctctagttga tactgcattt tggaatgtca gttgtccaaa ctgtagaaat    3780
taaataagga atcttaaatg catattataa tttgattgtt tcaccagtgt atgcagtggg    3840
atcagctact tgcatttaat ggacttacgt tggggtgtta tattcatctt gccttttcct    3900
acaactaaca tgtctattat attctctccg gaaacaaggc atttattgag tataattttt    3960
gtattgttgg catttattga atattctcaa ttttttctaa taggtgcgag caaaacacaa    4020
ggaggtgtgc cttcataaag atagtccact tggagaaacg attctagagt gctataattg    4080
tggatgccga aatgtctttc ttcttggttt catttctgct aaggcagaga gtgtcgttgt    4140
tctcctctgt agggaacctt gtcttagtgt taatgcattg aaggatatga actgggacct    4200
aagccagtgg tgcccgctca ttgatgacag gtgctttttg cagtggcttg ttaaggtctg    4260
gattctcttt cttgttctct cttttgatc  cttttggttt ttgttttctg tcctgtattt    4320
gtgacgtgtg gagtgctgca ggtcccctct gagcaagaac agttgagggc gcgccagatc    4380
agtgctcaac aaatcaacaa agtagaagaa ttgtggaaga caaatccaga tgctaccctg    4440
gaagatcttg agaagcctgg tgtagatgat gagcctcagc ccgttgcctt gaagtatgaa    4500
gatgcctatc aggttctcac tggatgatac tattgtatta tctcctctac cttttatgtg    4560
taataaatgc tgtgcaggaa ttgctttact atgtatttgt gagttgcctt cgtattgaca    4620
ttttaactaa gtttgccttc acccttctaa tgtagtatca aaacatattt gcaccattga    4680
tcaagctcga agctgactac gacaaggtat gtcaggtttt gaagatgatt ttacatgctg    4740
aagcgtgagt gcgtcaatga atactgaatt ttgtctatac aaatgttgat tttatgagga    4800
caattgtatt tatgcttgct tatctttttc ttcttgattc ttaacgtccg tgacaattga    4860
gttaaggcat tcaaagttac ttctctctat tgtcactctt gagtaaagat gtgagcgtac    4920
tactgtcacg acccaaaatc taaccatggt cgtgatggcg cttatcgtgt tacaaggcaa    4980
gcctactttt caaatatatta ctactaaacc gattataaga atttaataaa acatttcaac   5040
atttaaattt ttcataaact aaatcaactc taaatataat atagaaaaat acggnnnnnn    5100
```

```
nnnnnnnnnn nnnnnnnnnn nnnnnnnnnn nnnnnnnnnn nnnnnnnnnn nnnnnnnnnn    5160
nnnnnnnnnn nnnnnnnnnn nnnnnnnnnn nnnnnnnnnn nnnnnnnnnn nnnnnnnnnn    5220
nnnnnnnnnn nnnnnnnnnn nnnnnnnnnn nnnnnnnnnn nnnnnnnnnn nnnnnnnnnn    5280
nnnnnnnnnn nnnnnnnnnn nnnnnnnnnn nnnnnnnnnn nnnnnnnnnn nnnnnnnnnn    5340
nnnnnnnnnn nnnnnnnnnn nnnnnnnnnn nnnnnnnnnn nnnnnnnnnn nnnnnnnnnn    5400
nnnnnnnnnn nnnnnnnnnn nnnnnnnnnn nnnnnnnnnn nnnnnnnnnn nnnnnnnnnn    5460
nnnnnnnnnn nnnnnnnnnn nnnnnnnnnn nnnnnnnnnn nnnnnnnnnn nnnnnnnnnn    5520
nnnnnnnnnn nnnnnnnnnn nnnnnnnnnn nnnnnnnnnn nnnnnnnnnn nnnnnnnnnn    5580
nnnnnnnnnn nnnnnnnnnn nnnnnnnnnn nnnnnnnnnn nnnnnnnnnn nnnnnnnnnn    5640
nnnnnnnnnn nnnnnnnnnn nnnnnnnnnn nnnnnnnnnn nnnnnnnnnn nnnnnnnnnn    5700
nnnnnnnnnn nnnnnnnnnn nnnnnnnnnn nnnnnnnnnn nnnnnnnnnn nnnnnnnnnn    5760
nnnnnnnnnn nnnnnnnnnn nnnnnnnnnn nnnnnnnnnn nnnnnnnnnn nnnnnnnnnn    5820
nnnnnnnnnn nnnnnnnnnn nnnnnnnnnn nnnnnnnnnn nnnnnnnnnn nnnnnnnnnn    5880
nnnnnnnnnn nnnnnnnnnn nnnnnnnnnn nnnnnnnnnn nnnnnnnnnn nnnnnnnnnn    5940
nnnnnnnnnn nnnnnnnnnn nnnnnnnnnn nnnnnnnnnn nnnnnnnnnn nnnnnnnnnn    6000
nnnnnnnnnn nnnnnnnnnn nnnnnnnnnn nnnnnnnnnn nnnnnnnnnn nnnnnnnnnn    6060
nnnnnnnnnn nnnnnnnnnn nnnnnnnnnn nnnnnnnnnn nnnnnnnnnn nnnnnnnnnn    6120
nnnnnnnnnn nnnnnnnnnn nnnnnnnnnn nnnnnnnnnn nnnnnnnnnn nnnnnnnnnn    6180
nnnnnnnnnn nnnnnnnnnn nnnnnnnnnn nnnnnnnnnn nnnnnnnnnn nnnnnnnnnn    6240
nnnnnnnnnn nnnnnnnnnn nnnnnnnnnn nnnnnnnnnn nnnnnnnnnn nnnnnnnnnn    6300
nnnnnnnnnn nnnnnnnnnn nnnnnnnnnn nnnnnnnnnn nnnnnnnnnn nnnnnnnnnn    6360
nnnnnnnnnn nnnnnnnnnn nnnnnnnnnn nnnnnnnnnn nnnnnnnnnn nnnnnnnnnn    6420
nnnnnnnnnn nnnnnnnnnn nnnnnnnnnn nnnnnnnnnn nnnnnnnnnn nnnnnnnnnn    6480
nnnnnnnnnn nnnnnnnnnn nnnnnnnnnn nnnnnnnnnn nnnnnnnnnn nnnnnnnnnn    6540
nnnnnnnnnn nnnnnnnnnn nnnnnnnnnn nnnnnnnnnn nnnnnnnnnn nnnngatctc    6600
taacatgaag gcagacaagt tcaacaacaa gtaactatgt aaacacagat gatggccatg    6660
aggcctcacg ggacggacca agtctcgatc cctcgaggta tacacccaca cgcccatcac    6720
ctagcgtggg tatcatctcc aaacagtcac acgatatcaa attctccagg tttataccct    6780
caaagccaga gttaaaactg ttacttaact taacaacgta aaatcctact ccgggatgcc    6840
ctcgtctctg gactcggtct ccaaaagctc caaatctaac cataatctga ttaataccat    6900
tccacaataa aaactacaaa atatgccaaa aattcgaaac cggccaaaac ccgcccccgg    6960
gcccacgtct cgaaatcagt caaaaatggc agaataataa acctcgtcct ctcccgagtc    7020
taaccatata aaattcatca aatcggact ccgtttggtc cctcaaatcc tcacttaaac    7080
tctccaaaac tcaaaccta actccctcaa tttcactttg aaatcatcaa ttaaatccca    7140
aaaacgaaga tggattcatg aaatataacc aaaactgagt agagaacact taccccaatc    7200
cttatggtga aaatcgcccc caaatcgcc caaatccgag ctccccaact caaaatatga    7260
ccgaatgaac aaaccctcgt tttatatatt tttctgccag ctattctgcc tcgtttctcg    7320
tgccaaacga tcccgaaact cgttttttat gcctctaatg gattcgttgt gaaattttag    7380
tcaagttagg cttttgaatc actcaatttg accttatat gaagtagata tgtaggtttt    7440
aatatttgca aatcgtgcag attttttaaat acaccgtcag aggcaatttc gtaattaatc    7500
```

```
tgaaaaatct ggcaacctaa ttcttagtga aatgaccata aaatcctcat acgatgtcca    7560
aattcaacga ttcttttttgc tacgggtccg taattacaat ttacaatacg gatctaatgc   7620
ttcaatcaaa aaagaaatcg gagctcattt gttcaatatg atatcattta tgcttgaaga    7680
aacgacgtcg aaacataaga aaaacgagcg taacacaacc caaacctatc cgaaactctc    7740
ccgaggccct cgggacctca accaataatt ccaacaagtc atatatcact acccgaactt    7800
agttgaacct tcggaacacc caaaacaaca ccaaaacacc aaatcaacct cggattcaag    7860
cctaagaact tctaaacttc caactttcgc caattcaagc ctaattctac cacggacttc    7920
caaattacat tccggacaca cttctaagtc taaaatcacc caacgaagct aatcgaatca    7980
taaaaattca catccgaatt cgtttactca taagtcaact tccggttgac ttttctaact    8040
taacttttta actaagagac taagtgttca tttcactcca aaactactcc ggacccaaac    8100
ctaccaactc gatacaactc aacaccgctg aacaacacat aaagaagcag gaatgggaa    8160 acatggcttt aactctcaga acgactggcc ggttcgttac aactacttac ctaagtttac    8220
ttgatagtga gttttgtcca tacaaatgtt gatttatgc tgaatatcgt atttaagatt     8280
gcttttcttt ttcttcttga atcttaacct ctgtgacaat tgagctaaga cgtgtgaagt    8340
tacttctctc tgttgtcatt cttttttgaga atgtgatgtt ttcccttgtc aattaatctg   8400
cccatcgtgt cttcttcgtc tccaagtaga gtttatactt gtgttgagat actgcttaca    8460
agtttttgag ttcttttttc tgtttggtag atgatgaaag agtctcagag taaagacaat    8520
cttactattc gatgggatat tggtctcaac aagaagcgcg ttgcgtactt tgtcttccct    8580
aaggtatttt cttgttatt tttctgctat gattcttcta gattcttgga ctgttataga    8640
gcttattgct gtcatttact attaaatctt gatatgggaa atctcttgtg tctttcccta    8700
tctgaattga agatggtctg ctgttttta ggaagataat gagttgcgtc ttgtacctgg    8760
tgatgagcta aggctgcgat attcagggga tgcagtacat ccagcttggc aatccgtggg    8820
gcacgtggta tggacatttt gcttgatctc caactctttt cgagagggaa aataatttat    8880
ggagtatagc tagccataaa ccctcttaac aagtaaattg gttggaatga aaaaggctcc    8940
cagcatcatg gaaaattttc ttaaacgagc ttctcggaaa gctccctgct ttttgttttc    9000
ttgggttgtt aaaggcttct tttgcgattt ctagcctgag atattgattg actattcaat    9060
tttcaggtaa aattaactgc tcaagaggag gttgcgcttg aacttcgtgt cagccaggta    9120
ccttagtttt tagattgcta gtctcttcgc gattttctgt tttcttcttt caccatgttt    9180
tggcttgtac tttgggcctt ttctaaacta gtcctgtctt atcaggggt tcctgtcgat     9240 gtgacccatg ggcttagtgt tgactttgtt tggaaaagca cgagctttga tcggatgcag    9300
agtgcgatga aaacctttgc agtggatgag actagtgtca gtgggtgagt gagaatgtct    9360
ggtttctgtg tagaaagata aaaacaatt gtgaagattt catgtacttt taattaatta    9420
tcttacttgc ctaaggttta ttattccatc taaacctttt caaaaaggtg ttcatcgaat    9480
tggtttgtcc cttttttatt tgtttattgt aggtatcttg taatgcttat gatgattata    9540
catttagaga aatgactgct cttctcttaa ctttgcctcg ttgaatgttt aagatatact    9600 acatccttt tttggatgaa gcaataaggg atactgcatc ttttcttttg ttgcctagtc    9660
attgtatcct gaatgaaact ttgaattcat ctatgtagta caaggaatg tcatattcat     9720 ggatgtaaca acttactta tttgggtcaa ccagttgtaa cttttatcga tggagcattt     9780
agttttgcgt tctctttact tcttgtgcag gtatatttac catcacctgc taggtcatga    9840
```

```
agttgagatg cagatggtcc gcaatgcact tcctcgtcgt tttggtgccc ctggtcttcc    9900
agagcttaat gcatctcagg ttgagggcgc tgtctgtttg cttgaacctg ttacctcttt    9960
tccctcattt ctgaaaaagc atatttcctt tagcttcaat attgatcacg cttccaaacc   10020
tttttcaggg acaccttatt gaacgggatt ttttgacaat gaaaattctt agtagttctc   10080
taagtataca catgtatcaa acatgttatg atggcatgtt tgcttacagt tgagaattat   10140
agtgaatagt caaccctgat tgctgtgttg gttcatgtta cattgtgaaa cccattaaca   10200
agcacatgca atccaaattt tagttgctgt tttgttctct cttttcataa aattgccccc   10260
tcaatttcgg cagcttactc aattaagctt aatgcagaag tggtgcccca ttgtcagttg   10320
cttcccctca cccccttaac caaaaaaata ccccttcacc accaacagtg gaaagaggtt   10380
ctcaaaagga gttcttgatt ctggttgtct tattgatcca tgtttgcatc cttaggtttt   10440
tgctgtaaaa agtgttcttc aaaagcccat cagtttaatt caaggtccac ctggaacggg   10500
aaaaactgtc acctctgccg ccattgtgta tcatatggcc aaacaaggcc aaggacaggt   10560
aactttaagt cattttact tatatttgct ctaggtatta gtcgcttgat ataatggctc    10620
tttacaatca tttgcggact attatttcat caggttttgg tttgtgcccc cagtaatgtt   10680
gctgtggacc aattagcaga gaagataagt gctactggtc tgaaggtgag gcaccagcta   10740
tttctgtatc tccttcccac cctccaaccc aagaaaaata aagtgacgaa gattgaagac   10800
attttgaact gactgggaaa taactatttt ggtgtttaat gcatatttat gcagcacgtg   10860
tttctagtgg aagcatcttg cagaatgttg gactgttgtc cacctttgac atagtatata   10920
tatatatctc catcccctat cagctccttt tatggtattg atttaaagaa agagttctat   10980
ttatatcctc agatggatcg agtatggtta actgaaggat aaaaatgaat ctcctatatc   11040
catcccaatc ggccctgtcc caccagtggt agatgtaacc tcgatattac taggttcaac   11100
cgaacctact attttgacag gagcataaat atctatatgt aaaaatcact aaaatttact   11160
tcttaaccca taatttgaaa tgtgcaatgt gttcagtgcc aaaaacctta taggttgaac   11220
ccattgagtt ttaattctgg atccgcctct gtcagtccaa cccatgaata caaactgaag   11280
gcgaacgaag gaaattggag tctaaaagta ctggaaatat aataagaaat gtaataaaaa   11340
tgatcagaaa cttccaaata actctttttt ttttaatttt tatttgtgag aatattaggt   11400
cctttctcat ataattttct ttcttccagg tggtcaggct ctgtgccaag tcaagggaag   11460
ctgtcagttc tcctgtcgag catttaaccc ttcactatca ggttagtttt ttaatttgtt   11520
atcctcaaat atttttata tatcgttcta tttttaatga tatgttgtaa acttttgttt    11580
atacaggttc gccatcttga cacatctgag aagagtgaac tgcacaagtt acagcaactg   11640
aaggatgaac aaggtttgtg ttgctttcct ggattttctt tggcctcata tgtattgggg   11700
ggatttagca tttacatggt gatacttta gcatagtgct cggttttttt ttctctttct    11760
cattatatat cctttattag agcattctaa atatgtgatc atgattcaga gtcatttggt   11820
taatgaactt tcaggagagc tctccagcag cgatgagaag aaatataaag ctttgaagcg   11880
ggcaacagag agggaaatag ctcagagtgc tgatgtaatt tgttgcacat gcgttggtgc   11940
tggagaccct agattggcta acttcagatt ccgccaggtt ggtttacctt attactgaag   12000
atttgaggat ttcctaacta ttttagattt tcagtttctt attttttgttc ttatgtactc   12060
attctggatt cttgctgatt ttaacatttc tgttgtgtta aacctcttgg taggtgctta   12120
ttgatgaatc cactcaggct actgagcctg aatgtcttat tcctttggtt cttggcgcaa   12180
agcaggtcac tattgcaatt aatgtcatgt tgaaattcat ttatgaaaaa atttcatact   12240
```

```
gaaatatagt tcgatgttgg gtcttactgt gagttttgtg ctaggctgtt cttgtcggtg    12300
atcactgcca gcttggacca gtcattatgt gcaagaaagc agcccgtgct ggacttgctc    12360
aatctctatt tgagcgcctt gtgtttctag gagtgaagcc aattaggtta caggtgattg    12420
cctgtctgtt gatgtgttaa catgtctatc agggttggta gtggctgaag ttaaatttaa    12480
gattctcttt ttccagttat tctcttgttt ctcatatagt tggcatagtg attggaagtg    12540
ctcttcagtc atctatgaag acttgaggag tctgctttgc attttctttt ttttgggggg    12600
gtgggggggt gtgtggagta agatgttcct ggtattttaa ctcttcttca ctaatctgcc    12660
acttcccatt ttttttttgg gcggagctgc aacaaatcat gctaatttaa ggttttctga    12720
tttttctatg cttcatgtag cattatgtta ttcggtttat gtcattatct agtgtagctt    12780
gtgtatctga gctgttttga gtttctaagc ttctcattct agctgctttt atttgcttgc    12840
caagtagtaa ttgttaatcc cctcttgctt tttttttttt tttttacat tttgtttcct     12900 tggacgtaga gttgcctggt cacttcttct ttcagagtac tgtttatctt tatttagcta    12960 tttttttaaat ctgtaaagca tcagaattct tttattccat tactaatgtt gattatgctg   13020
tctatttgtt tgcaattcca ggtacaaatac cgtatgcatc ctgcattatc tgagtttcca   13080
tcaaatagct tttatgaagg tacactccaa aatggtgtaa ccatcaatga aaggcaatca   13140
acaggcattg atttcccttg gcctgtgccc aaccgtccca tgttcttta tgttcaggta    13200 ttatcagatt attttagctg attcttcttt gttttcgtt ttttgagttg tggaaaaacc    13260
tgtcattttt gttttgggat gttattgtga tggttatggt tacactaaag attgtttctc    13320
ctatatagtt tataggaact ttttcctggt ttactgatat attcaaattt gaatacttga    13380
tttgaatact tggtaattca tctatagatg ggacaagagg agatcagtgc tagtggaact    13440
tcctatctga atagaactga agctgcaaat gtggagaaga ttgtgactac atttcttaag    13500
ggtggagtag tccctagtca ggtaaattct tatatgcatc tttaaggttg aacaccttct    13560
ttttgtggcg aggatgtaat tattttaaat tcacagattg gggtcataac accatatgag    13620
ggtcaacgag catacattgt aaattacatg gcaagaaatg gttccttgag gcaacaactt    13680
tacaaggaaa ttgaggcaag cattaaatag atgagcttta tggtagtctt ggattcttaa    13740
tacttactgt gagtatttgc tatgttcagg ttgcaagtgt tgattcattt caagggaggg    13800
aaaaggatta tattattttg tcatgtgtca ggagtaatga acatcaggtt ggtttgcata    13860
tccattaatt ctctcttttt gatgcttcat gttttaacat attctgattt gattcgatct    13920
gttgaagatt tatgcatcct cctgtgaacc atacctctgt tcttttttc tctctaacct    13980 cccccccct cttctggtcc tttttggagt ttgtttaact tcatttgcaa aaagtttcag    14040 ttcttttta tttcggggtg caggaggtcg ggtggaattt ttgttaggcg ttaagatatg    14100
tttttgcaat aacttgcatg cttaatatat agtcagtgtg gatctctgac tctcttgtgc    14160
ttaagcttta atctattcca ccagttccca tatttcactg ttaaacttta agtattgaga    14220
acatctttta cttctctttt tagggcattg gattccttaa tgatccacgg aggcttaatg    14280
ttgcccttac acgtgctcgt tatggtattg ttatccttgg aaatcctaaa gttcttagca    14340
aacagcctct gtggaatggc ttgctgacac actacaaggt aatttcttca aaatgttctc    14400
ttgtaatgct tgttaggcat tttttcacta tttctctaca cttcggagaa gttatgaacc    14460
ggcaaagttg gcataatatc aggtggttaa tttttttggga taatatatca tgttgaattt   14520
gttaggcaat attgttactg tctgtaggct tggggacgta taaagtaacg tctcagtagg    14580
```

```
tttttcatgc tttgagatgc tcacacttta atgaatttgt ttctcaggag catgagtgct    14640
tggtagaagg tcctctgaat aacttaaagc agagcatggt tcaatttcag aagcccaaaa    14700
aggtacttat tgtggtcaaa tactcttcca aagttatatg tttgtgcttg attatgcatc    14760
agtactcaga tttcttgtaa cgtcgtttgc agatctacaa tgagcgcaga cttttctttg    14820
gtggtggacc tggaattcca ggtgacagtt ttggatctgc ttcaggcccc aacgctgaca    14880
ggagaaatag tcgttctagg ggtatggtgg atctgaactt tcccccactg actgttagtt    14940
acttgctgag atgttgtatg attggagcgt gtgtctcttt catctgataa tgtgtcagag    15000
acctgctttt gctttcttat tgtacagttt ttctcaaaga aactttggag taactagaaa    15060
attttcatta ttattataat ctcatggaat ttatatatgt atttgtttgt ttttgctgag    15120
gatatgattt tatgtgtagg ttcttatatg gcacctggtg tacccaacgg tactcagaaa    15180
cctggtcttc atcctgctgg ttatccaatg cctcgggttg cctttccacc ttaccatgga    15240
ggccctccac aaccgtatgc aattcctact cgtggtgctg tccatggccc tgttggagct    15300
gttcctcatg ttccacagcc aggtagccgg ggttttgggg ctggacgtgg caatgccaat    15360
gccccaattg gtagtcatct ccctcaccat caaggcgccc agcaacaggc cggaagtctt    15420
ggatctaact tcaactttcc tgcattggag aatccaaaca gccagcctttc tgttggagga    15480 cctttatctc agcctggata tgcttctaat gttagtaaat ttcagtttga ttttttcgat    15540
caatagtaga tgatttgctg taagtatttt ctctcttttg aattatagat tggtatccag    15600
gggccaggcc agacatttcg ggatggatat tctttgggta gcatgtcaca ggtgattgat    15660
tctgaacatt aaaattgtta ttttgattta atttttctat catatttacc ttagatttgt    15720
tcatcaggat ttcgtgggag atgatttcaa gagccagggg tctcatgttc catataacgt    15780
tgctgacttc tctacacagg ttcttgtcct gcacattttc tagtaattgt atattgggcc    15840
tgcacatcac tgccctttt atgcataatt atttgatttt cttgctccaa ttagtttgca    15900
taggcatagc aatattaact ggcctttttt tgttggtatt taggcttctc aaagtggata    15960
tgctgttgat tatgtaactc aaggagcaca ggctggtttt ccagggaact tcttaaacca    16020
gaattcgcaa tctggatact cccgttttgg ttcaggaaat gaattcatgt cacaggttaa    16080
ttttaattgt tcactccttt gccccttaat gtctcaaact ttaaggcctg gaaaacatgt    16140
atttaaatat gtgagtctgg aatgtattta aatatgagag tctggaagtt ttcacaagtt    16200
catcgtacat gatgggctga tctgttagct cttctgactg ggcggctttg gtagacaagt    16260
taattgaagt ggtctcttat gatttctttt ctcttgatct tcgggttgaa cttttgctta    16320
tcggactttt tatttttggt gcaggactac atggctcatg gatcccaagg tctctttact    16380
caagctggat acaataaccc gtcgcaagat gatggttcac agaatcattt tggcatgtcc    16440
aatgcatctc ttcagtctca ggttagttta ttaaataatt ctgcttgaga gttggctaaa    16500
ttactgaaca cgcacaaaat aggaagtatg gattaggcga agtccactag attgcacaaa    16560
tgattcttca cgggaatata atcaggggac ttcgcttgtt aaaaaatatt ttcttcttgc    16620
tattagttta tttcaactag tctaatgtga cttggatgat tgaggttttc cttggaatag    16680
cacttgaatt tgattccact ttttccagag ttcgcttaat ccactttact cccaaccatt    16740
tgctcactac aacacgcaac catttaacat gcaaagccaa cctcaacagc agcaagcccc    16800
acaaggccag ggcttccaaa atcagaaact tcactacaat agttgaagat cgcaggcttg    16860
tttatgtgat gggttatagt ttgcttccag cagtttggtt tatgtgtcaa cgcgtggacc    16920
atattatctg acctaagatg agattaagag tttgctaata attcaggtca aatggtgaca    16980
```

| | | |
|---|---|---|
| tatcccttgc cagtgattct gaatgttgag tcagagggct ggagtggtgg aaggctctct | 17040 |
| gctcaagtaa accatgcaca gcacaactgg tgctgagaaa ggaaaaataa cccatgttat | 17100 |
| cttcgtgaag ttttacgtat tgtttgaaga gagtaatact atttctccgg gagagtaagg | 17160 |
| ttacatggca tggtattggc cggaagggtg ggttattcag gacacggagc ttgctacttg | 17220 |
| cgcgttggaa ggagtacaac attgtttgaa gctgcgacca tatcttttgt acagtgtcca | 17280 |
| ggcgaaagtc agctaaccct ttcagctctt cctgacatgt agttaaactc tttagtattt | 17340 |
| gtattacgtg gataatgacg ataattatag atgtgtttat gtttcagcac ttgaggtatt | 17400 |
| gggtatataa gcagttatta gtcatttgat taaactggat tgcttgtaat ccagtatcat | 17460 |
| ttttttgtgg atttctttttt agcgtttgc ttggagtagt cggtgagaaa a | 17511 |

<210> SEQ ID NO 41
<211> LENGTH: 790
<212> TYPE: PRT
<213> ORGANISM: Artificial Sequence
<220> FEATURE:
<223> OTHER INFORMATION: interactor, Nitab4.5_0007831g0020.2 protein
      sequence

<400> SEQUENCE: 41

```
Met Ile Pro Asn Gly Val Glu Asp Glu Glu Lys Phe Leu Ala Ala Gly
1               5                   10                  15

Ile Ala Gly Leu Gln Gln Asn Ala Phe Tyr Met His Arg Ala Leu Asp
            20                  25                  30

Ser Asn Asn Leu Lys Asp Ala Leu Lys Tyr Ser Ala Gln Met Leu Ser
        35                  40                  45

Glu Leu Arg Thr Ser Arg Leu Ser Pro His Lys Tyr Tyr Glu Leu Tyr
    50                  55                  60

Met Arg Ala Phe Asp Glu Leu Arg Lys Leu Glu Ile Phe Phe Lys Glu
65                  70                  75                  80

Glu Thr Lys Arg Gly Cys Ser Ile Val Glu Leu Tyr Glu Leu Val Gln
                85                  90                  95

His Ala Gly Asn Ile Leu Pro Arg Leu Tyr Leu Leu Cys Thr Val Gly
            100                 105                 110

Ser Val Tyr Ile Lys Ser Lys Glu Ala Pro Ala Arg Asp Ile Leu Lys
        115                 120                 125

Asp Leu Val Glu Met Cys Arg Gly Ile Gln His Pro Leu Arg Gly Leu
    130                 135                 140

Phe Leu Arg Ser Tyr Leu Ser Gln Val Ser Lys Asp Lys Leu Pro Asp
145                 150                 155                 160

Ile Gly Ser Glu Tyr Glu Gly Asp Ala Glu Thr Val Val Asp Ala Val
                165                 170                 175

Glu Phe Val Leu Gln Asn Phe Thr Glu Met Asn Lys Leu Trp Val Arg
            180                 185                 190

Met Gln His Gln Gly Pro Ala Arg Glu Lys Lys Arg Glu Lys Glu
        195                 200                 205

Arg Ser Glu Leu Arg Asp Leu Val Gly Lys Asn Leu His Val Leu Ser
    210                 215                 220

Gln Ile Glu Gly Ile Asp Leu Glu Met Tyr Lys Glu Thr Val Leu Pro
225                 230                 235                 240

Arg Ile Leu Glu Gln Val Val Asn Cys Lys Asp Glu Ile Ala Gln Gly
                245                 250                 255

Tyr Leu Met Asp Cys Ile Ile Gln Val Phe Pro Asp Glu Tyr His Leu
```

```
                260                 265                 270
Gln Thr Leu Glu Thr Leu Leu Gly Ala Cys Pro Gln Leu Gln Pro Ser
            275                 280                 285

Val Asp Ile Lys Met Val Leu Ala Arg Leu Met Glu Arg Leu Ser Asn
290                 295                 300

Tyr Ala Ala Leu Ser Thr Asp Val Leu Pro Glu Phe Phe Gln Val Glu
305                 310                 315                 320

Ala Phe Ala Lys Leu Asn Asn Ala Ile Gly Lys Val Ile Glu Ala Gln
                325                 330                 335

Glu Asp Met Pro Ile Ala Gly Val Val Thr Leu Tyr Ser Ser Leu Leu
            340                 345                 350

Thr Phe Thr Leu His Val His Pro Asp Arg Leu Asp Tyr Val Asp Gln
            355                 360                 365

Ile Leu Gly Ala Cys Val Lys Lys Leu Ser Gly Lys Gly Lys Leu Lys
            370                 375                 380

Asp Ser Lys Ala Thr Lys Gln Ile Val Ala Leu Leu Ser Ala Pro Leu
385                 390                 395                 400

Glu Lys Tyr Lys Asp Ile Asp Thr Ala Leu Lys Leu Ser Asn Tyr Pro
                405                 410                 415

His Val Met Glu His Leu Asp Asp Ala Thr Ser Lys Glu Met Ala Asn
                420                 425                 430

Val Leu Val Gln Thr Ile Leu Lys Ser Lys Thr Cys Ile Ser Thr Ala
            435                 440                 445

Glu Lys Val Glu Ala Leu Phe Glu Leu Met Lys Gly Leu Ile Arg Asp
            450                 455                 460

Leu Asp Glu Asn Leu His Asp Glu Leu Asp Glu Glu Asp Phe Lys Glu
465                 470                 475                 480

Glu Gln Asn Ser Val Ala Arg Leu Ile Gln Met Leu His Asn Asp Asp
                485                 490                 495

Pro Glu Glu Met Leu Lys Ile Ile Ser Thr Val Lys Lys His Ile Leu
            500                 505                 510

Thr Gly Gly Pro Lys Arg Leu Pro Phe Thr Val Pro Pro Leu Ile Phe
            515                 520                 525

Asn Ser Leu Lys Leu Val Arg Arg Leu Gln Asn Gln Asp Glu Asn Ala
530                 535                 540

Pro Glu Glu Glu Ala Ser Ala Met Pro Lys Lys Ile Phe Gln Ile Leu
545                 550                 555                 560

Asn Leu Ile Ile Glu Ala Leu Ser Ser Val Pro Val Pro Glu Leu Ser
                565                 570                 575

Leu Arg Leu Tyr Leu Glu Cys Ala Glu Ala Ala Asn Asp Ala Asp Leu
                580                 585                 590

Glu Pro Val Ala Tyr Glu Phe Phe Thr Gln Ala Tyr Ile Leu Tyr Glu
            595                 600                 605

Glu Glu Ile Ser Asp Ser Lys Ala Gln Val Thr Ala Ile His Leu Ile
            610                 615                 620

Ile Gly Thr Leu Gln Arg Met His Val Phe Gly Val Glu Asn Arg Asp
625                 630                 635                 640

Thr Leu Thr His Lys Ala Thr Gly Tyr Ser Ala Lys Leu Leu Lys Lys
                645                 650                 655

Pro Asp Gln Cys Lys Ala Val Tyr Ser Cys Ser His Leu Phe Trp Val
                660                 665                 670

Asp Asp Gln Asp Asn Ile Lys Asp Gly Glu Arg Val Leu Leu Cys Leu
            675                 680                 685
```

```
Lys Arg Ala Leu Arg Ile Ala Asn Ala Ala Gln Gln Met Ser Asn Ala
        690                 695                 700

Thr Arg Gly Ser Ser Gly Ser Val Leu Leu Phe Ile Glu Ile Leu Asn
705                 710                 715                 720

Lys Tyr Leu Tyr Phe Phe Glu Lys Gly Val Thr Gln Ile Thr Val Ala
                725                 730                 735

Ser Ile Gln Ser Leu Ile Glu Leu Ile Thr Thr Glu Met Gln Ser Glu
            740                 745                 750

Asn Thr Thr Ser Asp Pro Ala Ala Asp Ala Phe Leu Ala Ser Thr Leu
        755                 760                 765

Arg Tyr Ile Gln Phe Gln Lys Asp Lys Gly Gly Ala Val Gly Glu Lys
    770                 775                 780

Tyr Glu Ser Ile Lys Ser
785                 790

<210> SEQ ID NO 42
<211> LENGTH: 2373
<212> TYPE: DNA
<213> ORGANISM: Artificial Sequence
<220> FEATURE:
<223> OTHER INFORMATION: interactor, Nitab4.5_0007831g0020.2 coding
      sequence

<400> SEQUENCE: 42
atgatcccta acggagttga agatgaagag aaatttctag cagctggaat cgccggcctt      60
caacagaacg ctttctacat gcatcgcgct cttgattcga ataatctgaa agatgcactc     120
aaatactcag ctcagatgct atcggagctc cgaacttcaa ggctttcccc tcacaaatac     180
tacgagctat atatgcgggc atttgatgaa ttgagaaagc tagaaatttt ctttaaggag     240
gagacgaagc ggggttgctc gattgttgag ttgtatgaac tcgtgcagca tgctggcaat     300
attttgccta actgtatctc actatgcaca gtggggtctg tgtacatcaa atccaaggag     360
gcgcctgcca gggatattct taaagatctg gttgaaatgt gccgtggtat acaacatcct     420
ttgcgcggac tcttcctgag gagttatctt tctcaagtca gcaaggataa attacctgat     480
ataggttctg agtatgaagg ggatgctgaa actgttgtgg atgctgtaga gtttgttctc     540
caaaatttca cggaaatgaa caaactctgg gttagaatgc aacatcaggg acctgctcgc     600
gaaaaggaga acgagaaaa agaaggagc gagcttcgtg atctcgttgg aagaacctg     660 catgttctca gtcaaataga aggaatcgac ctggagatgt acaaagagac tgtgcttcca     720 agaatttag agcaggttgt caactgtaaa gatgagattg cacagggcta tttgatggat     780
tgcataattc aagtcttccc tgatgaatat cacttacaaa ctcttgaaac attattgggt     840
gcttgtcccc agcttcagcc atctgttgat atcaagatgg tgcttgctcg gctgatggaa     900
aggctctcaa actatgctgc tttaagtaca gatgtttac cagagttttt ccaagtggaa     960
gcttttgcaa aactaaataa tgccataggg aaggtgatga agcacaaga agacatgcct    1020 attgctggag ttgtgacttt atattcatct cttctaactt ttactcttca gtacaccct    1080 gatcgtcttg attatgtgga tcagatcttg ggtgcatgtg ttaagaaact ttctggtaaa    1140
ggaaagctca agacagtaa agcaacaaaa cagattgtgg ctcttttaag tgctcccctg    1200
gagaagtata aggatattga tactgcatta agctgtcaa attatcctca tgttatggag    1260
caccttgatg atgcaactag taaagagatg gctaatgttt tagttcaaac tattttaaaa    1320
agtaagactt gcatttcgac agctgaaaag gtagaggcac tttttgaatt aatgaaagga    1380
```

```
cttatcaggg atttggatga gaatcttcat gatgagcttg acgaagaaga tttcaaggaa      1440
gagcagaact ctgttgcacg gcttattcaa atgcttcaca atgacgaccc tgaagagatg      1500
ctgaagataa tttctactgt gaagaagcat attctgacag gaggaccgaa gaggcttccc      1560
tttactgtcc ctccccttat tttcaattct cttaagttgg ttaggcgact gcagaaccaa      1620
gatgaaaatg ctccagagga agaggcatct gctatgccta agaaaatttt tcagattta      1680 aatctgataa ttgaggctct ctcaagtgtt ccagtacctg aactatcatt gaggttgtac      1740
ttggagtgtg ctgaggctgc caatgacgct gacctagagc ctgttgccta cgaattttc      1800 acccaagctt atatactata cgaagaagaa atttcggact ccaaagctca ggtgactgca      1860
atacacttaa ttataggaac tcttcagaga atgcacgtct ttggtgttga aacagggac      1920 acattaacac acaaggccac ggggtactcg gcaaaactcc tgaagaagcc tgatcagtgc      1980
aaggctgtct actcctgttc gcatctttc tgggttgatg atcaggacaa catcaaggat      2040
ggagagaggg ttttgctttg cttaaaacgg gctttaagaa ttgcgaatgc cgctcaacaa      2100
atgtccaatg caacccgagg cagcagtgga tcggtcttgc tctttataga aattctaaac      2160
aagtatttat atttctttga aaggggggtg acacagatca ctgttgcatc catccaaagc      2220
ctaattgagc taataacaac tgaaatgcaa agtgaaaata caacttcgga tcctgctgca      2280
gatgctttcc ttgcaagcac attacgatat atccagttcc agaaggataa aggtggagca      2340
gttggtgaga aatatgaatc catcaagtct tag                                   2373
```

<210> SEQ ID NO 43
<211> LENGTH: 12149
<212> TYPE: DNA
<213> ORGANISM: Artificial Sequence
<220> FEATURE:
<223> OTHER INFORMATION: interactor, Nitab4.5_0007831g0020.2 genomic
      sequence

<400> SEQUENCE: 43

```
atacgtaaaa gaacccgatg cccgccccgc cccgacccgc tcccgtacta tgtctggcag        60
ttggaacaaa gtaatggcaa ccaaaactga agtcaatacc aagaacataa atcccacaa       120 aaaactcgtc gatcgcgaat ttccccctc gaaatcgata aaaaaacgct atgatcccta       180
acggagttga agatgaagag aaatttctag cagctggaat cgccggcctt caacagaacg       240
ctttctacat gcatcgcgct cttgtaattt tcacaaaact cccccaaatt tctttatatc       300
tttatgtaca atgaaattac agttttattt ggtttacata acccctaatt ttgattttc       360 tttttatggt tattgaattg taggattcga ataatctgaa agatgcactc aaatactcag       420
ctcagatgct atcggagctc cgaacttcaa ggctttcccc tcacaaatac tacgagctat       480
gtgtgtactt tcactgatc agatcttaat tattgattaa ttaataaatt gaacttaat       540 ttcaaaattt gatttgttgc tctttaacct cagtattaaa actgtatcgc tgttgtttgt       600
ttgtttgttt gtttttatt tttgtttttt caataacttc aaatgcacat tgctgttatg       660
ctgaaaattt tatattccag catttgatta gaagctcctt aacctcggtg ttagaacatt       720
gttgtgtctt ttcttttcct tttttttttt taaattttaa ttcttttaaa atttttaaatg       780 cgcattgctt tgttagatat gcgggcattt gatgaattga gaaagctaga aattttcttt       840
aaggaggaga cgaagcgggg ttgctcgatt gttgagttgt atgaactcgt gcagcatgct       900
ggcaatattt tgcctagact gtaagttgta gtgatgatcc aactgtattt tccgctttag       960 ctcgatttt taaaagcttt atcttgtagt tcttcagcaa ctgatcttat gtttgtgaat      1020
```

-continued

```
tggcttaaag cttgtactgc ttaactatat tatatgtctc caaagagagg tacttttcgc      1080
ttaggttgtc aggaataatg tttcgtagga aaatcatgtg attaaagact caaatgaatc      1140
atatagaaaa cactatcaat gatggccgaa cagtcaggag gagaatacta tactccatgg     1200
gttataacat taggaaccta cacccaaaaa agcattgcca aaacagtaga gaaaatcaga     1260
aacgggttca gcgagtaagt ttttaactta catctaactt tgatgaaagc agttacaagt     1320
ttaggtagaa agagcagcta gtgtcagaga gacacatgaa gcgaagtatt tgagtatcgt     1380
tctgtttggc ctttgctgtg tttcttttaa gttcttttgc catgctaatc ttactgttgt     1440
cctgcgctca actgcttaca gacatctcct ctctaccttt gtttagcata ggttggatgt     1500
gcctttacaa ctcacatgga cacaagtgtt gctgctttaa cagtttggtt actgggaatc     1560
aagctagagc ttgcatacat tttattaaaa ctggaaaaat ttccaataag ttatttgaat     1620
tttttgggag aggactgccg tttggggtag ttaacagcag cctttcagat aatcaataaa     1680
tttttggact ggttttttgct gaagcaaact gtaagagtaa atgttttttt tttccttttt    1740
ttctttcttt atggtaaatg gaaattatgc tcctttttca tttgtttaga ttgggttggt     1800
gggagaggag ttcaagtagt tagaaggata gttgaactga atcagacgca acttcttatg     1860
ggaaggaact aggaagctaa aaagttgcat ttgataaagt aggataaagt catgttatgt     1920
aaggaaaggg gaagtttagg tgtcagggat cttgggctcc acaataaaag cttgctctct     1980
gtgaagatgg actgataccg ggaaggaaca atgtaaagat ttaaaggtta aatacggact     2040
acagaagtat ggagatacaa ctgatattac atctccccat ggtattgcat tcgaagcata     2100
ttgctccctt ctttgccaat ttatgtgacg ctctttcctt tttagtcagt cccaaaaaga     2160
atgacacatt tctttatttta gtaacaactt aactctaaac tccccatttt acccttatga    2220
gatgatttat agccacaatt gttttggct tattttgaac cataagtttt aaagtcatt      2280 ctttccatct ttgttaaact ctgtgccaag tcaaacgcca tcacataaat tggaatggag     2340
ggaagtaata gttgtgggga tgagttccaa gagtatacca gactaaaaat tggagatgga    2400
ggaagaatta atttctggca agagaaatgg tttagagagg atatttcagc tgccttagtc     2460
tcggagctgt atagtatggt gctgaacgga aactgtgtca ttgctgattg ttgggatggg    2520
attgcttggt cttctcagga tttagttgga gagtttcaac aagctactgg aaattactga    2580
gagcatatta ccgataagct cccagaatga ttccttctgt gtggatgggc aagagtgtat    2640
ggtattttca gtaaagtcga gctatcagtt aatggttaag aacatggctg caaacagtgc    2700
agattggtca tggaaaatgc tgtggaaaac taaagcccca actgaagttg cttttttcggt    2760 tgggtagcag cacctgaggc tttcttaaaa caggaagagt tacagaaaat aagctttaat    2820 ctatttttggt gctatttatg cagaggatgg tgaatcggtg aatcacttac tgctgagcaa   2880
atatgtatgg tgcaacaaca acaacccagt atattcccac aagtagggtc ttgggagggt    2940
agtgtgtacg cagaccttac ccctaccctg gggtagagag gctgtttccg atagaccctc    3000
gacacaagaa gatgaaatgc gacaatataa taataacaac aacataacca gaaagatagt    3060
accaacgagc taagaaccag aaaatatacc tggaaaacaa tattaataaa aagtgcagtg    3120
acaaggtcct agaaaatagt acgagcacca catgtaccac tagcatacta aaacacgaca    3180
caggccgact agacttacac acagaacgga gtagaaaaac gctcaattac ctgctaacct    3240 tcaacccctaa tgcacccccct ccatacccttc ctattaaggg ctatgtcgtc ggtgagctgg   3300
agtcgcgcca tgtcctgtct gatcacctct ccccaatact tcttaggtcg ccctctacct    3360
cttctcatac ccgtcagagc caactgctcg cacctcgtaa ccggagcatc taggtttctc    3420
```

```
ctctgcacgt gctcgaacga tctaagcctt acttcctgca ttttgtcttc catgggagcc    3480
acgcccactc ttgcccaaat atcttcattc ttaatcttat ccaacctcgt gtgcccgcac    3540
atccatctca acgtcctaat ttctgctacg ttcatcttct ggatatgggc aatcttgact    3600
ggccaacatt ctgccccata caacatggcc ggtctaacca ccgctttgta gagcctgcct    3660
ttaagttccg aggtaccttc ttgtcacata aaacgccaga tgctaacctc cgtttcatcc    3720
aatctggtgc gtgacatcct cgttgatctc ctcgtttccc tggataatcg acccaagata    3780
cttaaaactt ccttttttgt ggtcatgttc ctcaattttt atggggttca atgggtcatg    3840
caagcaaatg taagactgat tctgcatagt tggtagagtc aaaaagtggg aaaggagata    3900 aagggaaga cctggaagac cactcattta tgcataatgt ggaatatttg cttgagaga    3960 aacagaagat gcttcgaggg gaaggaagag aacatcccgc ttttgaaaaa tagatgtata    4020
caatgtctaa gatgcaatgc tgattttgct attaatattg atgcaatgct ggagtcttgg    4080
aattcttaca gcttcagagg atccttttcc agaaatttt tgtacattat tctttaataa    4140
aattttacct ttattgatca aaagaagatt tttactcgga ctaattttgt tcaagatcat    4200
gattaaaggt ggaatggtta taatcctgct tagctgcatt gtttcctttc ttctttagtt    4260
gttaacctat gtcaaagagg atgtgttcat tttatcatct ggttgctttt aagccagtct    4320
taaatcttgt tttctattat ttgctcatca ggatttctac agttcatatg ttgccttttt    4380
gtttctcagg tatctactat gcacagtggg gtctgtgtac atcaaatcca aggaggcgcc    4440
tgccagggat attcttaaag atctggttga aatgtgccgt ggtatacaac atcctttgcg    4500
cggactcttc ctgaggagtt atctttctca agtcagcaag gataaattac ctgatatagg    4560
ttctgagtat gaagggtaag ggtgttactc agctccacag tggtttacca tcaatttagt    4620
tacaagaatc atgtgtcaat gtccagtttt atgggtttcg tttacaatgt tctagctgag    4680
aggtataagt gcttgagaga gaaaaatact atgctgaagt gtcaacctga agacataaac    4740
actgacatga ctaagctaat tggcagtgcc tgcagtgtaa ccgtgtgtta agttgaattt    4800
atttaaataa agatgctagt agattatgtt gttcatggta accggttgtt gttgttttct    4860
tactgccata atgattaatt gaggatttcc tcaactatgt caacatagta tgatcttaac    4920
tcagaagaaa gaaatgaaa aagataataa actatcttac cttcattta agcttctttt    4980 atatgtaatc tcacctgtat tacgaatatt gttgttggat gcactaatgc cttgttccct    5040
cccacaggga tgctgaaact gttgtggatg ctgtagagtt tgttctccaa aatttcacgg    5100
aaatgaacaa actctgggtt agaatgcaac atcaggttgg ttgaaacatc tgtggatgct    5160
ataacatgct ctcatgcttt gacatgcata gtaccacaat gcttgcatgt catgaaggta    5220
aatgaaaatc atgagggcag aattcgtggt catgcaggtg ttttaatgct tgtgaatgat    5280
tcatactctt tgctgatcat gagttgaggc tagcatcggg cttctcatc tgcagggacc    5340 tgctcgcgaa aaggagaaac gagaaaaaga aaggagcgag cttcgtgatc tcgtatgagc    5400
tgttacttca tcatgtttac tagcacccaa ataagcaatg gaagtgcaca ctcatgcgag    5460
gattttcctt tttgctttta cttttggtag gttgggaaga acctgcatgt tctcagtcaa    5520
atagaaggaa tcgacctgga gatgtacaaa gagactgtgc ttccaagaat tttagagcag    5580
gtgattggtc taggaatgta gtggcctttc aataactttt tatggtttgt ttaagccata    5640
tgtgaactat tttctgactc aaaatgcgta acctcatggt gtgtttaggt tgtcaactgt    5700
aaagatgaga ttgcacaggg ctatttgatg gattgcataa ttcaagtctt ccctgatgaa    5760
```

```
tatcacttac aaactcttga acattattg ggtgcttgtc cccagcttca ggtgtgttat    5820
tttgctgttt tgtatcacta gcttttcatt aaatagacca aaagtgtaga aggaaaaatg    5880
tcatacctgg taggatccga ggagtgggat tggtttaata tctgcaacaa tgtaatataa    5940
tatgttggct atatcagatg aaagatttgg ttgtgaagat ttataaagag tattgtttgt    6000
ttacagcgtt tccaccttat actgaagttc attatctttt tttattggct tctgataaaa    6060
tctttgataa ttttgtcacc attgataaag tcatactggt gatgcaaatt tgtacattca    6120
ttttctttgt actgtctgtg acagttctaa gtatctgcca ttaaatgctt aacgtctatg    6180
agaatttgaa cttctgaaca ccatttccta tgtcattatt tcagccatct gttgatatca    6240
agatggtgct tgctcggctg atggaaaggc tctcaaacta tgctgcttta agtacagatg    6300
taagtattac attataaact ttctgtaatc ggatttttta catgtagtct ctaaatgatt    6360
tgttactgca ggttttacca gagttttttcc aagtggaagc ttttgcaaaa ctaaataatg    6420
ccatagggaa ggtaaacgag ataactaccc ttgactaaaa tgcaattctt gtttatgaag    6480
gcgtacttaa agaaaatatt cccaggcgtg gattttctac ctccaacatg tgaatattaa    6540
gtggaactca ctgaactttta aaagctagaa tcaattatct gactaattca aaaattaata    6600
agccaagaaa tagaaattga tcatagatct gtggatgtca ctggaaagtt aattcatgga    6660
gaccgtgctt gtcacaacaa tagagtggta atctttagat ttatgaatgc acagattctg    6720
attttcttcc aattttttgcc tccccaaact tatgcgcttt ccatgaagag gccaccaaac    6780
cttccatgac attctttcaa cttatttcct gttttctgac tggagggatt ctgcatacat    6840
cttttttcca atatcaatgg tggctttggc ttttcaagta gttcggatat catgcccgta    6900
tctctgttgt gcaggtgata gaagcacaag aagacatgcc tattgctgga gttgtgactt    6960
tatattcatc tcttctaact tttactcttc atgtacaccc tgatcgtctt gattatgtgg    7020
atcagatctt ggtaggtcaa ctcttattct ttcccttttt cttttttatct atattaaaat    7080 agttttgat aaggttgttt atgtcattta tgtttgttct tattccagaa tgaagattgc    7140
gtgtgaaaca gtttaacatt aaataaaaat taaaaaaaaa taagggaaga aacaaataga    7200
aacaacagaa ggttgactag aagctgtgag catttagata acttgcttgc ctgccttgtg    7260
catatgaaac ctgtaactta ctaatgacca ctctattctt atctttaggg tgcatgtgtt    7320
aagaaacttt ctggtaaagg aaagctcaaa gacagtaaag caacaaaaca gattgtggct    7380
cttttaagtg ctcccctgga gaagtataag gatattgata ctgcattaaa gctgtcaaat    7440
tatcctcatg ttatggagca ccttgatgat gcaactagta aagagatggc taatgtttta    7500
gttcaaacta ttttaaaaag taagacttgc atttcgacag ctgaaaaggt tagttccttt    7560
taattttagt tctttaaatt attctttatg ggtaatacta tagcctcttt attacttcaa    7620
acttactggt ctgtcaggta gaggcacttt ttgaattaat gaaaggactt atcagggatt    7680
tggatgagaa tcttcatgat gaggtgattg gggactctc tgcttatgca attagattcc    7740
tcatatctcc cgactttctt tctgctctat tcttagcggc taggctttct taaatttatt    7800
ttgcttaaat cagtatgtaa ttaagccaaa gtttctttaa cctcccattt tcagcttgac    7860
gaagaagatt tcaaggaaga gcagaactct gttgcacggc ttattcaaat gcttcacaat    7920
gacgaccctg aagagatgct gaaggtaacg agtgtatagt gatacctgtt tctagattct    7980
ttgcatattc ctctgaaggc tagcctctct acttgttatt gctggaaaag tttgttatat    8040
catgtagttc ttatagttcg gggttgagcg tggtcaactg tgttttaaat caaaacttta    8100
aagatgccta gaattgtttt tctctgttcc aaagttgaat gccatggttt cataggcatg    8160
```

```
acgttgattg agaactttt  tcttttgttc ttttggggat taaatggtgt aaaagtaggt  8220
ttcatatatc tttccaattt ccataatttg gaataattaa acagtaattt tacaaatgaa  8280
aaacatagta tcttttccag gacattggct gataccttct tgggacatca caaagtaaac  8340
caggacactt gcatttggga taaagtacct ttgttgtctc tgtttcatct cttctttcta  8400
tgacatgctt tctccaatat atatacccaa ccagaggcgg atccagaaat taaactttt   8460
gggttcaata tttaaggttc ttattattga accgtgaacc cactatattt ttaaacttat  8520
gagttcatat atactatttt tcgcaattct tgtggatgtt gcatttaaat ttatgctccg  8580
tgtcaaaagt tatggactca attgaacccg taactttcat cctacattcg cccctgtacc  8640
aaactcgtgc gcacaaccga tcagctaaat aagtatctct tataacagca atccttgatc  8700
ttcctagtca gcttataatg agagatatag aacgaagatg actcttgacc taagttgcac  8760
ctgattggtt ggatatgttc tattgaatcc ttctgatatt gatgtaatga aagcctttg   8820
cttgtgcatc tactgttaaa aaacatata  atgatgaagt atctgccaaa caagatagc   8880
ttttgctttt tgttggttct gttcgctttt catggtttct tttgttgatc cttttctttt  8940
tgaaaatatg agagggataa gttgccatct cagattctat tcatgagaat gccaaaaggc  9000
acttaggtac ttgagtacaa gactgaagac actttacatc cgctactaca ccacgtgata  9060
catctgtgct accaatgttc tcacattcaa ctctacacca tccttcagca atgtcgctgt  9120
tgcttggtgc ctctgcatct atccggatgg attttgtcac aacaagtggt gtagtagctt  9180
gaaagccttc cctgacaagt ctgctaccaa caagagcacg gcaaaaaaag ctagatttgc  9240
aatatgtatg ctcagatcta ggactagaac tgccaccaag gggtagataa attaacataa  9300
ccatggagat aaagggaaaa gaactaagac acaaacagat tagaagcaaa tggaactgcc  9360
aaagaaagga gtttataaag acaaaactgc tttgaaatgg gaccacagag agcagttgtt  9420
ttatggggag atggtctctc aaaaaatctc cttgctcttc gtagttaata agggaaatat  9480
gaaaaagaa  attgggaatg aagtcagtta aatgaagcag tagctgtaga gattgatatg  9540
acatgattga cgtgccaaag cttcaccagc tgtaaattca attcaagatt gacataaaaa  9600
ttcttgttaa attgagaatg aaattttcat tcctctagca agtagaaaag tgtgatgttc  9660
ttatttctt  ttatatgttt gttggtgcaa aataaaatgc ttcaatccgg tgttacatat  9720
ctatgtagcc ataaggttta tctctggcta tagctgttgg cttcttgctt ttcagatttg  9780
atatggtttg ctaattgctg atttgcagat aatttctact gtgaagaagc atattctgac  9840
aggaggaccg aagaggcttc cctttactgt ccctcccctt attttcaatt ctcttaaggt  9900
atgaattgac cactcaagga ctacaaaagg ggtgaagtgg tgatgaatgg cccatgcttt  9960
ttattcttaa aaagaaataa tttaagttac aaaattttg  aatgtgcatt ttaagatgat 10020
cctttcccaa tgcaactgct tgttcaaagg attaaataac agaaaaagga aatcaacccc 10080
ctccccttt  tctcagggag agagtttcca gtgtcataca gaactgaagt ttctgttgag 10140
ttactgatgt tgtaaatttc cttcttttca gttggttagg cgactgcaga accaagatga 10200
aaatgctcca gaggaagagg catctgctat gcctaagaaa attttcaga  ttttaaatct 10260
ggtaatatag ctgaatgggg ttatatgagt tatttggtca aatgtgatgc attgcatttc 10320
aagctctcga ctaaagctat tatgattctc agtcaaaaga ccaaaaaaat aaatcagctt 10380
tatgtctctt atatcccttt tctttattta gcttctattc cttcatttc  aattgttctg 10440
tgatactcat gattgtgcta actgctgagg caattgttat tacttataaa ttgcatatac 10500
```

-continued

```
cgtattccag ataattgagg ctctctcaag tgttccagta cctgaactat cattgaggtt    10560
gtacttggag tgtgctgagg tacattaatt tatccttgga tttgtgtaag attgtggaat    10620
cacaaattct aaaaaatatg ggtttactgc catgtgtgtt gctcaggctg ccaatgacgc    10680
tgacctagag cctgttgcct acgaattttt cacccaagct tatatactat acgaagaaga    10740
aatttcggta ggatttgctc attttatcat tactttatca tgatttctat ttgcttgact    10800
tcctggtatt tcgatatatc tacatttatt gtgcatttca tgcattgctt gattttctcta   10860 attccagttg aatggtttga taggactcca aagctcaggt gactgcaata cacttaatta    10920
taggaactct tcagagaatg cacgtctttg tgttgagaa cagggacaca ttaacacaca     10980
aggccacggg ggtaactatt ttaccacctc ttattttctt attcctgatt tcagcttcgt    11040
cattctatga ttgtaaccat ttcctcctcc ttttcttgat atcctccagt actcggcaaa    11100
actcctgaag aagcctgatc agtgcaaggc tgtctactcc tgttcgcatc ttttctgggt    11160
tgatgatcag gacaacatca aggatggaga gaggttcgta actctgccat gcacatgagg    11220
gatgaaattt acatttggcc tcccgtgcct ctcttattat gaacatttat tagcctgggt    11280
ttataccagc atgagatgtg atttatgtat ttgtgggtct tccctgactg agttttgccc    11340
ctttgagttc cgctccgtga tttcaagctt ttctgtatcc tttcatgttc ttcttatgtg    11400
gttgtttctt tttcattgat ccagggtttt gctttgctta aaacgggctt taagaattgc    11460
gaatgccgct caacaaatgt ccaatgcaac ccgaggcagc agtggatcgg tcttgctctct   11520 tatagaaatt ctaaacaagt aaaactacac tatacatcat tgtttgttta cctttcttgg    11580
cgacggtctc tgttttgcag gtcattaacg atagatacac ttaatcattt gtatgatctc    11640
aggtatttat atttctttga gaaggggggtg acacagatca ctgttgcatc catccaaagc   11700
ctaattgagc taataacaac tgaaatgcaa agtgaaaata caacttcgga tcctgctgca    11760
gatgctttcc ttgcaagcac attacgatat atccagttcc agaaggataa aggtggagca    11820
gttggtgaga aatatgaatc catcaagtct tagttataaa gacattttct tgcaaggagt     11880
ttgcattctt gatgttacag aagcagatta ttttgttttc caatacaaat tcattttcgc    11940 ctttttgattt gtctgttagt ggagattctg cactttacag caggctagcg gaagaagctg    12000
caaatatctg tatatcctaa ccatacttgt catgattttg attgttgtaa caattttttc     12060
tcgtagagat ctgactaaat tagaggctat ataattcaga tcaaacttgt gattgtgata    12120
ataactggaa taagtttgtt ttggagttg                                      12149
```

<210> SEQ ID NO 44
<211> LENGTH: 148
<212> TYPE: PRT
<213> ORGANISM: Artificial Sequence
<220> FEATURE:
<223> OTHER INFORMATION: interactor, Nitab4.5_0002978g0020.2 protein
      sequence

<400> SEQUENCE: 44

Met Ala Glu Val Glu Tyr Ser Cys Phe Val Gly Gly Leu Ala Trp Ala
1               5                   10                  15

Thr Thr Asp Arg Thr Leu Ala Asp Ala Phe Gly Thr Tyr Gly Glu Val
            20                  25                  30

Leu Asp Ser Lys Ile Ile Asn Asp Arg Glu Thr Gly Arg Ser Arg Gly
        35                  40                  45

Phe Gly Phe Val Thr Phe Lys Asp Glu Lys Cys Met Arg Asp Ala Ile
    50                  55                  60

Glu Gly Met Asn Gly Gln Glu Leu Asp Gly Arg Ser Ile Thr Val Asn
65                  70                  75                  80

Glu Ala Gln Ala Arg Gly Ser Gly Gly Gly Gly Gly Tyr Gly Gly
                85                  90                  95

Gly Arg Arg Glu Gly Gly Gly Gly Tyr Gly Gly Gly Gly Gly
            100                 105                 110

Tyr Gly Gly Arg Arg Glu Gly Gly Gly Gly Tyr Gly Gly
        115                 120                 125

Arg Arg Glu Gly Gly Gly Gly Tyr Gly Gly Gly Tyr Gly Gly
    130                 135                 140

Gly Gly Arg Tyr
145

<210> SEQ ID NO 45
<211> LENGTH: 447
<212> TYPE: DNA
<213> ORGANISM: Artificial Sequence
<220> FEATURE:
<223> OTHER INFORMATION: interactor, Nitab4.5_0002978g0020.2 coding
      sequence

<400> SEQUENCE: 45
atggctgaag tagaatacag ttgcttcgtc ggtgggctcg catgggctac caccgataga      60
accttagctg atgctttcgg tacatacggc gaagttctcg actcgaagat cattaacgac     120
agagaaactg gcagatctag aggatttggc tttgttacct ttaaggatga gaaatgcatg     180
agggatgcaa tcgaagggat gaacggtcag gaacttgacg gccgtagcat taccgttaac     240
gaagctcagg ctcgtggaag tggaggcggc ggcggtggtt acggaggtgg ccgacgtgaa     300
ggaggaggcg gtggttacgg aggtggtggt ggtggctacg gaggtggccg acgtgaggga     360
ggaggcggtg gctacggagg tggccgacgt gaaggaggag gcggtggtta cggaggtggc     420
ggttatggcg gtggtggtcg ttattag                                         447

<210> SEQ ID NO 46
<211> LENGTH: 1070
<212> TYPE: DNA
<213> ORGANISM: Artificial Sequence
<220> FEATURE:
<223> OTHER INFORMATION: interactor, Nitab4.5_0002978g0020.2 genomic
      sequence

<400> SEQUENCE: 46
accccatctc ttctttctga tattttcctt tagggtttat cctcttctct cttttctcag      60
tgtagtaaaa tggctgaagt agaatacagt tgcttcgtcg gtgggctcgc atgggctacc     120
accgatagaa ccttagctga tgctttcggt acatacggcg aagttctcga ctcgaaggtc     180
cgtttgttgc gcagagcaga aatcgaatcc gggcccattt tttggctttg ttgatgacct     240
tctgttactg attactgttt attaatctct ggtttacttg attcatctgt tactgttact     300
gttactgtta ttactgttat acccttgaaa cggtacgttc cgtctttttt ctcttttgt      360 caagagatga agatagatcg gttaattatt ttgcgtgtaa acgttgtaga tctgttagat     420
ctgagcttag ttttgtttta cttttatttt tcagatcatt aacgacagag aaactggcag     480
atctagagga tttggctttg ttacctttaa ggatgagaaa tgcatgaggg atgcaatcga     540
agggatgaac ggtcaggaac ttgacggccg tagcattacc gttaacgaag ctcaggctcg     600
tggaagtgga ggcggcggcg gtggttacgg aggtggccga cgtgaaggag gaggcggtgg     660
ttacggaggt ggtggtggtg gctacggagg tggccgacgt gagggaggag gcggtggcta     720

```
cggaggtggc cgacgtgaag gaggaggcgg tggttacgga ggtggcggtt atggcggtgg    780
tggtcgttat tagattaaat ttacttaatt ttggcctatt gttaaattgg cctttagatt    840
agtatccatt actgttttag tgtggttggt gttattgtcc tttatatttg gttaagatac    900
tgtgaatctg tattttacaa agttccatgg aatcaagtaa atgatggttt acgaaataac    960
tgtgtcggct tcttagttca ttactagttg aggaactctc ttatattcat tactttttaa   1020
atgaagttta aaggattaaa ttaattgagt tattaaagag tgagtacttg              1070
```

<210> SEQ ID NO 47
<211> LENGTH: 719
<212> TYPE: PRT
<213> ORGANISM: Artificial Sequence
<220> FEATURE:
<223> OTHER INFORMATION: interactor, Nitab4.5_0005552g0010.2 protein sequence

<400> SEQUENCE: 47

```
Met Glu Thr Ala Asp Ser Thr Arg Thr Phe Val Arg Asn Val Lys Arg
1               5                   10                  15

Val Ile Val Lys Val Gly Thr Ala Val Val Thr Arg Thr Asp Gly Arg
            20                  25                  30

Leu Ala Leu Gly Arg Leu Gly Ala Leu Cys Glu Gln Ile Gln Glu Leu
        35                  40                  45

Asn Ser Gln Gly Tyr Glu Val Ile Leu Val Thr Ser Gly Ala Val Gly
    50                  55                  60

Val Gly Arg Gln Arg Leu Arg Tyr Arg Lys Leu Leu Asn Ser Ser Phe
65                  70                  75                  80

Leu Asp Leu Gln Lys Pro Gln Ser Glu Leu Asp Gly Lys Ala Cys Ala
                85                  90                  95

Ala Val Gly Gln Asn Gly Leu Met Ala Leu Tyr Asp Ser Leu Phe Ser
            100                 105                 110

Gln Leu Asp Met Thr Ser Ala Gln Leu Leu Val Thr Asp Asn Asp Phe
        115                 120                 125

Arg Asp Pro Asp Phe Arg Arg Gln Leu Asn Asp Thr Val Asn Ser Leu
    130                 135                 140

Leu Ser Leu Lys Val Ile Pro Ile Phe Asn Glu Asn Asp Ala Ile Ser
145                 150                 155                 160

Thr Arg Lys Ala Pro Tyr Glu Asp Ser Ser Gly Ile Phe Trp Asp Asn
                165                 170                 175

Asp Ser Leu Ala Ala Leu Leu Ala Leu Glu Leu Lys Ala Asp Leu Leu
            180                 185                 190

Val Leu Leu Ser Asp Val Glu Gly Leu Tyr Ser Gly Pro Pro Arg Asp
        195                 200                 205

Pro Asp Ser Lys Leu Ile His Thr Tyr Ile Lys Glu Arg His Glu Thr
    210                 215                 220

Val Ile Thr Phe Gly Asp Lys Ser Arg Val Gly Arg Gly Gly Met Thr
225                 230                 235                 240

Ala Lys Val Lys Ala Ala Met Tyr Ala Ala Tyr Ala Gly Ile Pro Val
                245                 250                 255

Val Ile Thr Ser Gly Phe Ala Val Asp Asn Ile Ile Lys Val Leu His
            260                 265                 270

Gly Glu Cys Ile Gly Thr Leu Phe His Arg Asp Ala Asn Lys Trp Ala
        275                 280                 285

Ser Thr Gly Glu Ile Gly Ala Arg Glu Met Ala Val Ala Ala Arg Glu
```

-continued

```
                290                 295                 300
Cys Ser Arg Arg Leu Gln Ala Leu Ser Ser Gln Glu Arg Ser Lys Ile
305                 310                 315                 320
Leu Gln Asp Met Ala Asp Ala Leu Glu Ala Asn Glu Lys Ala Ile Leu
                    325                 330                 335
Ala Glu Asn Glu Ala Asp Val Val Ala Gln Gln Ala Gly Tyr Glu
                340                 345                 350
Lys Ser Leu Ile Ser Arg Leu Ala Leu Lys Pro Gly Lys Ile Ser Asn
                355                 360                 365
Leu Ala Asn Ser Val Arg Val Leu Ala Asn Met Asp Glu Pro Ile Gly
                370                 375                 380
Arg Ile Leu Lys Arg Thr Glu Val Ala Asp Gly Phe Ile Leu Glu Lys
385                 390                 395                 400
Ser Ser Ser Pro Leu Gly Val Leu Leu Ile Ile Phe Glu Ser Arg Pro
                    405                 410                 415
Asp Ala Leu Val Gln Ile Ala Ser Leu Ala Val Arg Ser Gly Asn Gly
                420                 425                 430
Leu Leu Leu Lys Gly Gly Lys Glu Ala Lys Arg Ser Asn Ala Ile Leu
                435                 440                 445
His Lys Val Ile Thr Ser Ala Ile Pro Gly Thr Val Gly Glu Arg Leu
            450                 455                 460
Ile Gly Leu Val Thr Ser Arg Glu Glu Ile Pro Glu Leu Leu Lys His
465                 470                 475                 480
Asp Asp Val Ile Asp Leu Val Ile Pro Arg Gly Ser Asn Lys Leu Val
                    485                 490                 495
Ser Gln Ile Lys Ala Ser Thr Lys Ile Pro Val Leu Gly His Ala Asp
                500                 505                 510
Gly Ile Cys His Val Tyr Val Asp Lys Ser Ala Asp Met Asp Met Ala
            515                 520                 525
Lys Arg Val Val Asp Ala Lys Thr Asp Tyr Pro Ala Ala Cys Asn
530                 535                 540
Ala Met Glu Thr Leu Leu Val His Lys Asp Leu Ala Gln Asn Gly Gly
545                 550                 555                 560
Leu Asn Asp Leu Ile Val Glu Leu Gln Thr Lys Gly Val Ser Leu Tyr
                    565                 570                 575
Gly Gly Pro Lys Ala Ser Ser Leu Leu Lys Ile Pro Glu Ala Arg Thr
                580                 585                 590
Phe His His Glu Tyr Gly Ser Leu Ala Cys Thr Val Glu Val Val Glu
                    595                 600                 605
Asp Val Tyr Ala Ala Ile Asp His Ile His Gln His Gly Ser Thr His
                610                 615                 620
Thr Asp Ser Ile Ile Thr Lys Asp Gln Glu Val Ala Glu Ile Phe Leu
625                 630                 635                 640
Arg Gln Val Asp Ser Ala Ala Val Phe His Asn Ala Ser Thr Arg Phe
                    645                 650                 655
Ser Asp Gly Phe Arg Phe Gly Leu Gly Ala Glu Val Gly Ile Ser Thr
                660                 665                 670
Ser Arg Ile His Ala Arg Gly Pro Val Gly Val Glu Gly Leu Leu Thr
                675                 680                 685
Thr Arg Trp Leu Ala Arg Gly Thr Gly Gln Ile Val Asp Gly Asp Lys
                690                 695                 700
Ala Val Val Tyr Thr His Lys Asp Leu Ser Gly Leu Glu Ile Ala
705                 710                 715
```

<210> SEQ ID NO 48
<211> LENGTH: 2160
<212> TYPE: DNA
<213> ORGANISM: Artificial Sequence
<220> FEATURE:
<223> OTHER INFORMATION: interactor, Nitab4.5_0005552g0010.2 coding
      sequence

<400> SEQUENCE: 48

| | | | | | | |
|---|---|---|---|---|---|---|
| atggagacag | ctgattctac | tcggacattt | gtcaggaacg | tgaaacgagt | aattgtcaag | 60 |
| gttgggactg | cagttgtgac | acggactgat | ggaagattag | cacttggaag | attgggagcg | 120 |
| ctctgtgagc | agattcagga | gcttaactcg | caaggctatg | aagttatttt | ggtgacttca | 180 |
| ggtgctgtag | tgttggtcg | tcagcggctt | agatatagga | agttgctgaa | tagcagtttt | 240 |
| cttgatcttc | aaaagcccca | aagtgagctt | gatggcaaag | cttgtgctgc | tgtgggccag | 300 |
| aatggcctta | tggctctgta | tgattcattg | ttcagtcagt | tggatatgac | ttcagctcag | 360 |
| cttttggtga | ctgataatga | ctttagggat | ccagatttta | ggagacaact | caatgacaca | 420 |
| gtaaactctt | tgctgtctct | taaagttata | cctatattta | atgagaatga | cgctatcagt | 480 |
| acgcggaaag | ctccttatga | ggactcttct | ggaatatttt | gggacaatga | cagtttggca | 540 |
| gctctactag | cttttggaatt | aaaagctgat | cttctagttc | tgttgagtga | cgtagagggt | 600 |
| ctttatagtg | gccctccccg | tgatccagat | tcgaagttaa | ttcacacata | cattaaggag | 660 |
| agacatgaga | cagtgattac | ttttggagac | aagtccaggg | tgggaagagg | gggcatgact | 720 |
| gccaaagtaa | aagctgctat | gtatgctgct | tatgctggca | ttcctgttgt | cataaccagt | 780 |
| ggcttcgctg | tcgataacat | cattaaagtg | ctacatgggg | aatgtatcgg | caccctcttt | 840 |
| catcgtgatg | ccaataaatg | ggcttcaact | ggagagatag | tgctcgtga | gatggcagtt | 900 |
| gccgcaaggg | aatgttccag | gcggcttcag | gcactttctt | cccaagaaag | gagtaaaatt | 960 |
| ttgcaggata | tggctgatgc | attggaagca | aatgaaaagg | caatccttgc | tgagaatgaa | 1020 |
| gctgatgtgg | ttgctgctca | acaggctgga | tatgagaagt | ctttgatatc | tcggctggca | 1080 |
| ttaaagccag | gaaaaatttc | taatcttgca | aattcagttc | gtgtgcttgc | taacatggat | 1140 |
| gagcccattg | gtcgcatttt | aaagagaacg | gaggttgctg | atggattcat | cttggagaaa | 1200 |
| tcatcatctc | cattaggcgt | tctattgatt | attttgagt | cacgaccgga | tgcacttgta | 1260 |
| cagatagctt | ctctagcagt | ccgaagtggg | aacggcctct | tgttgaaagg | aggaaaggag | 1320 |
| gccaaaagat | caaacgctat | cttacacaag | gtgattacct | cagcgattcc | tggaactgtt | 1380 |
| ggtgaaaggc | ttattggact | agtgacttct | agagaagaga | tccctgaatt | gctcaagcat | 1440 |
| gatgatgtga | ttgatcttgt | tattccaaga | ggtagcaata | aacttgtttc | tcaaattaag | 1500 |
| gcatcaacaa | aaattcctgt | tcttggccat | gctgatggaa | tttgccatgt | ttatgttgac | 1560 |
| aagtctgctg | acatggatat | ggcaaagcgg | gttgttgtgg | atgcaaaaac | ggattatcct | 1620 |
| gcagcctgta | atgcgatgga | aacacttctt | gtgcataagg | atttggcaca | aaatggaggt | 1680 |
| cttaatgacc | tgattgtgga | acttcaaaca | aaaggggttt | ctttatatgg | tggaccaaaa | 1740 |
| gcaagctccc | tgctcaagat | tccagaggcg | cgtacttttc | atcacgaata | tggttcactg | 1800 |
| gcttgcactg | tggaagttgt | tgaagatgta | tatgctgcaa | tagatcatat | acatcagcat | 1860 |
| ggaagtaccc | acactgatag | cattattacc | aaagatcagg | aagttgctga | aatattttta | 1920 |
| cgtcaggttg | acagtgctgc | tgtatttcat | aatgcaagca | caagatttag | tgatgggttc | 1980 |
| cgcttttggac | tgggtgcaga | ggttgggatt | agcacaagtc | gtattcatgc | tcgtggccca | 2040 |

```
gttggagttg aagggttgct aactacgaga tggcttgcaa ggggaactgg acaaattgtt      2100
gacggtgata aagcagttgt ctacactcac aaagaccta gtgggcttga gattgcataa      2160
```

<210> SEQ ID NO 49
<211> LENGTH: 19454
<212> TYPE: DNA
<213> ORGANISM: Artificial Sequence
<220> FEATURE:
<223> OTHER INFORMATION: interactor, Nitab4.5_0005552g0010.2 genomic
      sequence
<220> FEATURE:
<221> NAME/KEY: misc_feature
<222> LOCATION: (8815)..(8839)
<223> OTHER INFORMATION: n is a, c, g, or t

<400> SEQUENCE: 49

```
atgaaaatgt gttggataaa aagcaaaata aggtaaggga aaacgacttt ccacaacaaa        60
aacaaacaat agtggaggaa aacgtgctga gcaatcccca agttccaata cacgcccgta       120
caaaacccaa atccccaaa tcgaagtcgg attaagtaga actagagaac tggctgaagg        180
cagtagactc cacatatttc tgctgccgtt ttgcagtcta catttctttc tctctcttct       240
gagctaaaaa tggagacagc tgattctact cggacatttg tcaggaacgt gaaacgagta      300
attgtcaagg tctcaacttt atcctccttt tttcctctaa tttcttttcc ttattattgc      360
ttaatccctg cattgcattt ggccctgatt ttcttttgta gaataattct tgtcagattg      420
gaaagagtcg tctgtcctta atgaagattg attttagtta gctatcatac ttatgtttat      480
tgtatgtata aggatttaac ttatatagtg ggacaatgag tgtaatttaa ccttgtttta     540
acatattttc aggttaccaa tccgtactta acattgatat ttacttgtaa ttagttttta      600
agtgacttga ttgttaagta cgtgtttaa ttagctattt gactgggcac gaaatttaag      660
aaaagaaatt aaattttttt gaaacttgtg attttaaata tgccataata cttgtaggtt     720
atagaagctt tcccattaag gtaaaatgga agtttaact taaattgttt ccaaattctt      780
ttcaaaacag attaaaaagg aaatagggtc atataagctg gaagagaggg gataattttt     840
acactgtcaa tgtacaaaag ttaaaatcat tgtgtatgtt gttccttcta ttccctgtct     900
gttattttag tttttcta atatattgct aacaaattta attttgatg tcattttaa      960 aggtgggac tgcagttgtg acacggactg atggaagatt agcacttgga agattgggag    1020
cgctctgtga gcaggtgaat cttatactcc ctctgtttca atttatgtga cataatttga    1080 cttgaatgg agtttaataa aaatggaaga cttttgaaac ttgtggtctt acttgccata    1140
atatttgggt gtctataaga catttgaaac ttgtggtctt aaacattcca taacattgt     1200 tggctataaa agcttctcat taagggtaaa ttggaaagtt caagttaag ttgttcccaa    1260 atagagaaat ttttcattct tttttgcaat aagtaaattg tgtcacatat attgaaacag    1320
agggagaaat agtttgattg ttagtatata tctgcatctt ctaaagctta ctggttttgc    1380
tgcaaactgc attacagatt caggagctta actcgcaagg ctatgaagtt attttggtga    1440
cttcaggtgc tgtaggtgtt ggtcgtcagc ggcttagata taggaagttg ctgaatagca    1500
ggtttctacc atgtccttgc tgtcaaataa gatatttact tagtaaatag gttatataac    1560
tagaattgtt aataaacaag tttaactcaa atgtaacttg acttattagt aagagctaac    1620
cttgatggta tagttgatat tgaattatgc aaatgaacca caaacatatc tgaagtactc    1680
tatccatccc attttatatg gctatatttg attgtgcatc gacttaagat attaattaac    1740
acattatatt agtgatggta gaagaaaaca ttaaagcaaa aagaaaagtt agtttgatag    1800
```

```
aaaaaatatc aagtcagttt aaaatttgaa tagtttaatg aatttgagtt ctggaaaatt   1860
gtaaaaattg tataaagata tggtgtcaat cottttggga tctcaaaatg gaaagaaggg   1920
tcatatgaac tgggtcttag gttgtaactc gttcatagat atatatattg gttgtactaa   1980
tgatctgaat aataaagtaa tgctctatat atatctcact ctgtgaatca gaagttactt   2040 gaaaagaat caatattctt accttttgat ttgatgtagt actgaaaggg tattaaactc    2100
tatcttttat cctcagtgac aagattccaa cgataggatt tgaatattcc agtatctgca   2160
atttactatt aactaccaag tcatcatatt tgcagttttc ttgatcttca aaagccccaa   2220
agtgagcttg atggcaaagc ttgtgctgct gtgggccaga atggccttat ggctctgtat   2280
gattcattgt tcagtcaggt tgaagcacag ttcttggaac tttttgttt gttctaactc    2340 ttgatttgtt tatcataacc acataaccgt ccttagctta aaggattgtc tactgacttt   2400
ttattctttg taccatcttt atacagttgg atatgacttc agctcagctt ttggtgactg   2460
ataatgactt tagggatcca gattttagga gacaactcaa tgacacagta aactctttgc   2520
tgtctcttaa agttatacct atatttaatg agaatgacgc tatcagtacg cggaaagctc   2580
cttatgaggt gtgtctctct gattttacac tgtagttgct gtcttcttgc ccttttttgt   2640
gaaagtgatg tacttttaag gttttgcacc tcttaagcac aaagaagaga gaaaaataaa   2700
agcaccccgt taaatttttt caaaaaacta gtgaaagcgt tcttcaaaact cacgtaaaaa   2760 gaatgtaaga tgaaaagaac cttaccactg ttcttctgga ggaagaatga aataaaagat   2820
aaatcacgtt tttgaagcaa gagcttagaa aaactaatca ccaatgttta ttttcagtat   2880
attgagccct ttaaataggc cttacaatga gtaaaattga taaggttaag gaaaactaat   2940
cctaattaaa ctagaataag aataaggcga agaaaaccta tcctaactaa aataggaaga   3000
agaattctag taggaatgga ctaccaatta acaatcccac tttgactaga accataaata   3060
taatcctact aaaacaagaa ttaagaaatc ctaatattta aggaaaggaa atcctaatct   3120
tgaatggatt cttggacttt caatttcttg agattcttgg gcctcaattg gaccagggct   3180
aattagtgta accatttaa atttgtggcc caattctcca aatccattgg caccttcatg    3240
aacccaataa gcctccattg ttgtagaaaa catggcctcc atgctactct aacatcacgt   3300
cttgagcttg tatgttcatc agaaagttcc tctcattagt agataggtca caatgtttct   3360
tgctgtaggg ctgaccagtt gcgtaattgg tcaatccatg cgttggaact agaaatccct   3420
tgagtaatgt tcatgcatct atttcaagta aacttcatca tgtgctgtta ttaactaatc   3480
aaaaataaag aactcatttg ttgattttac agtcgacata tacatatatg gttgtctgat   3540
atatgcttct actcatcagt tctctgttat tattctcatt gttgtttcct gggattggga   3600
ggggaatgta ttaagatagt gcatgtgacc atgcacggca tttaaagttg gtttctgcca   3660
ctttggtccc aaaatttcat ctttgcttta atgagctttt gtttggttga tcctgctgt    3720 tctccaaatc tgtaatatga tttcgagttc tagcaagtat ttctagatat aatatcttat   3780 atctttcat ttcctcagct catggtttta ttgtaataat gaacacttct tgtaggactc     3840
ttctggaata ttttgggaca atgacagttt ggcagctcta ctagctttgg aattaaaagc   3900
tgatcttcta gttctgttga gtgacgtaga gggtctttat agtggccctc cccgtgatcc   3960
agattcgaag ttaattcaca catacattaa ggagagacat gagacagtga ttacttttgg   4020
agacaagtcc agggtgggaa gagggggcat gactgccaaa gtaaagctg ctatgtatgc    4080 tgcttatgct ggcattcctg ttgtcataac caggtctgat actagtattt acgcaattgg   4140
```

```
aattcttaat atttatgtgc atcagtttta cacttgttca tttaaaatat tcaagtgttg    4200
tcttcttagt agagtggaca ggatttgtga tacctcttta tatatgggct ttgccctttt    4260
ttgtcaataa aaataatata actgtccaaa gagaagcatt taggatgacc ttaaaagtgc    4320
aaaaaaagtc tgaattaaaa gttgaattta tagctttgtt ggggatgcac aagaaaatct    4380
gaggtacctg actggagctg aaaggaaaat gctgtcattg agtctgtatc aaagttgaat    4440
ttatagctta cggtaggaaa tgcagaagaa tctgaggtat tttactggag ctgaaagaga    4500 aaagatgtc attctactgt gataaaacat gacaattgat ctgctgaaag cacaaacagg    4560
cacacaagaa aaaaaaaaga agaaaaaagt aaaaaaaata aaaagaagc aaaagcaaga    4620 acaaacatga ggtaaaaccg attctgtatt gcatagcctg cattatgaag aatgcatttt    4680
gagtagtata accatttctt taaaaaacaa ttcttgttat ctttgagtga accgcttggg    4740
cgttaattga gtgggttggg gcagttgact tttaggtgaa cctgcttcca gaaaatttgg    4800
cttctagttg ttgatgctta attaagaaaa gacgctcttc agcaacgaaa gtatgccaac    4860
ggtagagaag tttgagctct ttatgctgcc atattatttg tgtaaatatt gggtatatca    4920
agtggctaat atatgcctgt aatatttcat ttcaaaattg attgaatttc aggctaagca    4980
gtttataatt gaaaaattaa aacgggtaga cttttttataa atctgtcgca tatgagacta    5040
ctgtattcta ttgttgaata atattatgcc gcttgtgacc attaatgtcc atagatagtg    5100
agaaaggcaa atgtaataat tttctaatta tgtgtggtta aggacctagc aagagtgtgt    5160
gtgtataggg tcttgctaac ctactacatt gttgtagtaa gttagcattg tatacatatt    5220
tcatttctcc aaaatacccc cgcgttttct ttaatagtaa ggacatcttt gtctttaaa    5280 tctattaggg caatcatctc cattcggcaa actttccgtc ctcgtgaatc tttaatcccg    5340
tttttgctga aaactgggaa ttcttttgtta ttaatgcaac aaatttcctt ttagcaattt    5400
atcaatgttg ggcttcaatt gattttttgt tcttttccga aaaaaatttg aatcaagttc    5460
ttaacaaaaa gacagagaaa tcattatgtt ttgatctgta atactaagcc ccatttcgat    5520
tcaagatctg ttcagatcaa aatccggcta tggttaatct tcaaaatgcc ggtcaaaccg    5580
acttagaatg ttgacgagaa aaacaaggaa agaggatgta gagcttgctc tgcatcactt    5640
aatcgacctc ccaaggcatt gtcttccact tcatctgagt agaaattggg gaatttgggt    5700
gaattcatga atgattaaga ttggactaca aatccgatat agaaaattga agatgcaact    5760
tggattgaaa agaggaagct taagtagcat tatgttctgg cattggattc ttactcatac    5820
tagattgttc ttttgccgag tatcgataaa atgataagag gaaaaggta tacggttcca    5880 attttataaa agttatgaat aggttagatt tagacatata aagttctgaa gataaaaaaa    5940
tctctcacaa aaacatcaga ttgcaactcc ttcatagatc ggaagaggaa gctaaagaga    6000
atgctagaat gagaaaatga gaaaaagggg agaagaattt gggtttaagt tttcagtaga    6060
agacaaaaat gcgcttgcca ttaatgtgtt gctgaaccac tattaagggt atttaagtga    6120
aaccaaatat gtatacaatg ctaacctact acaactatgt agtaggttag caaaacctat    6180
ataaggtctt gctaacctac tacattgttg tagtaagtta gcattgtata catatttcat    6240
ttctccaaaa tacccccatg tttttcttaa tagtaaggac atcttgtctc tttaaatcaa    6300
ttagggcaat catctccatt cggcaaactt tccgtcctcg tgaatcttta atcccgtttt    6360
tgctgaaaac tggaattctt tgttattaat gcaacaaatt tcctttagc aatttatcaa    6420 tgttgggctt caattgattt tttgttcttt tccaaaaaaa attgaatcaa gttcttaaca    6480
aaaagataga ggaatcatta tgttttgata tgtaatacta agccccattt cgattctaga    6540
```

```
tctgttcaga tcaaaatcca gctatggtta atctttaaaa tgctggtcaa accggcttag    6600
aatgttgacg agaaaaacaa ggaaagagga tgtagagctt gctctgcatc acttcatcga    6660
cttcccaagg cattgtcttc cacttcatct gtgtagaaat agggaaattt gggtgaaatt    6720
catgaatgat taagattgga ctacaaaacc gatatagaaa attgaagatg cagcttggac    6780
tcaaaagagg aagcttaagt agcattatat tctggcattg gattcttact catacgagat    6840
tgttcttttg ccgagtatcc ataaaatgat aagaggaaaa aggtatacgg ttccaatttt    6900
ataaaagtta tgaataggtt agatttagac atataaagtt ccgaagataa aaaaatctca    6960
cacaaaaaca tcagattgca actccttcat agatcggaag aggaagctaa cgagaatgct    7020
agaatgagaa aaaggggaga agaatttggg tttaagtttt cagtagaaga caaaaatgca    7080
cttgccatta atgtgttgct gaaccactat taagggtatt taagtgaaac caaatttgta    7140
tacaatgcta acctactaca actatgtagt aggttatata tatatatata cacacacaca    7200
cacatacata ctccctccgt ttcaatttat gtgaccctat ttgattgaac acagtgttta    7260
agaaaaaaga gaagactttt gaacttgtgc tgtaaaatga aacgtatatt ttgtgtcgct    7320
ataaatcatt gcataaaggt aattatttcc aaatatgaag aggtcattct ttttggcacg    7380
gactaaaaag gaaataggtt cacataaatt gaaaccaata taataatgag tctaaatcta    7440
aattgtatta catatagttg ggtatataga aggggagcct tggcgtaact ggtaaagttg    7500
ctgccatgtg accaggaggt cacagcttcg agccgtggaa acagcctctt gcagaaatgc    7560
agggtaaggc tgcgtacaat agaccattgt ggtccggccc ttccccggac cccgcgcata    7620
gcgggagctt agtgcacccg gttgcccctta tatagttgtt ctaaatctag gaaccaatat    7680
agtagtgagt ctaaacctaa attagtagta gtttactttt aattctagta ctaaaattat    7740
attctactta gagtagatga taataacctt cgtactaatt atagtttttt tctatgtaaa    7800
tcaaaataat tatttctatt ttgttctaga taaataaaat gtattcccag atctattata    7860
gagtacaatc ttgtatcttt atttaactta aattcttcta gatcttcgct cagattttga    7920
gcaaatattt ctatattgta gtttgaagca aatatttaga cgcaatgtaa tgaagtaatg    7980
aactactaca aaaggctagt cttctcatgg agtttgagga catagcaaaa tatgaagaga    8040
tagtatggag gcagaaatcc agaatattat ggctaaagga aagaaacaaa aatttaaaag    8100
ttgcccaaaa aatggcaagt tctcatgaaa gattcaacta cataaatgat gcaagatcaa    8160
gaaggtcagg agtccaagaa attcaagaag tctaagaatc catttaagat taggattttt    8220
tctccataaa aattaggatt tcttatttga tgtttcctag taatttgatt cttgatttag    8280
taggattgaa ttttgtagct ctagtcaaac taggattgtt agttggtatt ctactcctaa    8340
tagaattctt tttcttttttt agttagaata tgttttttctt aaccttattg ttattctggt    8400
ttaattatga ttagttttttcc ttaacatgat caatttttact cattgtaagg cctatttaaa    8460
gggcttagta tgttgaaaat aaagattggt gattagtatt gtgatatcac aacgaagta    8520 tgccttatac attcttgagg agataggaat gccgggctgt agacccattc acactcatgt    8580
ggattcgaat tctaaacttt cgccaggacc cggggaatca ctaaacgatc tggaagatat    8640
aggcggctgg ttggtaagtt aaaattacctc acaggtacta gacttgacaa ttcttttcct    8700
gtgagtgttg tgagtcagtt tatggattct ccctgtgata gtcattggaa tgcaattgtg    8760
tatataaaat cagcccccaaa caaaggatta ttgttcgtag atcgaggcca tgagnnnnnn    8820
nnnnnnnnnn nnnnnnnnnt aataaattga aacggaggga gtagttaata catcaatcaa    8880
```

```
taatgtaatt ttccgattat tttacaacaa ccttttggt tatcaaaaat gtaattttcc      8940
gattatttt cacaagtacc aagggcccaa tattataaat attcagataa tcaagggagt      9000
gaagaggaca aaactgatga atacaatatc aaagagacaa ggaacatgca ttggatccac      9060
aagttgagga tttactacca aagttttatg atgatccatt ggagtatcta gccatgtgtg     9120
tcattgactt tccgtctttc agagatgctc aacacaatgt tgacttgatt gttgattcta     9180
tccattgtag tatctagcca tgtgtcattg actttccgtc tttcagagat gctcaacaca     9240
atgttgactt gattgttgac tctatcattc caaacaagtc agcatattgc gttaatccta     9300
aagtccataa aaatatgcat gaacaagagg aaggattact taaaaaatag tggataatgg     9360
agagtttgag gtatattgga gaaacaagat gtcttcactt gataaatata tatggccatc     9420
atcaaatttt ggtgtacaat cattgcaatt gatgcattcc cacgaagagc gctgatctct     9480
atacttaatt caaagctaga cacggagtta gctaagtttt atgaagttct aacaccaata     9540
acttcttatt gaaagttgaa gtttgatagt caacatagaa atattacatg gagaaggctt     9600
agtagaaagt tgaaacttag aaagtgggat ttagttcgac ccaagtgcta aggttcactt     9660
acaacatgaa gaagctccat aaataagcta gcaaaatata acttgaaacc tagtgagcac     9720
tgggtcccca ttccttaata tagcaaatct tgcaccatct atggaagttg ttagactaga     9780
ggacgagtct ttttcaacta ggggagaatg cgaaatcaag aaggccaaga attcagggaa     9840
ttcaagaatc cattcaagat tagaatttct ccatcaagat taggatttct tatttcctgt     9900
tttctagtaa tttgattctt gatttagtag gcttatattt ttgtagtcct agtcaaacca     9960
gaattgttag ttggtattct attcctacta gaattctttt ttctttttta gttaggatat    10020
atttttctta accttattct tattctagtt taattaggat taattttcct taacatcatc    10080
aattttactc attgtaagca ctatttaaat ggctcaatat gctgaaaata aagattggta    10140
attaattttt ctatgatctt gcttcaaaaa cgtgatttac tttttatttc attgttcttc    10200
gcttattcaa cgtttcttgc aatcttgctg gattgcggaa cgtgtgggtg aggtttctttt    10260
tcatcttaca ttcttctaat atgagtttga agaacgcttt cactagtttt gtggaaaact    10320
ttagtggggt ttttttgttt ttcttttcttc tttatgtgtg agaggtgcaa aaccttgaaa    10380
gtacatcaga catcctatgg ttcaaggcga gaccattact aatctagatg atatcaaaag    10440
ggagattata gcctattatc agaatctata tgctgaaaca gaatcttgga ggcctgatat    10500
aaaacaaaat gggtgggtca agcattagag aggaggaaag ggagtggatg caaagagact    10560
ttgaagaaca agaagtactg gaaagtttga aattatgtga agcagacaag atggatacaa    10620
cttagagacc aatacttcat ggagaaaggt aatatatgtg tagtttgaca agattgaata    10680
ggggtgcaaa agatctgtta atagtccata tgtgggtggg tgtcgcaatt ttggaattct    10740
cttgtggtta acactagcat aaaggtgggt aatggaagac actttatttt agagtgataa    10800
ttggttagga catgatccac ttaaagagat gtttcccgaa ttctatggta ttgccaccat    10860
acctgaaatt aaagtggaag aagcccgggg actgcatggc tggaatatca cttttagaag    10920
agggttcagt gattgggaaa tgggaagaaa tgctgacttc tttaaagctt tggaagtttt    10980
ctagggtctc actgatcatg aagataccttt actatggaac aaatgtaaga attggagcta    11040
cactttcaaa tctgcctatc ttgtgctttc aaataaaggc cagcatagtg agggatggtc    11100
atggaagaat atggaaagct aaagctcccct ttaaggtggt ctatttctca tggctgggta    11160
gcaagagaag catgcttgcc tcaagaaaaa ctgaaaagaa ggggatttca gttatgtggt    11220
agagatccgg aaacaaacag ccatttgttc ctgcattgtc ctatcactag gcaactgtgg    11280
```

```
aaaccgttcc ttaacattgt gggcctcagg tggaccatgc cttcaactac tgaggagctt   11340
ttgaagtctt ggaataacaa tggaggttca cttagacaga aggcatggtg gaggctgata   11400
cctgcttgca tttagtggac agtatggaaa gagaggaata catgagtttt tgaagatata   11460
tataatcccc tccaaaatat caagatgaat tgtattcttt tgttttattt ttggtgtaaa   11520
gaaagtcatg tagataatac agagtccttg gttgacatgt taggctttt gtaacttcga   11580 tggatcagtt ttgatttatc caccttgtac atatggtttt ctgcattgcc ttagtgcgtt   11640
ttctaatata ttgttacaag tctcaaaaag attagaggtt ctcatctcag acttaaccta   11700
gtcagaaccc aaaagtata accaaaacaa taaatcagcc tacagagtga atattttagt   11760
cgtcgtagga aagtgcttc tatttatgta tgataacact ttgtaaagtt tctcattcta   11820
atgcatttta agcattgata atcctaatgt tgtaagttca atggttggaa aacataaaaa   11880
tttctattca tccacccagg attctaagaa gatgggtgca ctattacaaa gaggtgaatc   11940
tagaagttat atttgtaagt tattaccatc tatgttgctc ggactcttcg aagatgtggc   12000
cggatacgtg tcggatcctc caaaagtagt gcattttga aggatccgac acgggtgcgg   12060
ttacattttg gagagtcctt gcaacataga ttaccatgaa cctaaaggtt aaagttatag   12120
gttaataggt taagttatag gtgaatctat taccatttag aaattatagc ttgaaattaa   12180
aaatttcgtg caattttaga gattttaac atatatatac ctatactcca tataaaaaat   12240
attgggtcat tgaaccgtgt tatatcatcc actgctatta gttttaatta tttaaaatct   12300
tgctatgaca aaaggagatc aaggatttca atgtcttaga tatggggatt ttgaatgaat   12360
aaattaaatt aaaaatgaaa gaaaagaaa agaaaatac ttaattaaaa taaaatalggg   12420 gacactagat atgccttcaa actgagattt aaacctctag ttcacttgga aaggtgcacc   12480
caataatcat tgttttaaag gactctttga gctggggtgc acacatgtat atttaagcaa   12540
ttttaaagaa atataacatt attatacatg gtatagagag acgagtatgg gttcatgtgc   12600
cccatgctcc aacacataga tactcccttg catccaccaa cagatctgtt aacacttgac   12660
acattctgga gaagaccacc ttcgaatcaa tttagactgt tctctaatcc tcaaaaacag   12720
attcctgcag gcctctttt tggtaattaa cctttgttgt atacagttta tcagaagtcc   12780
tactacaatt gaagatactt tatgctctct tctattccaa aaaaaaaagt tgggtgcatt   12840
aactgctaaa agagattact ctatttcatc cttggacttt taccttggaa atataaagtt   12900
actgtcaaaa atgtcgacta tggagcttag ctagaaagaa taactatgtt atgaagaact   12960
tttccaagct gtggctcagt ggatgaagct gggataaaga tcataggaga ccatggtcta   13020
aaatccagca gaggccaagt gaacaaagtt accctagcct gtatatgtat tggtgggagg   13080
atgtaattac ccggtggaat agttgaggta cgtgcaagct ggtccaaaac accaataaaa   13140
caccattgct atttaaaag aaaagggtgc tagcagaaca agatggtgat agtaagtggt   13200
taggttgaaa acgaatgcaa taaaataagg ctgaaaaacg aatgcaaatc agtacatgag   13260
taaagcgtat tatatgtagc aaagcattgt tcttcagatg ttcagtgtga aagctgattt   13320
ctctaagttt cttgctccct ttacctaaaa tttctgctga ttctttctct ctatccgtct   13380
gtgtgcgttc gcggggataa gtggcttcgc tgtcgataac atcattaaag tgctacatgg   13440
ggaatgtatc ggcaccctct ttcatcgtga tgccaataaa tgggcttcaa ctggagagat   13500
aggtgctcgt gagatggcag ttgccgcaag ggaatgttcc aggcggcttc aggtatatct   13560
agagagacat ctggctgtaa cattttgtaa accgcatgga tgtgaatatt tattctttgt   13620
```

```
tccttcacct ccaggcactt tcttcccaag aaaggagtaa aattttgcag gatatggctg   13680
atgcattgga agcaaatgaa aaggcaatcc ttgctgagaa tgaagctgat gtggttgctg   13740
ctcaacaggc tggatatgag aagtctttga tatctcggct ggcattaaag ccaggaaaag   13800
taagagcgtg ctcactttgc aacttagtct gaatgatcat gtaccttttt agtattcttg   13860
ctgaaagggc tactcctttg tcatagattt ctaatcttgc aaattcagtt cgtgtgcttg   13920
ctaacatgga tgagcccatt ggtcgcattt taaagagaac ggaggtaagc aaatcacacc   13980
aaatatatgt ggcatgtagt ttttaataca tgaggaatag agaacaaatt gtgaaggagt   14040
cttgtgaagt acttctttaa gaaaaaactt ctgcactctc agacgattta gtgggtattg   14100
tacaatgtcc attgacaatt atatttaatg gtatagccaa agctattttg ttgttgtttt   14160
gtttcttggc catgaaaaga actgggctga cttgttggaa tattgggagc aacagagatg   14220
tcgatttgta actagaaacc tttattgatc agtgttcagt tattagcctt tagtttcaga   14280
gtgagatgtt gatttaatgt ctggaatatt gtcgtctcgt ccaggttgct gatggattca   14340
tcttggagaa atcatcatct ccattaggcg ttctattgat tatttttgag tcacgaccgg   14400
atgcacttgt acaggtaagc aatgctggca aaagaagtt ttccactagc aggaaggttc   14460
tgctgcatgt ccaatataaa ttagtagggt tctctttta gtagttatga aacactttt    14520 ctttactaat ggcggggaca atggtgatta acatatgtct gtatatgtaa acttcacgga   14580
attctctgca tgcttgaatt gcatgtcctt ggattattcc tttacagttc acaaactcgt   14640 tgcactttt ttgcatgact agatagcttc tctagcagtc cgaagtggga acggcctctt    14700
gttgaaagga ggaaaggagg ccaaaagatc aaacgctatc ttacacaagg tttaactgat   14760
atcttacacg ctatcataca ctcttcactg aagcttcacg tttccatcat ttcatgtcca   14820
gctttgtcac cttctcctct tttcttttt cgtcttaggt gattacctca gcgattcctg    14880
gaactgttgg tgaaaggctt attggactag tgacttctag agaagagatc cctgaattgc   14940
tcaaggtacc tgccaaatat cttaaatgag aaacttatat tctccctctc tttcttttt    15000 aggaaatcat gacctacact ggacatgagt ttggttctta gtttattttt cttgcatccc   15060
gcagcatgat gatgtgattg atcttgttat tccaagaggt agcaataaac ttgtttctca   15120
aattaaggca tcaacaaaaa ttcctgttct tggccatgct ggtaattatg tgttacttga   15180
gtattggtta cttgctagac tcaatctctg ctttgatgtc acggattctt ttcctgcgat   15240
ggtaatatta ctatgtttgc ttccagatgg aatttgccat gtttatgttg acaagtctgc   15300
tgacatggat atggcaaagc gggttgttgt ggatgcaaaa acggattatc ctgcagcctg   15360
taatgcgatg gtagtttgtt atactttttc ataaaacagt gtccagtttt aaccaggtag   15420
tttattgatt tcttttcttt tttggttttt ttgcaataaa attgtttcat tgctttccct   15480
ggtaggaaac acttcttgtg cataaggatt tggcacaaaa tggaggtctt aatgacctga   15540
ttgtggaact tcaaacaaaa ggtagaactt ctttttcaaa ttctttgtgt aattaaagct   15600
tctatatgat tactgtggag tcttgacttg aaagtaggga aaatagaatc tgagggtatt   15660
tctgatagca aaatctgctt tgtaatgatt attttttgtta atctcagttt agcgttgagt   15720
tgcatcaccc atgaaaacac tcttgttgtt gagtctcatc tataatgaac agctatgttg   15780
cacggactct ccaaaatgct gcctaatagt tttcacacag ttttgcgtac taaccattct   15840
gtcctaatag ttttagaata tggtaaatgc tgtcttccct caactttctt tttttgttga   15900
gaaaagtgac cgactatcct cacattcctt ggccctgaaa ataaagttta attggattga   15960
agaaatgtga actgatgttt gcatttgtgg caggggtttc tttatatggt ggaccaaaag   16020
```

```
caagctccct gctcaagatt ccagaggcgc gtacttttca tcacgaatat ggttcactgg   16080
cttgcactgt ggaagttgtt gaagatgtat atgctgcaat agatcatata catcagcatg   16140
gaaggtgtta tgtttgccta acttttatct tttacaaggc tgcattatga ttcttttctt   16200
tttcaaatta tttcatattg gagctcttat actatgcaaa cttttgcaat ccttatttt    16260 atacacaact cattggcagt acccacactg atagcattat taccaaagat caggaagttg   16320
ctgaaatatt tttacgtcag gttgacaggt acattctcat gttttcaact tcatctttcg   16380
tcatgactga tgagtagttt cttcaatctg atatactaag acctctggaa tttcattaat   16440
ttctgatagt aagttttgcc cattattgtt aatcatttaa ttgggggaac tactactacc   16500
atccctgctt aaacatgttt gatcttcact tttcagtgct gctgtatttc ataatgcaag   16560
cacaagattt agtgatgggt tccgctttgg actgggtgca gaggtatata atctatcagt   16620
ggttccaaat tgtctttttgg tatcataatt tcatatttgt aagtatcttg attgcttttg   16680
gttgaatagg ttgggattag cacaagtcgt attcatgctc gtggcccagt tggagttgaa   16740
gggttgctaa ctacgagatg gtatatctgt tgtcaactct cttttgatttt caatccctgt   16800 tttctacatc attctggctt taagtcctat ctggaaaaact accactcttg agagattgcc   16860
ctcggaacaa gagacttctc aaatctctgg caattcacgt atcccttatg ataaaagaga   16920
aaatagaagt aaagaagatg acgttgtcag ttaaatctct ttatgttagt cgaaaatgaa   16980
gtctctcagc ttgacctaga tcccatgggt tccctataag acatgtcctc cagctttatt   17040
gcatttgcta caacttcttg tttatctttg tctgtttgct gcatgaactt ggttattact   17100
tcattacagg atcacatctg actgaactgg ccccaattta gttttttttct tgaccaaaac   17160 cagtctttta tatcaagtgt agccagatct ctgtgcataa ttgcatatcc agcctgcagt   17220
ccgttgcccg gtagttttcc tacttggcaa gatttggatg tggtaggcca aaggacatac   17280
atcacaaaac tccttagcta gttcatattg tttaagtaaa aagtccaaaa agagttggaa   17340 ctttttaagtt cttgagcacg gctgtcgagt aaagtcaaag aattactata tttccctcga   17400
tcagaaagag gtattacatt tctgcttata cattgaacgt gtgtgtgtgt gtgtgtgtgt   17460
gtgtgtgtat acccttcttt gtttgtgcct tcttctatta gacgcatgct tttattgcat   17520
gttgcacata aagcccggca gacgcttgac ttttttttctt tctttttgct tggaaaatac   17580
tggaaaatca cacgaaaatg gatgcgcaaa tgatcatctc tgactaaatt ggagatggag   17640
acctaatctc aagaatctac tctatagttg ctgtatgtcc tttttttgcca tgagctcttg   17700 attcttatca gaaatctttc ttgactctct tctttagcag tgttatgaaa tagtctggta   17760
agacaaattt cacttagatt gactgctgtt caagatgcat gaatgcttta tccccaaagt   17820
ggaaaaagag agatcagagg catgaatttg cggtggtttt actgggtgta tggcatgtgt   17880
aagaggaaga gtttagtagc tgtacaaaat ttaggccaaa tacataagtg gccacctaaa   17940
attgccacga ttttttcatgc acttcaacta aggctttcct attagtcact taaagtatat   18000
ctaaaatgtg tctattgagc acttcattga tcatgtatga atgggatgaa gacatgtgtt   18060
atttcgacca aaataatcc cactataaac agcttctaca accagagaaa aaccaacagt   18120
atctgagcaa acaacaacca aaaatatcc gaccagcagc ggccatcgaa aaaaactcga   18180
gcctggtcca aaaattaatt ctccggcgaa cctgtacaac gagccgaccc tttgtctcct   18240
tttgttctat tctctcctca tttcagatgc acattaaaaa atccttgcac cttcaaaata   18300
atataagaga accattgagt ttgaccggat atctattcca gttctctcaa tgacaacgag   18360
```

-continued

```
agctttgacg gcgctgatga tgaagaagat tttgagaata agctgaagga gattttttag    18420
gaaataagga atgattcttt gttgttctcc tcggtcttgt gtaataaatg aaattggaga    18480
taaagattag aggatggtga aaatgatctc aaaataaaat ttctctgaga atggttgctg    18540
gtggaattgg aaagtttgta aggaatgatt ctttgttttg gtgcttaggt ggtactgctg    18600
gccggtcatc gacgatccta agttgagtgg ccgatgggtt tattgtggtg ttctggtgaa    18660
gaaactaaaa aaataaaatt ttaattacaa ataaaaatat taggctcatc acgcaaagag    18720
aactgttatt cacataacat gacatgtcat cattttgtgt ttaatagcac acatttattg    18780
aagttgggac tgcctaatag gaaagagcct aagttgaagt gctaaaatga aaatcgcgg    18840
caatatgtat ttggcctgaa atatatgcta agttttggat tccagtacct acttttacct    18900
ctgcttttc agccgtttct ttcttgattt cttataaagg aatttgtctt tgttaaagtt    18960
ttcttaaggt cgtttagtta gtttccttgg gcataacaca cttatattca ttctgcatttt   19020
tgaacatgaa ttttgttcaa attatttggc caatgctgca attttctgta ggcttgcaag    19080
gggaactgga caaattgttg acggtgataa agcagttgtc tacactcaca aagaccttag    19140
tgggcttgag attgcataat tgaaagcatt ggttgtccca gttatgtttt acgaagatct    19200
tctgttgtac tattggatgt gggtaaagca ggtttgatgc ttactctctg tacgttccag    19260
tcatggattg acttatgatc atttgcatac tacaggtcaa aaattatttt gtataacaaa    19320
gtttcactgc tgcataggtt ataacttgta gcattataaa ctcgcagtct attttgtctg    19380
gcaaaggttt ccaattatga taaaatagga atgtgttcca aagaattttt ttttcataga    19440
aaagaatttg agtt                                                     19454
```

<210> SEQ ID NO 50
<211> LENGTH: 562
<212> TYPE: PRT
<213> ORGANISM: Artificial Sequence
<220> FEATURE:
<223> OTHER INFORMATION: interactor, Nitab4.5_0003679g0060.2 protein
      sequence

<400> SEQUENCE: 50

Met Ala Ile Glu Asp Asn Glu Ser Cys Gly Ser Arg Val Val Asp Ser
1               5                   10                  15

Ala Thr Thr Ser Gly Arg His Gln Arg Lys Lys Leu Glu Val Tyr Asn
            20                  25                  30

Glu Val Leu Arg Arg Leu Lys Glu Ser Asn Asn Val Glu Ala Leu Glu
        35                  40                  45

Pro Gly Phe Asp Asp Glu Leu Trp Ala His Phe Asn Arg Leu Pro Thr
    50                  55                  60

Arg Tyr Ala Ile Asp Val Asn Val Glu Arg Ala Glu Asp Val Leu Thr
65                  70                  75                  80

His Lys Arg Leu Leu His Leu Ala His Val Pro Ala Asn Arg Pro Ala
                85                  90                  95

Phe Asp Val Arg Leu Val Gln Val Ala Ser Val Pro Asp Gly Asn Leu
            100                 105                 110

Arg Asp Ser Phe His Ser Ser Phe Ala Lys Lys Glu Val Ser Arg Ser
        115                 120                 125

Val His Pro Pro Ala Phe Gly Ser Ser Pro Asn Leu Glu Ala Leu
    130                 135                 140

Ala Cys Glu Ala Ile Lys Ser Glu Val Gln Asp Glu Asp Thr Ala Ala
145                 150                 155                 160

Pro Cys Ala Asn Phe Ser Arg Pro Met His Glu Ile Thr Phe Ser Thr
                165                 170                 175

Asp Asp Lys Pro Lys Leu Leu Ser Gln Leu Thr Ser Leu Leu Ala Glu
            180                 185                 190

Leu Gly Leu Asn Ile Gln Glu Ala His Ala Phe Ser Thr Val Asp Gly
        195                 200                 205

Tyr Ser Leu Asp Val Phe Val Asp Gly Trp Pro Tyr Glu Glu Val
    210                 215                 220

Val Arg Leu Arg Thr Ala Leu Glu Arg Glu Ile Leu Arg Asn Glu Lys
225                 230                 235                 240

Ser Trp Pro Ser Pro Ser Gln Ser Phe Ile Lys Gln Glu Gln Asp Leu
                245                 250                 255

Ile Lys Arg Glu Phe Asp His Leu Thr Ile Pro Phe Asp Gly Ile Asp
            260                 265                 270

Val Trp Glu Ile Asp His Gln Leu Leu Lys Phe Glu Tyr Lys Ile Ala
        275                 280                 285

Ser Gly Ser Tyr Gly Asp Leu Tyr Lys Gly Thr Tyr Cys Ser Gln Asp
    290                 295                 300

Val Ala Ile Lys Ile Leu Lys Ser Glu Arg Leu Asn Thr Glu Leu Gln
305                 310                 315                 320

Thr Glu Phe Ala Gln Glu Val Tyr Ile Met Arg Lys Val Arg His Lys
                325                 330                 335

Asn Val Val Gln Phe Ile Gly Ala Cys Thr Arg Pro Pro Asn Leu Cys
            340                 345                 350

Ile Val Thr Glu Tyr Met Ser Gly Gly Ser Val Tyr Asp Tyr Leu His
        355                 360                 365

Lys Arg Lys Gly Ser Phe Lys Leu Pro Thr Leu Leu Lys Val Ala Ile
    370                 375                 380

Asp Val Ala Lys Gly Met Asn Tyr Leu His Gln Asn Asn Ile Ile His
385                 390                 395                 400

Arg Asp Leu Lys Ala Ala Asn Leu Leu Met Asp Glu Asn Glu Val Ile
                405                 410                 415

Lys Val Ala Asp Phe Gly Val Ala Arg Val Lys Ala Gln Thr Gly Val
            420                 425                 430

Met Thr Ala Glu Thr Gly Thr Tyr Arg Trp Met Ala Pro Glu Val Ile
        435                 440                 445

Glu His Lys Pro Tyr Asp His Lys Ala Asp Val Phe Ser Phe Gly Val
    450                 455                 460

Val Leu Trp Glu Leu Leu Thr Gly Lys Leu Pro Tyr Glu Tyr Leu Thr
465                 470                 475                 480

Pro Leu Gln Ala Ala Ile Gly Val Val Gln Lys Gly Leu Arg Pro Thr
                485                 490                 495

Ile Pro Lys His Thr Pro Arg Leu Ala Glu Leu Leu Glu Thr Cys
            500                 505                 510

Trp Gln Gln Asp Pro Thr Ser Arg Pro Asp Phe Ser Glu Ile Val Asp
        515                 520                 525

Ile Leu Gln Gln Ile Ala Lys Glu Val Gly Asp Glu Arg Ala Asp Arg
    530                 535                 540

Cys Lys Glu Lys Ser Ala Gly Gly Phe Phe Ser Ala Leu Arg Arg Gly
545                 550                 555                 560

His His

<210> SEQ ID NO 51

<211> LENGTH: 1689
<212> TYPE: DNA
<213> ORGANISM: Artificial Sequence
<220> FEATURE:
<223> OTHER INFORMATION: interactor, Nitab4.5_0003679g0060.2 coding sequence

<400> SEQUENCE: 51

```
atggcgatag aggataacga gagttgtggg agtagagtgg tggattcggc gactaccagt      60
ggtcgtcatc agagaaaaaa attggaggtc tacaatgagg ttttacggag gcttaaggaa     120
tcaaacaacg tcgaggcttt agaacctgga tttgacgatg aactttgggc tcacttcaat     180
cgtctaccta ctcggtacgc aatagatgtg aatgtcgaaa gggcagaaga tgtactcaca     240
cacaagcgat tgctacatct tgcacatgtt ccagctaata gacctgcctt tgatgtccgg     300
ttggtgcagg ttgcttcggt tcctgatgga aacttaagag attcttttca ttcgagcttt     360
gcaaagaagg aagttagcag aagtgtccat cctccacctg cctttggttc ttctcctaat     420
ctcgaagccc ttgcttgtga agcaatcaaa tctgaagttc aagacgaaga tactgctgct     480
ccttgtgcaa atttttcgcg gcccatgcat gaaattacat tttcaacaga tgacaagcca     540
aagcttctta gccagttaac ttcattacta gctgagcttg gctgaacat ccaggaagcg      600
catgcctttt ccactgtgga tggctactcc ctagatgtct tgttgttga tggttggccc      660
tatgaggaag ttgtgcgact tcgaactgca ttggagaggg aaatcttgag aaatgagaaa     720
tcatggccaa gcccgtcaca atcgttcata aagcaggagc aagacttgat caaacgtgaa     780
tttgaccatt tgacaatacc ttttgatggc attgacgtct gggaaattga tcatcagctt     840
ttaaaatttg aatacaagat tgcatctggt tcatatggtg acttatacaa aggtacatac     900
tgcagtcagg atgtagctat caaaatccta aatctgagc gcttgaacac agaattgcag      960
acggagtttg cccaagaagt gtatatcatg agaaaagttc gtcacaaaaa tgttgtccaa    1020
ttcataggg cttgtaccag gcctcccaac ttgtgtatag taacagagta catgtctggg    1080
ggaagcgtat atgactattt acacaaacga aagggcagtt taaactacc taccctgctt    1140
aaagtagcga ttgatgtagc taaagggatg aactacctgc atcaaaataa tattatacat    1200
agggacttga aggctgccaa tctactgatg gatgaaaatg aagtcattaa agtggctgat    1260
tttggtgttg ccagagtgaa ggcacaaaca ggtgtaatga cggcagaaac cgggacttat    1320
agatggatgg ccccggaggt aatagaacac aagcctacg atcacaaagc agatgtattc    1380
agttttgggg ttgtgctatg ggagttgctg acagggaagc ttccatatga gtacttgacc    1440
ccattgcaag ctgctattgg agtggtccag aagggtttgc gaccaactat acccaagcac    1500
actcctccca gacttgctga gctgctagag acatgctggc aacaagaccc gacatccagg    1560
cctgactttt ctgaaatagt agatattttg cagcaaatag caaagaggt tggagatgaa    1620
agagcagatc gttgcaagga gaagtcagct ggaggattct tttcagccct tagacgtgga    1680
catcattga                                                            1689
```

<210> SEQ ID NO 52
<211> LENGTH: 10865
<212> TYPE: DNA
<213> ORGANISM: Artificial Sequence
<220> FEATURE:
<223> OTHER INFORMATION: interactor, Nitab4.5_0003679g0060.2 genomic sequence

<400> SEQUENCE: 52

```
attcatcacc taaattttgc caaagctaag aatattaagc aaagcaaaaa aaaaagggga      60
```

```
atgtaattag cacgcaaaaa aagcagatcg aagataagca gatccacgtc aacttgactg    120
tgccaattaa aatcccacct ttaccccgag tcaaaaaagg gttatacaat acatacatac    180
atgattcatt tcatgtaccc acccccccca cacacagaga gagggaaaaa cgatatgacc    240
aatgggaatg aaaccttcct caaaaccact cccccaccg ccatttgttt cttaataatt    300
cttctcagtt ttcttttcaca aattaaacat gcatctttga tataaagtag aatttgaatt    360 ctgtaattt ccatctccat aacgaagatt cactttacgt aaactgcacc gcggccatta    420 ttttttcattc cggaggaatt taagactagt gagagaggtg aaatggcgat agaggataac    480
gagagttgtg ggagtagagt ggtggattcg gcgactacca gtggtcgtca tcagagaaaa    540
aaattggagg tctacaatga ggttttacgg aggcttaagg aatcaaacaa cgtcgaggct    600
ttagaacctg gatttgacga tgaactttgg gctcacttca atcgtctacc tactcggtaa    660
ctttaccttt ctacctctct ctatgtatta atccgtacaa ttatatacgt tttatgcggt    720
tttctataga cgataatata tgactactga catatgatct caaatgtacc gttgtcgttc    780
gcatttgttg tgcctttggg agattggatt attttttggtc gacagtttca atcttcttat    840
caagttagaa gtcgataatg ccagttatcg tttccagctt cctcttctgg tcttaaattt    900
ttaggtttta cttgccgaaa agtttgctat cttagcttgt taaaatttcg atgaaccagt    960
tgaatttgct aagcagttca catttgtgca gatgtattaa tgtgcgtgtt ttagatgcac   1020
gacgttgcga aacgctgaat acttttttt tttggagaag tgcatactta tgtgccgcca   1080
aaattgattg atcaataaac gaataccta tttttgcatt taaggtacgc aatagatgtg   1140
aatgtcgaaa gggcagaaga tgtactcaca cacaagcgat tgctacatct tgcacatgtt   1200
ccagctaata gacctgcctt tgatgtccgg ttggtgcagg taattaaact actcttgcaa   1260
gataacacct tttagttgct ttgctcttga tatcgcatac atttaaatca agcatgcctt   1320
tttctggagt taaggaggat attttagatg ttcgttcact ctgactagct agttcaatag   1380
accaacacat ctccgtgtaa tcttggtcct ttgtatttt tgtttattgt tgcttgtcca   1440
gtacctaatt attcccagta tatgctagtt atggattgaa tcaaacttgg cattgtgcag   1500
gttgcttcgg ttcctgatgg aaacttaaga gattctttc attcgagctt tgcaaagaag   1560
gaagttagca gaaggtatca ccttcgtgac attctacctg aaaacgattt cccataggac   1620
gctgtatttc tttggttact tagtgattca ttgaagcctt ttctgttgt ttaatataat   1680 cttgaattct tacttgtcat tgactgtgct aaataaccgc ttccattttg atacatagtg   1740
tccatcctcc acctgccttt ggttcttctc ctaatctcga agcccttgct tgtgaagcaa   1800
tcaaatctga agttcaagac gaagatactg ctgctccttg tgcaaatttt tcgcggtata   1860
gaattttttt tcttttgtg cattccgctt cgacgagtat atattatgaa gcataaaatt   1920
gtaaataatt ttgcaggccc atgcatgaaa ttacattttc aacagatgac aagccaaagc   1980
ttcttagcca ggtaattgat gtgcttattt attcaataca ctatctgctt gatagaaatg   2040
tactctatct gttggcagag gtgggatgtg gtaagctttt tatttgacat tgaaaaaatg   2100
tccatttatt attgaaaacca attgttgacc catgaacatg tataatattt aattctttat   2160
gtagaaatgt aattcaggga ccttgatgta tgaagggctg aggcttttgt ctgttccttt   2220
gtttcatgaa agaacacaac tctcatcttg ctgcagattt caaaatgatg catgatttgg   2280
aatgtgcaag taaaacagac ataattgtat ttggtgacac caaaattgat aaatattgcc   2340
tgcctacttg gcattgtgat gcagtgagaa aggattgtgt attgcaagaa aagaagtagt   2400
```

```
tctttatatc agtttatatc tcatgataag gaaatctgag acaataatga acctttgaat    2460
atgacagtta acttcattac tagctgagct tgggctgaac atccaggaag cgcatgcctt    2520
ttccactgtg gatggctact ccctagatgt ctttgttgtt gatggttggc cctatgaggt    2580
acatctctga cgttatatcc tcactttgat ctgggttcgc ttaggtgcct gttatatttt    2640
gtgacctaac atcaagaagt gacagataat gtatgcatgg tttaaagttc tgtattatgg    2700
tcgctttcag ctcaactaaa aattgagtaa ccacttttaa actatgtaaa gtttatgaga    2760
atttcatcaa attatttagg ctacataatt taaaaggaat ttgataattc tgattaaaaa    2820
ataatataaa ggatttgtac ttgtacatct agaaaattca gttataaata cttttaacat    2880
taagatttca ataaatcaaa gtgcataaag gtttacgtat gacaatcgac tatgataaaa    2940
catattggag tataactatg ttgaattcaa tgagagtata tcatacactt tcatttaact    3000
attattatgt cattaggttt ttgttttgtt ttttgttat ttcgtaagaa aaaatgtgac    3060
ataaatttaa taagagtgtc ccgctttcag cttaccttgg gaaatgatta tgtcttgctt    3120
tcttgattat tactttgtat atatcacagt catgattctc tacttcactt attaggaaat    3180
gagttttaaa aggtctacag taaaataatc ttttgaagt gttggttcgc caattaactt    3240
tttccggcat aggaatcctt tctgtagttg gcttgttgag ttctaggcta cactgttgca    3300
cctctaaatt cagtgcataa actgggagta ttttacattt caaacagaag tgaatgaaat    3360
tctgtgctcc aatgcttcat atttgtagca ccaattccag cattcagtgt gagccccatg    3420
gtaggtgcca attttatttt ttttttctaa ttgaaaaagt aaaatcactc tgttatggtt    3480
tctcggtcat ggtcggggtt gtctattata ttccttctga tgtcatgtgt ccaatggaac    3540
atttatttct gtttcttatc aggaagttgt gcgacttcga actgcattgg agagggaaat    3600
cttgagaaat gaggtacttt cctgttattt tgttctatat aatgacattt gatattctgc    3660
cgagatttct ggatatgttt tttctgcact agttaaatcc caactaatgt acaaaggact    3720
ttggtaagaa cagatttctg gtcgttttct gaatgattat acttttggag ttactaggat    3780
tagtcatttc cttgttctcc tcgacgagca atataagatt tagccagttg tctgtaagtt    3840
ttgtgtactt atcattttaac gaggtgtagc tccattcaga aatcatggcc aagcccgtca    3900
caatcgttca taaagcagga gcaagacttg atcaaacgtg aatttgacca tttgacaata    3960
ccttttgatg gcattgacgt ctgggaaatt gatcatcagc ttttaaaatt tgaatacaag    4020
attgcatctg gttcatatgg tgacttgtaa gtttgttatg agctatatca ttcctctgac    4080 catttttagtt tcctggagac ttaattaatt aggtaattgt ttcagataca aaggtacata    4140
ctgcagtcag gatgtagcta tcaaaatcct aaaatctgag cgcttgaaca cagaattgca    4200
gacggagttt gcccaagaag tgtatatcat gaggtctgtc tggttatacc tccctatgaa    4260
gcttatggct attatctttg atttctttct ctatgcttaa aatatgttca gacaatatat    4320
ggtattattg tcacattgct atatcctta cttttcagga caagtataag attacacacc    4380
atgtcaagtc gttatcttc ctctgatact gtatttcttt tgtacttgca gaaaagttcg    4440
tcacaaaaat gttgtccaat tcataggggc ttgtaccagg cctcccaact tgtgtatagt    4500
aacaggtagt aaatgtcgta ttcagatcac ccaacttgca gaattgtttc aaaatcgccg    4560
actatcactg ttttcaaaac catttcctgt atcagtttca gtaggagttc acttaatgtt    4620
tatttatctt tcatttcttt gactgtagag tacatgtctg ggggaagcgt atatgactat    4680
ttacacaaac gaaagggcag ttttaaacta cctaccctgc ttaaagtagc gattgatgta    4740
gctaaaggga tgaactacct gcatcaaaat aatattatac ataggggactt gaaggctgcc    4800
```

```
aatctactga tggatgaaaa tgaagtaaga cgcaatttc  agtaaggctg aaaatcttat   4860
actttgtgtg ctgtcttatt gctagatgtt tttagtcgct gatgttacgt atattgatga   4920
ttgatcaact ttctagagta attttttatca tgtccaacta actatgcttg taaatattga   4980
tttcccattt tcatttgcaa atgtagaacc attagctagt acacaaggcc ctaccacatg   5040
aaagaggttt atttctgaac gactataggg aagttattgg agatgccacc acaggatacg   5100
gagcgctgcg tattttatat accactgata acattttgtt atcactcttt tgcttagcga   5160
taatgggctg cttgaacttt gggacatttt ccaaagtttt tattatcagc ctataggaaa   5220
tctgctaaag gcaaatcatt gtggttgcat tagatctatg aaataggata tgactgtgtt   5280
ttatttcgag tccgtgaaaa acatattgct tttcttgaaa atattgagaa cacaagcagg   5340
ttgaaacaca ctgacgatct gtcctcatcg tggtcttta  gtgatagaac caggatggaa   5400
agaactgaga ggcacttaag gctattttg  tataaagata ggaaagaatt aaatgctaaa   5460
gcggaagtaa caaaacatta gcaagtccaa agcctccttg actgaaaaac agtgtctaaa   5520
aggcagacat gatgtaattc aatttgtagt ttctgttacc tccgtgtctg agattgtaga   5580
acgactccac ttctccctta cagccagatt ctaatattgg tgaccaaatt gcgcgaaatg   5640
cattaatgat gcaattgcca tcttttatcc caaaatttca ttgttgtagc tttcaattaa   5700
gcttcagctt gaaattcagt tcataacagt ggagttcaaa gtgtgccaaa ttaagggtgt   5760
aatctttcat tcatcccatg ttcttcaat  tgtactctag ttttcaacta gtttcactt    5820 tgaaatccct tttaatttga cttaaatcat ttggttagtg tacttagaca taataaaata   5880
tgtgttgtag gcatgtgtgg gttcattagt ccttcatcca ccttatgttc tgaatcagtt   5940
agtggtaaat tttgagtcta aaattagttt tcagctgttt gtaatcaata gtttgctata   6000 atttctcgc  agaatatatc gatcatgtta ttttttcaac tgagaattac tcattgatgc   6060
ttcactatgg gttaaattac ccaatacacc tttttatccg ctttttatttt cttaagtggg   6120 tttcaaaaat aattatattc aagctctctt ttgttagttt agtctaggcc aatcttaacc   6180
caaattagtt ggttgcttat caagttttac ctaatgtctt ttttcaggtc attaaagtgg   6240
ctgattttgg tgttgccaga gtgaaggcac aaacaggtgt aatgacggca gaaaccggga   6300
cttatagatg gatggccccg gaggtaggcc tatcattcaa atcttaagat aggaaattta   6360
atccgaaatc tcccaaacca ggcttaagcc ttaagataga agttagttat gagtgagcag   6420
aattttggtg cagatcttaa atttagccat ctatattgtt taggatttag gcggtattaa   6480
ttgattgtac acacagtagt gagtagactg ttgaaggtga tttaagagaa ggaagggatg   6540
gaagaagagg aatagagaga gggagcagtc cttatgtcaa gagggtggag tcttaactaa   6600
gatttgttca ttataagaat tatataatac aaagacgtgt agactctatt tgatctctca   6660
aagaattcga tagcttgtgg taccaattat gaatccattc aaggtaacag cagttgttac   6720
aatggaggct gaaggtacta aagttatgtg tgaaggcaga ccaatacgaa agcaatatgc   6780
gacatggttc ctctaaatag atacagaaag agctacatac atatgatagg tgtagtatca   6840
gaggtatatg ttgcatcata tttaccaaga actagatagc tagtactacc aatcatgact   6900
tgtgttaggt aagagagtct gcaattactg acacaagctt ccttctgga  cctccccatc   6960 caaataactc gcgtgagtcc tagataatgt gccgagatgt tacgttatta aattgctgca   7020
tggcaagtct ctagtgatct tggcaaagga tattttgttt ttttagtacc agaattgtgt   7080
gttactagaa tcagagagct gactgtgggg taccttactg caccatttg  ggctgcaact   7140
```

```
gcataaggga tgagtatcag aaaaagtttt gtgctttcta agctctaat  atcctttctt   7200 gtagattcta gatacaaact tatcaaaaat ggttaaattg gaacaaaac  acagtttatg   7260 atggagcatg agttttctca tatttccata actggaatta gaggcaattg aaactgtacc   7320
ttttagcttt ttcttgtttg aattttgttt cattggagtg ttgtgagata caagcactga   7380
tatcaactct ctgcccagtt gattgatgca caacaacaac aaacccagtg aaggtgtggg   7440
gaggataatg tgtacacaga ccttacccct accccggaag gtcagagagg gagaggttgt   7500
ttctgataga ccctcgacta gagagtagat gaaatgcgct ttataggaat atcacatata   7560
cataaagaag cataggccac aagtagtaac aacaacagta tattaaaaaa ccaaagcgaa   7620
agatgccaat caaacaacaa gtaaagatag cagtctatga gtaaagggga taccatacta   7680
atactaatgc tataggtctg gaaaagaaag agcagcgcgc tcgactaccc actagccttc   7740
taccctaata ctcgacctcc acaacctcct atcaagggac atgtccgcag taagctccag   7800
ctgcgtcata tcctgcctaa tcacctctcc ccgatacttc ttcggcatgc tactacccctt  7860 cctcatacccc attgttgcta acctctcaca catcataact ggggcatcaa tgtttctcct   7920
ttgtccgaac catctcagac tcgcctcccg catattatcc tccacggagg ccactttcgc   7980
cttttctcaa ataactccat tcctaatctt atcaaatcgg gtatgcccgc acatccattg   8040
caatattctt atttcagcta cttttatctt ttggacatga gagttcttga ctggccaaca   8100
ctctactcca tacaacatag tcggtctaac caccactcta tagaacttac ctttaagttt   8160
taatggaata ttcttattac acaagacacc ggaagcgaac tccatttcat ccaccctgac   8220
acgatacgat gtgtgacatc ctcatcaacc tccctatttc tttgtattat tgacccaaga   8280
tacctaaaac ttactctctt ggggatgact tgtgtatcaa gcctcacctc catgtccgct   8340
tcctgggtta cgtcgttgaa tttgcactct aagtattccg tcttggtcct gctcaacttg   8400
aaacctttag actccagggt ctccctccaa acctacagtc tcttgttaac acctcccaac   8460
gtctcatcaa tcagaacttt gtcattagca aataacatac accatgacac ctcccttgaa   8520
tgtgtcgcgt aggtgcgtct atcaccaagg aaaatagaaa cgggctaaga gctgatccct   8580
ggtgcaactc tatcacaacc agaaagtgtt ccgagtctcc tcccgttgtc ctaaccaggg   8640
tattacctct atcatacatg tccttaatca ccctaatata ggctaccgtg accccttag    8700 cctccaagca tctccatagc acctccctcg ggactttgtc gtatacttt  tctaggtcaa   8760 tgaacatcat atgcaagtcc tttatctccc tatacctctc caccaatctc ctcacgaggt   8820
gagtggcttc cgtagtcgaa cgaccccgaca tgaaacgaa  ctggttctca aaaatagata   8880
caactctcct caccctcact tcaaccatcc tctcccaaac tttcatcgta tggctggctc   8940
ttaatatgtt gactatagtg gtgatatctt gtgttttgt  tgtttggagt ggcttagaat   9000
tgaggtattt cattggttgt tactggccaa gaggatccag atgtgttagg taactcctag   9060
gtgtcagtgg tgattgatga aatttaatga ggttgagctt atttagtggg tacacgcaat   9120
gctgatcaat gattttatga ctgcttgtat aagatttgtg ttaaaaactc ctgttattt    9180 tgtataagat ttgtgtcatt gtaagcatca ctgcagttgc ttgaatagta attgaactag   9240
atggagcatg gaagggtta  tagaaactcg gccaaaaaca atcagttagt tatttgtgac   9300
agttacttaa atcagttaat gtgcgagtta cttccgttat tttctcaatg agattttata   9360
taactagttg tgcagttagc atggctgcat tggcttattt cagatctttc ttcttgaagg   9420
taatagaaca caagccctac gatcacaaag cagatgtatt cagttttggg gttgtgctat   9480
gggagttgct gacagggaag gtactgatat gtgattggaa attttgggt  tagcccgttt   9540
```

```
ttgttggttg tttctcttggt atatacttat attcacttga ttttgttaa ccagcttcca    9600 tatgagtact tgaccccatt gcaagctgct attggagtgg tccagaaggt aatgcttctt    9660
ttatttgatt ttattttatt tgtaatatcg tatgaccata atggttgatt gcatattgcg    9720
cgctcatcac atgcatgcgg gcgcacatag aaaagatatg cacaaatgat ttgatattaa    9780
ttttctaatt gctgccaggg tttgcgacca actataccca agcacactcc tcccagactt    9840
gctgagctgc tagagacatg ctggcaacaa gacccgacat ccaggcctga cttttctgaa    9900
atagtagata ttttgcagca aatagcaaaa gaggtatttg tctctgctca ggcattggcc    9960
agttaataat tattttctt ggtgataaat gtacagtaca cgtcacaaat tggatttact   10020
gggatttaaa agggtattga ttttctttgg ccgaacatct tttggtcacg atttacaatt   10080
ttctgtcaaa ttgccacctc atgccgataa tataaattgt attaatggct ggggaaaaaa   10140
gagttcactc tccttgaact tcttaagagt tggcagtccc ttcttcagct tccctagaat   10200
aataactatc ctcatttgtg ctttgctttt aattttcata atttctctgc acacaaagat   10260
ggatttaaat agtactctca taacataaac tgtaacaaag gaagtagttt attaactcgg   10320
caacactcga catgtgggtc aggttggaga tgaaagagca gatcgttgca aggagaagtc   10380
agctggagga ttcttttcag cccttagacg tggacatcat tgagtagatg cacacataca   10440
gaatgttgat aaagttttga ttttttagcct catttatcca gactgtacag ttttttttcca   10500 gatcaatgtt cccatggtca aaaggaagtt attatttcca attctttgaa caaattcctt   10560
ttataagcaa ctttcttttg gcagctccgt cagaagcttt cggagttgga tcaaattaga   10620
ttaatataat tttgcgacta ctccatcaac atcaacatcc acatccacat cattattcat   10680
tccccacgat cacgatatgt ttcgtattcc ctgaaagtaa tggtaggttt cccgtatatt   10740
gttgtttccg ctttctagtt gttttgcgtg tgtttcactg tttatgtgat atttgacctt   10800
tatatcgtgg ttttaggttt atggcatcga ttatgtgcgc tatgaaagaa atgaatttta   10860
aactt                                                               10865
```